(12) United States Patent
Cheng et al.

(10) Patent No.: US 10,030,103 B2
(45) Date of Patent: *Jul. 24, 2018

(54) STABLE HELICAL IONIC POLYPEPTIDES

(71) Applicant: The Board of Trustees of the University of Illinois, Urbana, IL (US)

(72) Inventors: Jianjun Cheng, Champaign, IL (US); Hua Lu, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/006,118

(22) Filed: Jan. 26, 2016

(65) Prior Publication Data

US 2016/0215093 A1     Jul. 28, 2016

Related U.S. Application Data

(63) Continuation of application No. 13/990,739, filed as application No. PCT/US2011/062656 on Nov. 30, 2011, now Pat. No. 9,243,040.

(60) Provisional application No. 61/418,269, filed on Nov. 30, 2010.

(51) Int. Cl.
| | |
|---|---|
| *C08G 69/48* | (2006.01) |
| *C08G 69/08* | (2006.01) |
| *C08G 69/10* | (2006.01) |
| *C08G 69/22* | (2006.01) |
| *C08L 77/02* | (2006.01) |
| *C08L 77/04* | (2006.01) |
| *C07K 14/00* | (2006.01) |
| *C08G 63/08* | (2006.01) |
| *C08G 63/68* | (2006.01) |
| *A01N 43/36* | (2006.01) |
| *A61K 31/785* | (2006.01) |
| *A61K 47/34* | (2017.01) |
| *A61K 47/59* | (2017.01) |

(52) U.S. Cl.
CPC ........... *C08G 69/48* (2013.01); *A01N 43/36* (2013.01); *A61K 31/785* (2013.01); *A61K 47/34* (2013.01); *A61K 47/595* (2017.08); *C07K 14/001* (2013.01); *C08G 63/08* (2013.01); *C08G 63/68* (2013.01); *C08G 69/08* (2013.01); *C08G 69/10* (2013.01); *C08G 69/22* (2013.01); *C08L 77/02* (2013.01); *C08L 77/04* (2013.01)

(58) Field of Classification Search
None
See application file for complete search history.

(56) References Cited

U.S. PATENT DOCUMENTS 5,245,056 A    9/1993  Karpf et al.
5,516,758 A *  5/1996  Stevens ................ A61K 31/785
                                            514/2.4
5,840,833 A    11/1998 Kahn
6,271,198 B1   8/2001  Braisted et al.
7,723,469 B2   5/2010  Walensky et al.
9,243,040 B2 * 1/2016  Cheng ............. A61K 47/48207
2006/0147177 A1 7/2006 Jing et al.
2006/0287457 A1 12/2006 Nishiguchi et al.

FOREIGN PATENT DOCUMENTS

JP     63-96200 A      4/1988
JP     63096200   *    4/1988
WO     02/22660 A2     3/2002

OTHER PUBLICATIONS

Engler et al. Highly efficient "grafting onto" a polypeptide backbone using click chemistry. Angew. Chem. Int. Ed. 2009, 48, 9338-9334.*
Christos Mitsos. Isosteres in Medicinal Chemistry. Group meeting Feb. 1, 2006; https://www.scripps.edu/baran/images/grpmtgpdf/Mitdsos_Feb_06.pdf.*
Uemura et al. Short Polymers of Arginine Rapidly Translocate Into Vascular Cells. Circ J 2002; 66: 1155-1160.*
Beevers et al., "Helical membrane peptides to modulate cell function," Chemical Society Reviews (Mar. 10, 2010) 39: 2146-2157 (DOI: 10.1039/b912944h).
Engler et al., "Highly Efficient "Grafting onto" a Polypeptide Backbone Using Click Chemistry," Angew. Chem. Int. Ed. (2009) 48: 9334-9338 (DOI: 10.1002/anie.200904070).
He et al., "DNA threading bis(9-aminoacridine-4-carboxamides): effects of piperidine sidechains on DNA binding, cytotoxicity and cell cycle arrest", Bioorg Med. Chem. (Apr. 15, 2008) 16(8): 4390-4400.

(Continued)

*Primary Examiner* — Marcela M Cordero Garcia
*Assistant Examiner* — Jia-Hai Lee
(74) *Attorney, Agent, or Firm* — Haukaas Fortius PLLC; Michael H. Haukaas

(57) ABSTRACT

The invention provides polymers comprising Formula I:

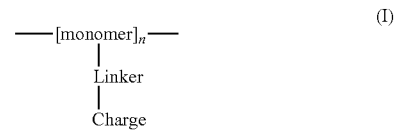

wherein monomer is a repeating unit comprising 2, 3, 4, 5, 6 or 7 carbon atoms and the monomers are linked together through amide or ester bonds; n is about 6 to about 1000; and Linker is an optionally substituted carbon chain that is optionally interrupted by moieties such as oxygen, nitrogen, sulfur, phosphorus, or silicon. Charge is a moiety having a positive or negative charge on a heteroatom, such as nitrogen, oxygen, phosphorus, or sulfur; where the Linker separates the monomer and the Charge by at least six linear atoms. The invention also provides methods of preparing the polymers and the copolymers and methods of using the polymers and copolymers, for example, as drug delivery systems, as membrane penetrating peptides, and as therapeutic agents.

22 Claims, 88 Drawing Sheets

(56) References Cited

OTHER PUBLICATIONS

Itaka et al., "Supramolecular nanocarrier of siRNA from PEG-based block catiomer carrying diamine side chain with distinctive pKa directed to enhance intracellular gene silencing", J. Am. Chem Soc. (Oct. 27, 2004) 126(42): 13612-13613.

Lu et al., "Hexamethyldisilazane-Mediated Controlled Polymerization of α-Amino Acid N-Carboxyanhydrides," J. Am. Chem. Soc. (Oct. 27, 2007) 129: 14114-14115 (DOI: 10.1021/ja074961q).

Luijten et al., "Cross-linking-induced permanently perpendicular helix orientation in surface-grafted polyglutamate films", Langmuir, American Chemical Society (Jun. 14, 2007) 23: 8163-8169.

Niidome et al., "Chain Length of Cationic α-Helical Peptide Sufficient for Gene Delivery into Cells," Bioconjugate Chem. (Jul. 30, 1999) 10: 773-780.

Nowak et al., "Rapidly recovering hydrogel scaffolds from self-assembling diblock copolypeptide amphiphiles", Nature (2002) 417: 424-428.

Sanborn et al., "Extreme Stability of Helices Formed by Water-Soluble Poly-N-Substituted Glycines (Polypeptoids) with α-Chiral Side Chains," John Wiley & Sons, Inc. (2002) pp. 12-20 (DOI: 10.1002/bip.1058).

Tang et al., "General Route toward Side-Chain-Functionalized α-Helical Polypeptides," Biomacromolecules (May 13, 2010) 11: 1585-1592.

Vaz et al., "Comparison of Design Strategies for Promotion of b-Peptide 14-Helix Stability in Water," ChemBioChem (2008) 9: 2254-2259.

Wyman et al., "Design Synthesis, and Characterization of a Cationic Peptide That Binds to Nucleic Acids and Permeabilizes Bilayers," Biochemistry (1997) 36: 3008-3017.

International Search Report and Written Opinion for corresponding International Application No. PCT/US2011/062656 dated Apr. 5, 2012.

\* cited by examiner

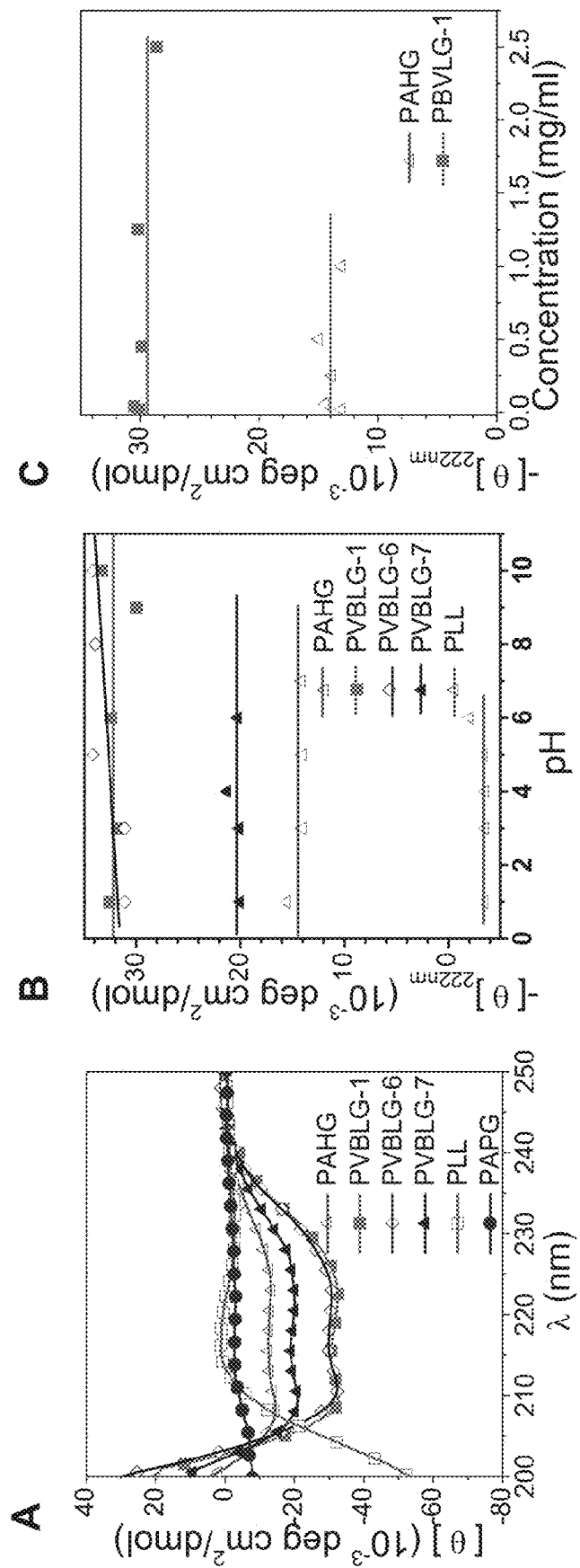
Figure 3A-C

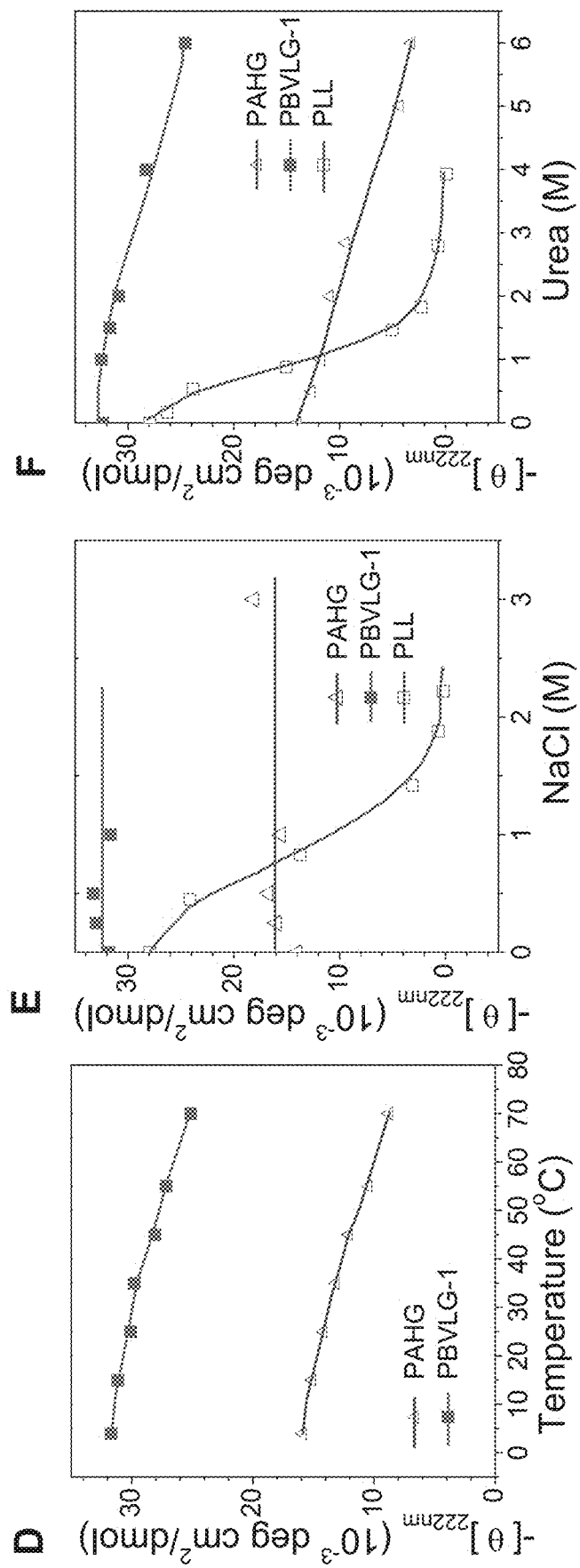
*Figure 3D-F*

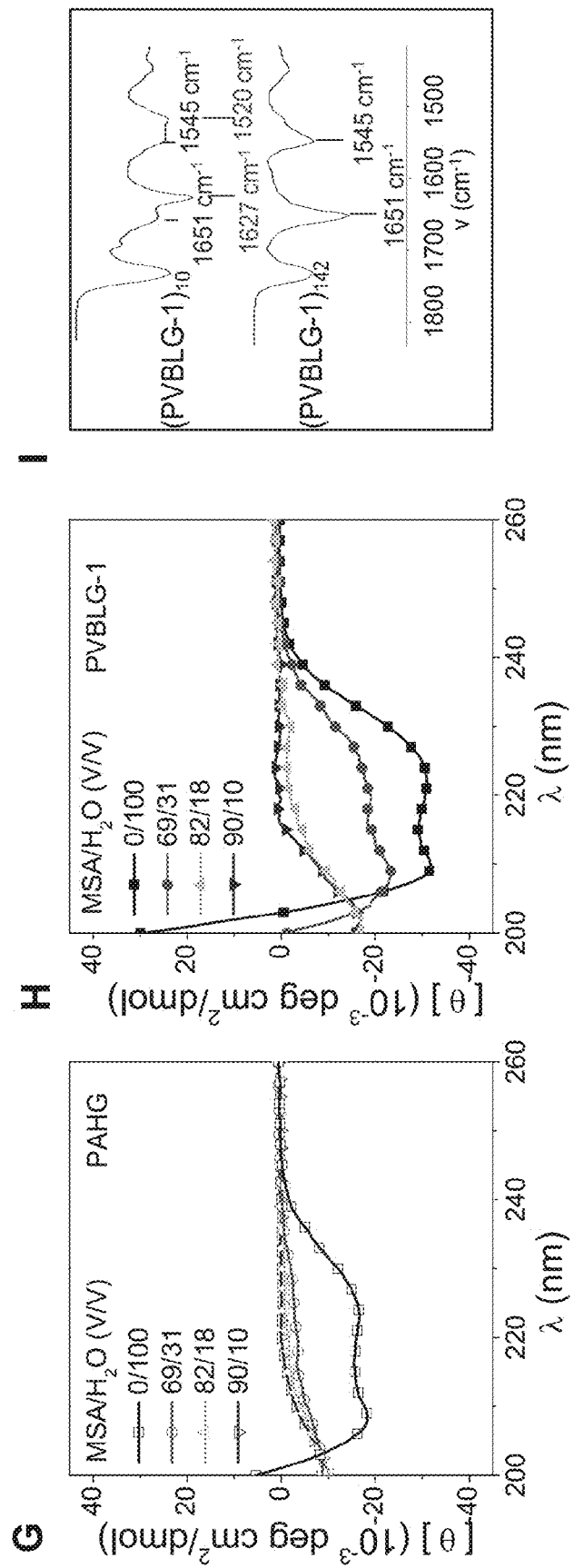
Figure 3G-I

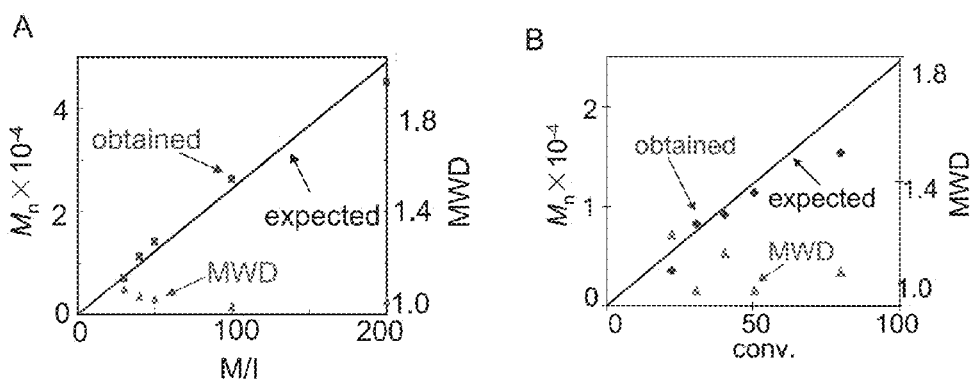
*Figure 4A-B*
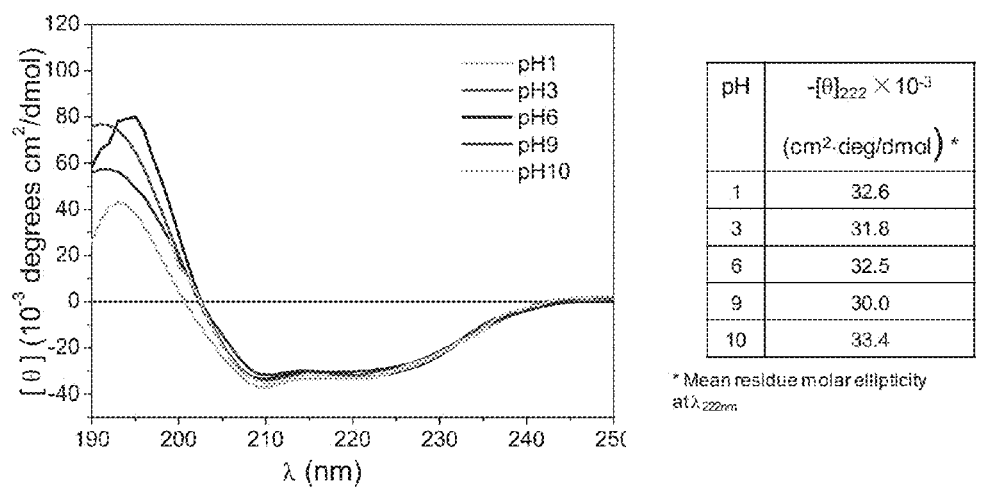
*Figure 5*

(PVBLG-2)₄₅

(PVBLG-3)₄₅

(PVBLG-4)₄₉

(PVBLG-5)$_{40}$ (PVBLG-6)$_{44}$ (PVBLG-7)$_{40}$

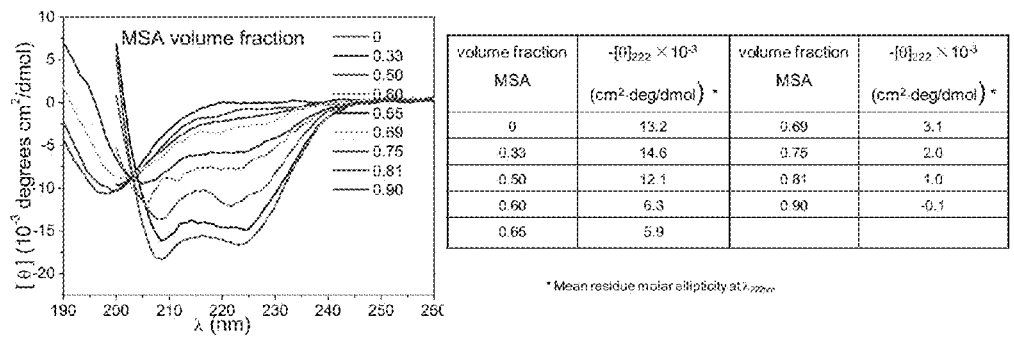
*Figure 25*
A
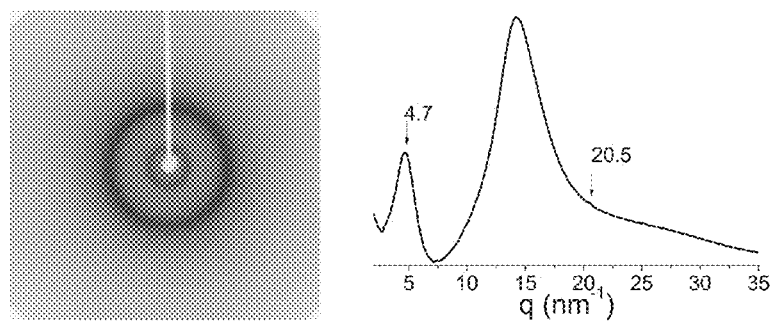
B
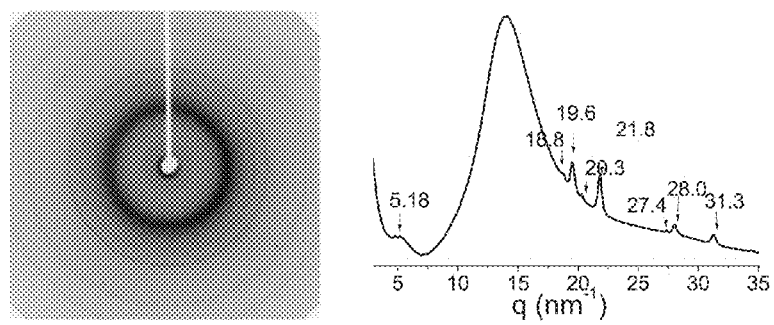
*Figure 26A-B*

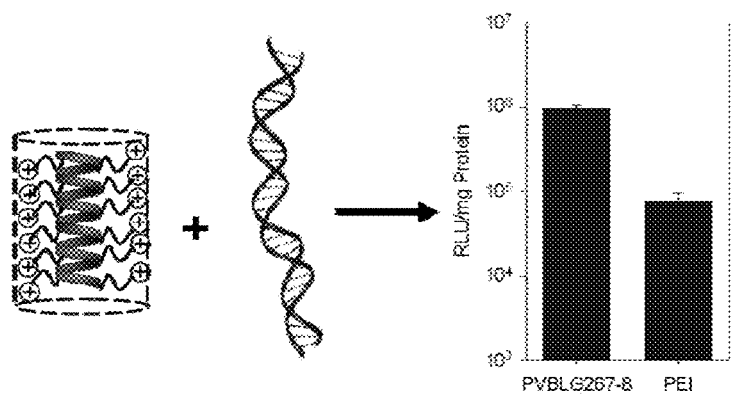
*Figure 27*
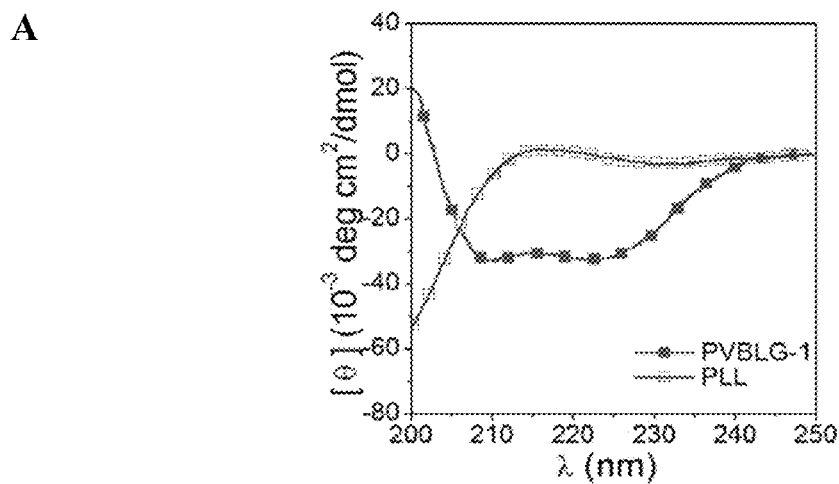
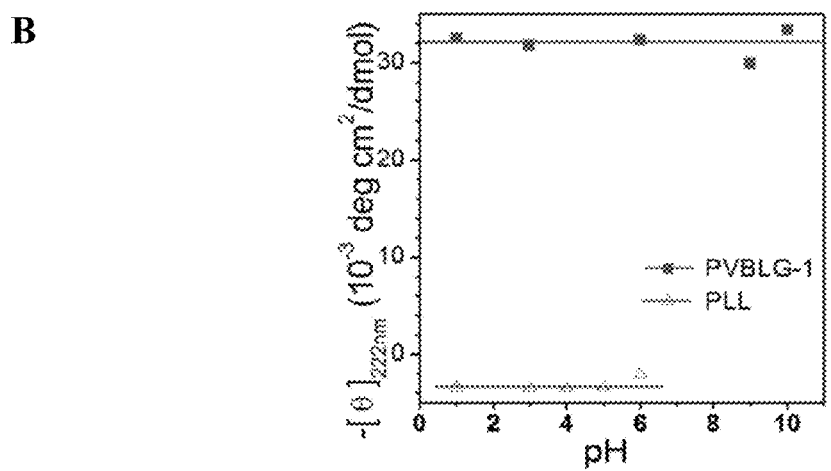
*Figure 28A-B*

C
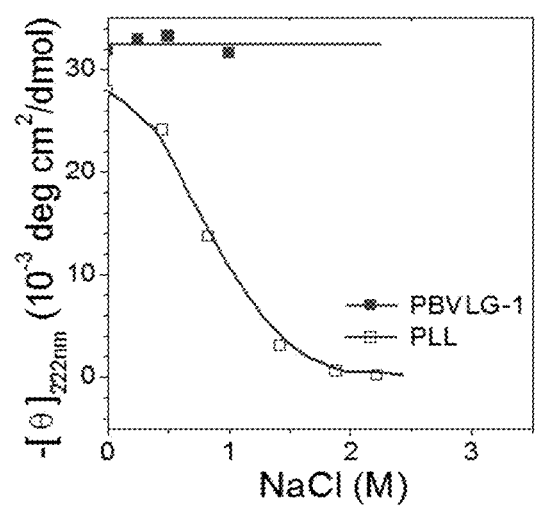
D
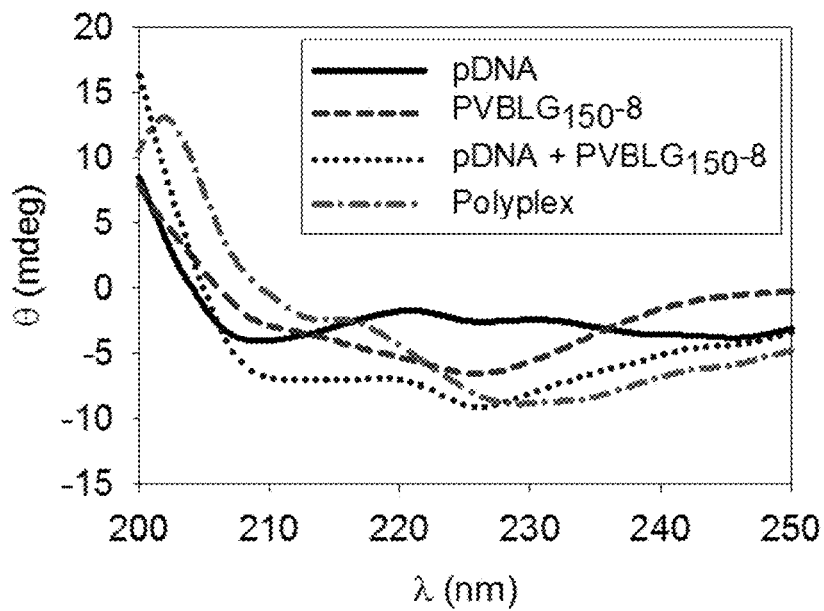
*Figure 28C-D*

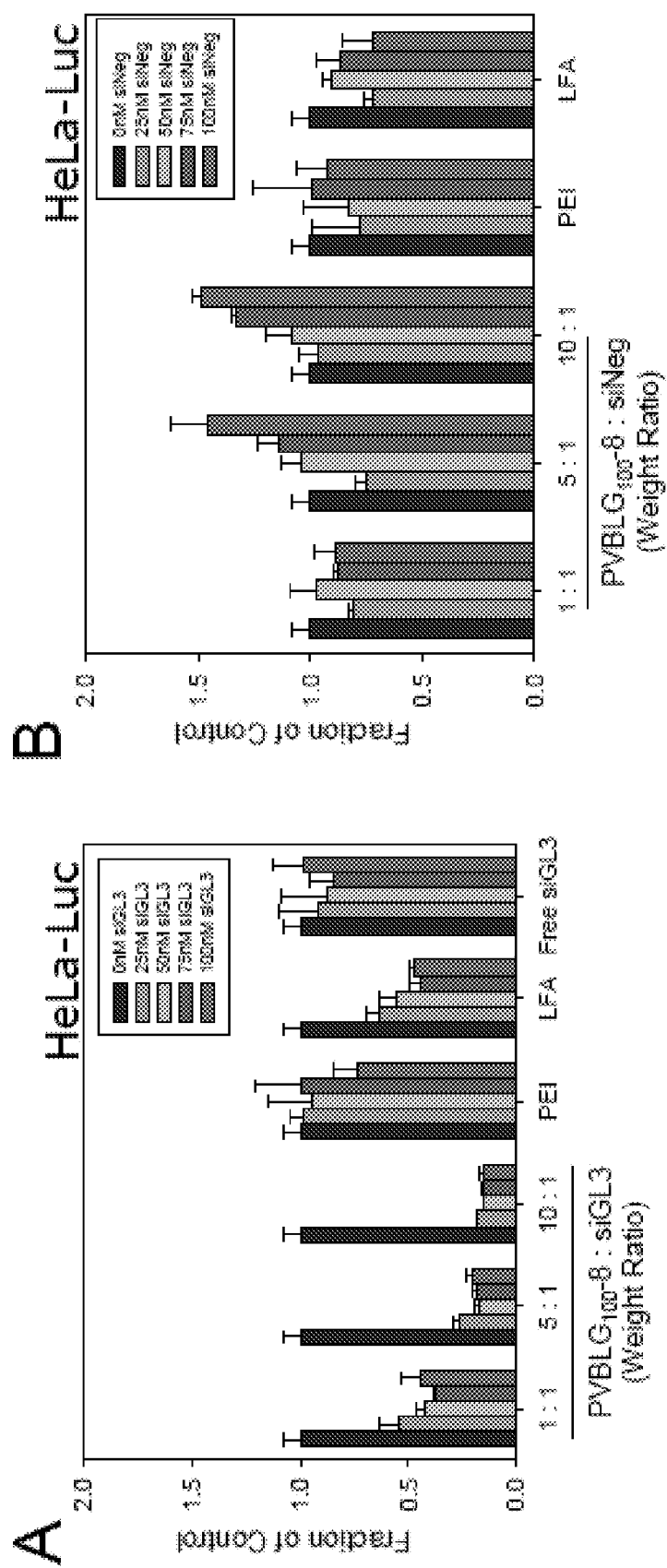
*Figure 32A-B*

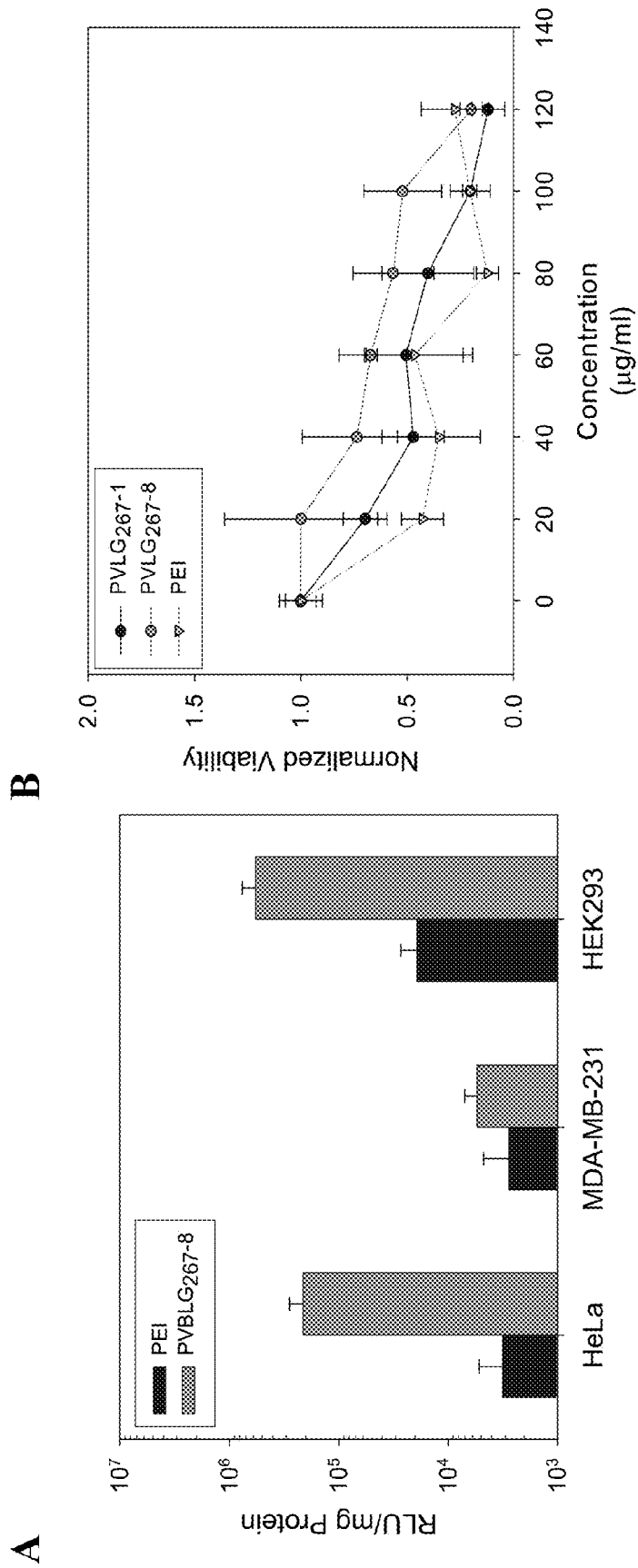
*Figure 33A-B*

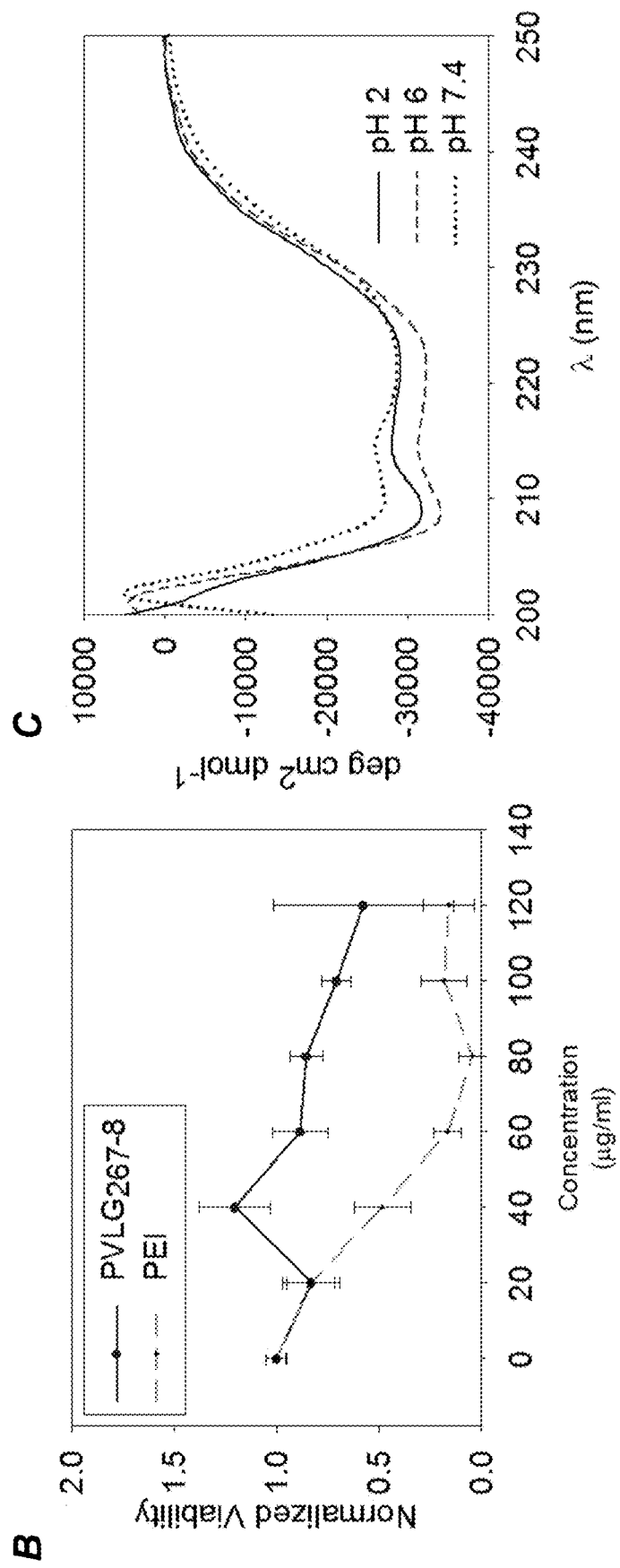
Figure 34B-C

PVBLG$_{267}$-8

PVBLG$_{267}$-9

*Figure 41A-B*

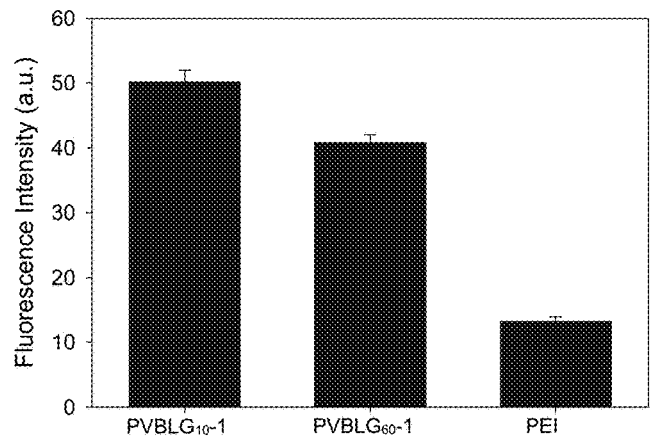
*Figure 42*
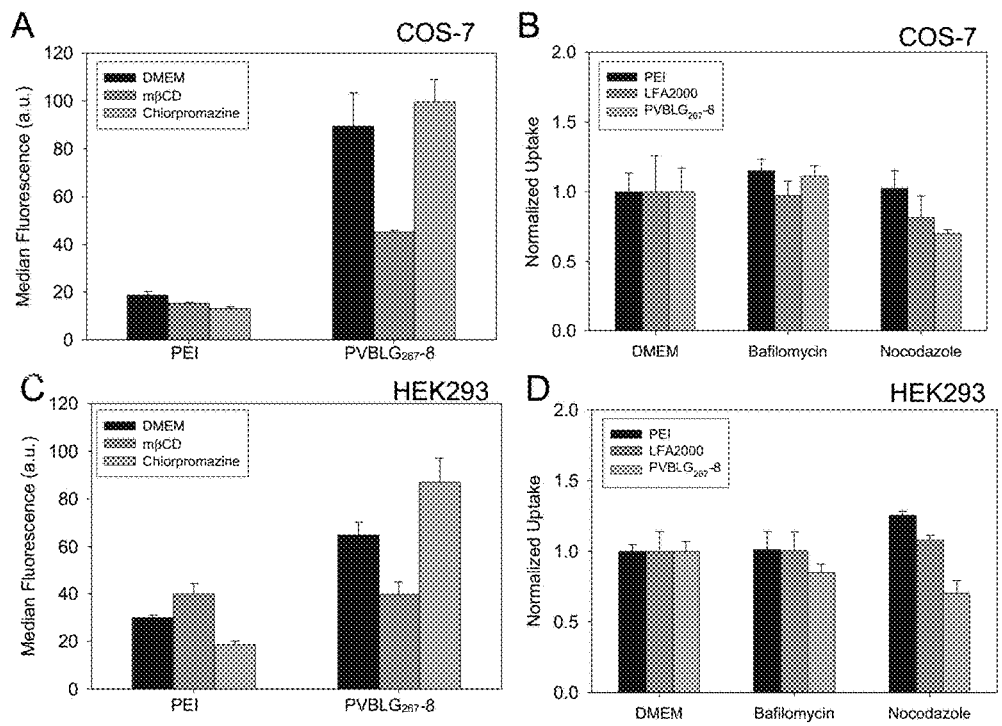
*Figure 43A-D*

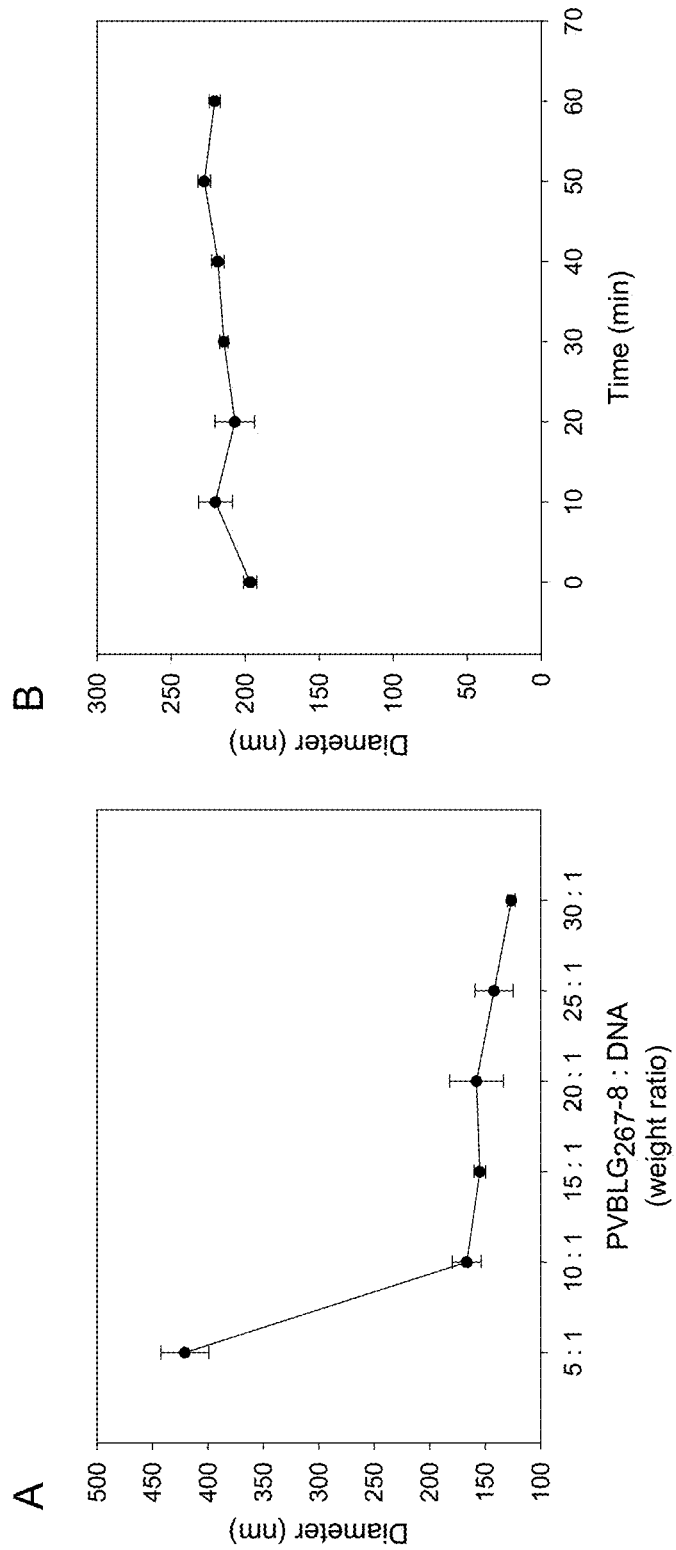
*Figure 44A-B*

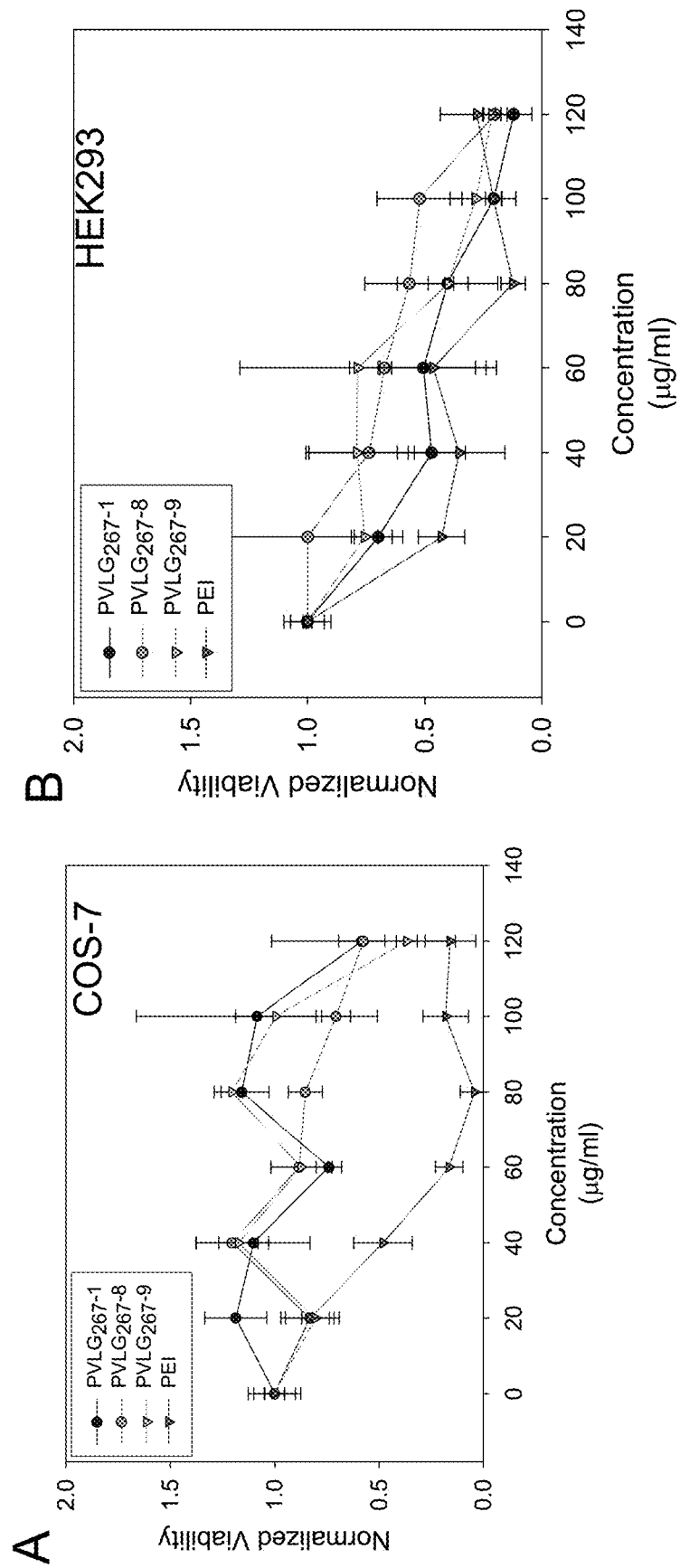
*Figure 45A-B*

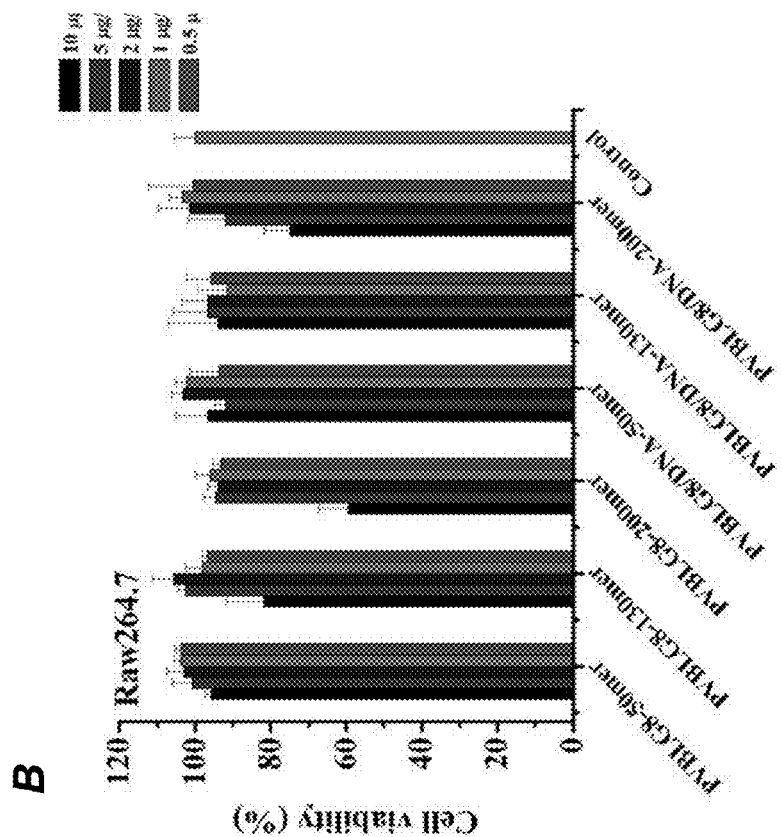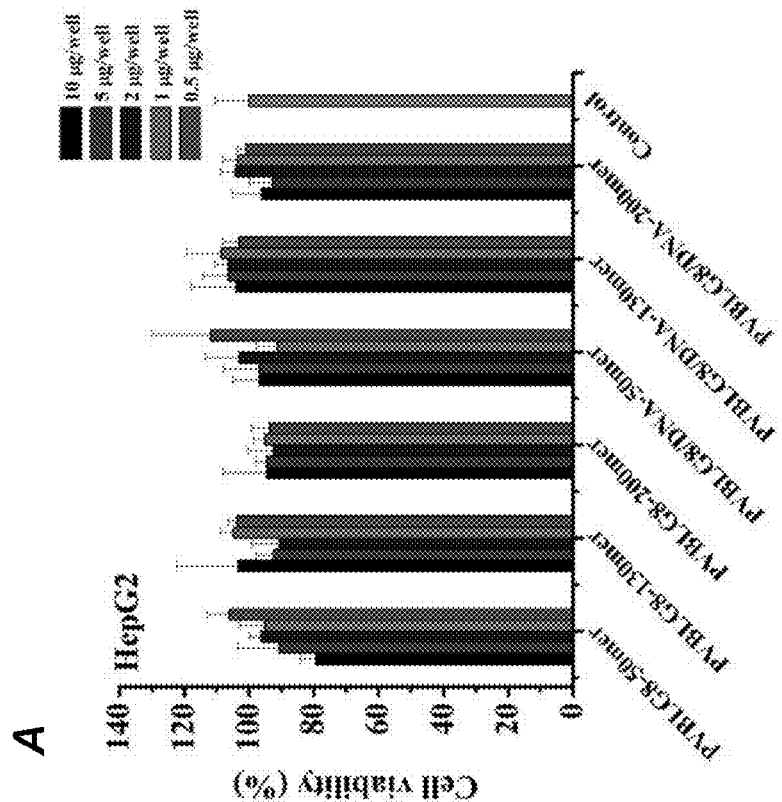
Figure 69A-B

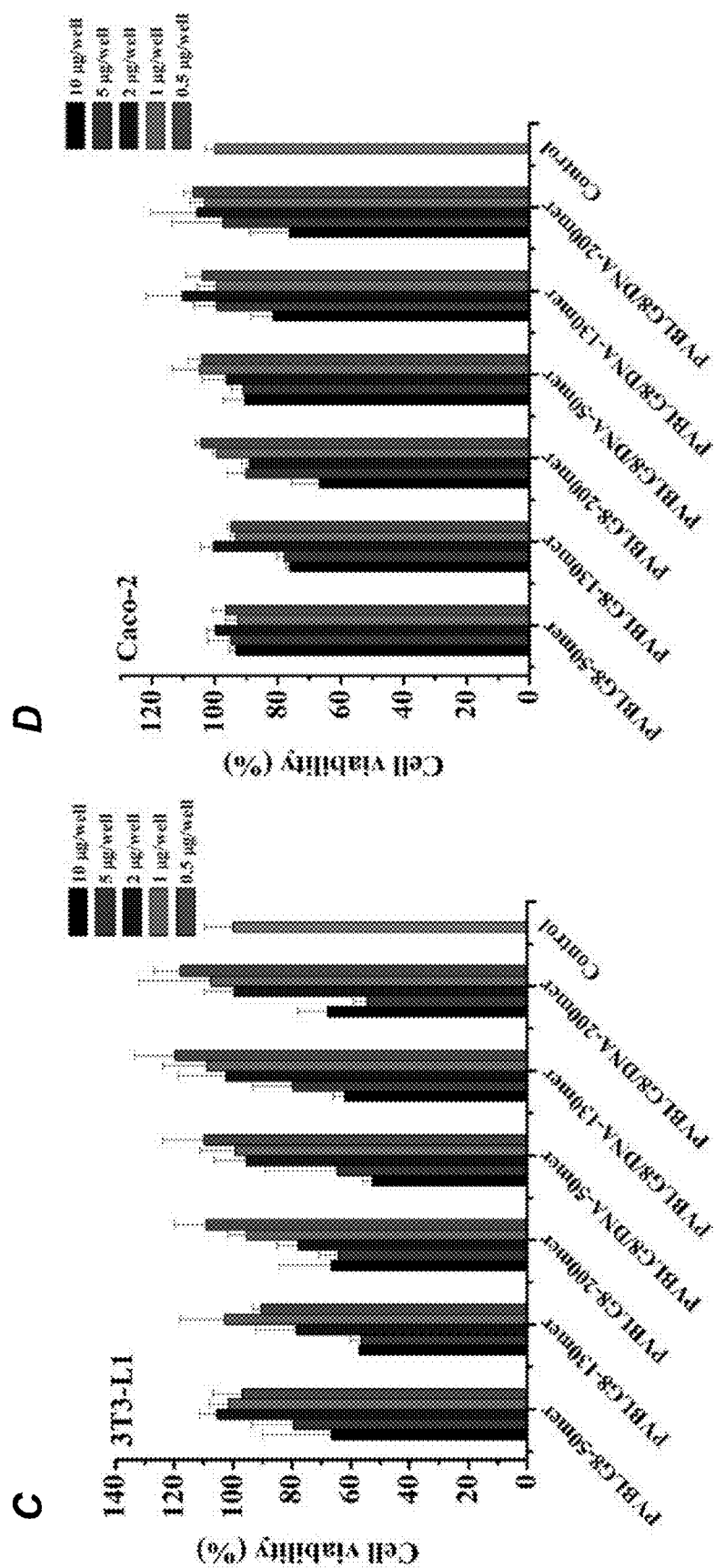
Figure 69C-D

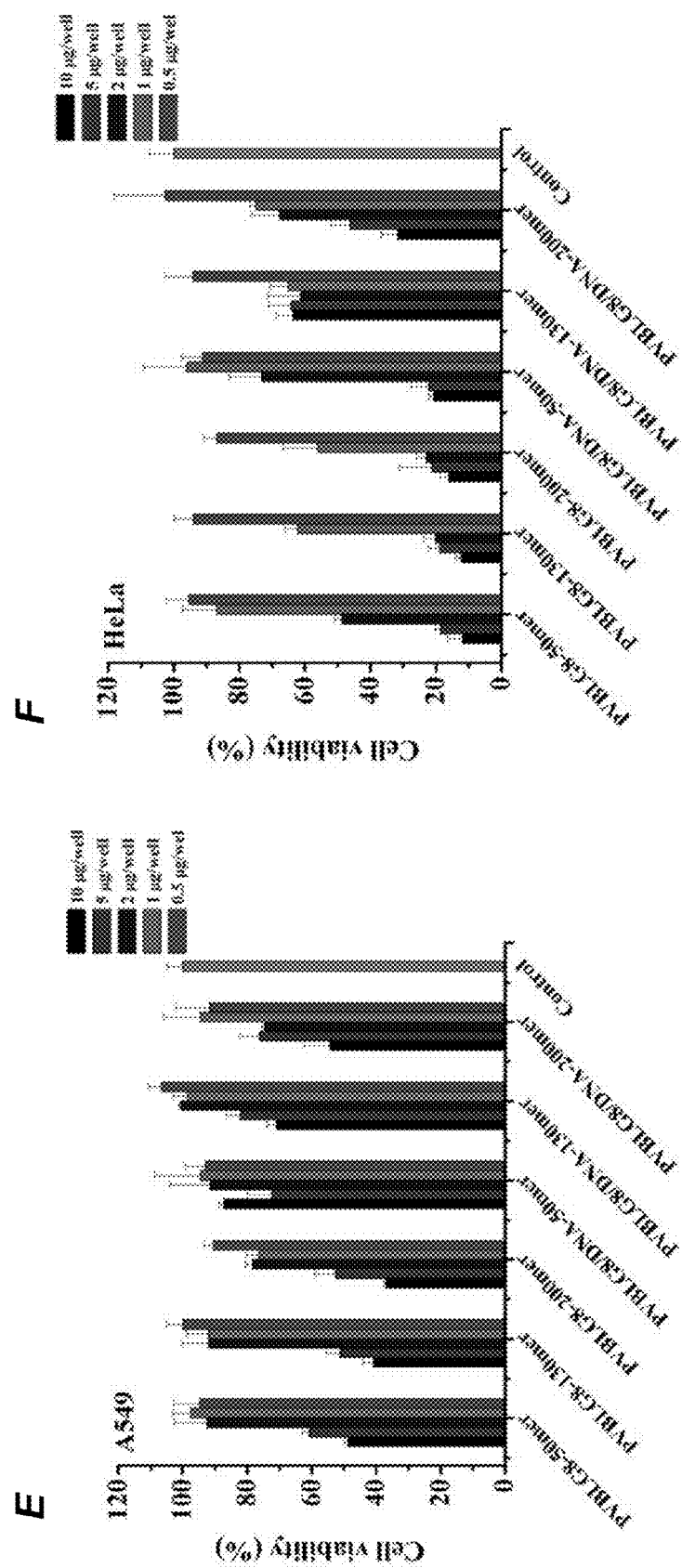
Figure 69E-F

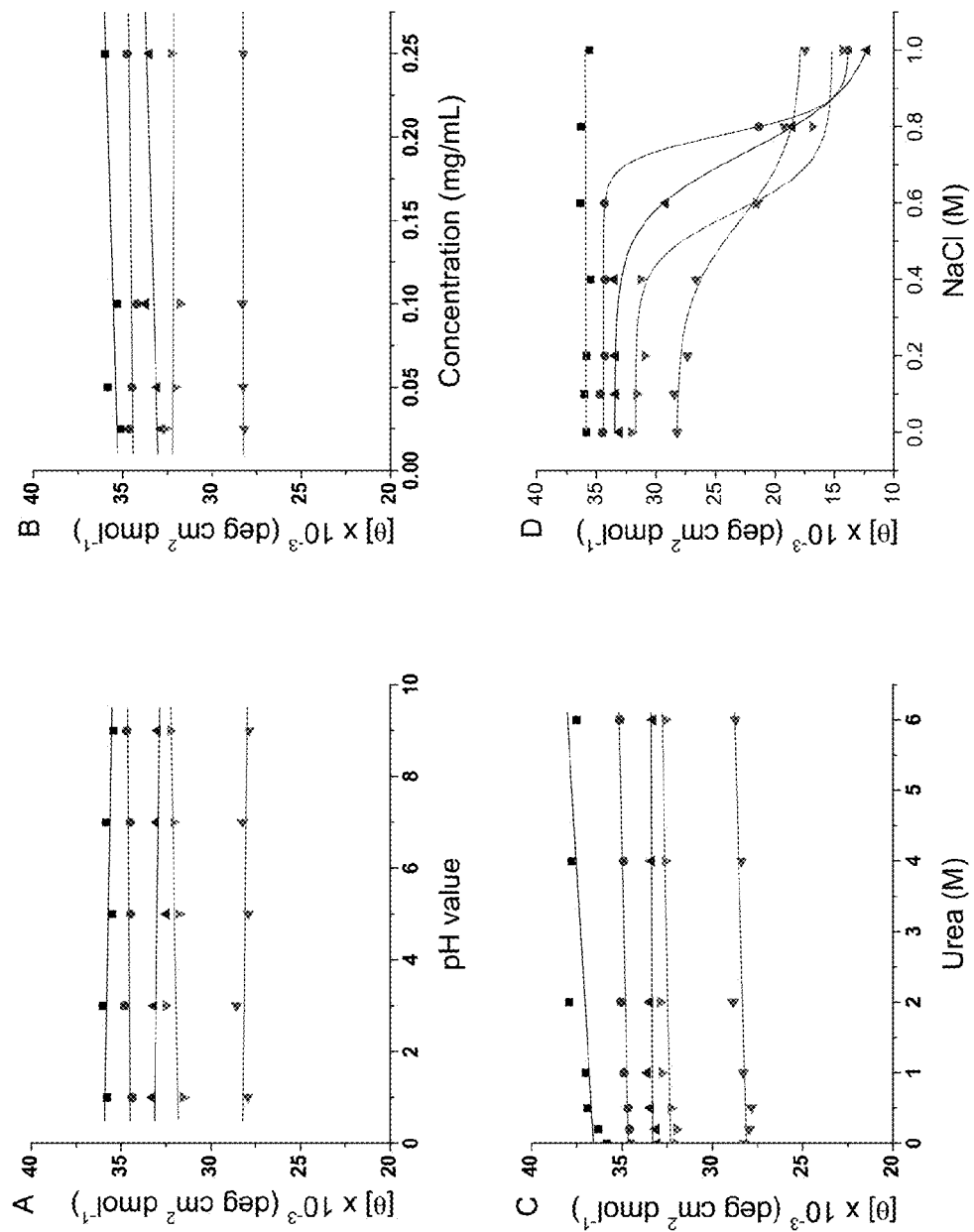
Figure 70A-D

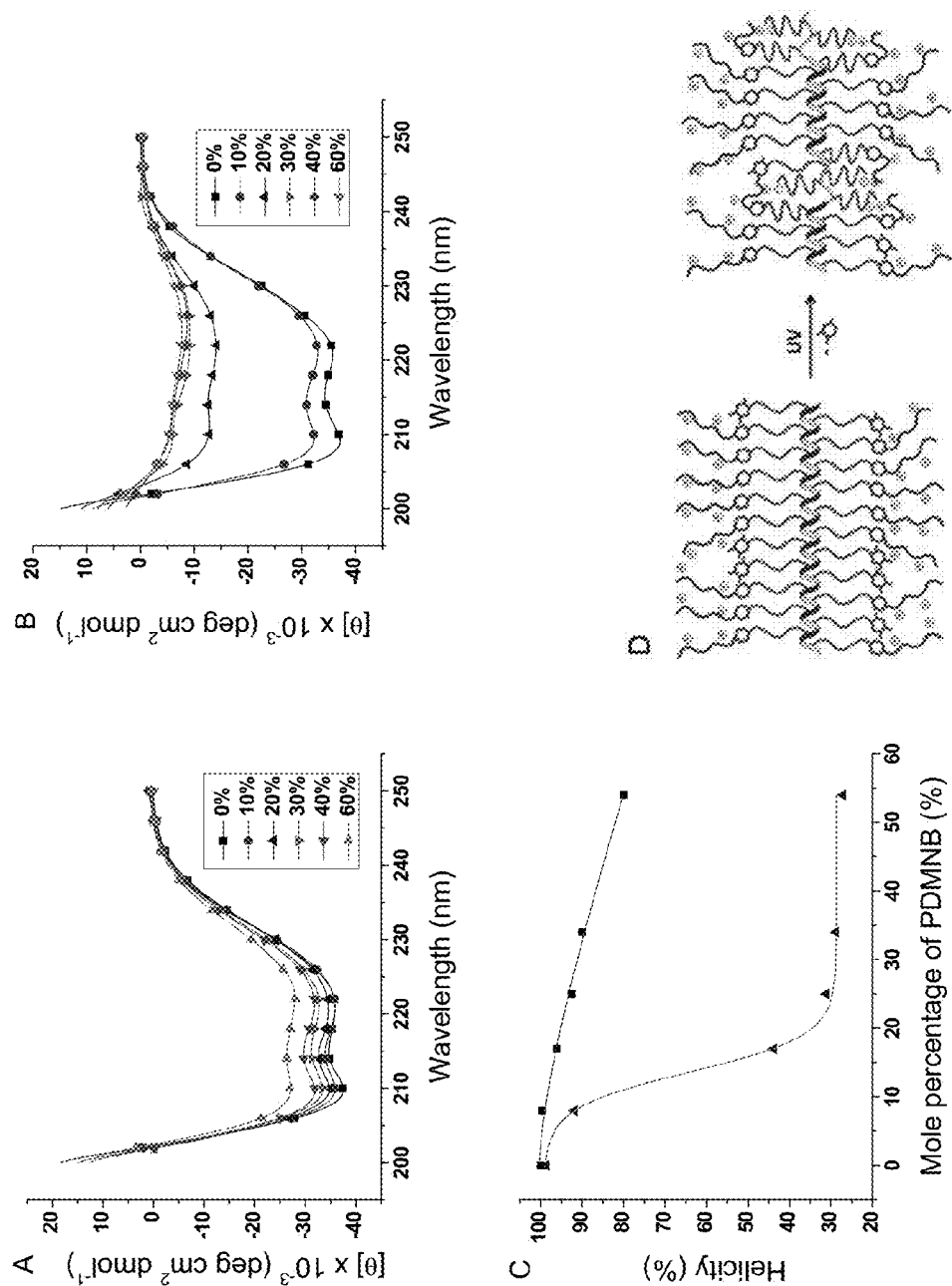
Figure 71A-D

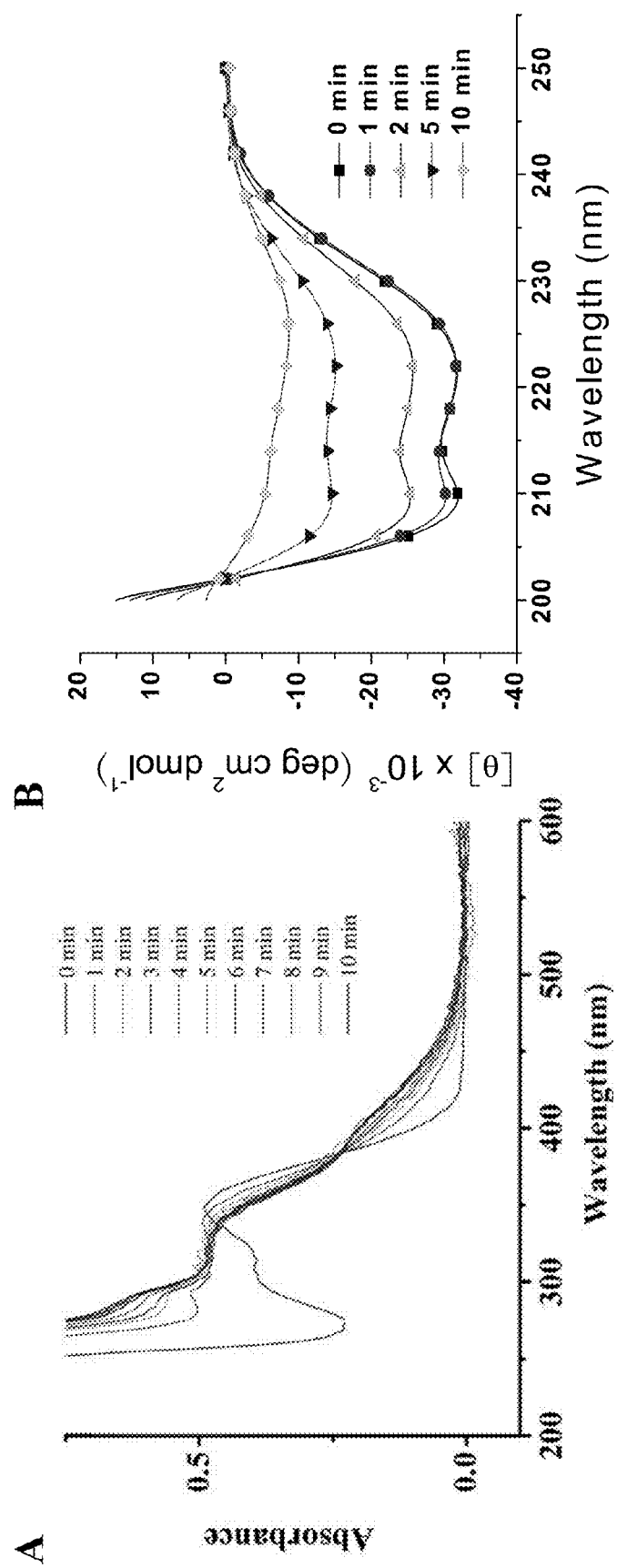
*Figure 72A-B*

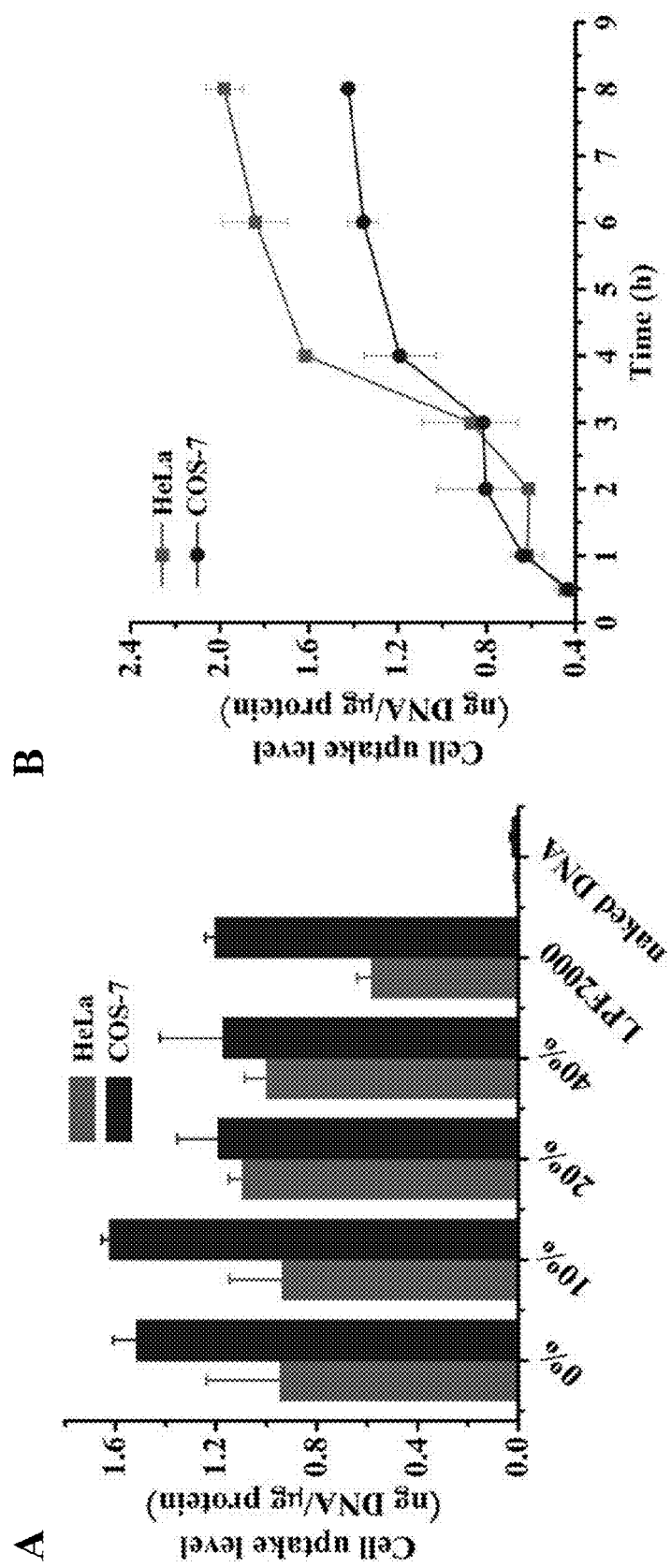
*Figure 74A-B*

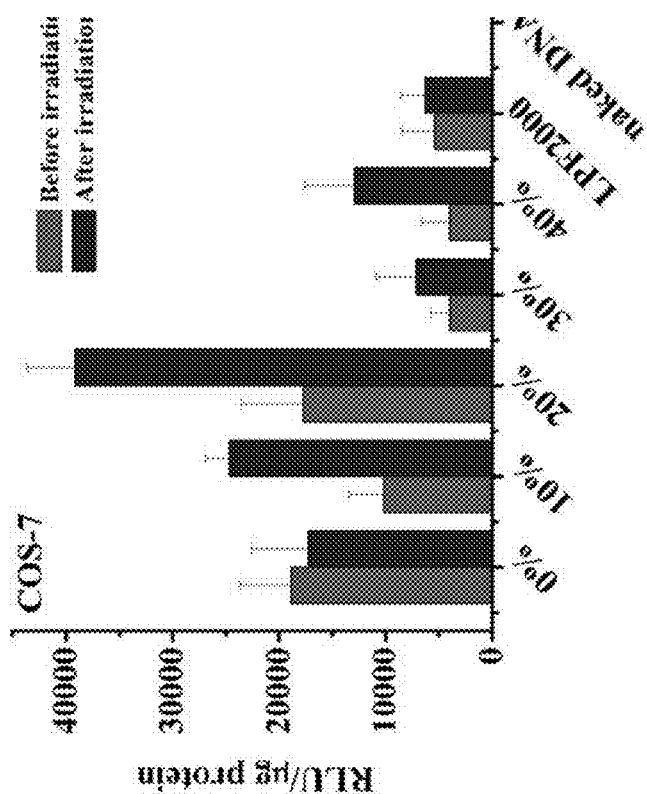
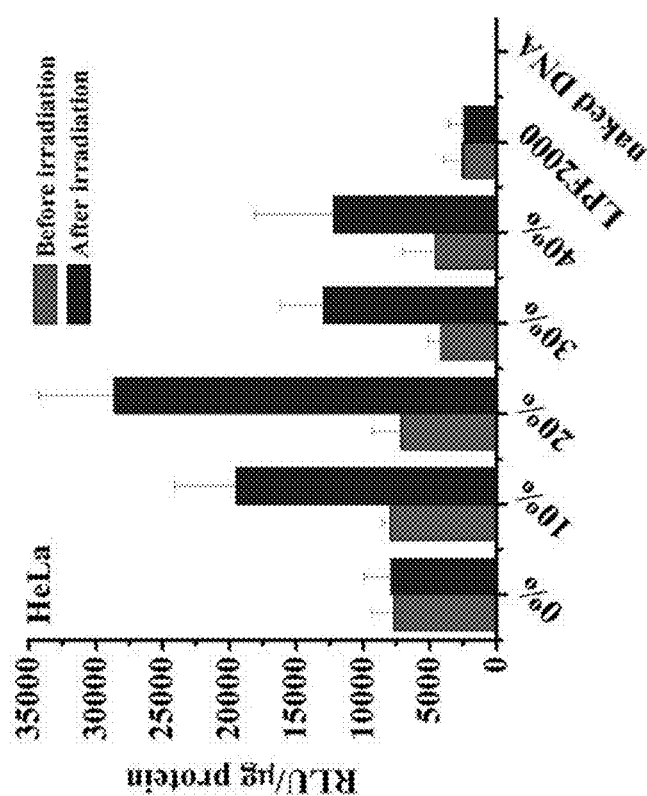
Figure 76B

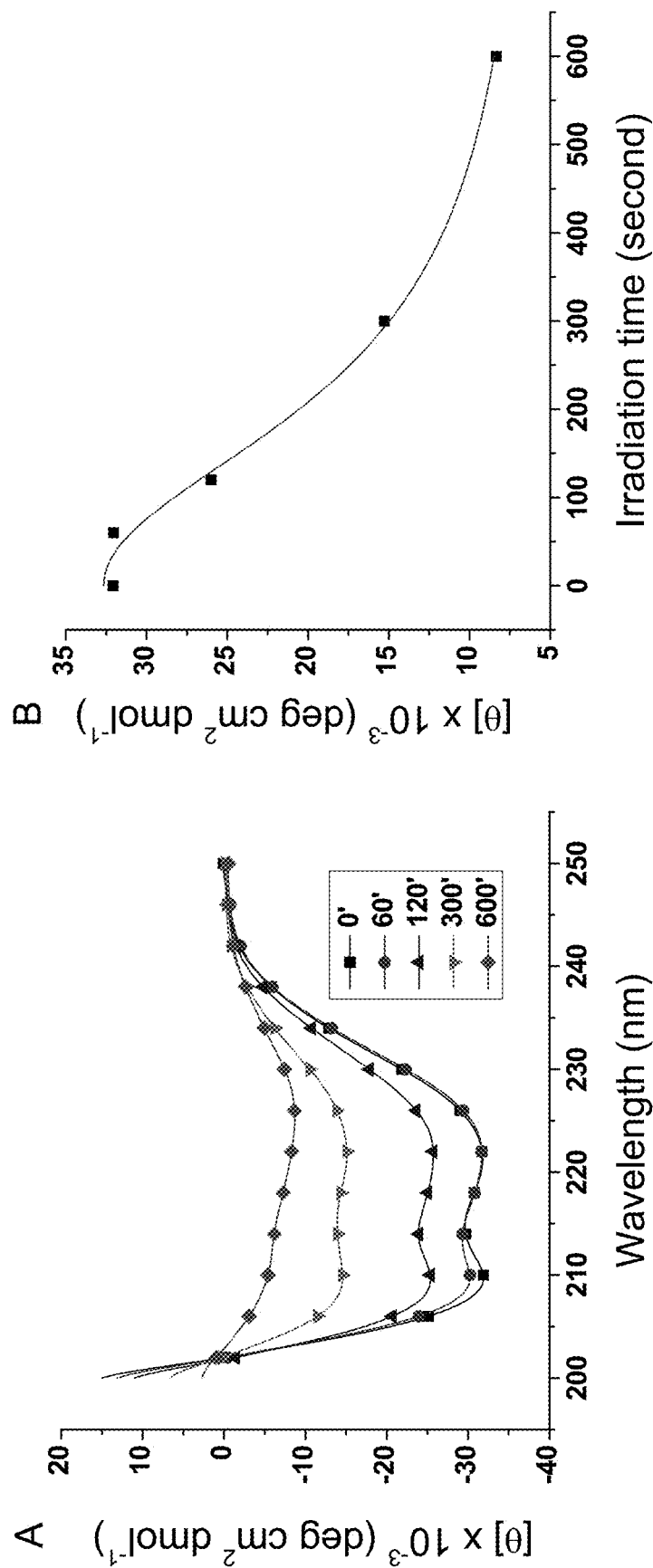
Figure 77A-B

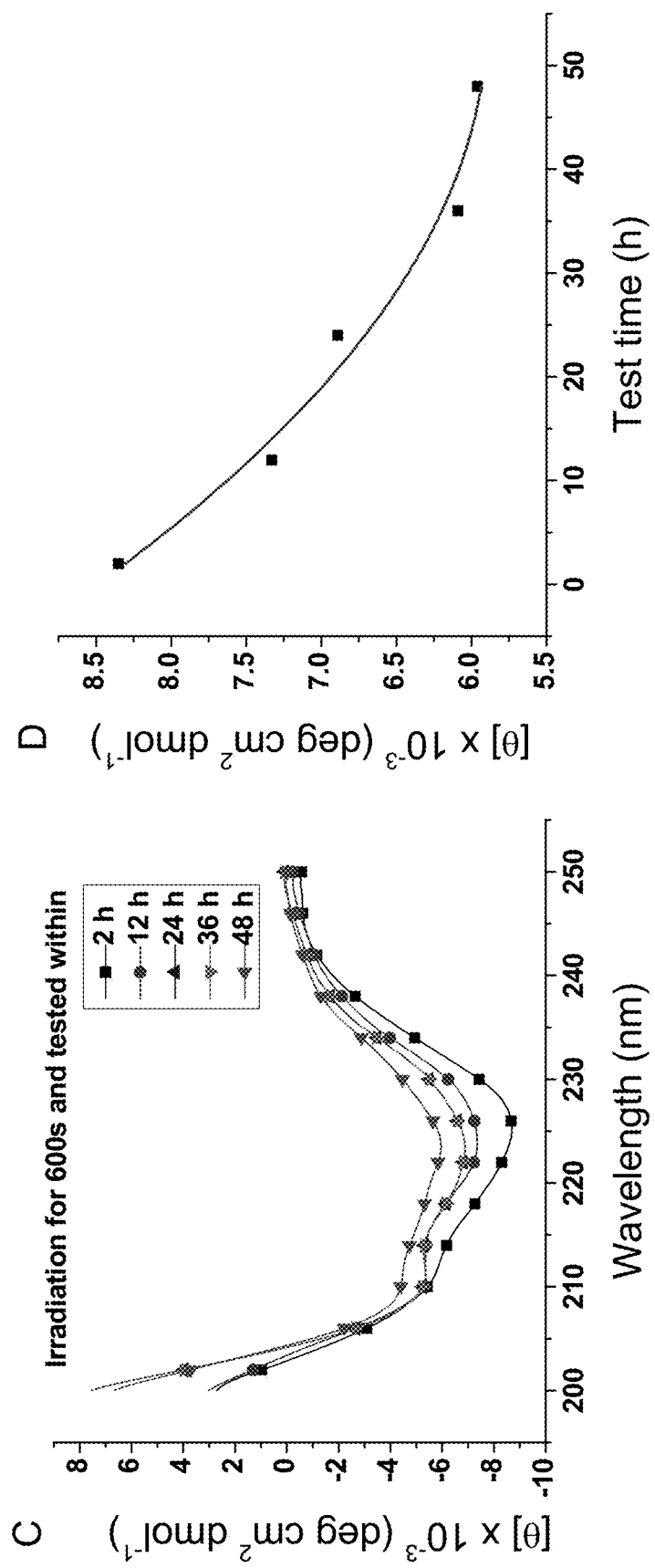
Figure 77C-D

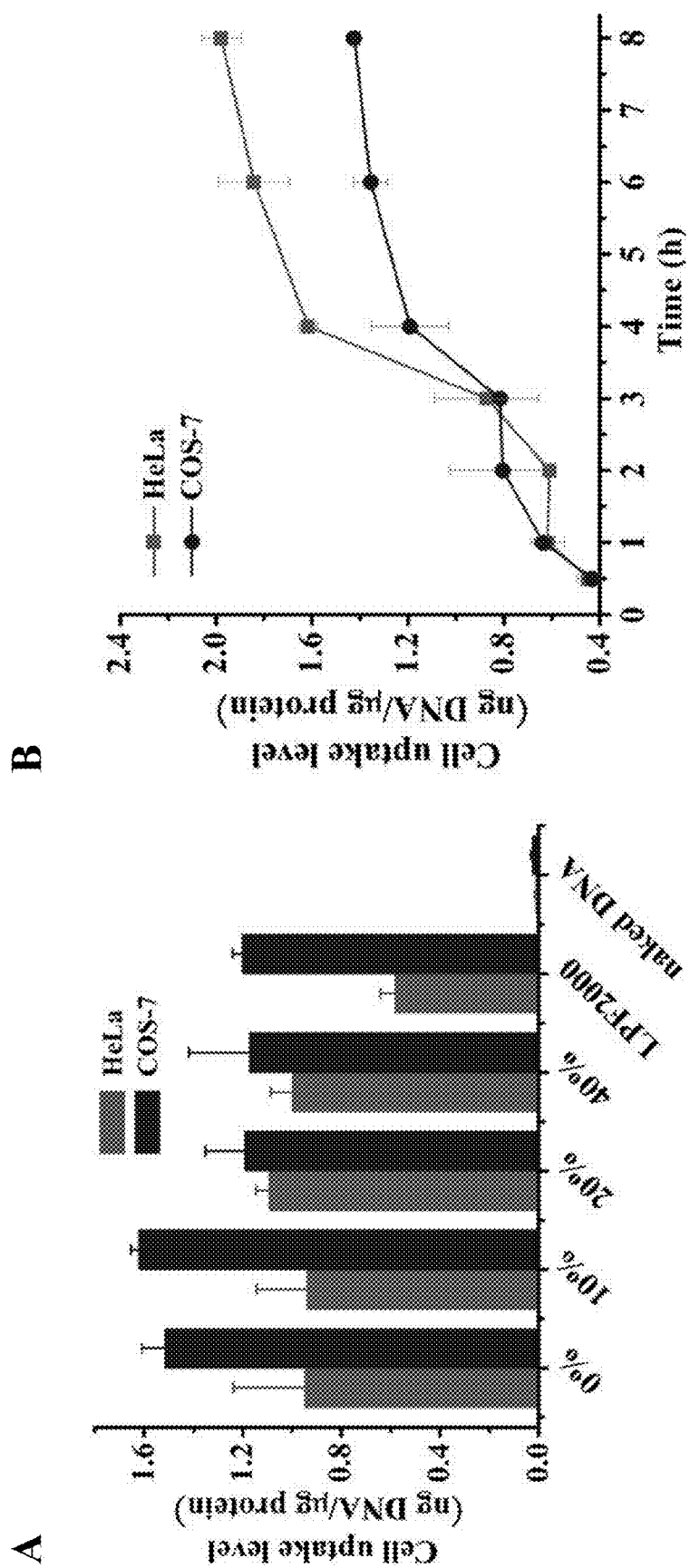
*Figure 78A-B*

STABLE HELICAL IONIC POLYPEPTIDES

RELATED APPLICATIONS

This application is a continuation of U.S. patent application Ser. No. 13/990,739, filed Jun. 24, 2013, which issued on Jan. 26, 2016 as U.S. Pat. No. 9,243,040, which application is a National Stage Application of PCT/US2011/062656, filed on Nov. 30, 2011, which claims priority under 35 U.S.C. § 119(e) to U.S. Provisional Patent Application No. 61/418,269, filed Nov. 30, 2010, which applications are incorporated herein by reference.

GOVERNMENT SUPPORT

This invention was made with government support under Grant No. CHE-0809420 awarded by the National Science Foundation and Grant Nos. 1R21EB009486 A and 1R21CA139329 Z awarded by the National Institutes of Health. The government has certain rights in the invention.

BACKGROUND OF THE INVENTION

The α-helix, the most prevalent type of secondary structure found in proteins, forms the cornerstone of the three-dimensional architecture of proteins and regulates numerous biological activities. Water-soluble peptides that adopt stable α-helix conformations are attractive motifs because of their importance in basic science and their broad utility in medicine. As a motif with a unique folding/unfolding property and a rigid, rod-like morphology, the α-helix has been the subject of intense study and has been broadly used as a building block in the design of therapeutics and molecular assemblies (see for example, Zhang, *Nat. Biotechnol.* 21, 1171-1178 (2003); Hartgerink et al., *Science* 294, 1684-1688 (2001); and Nowak et al., *Nature* 417, 424-428 (2002)).

Polypeptides bearing an α-helical conformation can be made entirely of hydrophobic amino acids such as alanine and leucine because such polypeptides have high helical propensities due to the hydrophobic amino acids (Chakrabartty et al, *Protein Sci.* 3, 843-852 (1994); Levy et al., *Proc. Natl. Acad. Sci. U.S.A.* 98, 2188-2193 (2001); Dobson et al., *Angew. Chem., Int. Ed.* 37, 868-893 (1998)). However, the usefulness of these structures is limited because of their poor aqueous solubility and processability.

Incorporating charged amino acid residues to improve peptide solubility, however, usually leads to reduced helical stability due to increased side-chain charge repulsion and the disruption of intra-molecular hydrogen bonding. Access to stable, water-soluble α-helical polypeptides would facilitate peptide research and provide useful tools for developing new peptide applications.

SUMMARY

The invention provides polymers comprising Formula I:

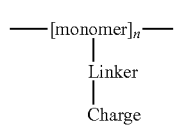

(I)

wherein each [monomer] is independently an organic unit of 2, 3, 4, 5, 6 or 7 carbon atoms wherein the organic units are linked together through amide or ester bonds;

n is about 6 to about 1000;

each Linker is independently an optionally substituted carbon chain that is optionally interrupted by oxygen, nitrogen, sulfur, phosphorus, or silicon; and each Charge is independently a moiety having a positive or negative charge on a heteroatom, wherein the heteroatom is nitrogen, oxygen, phosphorus, or sulfur;

wherein the Linker separates the monomer and the positive or negative charge of the heteroatom by at least six linear atoms; or a salt thereof.

The polymer can be in the form of a helix, a sheet, or a combination thereof. The secondary structures of the polymers can exhibit stability greater than an α-helix or β-sheet formed from corresponding polypeptides of naturally occurring amino acids, for example, that do not have a charge separated from the polymer backbone by at least six linear atoms.

In one embodiment, the polymer is a polymer of Formula IIa:

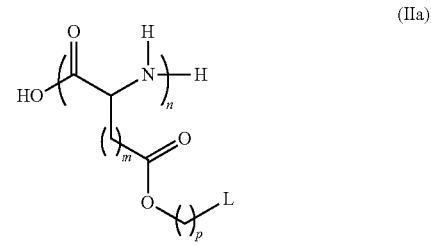

(IIa)

wherein n is about 6 to about 600;

m is 1 to about 10;

p is 1 to about 16;

L is —$R^1$, or —NH—$R^2$, -Ph-$CH_2$—NH—$R^2$;

$R^1$ is a moiety having a positive or negative charge on a heteroatom, wherein the heteroatom is nitrogen, oxygen, phosphorus, or sulfur, such as a Charge group of Formula I; and $R^2$ is —C(=O)-pyridine, sugar, phenyl, phenyl meta para substituted with a crown ether moiety; or ($C_2$-$C_{10}$)alkyl optionally substituted with one or more hydroxy, pyridine, piperidine, or pyrrolidine groups;

or a salt thereof.

In another embodiment, the polymer comprises Formula IIIc:

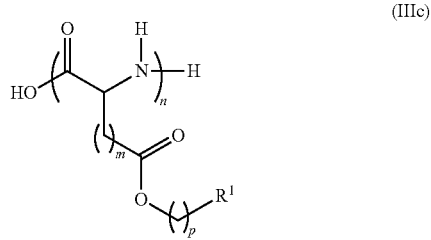

(IIIc)

wherein $R^1$ is a moiety having a positive or negative charge on a heteroatom, wherein the heteroatom is nitrogen, oxygen, phosphorus, or sulfur;

n is about 6 to about 600;

m is 1 to about 10; and p is 1 to about 16.

The polymer can be included in a composition, for example, an aqueous composition optionally including isotonic agents, buffering agents, and the like. The invention also provides methods of using the polymers disclosed herein. Examples include methods for delivering DNA or RNA to a cell, methods for transfecting organs of a subject, such as a mammal, methods for inhibiting bacterial growth, and methods for causing pore formation in a cell.

The invention further provides methods of preparing a polypeptide or polyester having charged side chains comprising initiating ring-opening polymerization of a compound of Formula X:

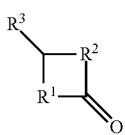

wherein
$R^1$ is O or NH;
$R^2$ is $CH_2$ or —C(=O)—O— so as to form an anhydride moiety; and
$R^3$ is a carbon linked to an olefin or a protecting group (e.g., through a linking group); with a polymerization initiator to form a polypeptide or polyester, and oxidizing the olefin or removing the protecting group to provide a polypeptide or polyester having charged side chains, at suitable pH levels and in the corresponding suitable environment, such as at a pH of approximately 6-8, or about 7, for example, to provide a polymer of Formula I. In various embodiments, the side chain can be separated from the polypeptide or polyester backbone by at least 6 linear atoms.

The invention therefore provides novel polymers of the formulas described herein, intermediates for the synthesis of the polymers, as well as methods of preparing the polymers. The invention also provides polymers that are useful as intermediates for the synthesis of other useful polymers and compositions. The invention provides for the use of the polymers for the manufacture of medicaments useful for the treatment of bacterial infections in a mammal, such as a human, as well as for the delivery of genetic information, such as DNA or RNA, to a mammal.

The invention further provides for the use of the compositions described herein for use in medical therapy. The medical therapy can be treating cancer, for example, breast cancer, lung cancer, pancreatic cancer, prostate cancer, or colon cancer, for example, by cell transfection or cancer cell growth inhibition. The invention also provides for the use of a composition described herein for the manufacture of a medicament to treat such cancers. The medicament can include a pharmaceutically acceptable diluent, excipient, or carrier. The invention further provides for the use of a composition described herein to prepare a medicament for treating cancer in a mammal, such as a human. The invention additionally provides for the use of a composition described herein for the inhibition of bacteria and for the treatment of bacterial infections.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

FIG. 3A-I. Characterisation of charged polypeptides. PAHG and PVBLG-X, polypeptides with long charged side chains, adopt very stable α-helical conformations at low pH, at elevated temperature, or in solution containing high concentration of salt or denaturing agents (e.g., urea or methanesulphonic acid (MSA)). a, CD spectra of various charged polypeptides in water (pH=3). b, pH dependence of the residue molar ellipticity (at 222 nm) for $(PAHG)_{57}$, $(PVBLG-1)_{60}$, $(PVBLG-6)_{44}$, $(PVBLG-7)_{40}$ and $(PLL)_{75}$. c, Concentration dependence of residue molar ellipticity at 222 nm for $(PAHG)_{57}$ and $(PVBLG-1)_{60}$ at pH 3. d, Temperature dependence of residue molar ellipticity at 222 nm for $(PAHG)_{57}$ and $(PBVLG-1)_{60}$ at pH 3. e, Salt dependence of residue ellipticity at 222 nm for $(PAHG)_{57}$ and $(PBVLG-1)_{60}$ at pH 3 and $(PLL)_{75}$ at pH 10. f, The helical stabilities of $(PAHG)_{57}$ and $(PVBLG-1)_{60}$ at pH 3 and $(PLL)_{75}$ at pH 10 in the presence of urea. g and h, CD spectra of $(PAHG)_{57}$ (g) and $(PVBLG-1)_{60}$ (h) in a mixed solvent of MSA and $H_2O$. i, FT-IR spectra of $(PVBLG-1)_{10}$ and $(PVBLG-1)_{142}$.

FIG. 4A-B. Controlled polymerisation of VB-Glu-NCA. a, The molecular weights (MWs) and molecular weight distributions (MWDs) of PVBLGs derived from the ring-opening polymerisation of VB-Glu-NCA initiated by hexamethyldisilazane at various M/I ratios in DMF (containing 5% nitrobenzene). b, The MWs and MWDs at various VB-Glu-NCA conversions at an M/I ratio of 100:1 in DMF (containing 5% nitrobenzene). The black curve line indicates the correlation of the theoretical MW with the M/I ratio in a or with the conversion of VB-Glu-NCA in b; the squares are the obtained MW; the triangles are the obtained MWD.

FIGS. 5-17 illustrate CD spectral analysis of $(PVBLG-x)_n$ at various pH measurements in various solutions.

FIG. 5. The overlay of the CD spectra of $(PVBLG-1)_{60}$ at pH 3, 6, 9 and 10 in 25 mM NaCl solutions (c=0.028 mg/mL). The $-[\theta]_{222}$ of $(PVBLG-1)_{60}$ ($\sim32\times10^3$ $cm^2 \cdot deg/dmol$) is much larger than that of $(PAHG)_{57}$ ($\sim14\times10^3$ $cm^2 \cdot deg/dmol$, FIG. 20), and remains unchanged between pH 1 and 10.

FIG. 6. The overlay of the CD spectra of $(PVBLG-1)_{60}$ at various concentrations ranging from 0.02 mg/mL to 2.5 mg/mL in aqueous solution. These experiments showed that $(PVBLG-1)_{60}$ stays monomeric in aqueous solution.

FIG. 7. The overlay of the CD spectra of $(PVBLG-1)_{60}$ in aqueous solution (pH=3) at various temperatures ranging from 4° C. to 70° C. These experiments showed that $(PVBLG-1)_{60}$ adopts helical structure with remarkable thermal stability.

FIG. 8. The overlay of the CD spectra of $(PVBLG-1)_{60}$ in aqueous solution with different NaCl concentrations ranging from 0 to 1 M (c=0.028 mg/mL). These experiments showed that the helical conformation of (PVBLG-1)$_{60}$ has unusual salt stability.

FIG. 9. The overlay of the CD spectra of (PVBLG-1)$_{60}$ in aqueous solution with different urea concentrations ranging from 0 to 4 M (c=0.028 mg/mL). These experiments showed that the helical stability of (PVBLG-1)$_{60}$ is remarkable, and remains nearly unchanged with 1.5-2 M urea and still has 76% of its original helical contents against 6M urea.

FIG. 10. The overlay of the CD spectra of (PVBLG-1)$_{60}$ in aqueous solution with different MSA concentrations ranging from MSA volume fraction of 0% to 90% (c=0.028 mg/mL). These experiments showed the typical pattern of (PVBLG-1)$_{60}$ α-helix disruption with the addition of MSA, a very strong denaturing agent. (PVBLG-1)$_{60}$ also has amazing stability against MSA and can adopt 58% of its original helical content with a MSA volume fraction of 69%.

FIG. 11. The overlay of the CD spectra of PVBLG-1 at pH=3 (left) and the plot of the $-[\theta]_{222}$ of (PVBLG-1)$_{DP}$ versus of the degree of polymerization (DP or the PVBLG-1 chain length (right).

FIG. 12. CD spectral analysis of (PVBLG-2)$_{45}$.
FIG. 13. CD spectral analysis of (PVBLG-3)$_{45}$.
FIG. 14. CD spectral analysis of (PVBLG-4)$_{40}$.
FIG. 15. CD spectral analysis of (PVBLG-5)$_{40}$.
FIG. 16. CD spectral analysis of (PVBLG-6)$_{44}$.
FIG. 17. CD spectral analysis of (PVBLG-7)$_{40}$.

FIGS. 20-25. CD analysis of (PAHG)$_{57}$ under various conditions (R=H, TMS, etc.).

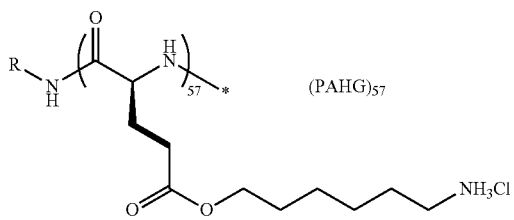

Figure 20:
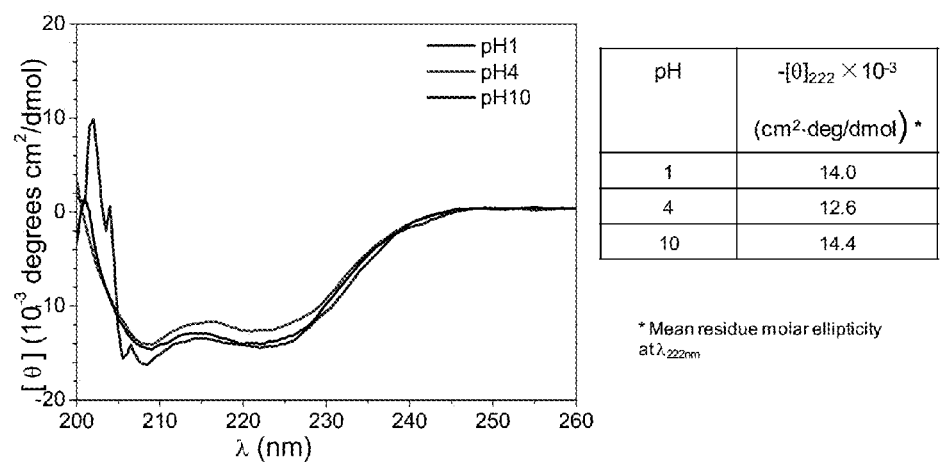

FIG. 20. The overlay of the CD spectra of (PAHG)$_{57}$ at pH 1, 4 and 10 in 25 mM NaCl solutions. (polymer conc.=0.028 mg/mL).

Figure 21:
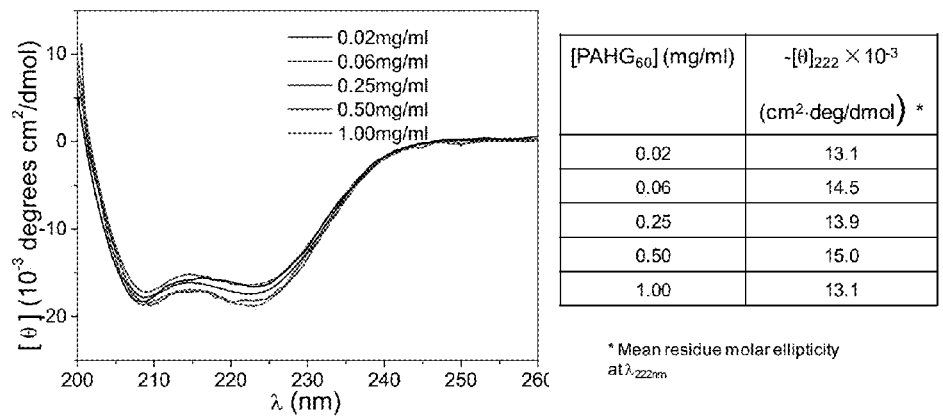

FIG. 21. The overlay of the CD spectra of (PAHG)$_{57}$ at various concentrations ranging from 0.02 mg/mL to 1 mg/mL in aqueous solution. These experiments showed that (PAHG)$_{57}$ remains monomeric in aqueous solution.

Figure 22:
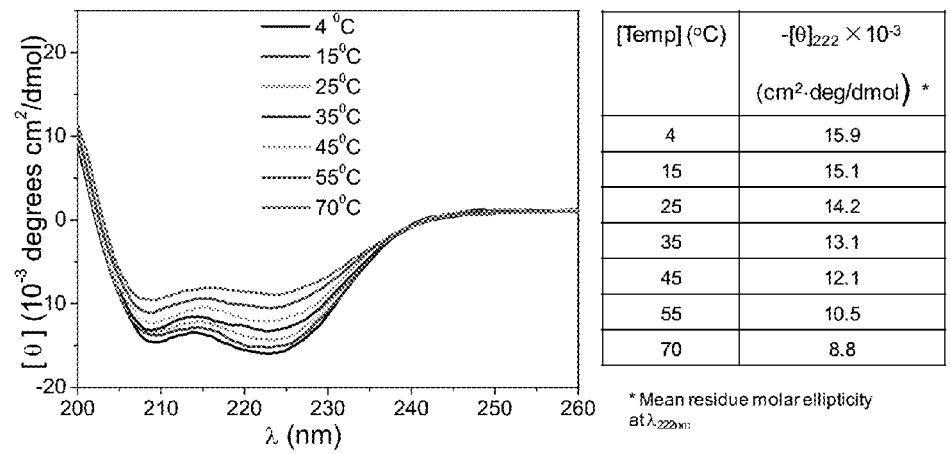

FIG. 22. The overlay of the CD spectra of (PAHG)$_{57}$ in aqueous solution (pH=3, the concentration is 0.02 mg/mL) at various temperatures ranging from 4° C. to 70° C. These experiments showed that the helical stability of (PAHG)$_{57}$ was compromised at extreme elevated temperatures.

Figure 23:
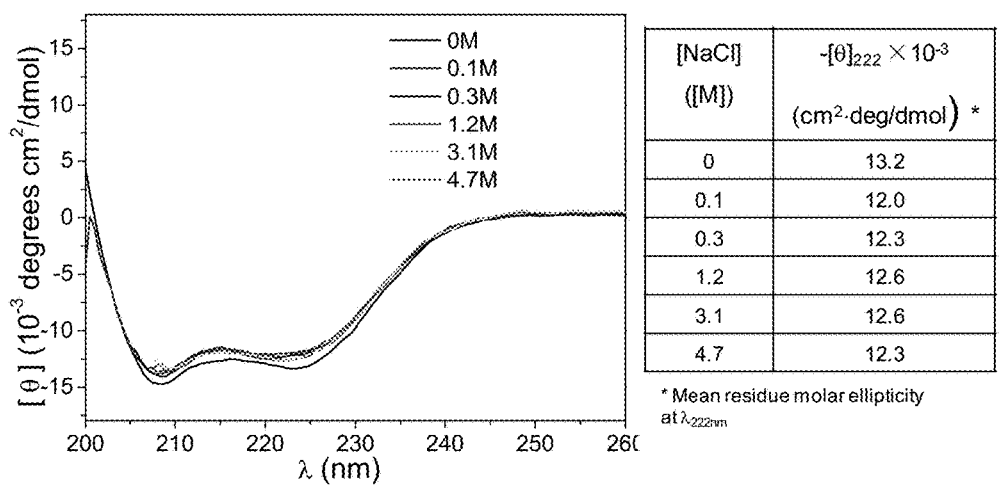

FIG. 23. The overlay of the CD spectra of (PAHG)$_{57}$ in aqueous solution (pH=3) with different NaCl concentrations ranging from 0 to 4.7M (c=0.028 mg/mL). These experiments showed that the helical conformation of (PAHG)$_{57}$ has unusual salt stability.

Figure 24:
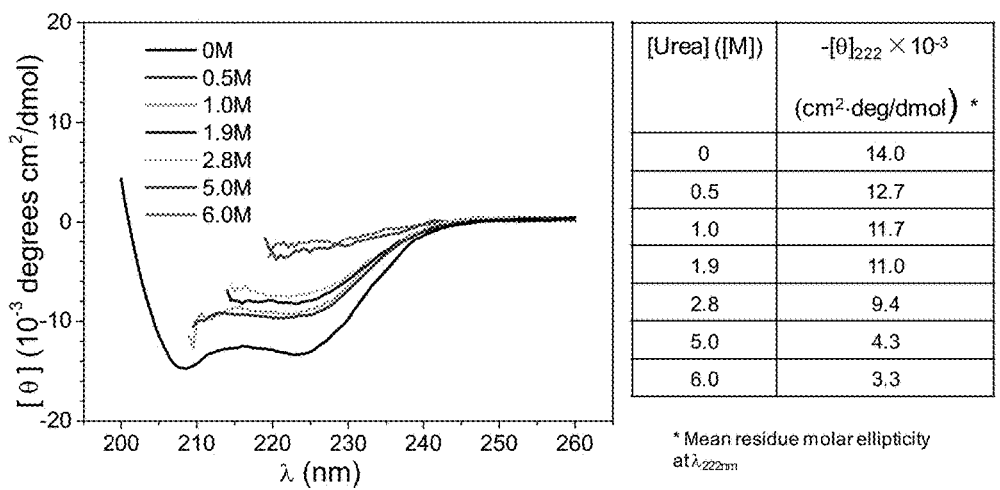

FIG. 24. The overlay of the CD spectra of (PAHG)$_{57}$ in aqueous solution with different urea concentrations ranging from 0 to 6.0 M (c=0.028 mg/mL). These experiments showed that the helical stability of (PAHG)$_{57}$ was compromised with increased concentration of urea, a helix-disrupting agent.

FIG. 25. The overlay of the CD spectra of (PAHG)$_{57}$ in aqueous solution with different MSA concentrations ranging from MSA volume fraction of 0% to 90% (c=0.028 mg/mL). These experiments showed the typical pattern of (PAHG)$_{57}$ α-helix disruption with the addition of MSA, a strong denaturing agent.

FIG. 26A-B. Wide-angle X-ray Scattering pattern of (a) PAHG and (b) (PVBLG-1)$_{180}$.

FIG. 27. In vitro transfection of COS-7 cells with PVBLG$_{267}$-X polypeptides compared to polyethylenimine (PEI MW=25 kDa).

FIG. 28A-D. (A) Circular dichroism (CD) spectra of PVBLG-1 and PLL in water (pH=1). (B) pH dependence of the molar residue ellipticity (222 nm) for PVBLG-1 and PLL. (C) Salt dependence of the molar residue ellipticity (222 nm) for PVBLG-1 and PLL in water (pH 3). DP=~60. (D) CD spectra of free plasmid DNA (0.05 mg/mL), free PVBLG$_{150}$-8 (0.05 mg/mL), the numerical addition of the free DNA and PVBLG$_{150}$-8 curves as well as the actual polyplex formed by mixing plasmid DNA and PVBLG$_{150}$-8 at a 1:1 weight ratio (concentration of DNA and PVBLG$_{150}$-8 were 0.05 mg/mL and 0.05 mg/mL after mixing). For comparison and simplicity reasons, the raw data instead of normalized spectra are shown.

Figure 29:
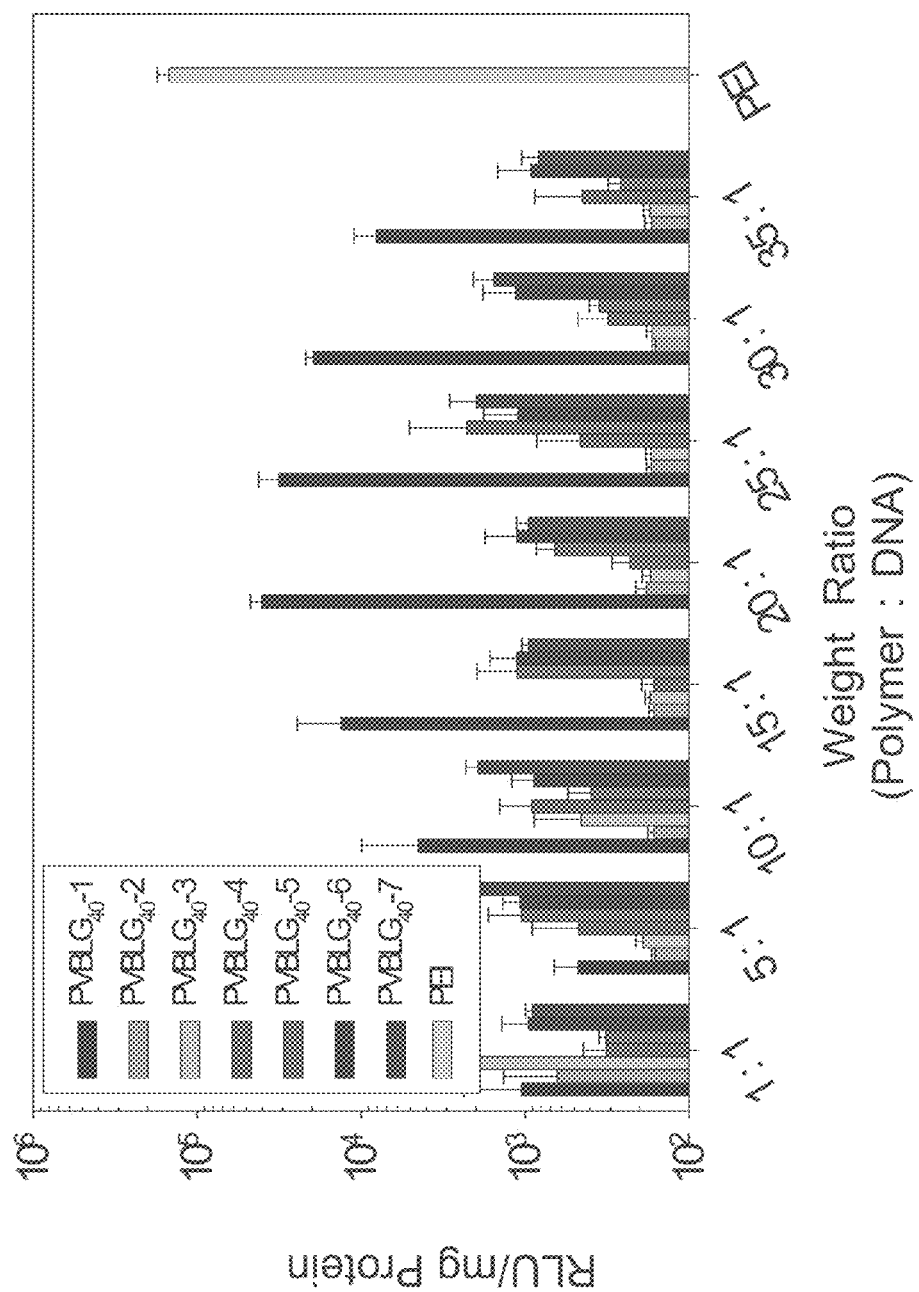

FIG. 29. In vitro transfection COS-7 cells with PVBLG$_{40}$-X polypeptides.

Figure 30:
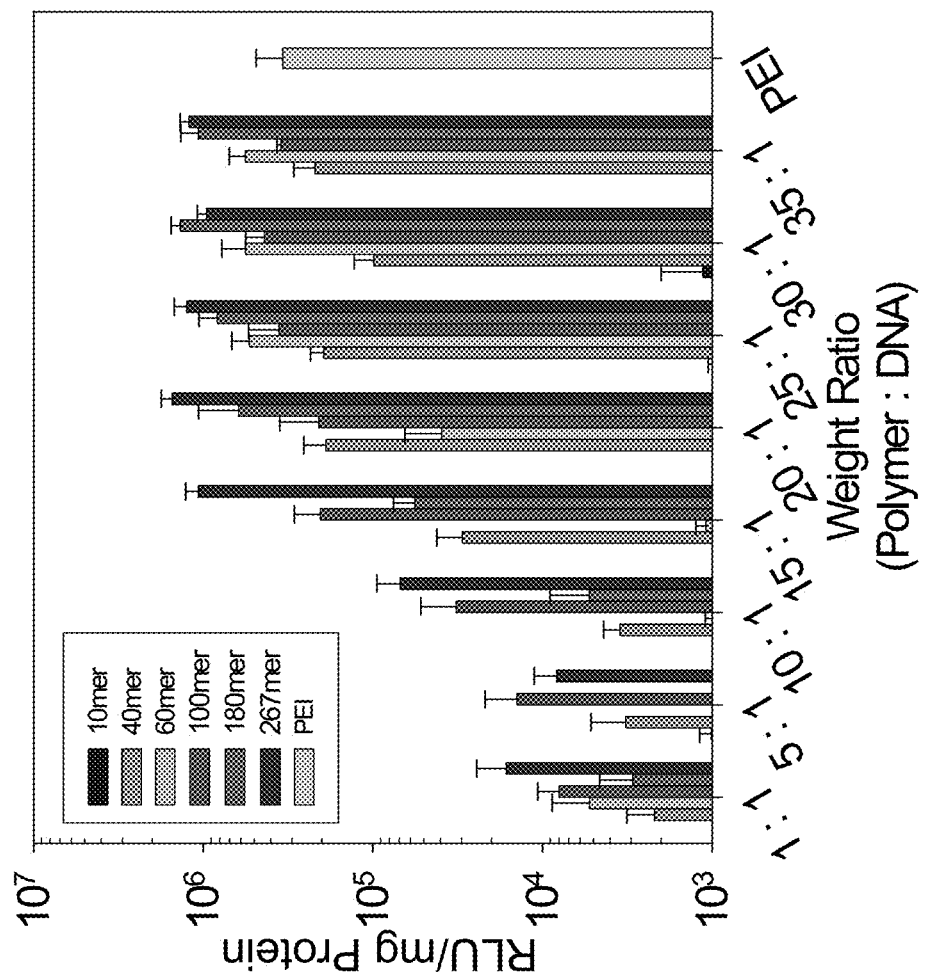

FIG. 30. In vitro transfection of COS-7 cells with PVBLG$_n$-1 polypeptides (n=10-267).

Figure 31:
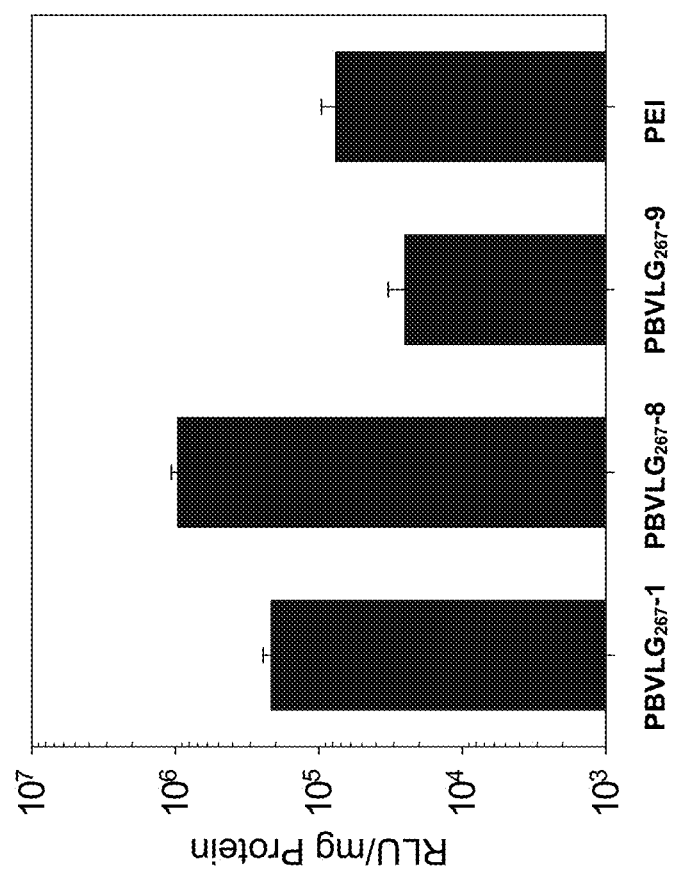

FIG. 31. In vitro transfection of COS-7 cells with PVBLG$_{267}$-X polypeptides.

FIG. 32A-B. (A) In vitro transfection of HeLa-Luc cells with PVBLG$_{100}$-8 and siRNA (siGL3). 25-kDa branched polyethylenimine (PEI), lipofectamine 2000 (LFA) and naked siGL3 were included as controls. (B) In vitro transfection of HeLa-Luc cells with PVBLG$_{100}$-8 and negative control siRNA (siNeg). 25-kDa branched polyethylenimine (PEI), lipofectamine 2000 (LFA) and naked siGL3 were included as controls.

FIG. 33A-B. a) In vitro transfection of HeLa, MDA-MB-231 and HEK293 cells with 25-kDa branched PEI and the top-performing PVBLG$_{267}$-8 polymer. b) In vitro transfection of HEK293 cells transfected with complexes of 25-kDa PEI or PVBLG$_{267}$-8 in the presence of intracellular processing inhibitors.

Figure 34A:
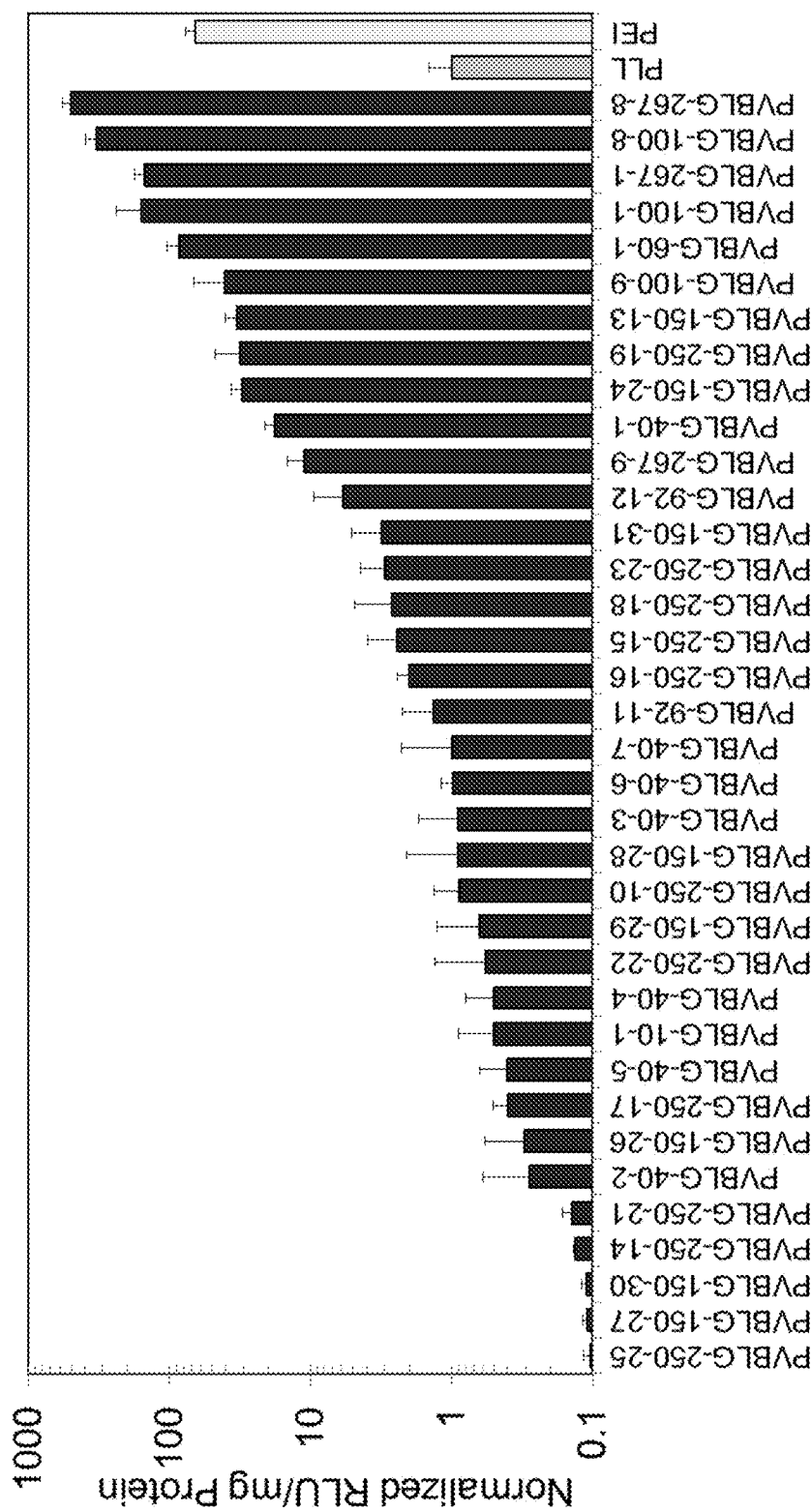

FIG. 34A-C. a) In vitro transfection of COS-7 cells with PVBLG$_n$-X polypeptides. 22-kDa poly-L-lysine (PLL) and 25-kDa polyethylenimine (PEI) were included as controls. b) Viability of PVBLG$_{267}$-8 and PEI in COS-7 cells. c) CD analysis of PVBLG$_{267}$-8 at pH 2, 6 and 7.4.

Figure 35:
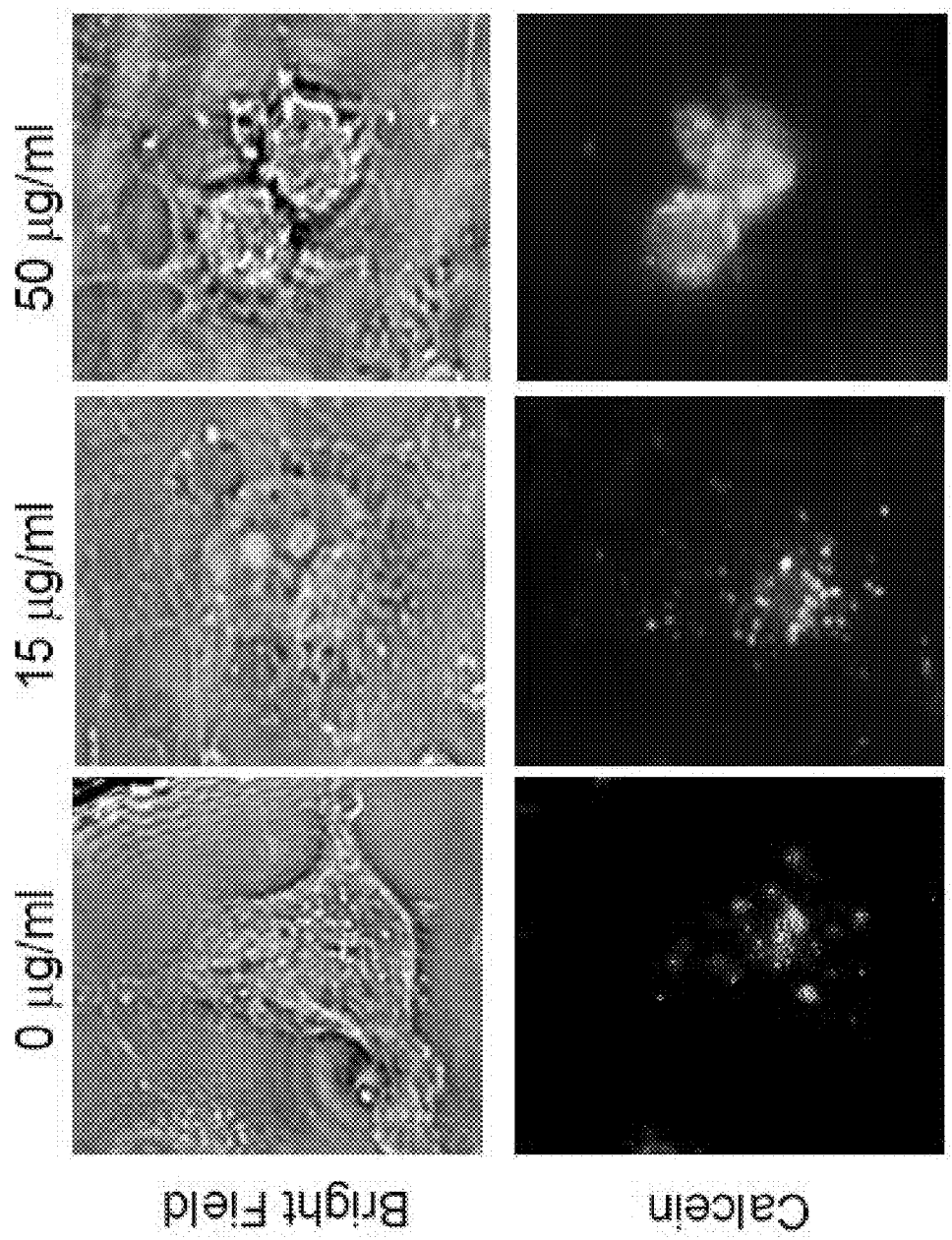

FIG. 35. Calcein uptake in COS-7 cells treated with various concentrations of PVBLG$_{267}$-8.

Figure 36:
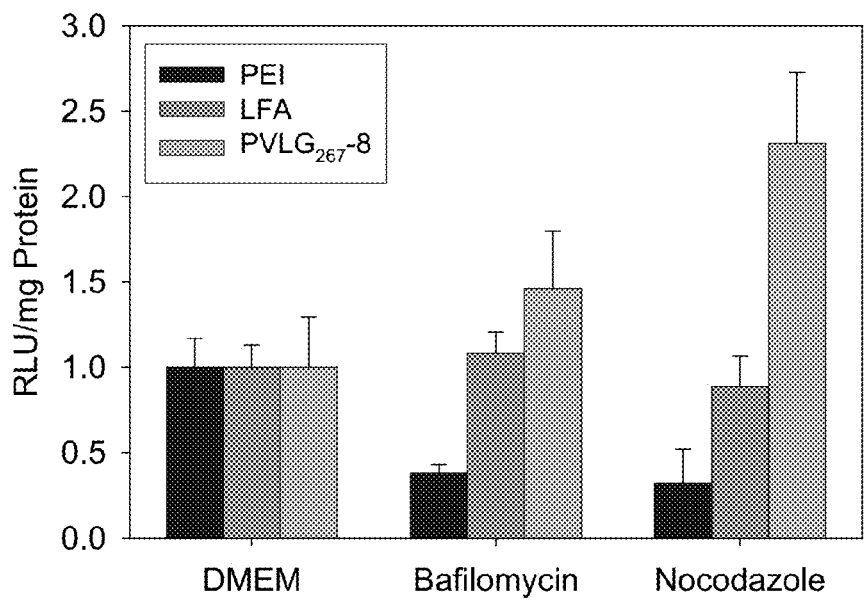

FIG. 36. In vitro transfection of COS-7 cells transfected with complexes of 25-kDa PEI (left bar), lipofectamine 2000 (LFA2000) (middle bar) or PVBLG$_{267}$-8 (right bar) in the presence of intracellular processing inhibitors.

Figure 37:
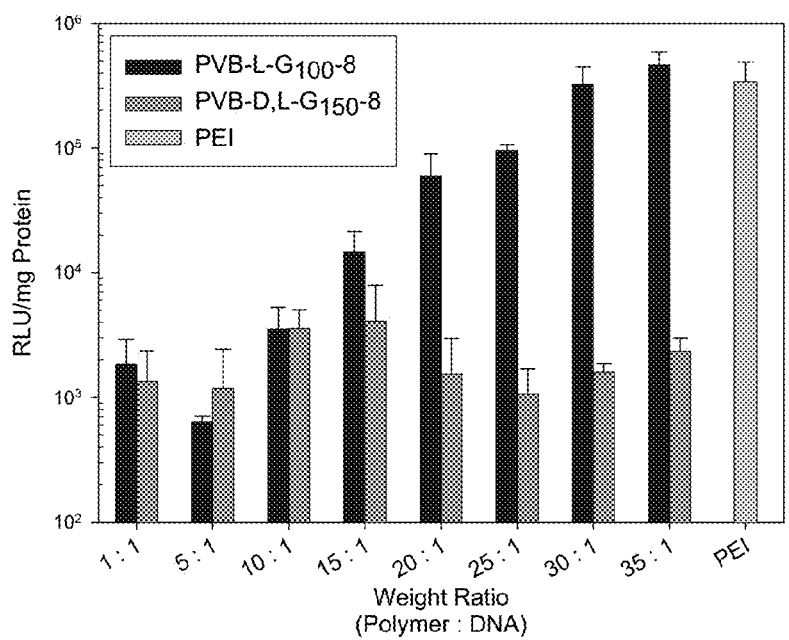

FIG. 37. In vitro transfection COS-7 cells with PVB-L-G$_{267}$-8 (left bar) and PVB-D,L-G$_{267}$-8 (right bar) polypeptides. 25-kDa PEI was included as a control.

Figure 38:
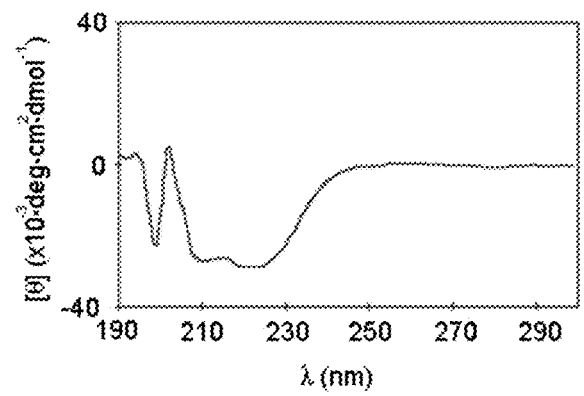
Figure 39:
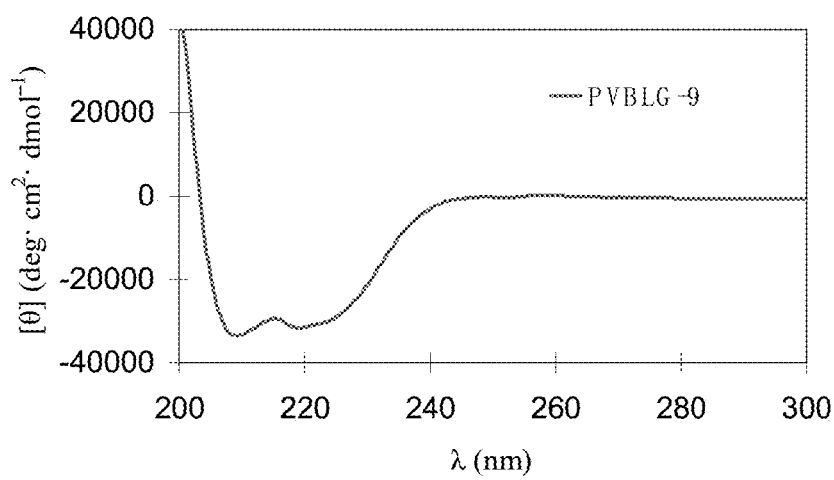
Figure 40:
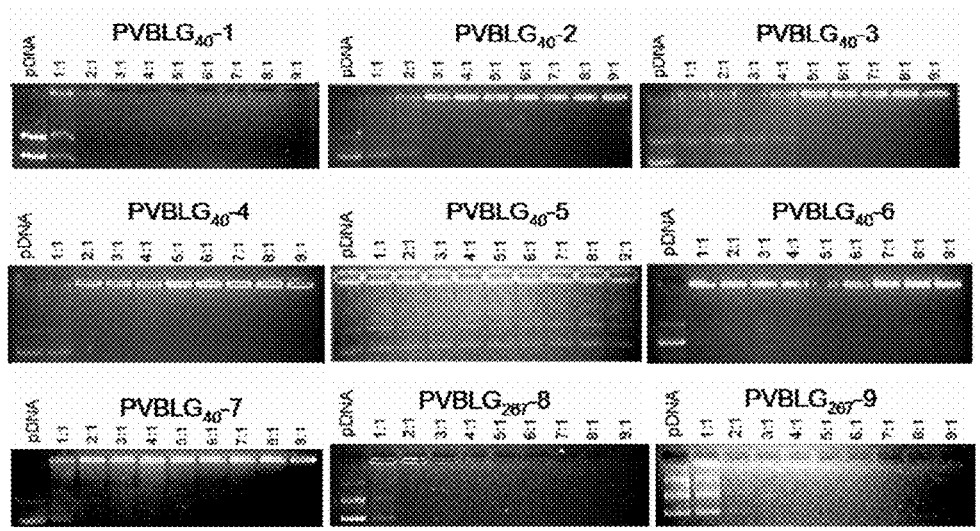

FIG. 38. CD spectral analysis of PVBLG$_{267}$-8.
FIG. 39. CD spectral analysis of PVBLG$_{267}$-9.
FIG. 40. Gel retardation analysis evaluating the ability of the various PVBLG$_n$-X polymers to bind and condense DNA at various weight ratios. The numbers above the lanes correspond to the polymer:DNA weight ratio tested. Of the nine polymers tested, only PVBLG$_{40}$-5 was unable to bind and condense DNA at weight ratios up to 9:1.

Figure 41:
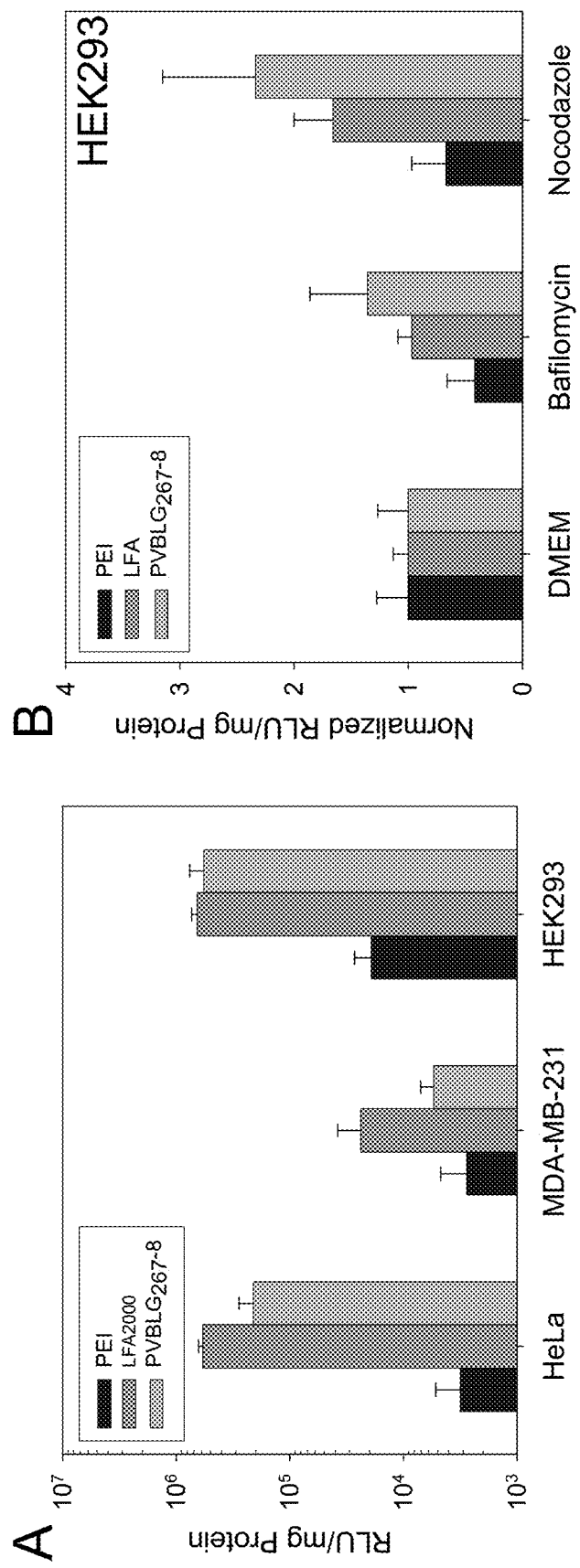

FIG. 41A-B. (A) In vitro transfection of HeLa, MDA-MB-231 and HEK293 cells with and 25-kDa branched PEI (left bar), lipofectamine 2000 (LFA2000) (middle bar), and the highly effective PVBLG$_{267}$-8 polymer (right bar). (B) In vitro transfection of HEK293 cells transfected with complexes of 25-kDa PEI, LFA2000 or PVBLG$_{267}$-8 in the presence of intracellular processing inhibitors.

FIG. 42. COS7 cell uptake of YOYO-1 labeled complexes formed with either 25-kDa PEI or PVBLG$_{10}$-1 or PVBLG$_{60}$-1. The observation that both PVBLG$_{10}$-1 and PVBLG$_{60}$-1 show enhanced uptake compared to PEI while only PVBLG$_{60}$-1 has comparable transfection efficiency compared to PEI indicates that the increased performance of the PVBLG$_n$-X polymers is likely not due solely to enhanced uptake.

FIG. 43A-D. (A) COS7 cell uptake of YOYO-1 labeled complexes formed with either 25-kDa PEI or PVBLG$_{267}$-8 in the presence of endocytic inhibitors (left bar=DMEM; middle bar=mβCD; right bar=chlorpromazine). (B) Normalized COS-7 cell uptake of YOYO-1 labeled complexes formed with either 25-kDa PEI or PVBLG$_{267}$-8 in the presence of intracellular processing inhibitors (left bar=PEI; middle bar=LFA 2000; right bar=PVBLG$_{267}$-8). (C) HEK293 cell uptake of YOYO-1 labeled complexes formed with either 25-kDa PEI or PVBLG$_{267}$-8 in the presence of endocytic inhibitors (left bar=DMEM; middle bar=mβCD; right bar=chlorpromazine). (D) Normalized HEK293 cell uptake of YOYO-1 labeled complexes formed with either 25-kDa PEI or PVBLG$_{267}$-8 in the presence of intracellular processing inhibitors (left bar=PEI; middle bar=LFA 2000; right bar=PVBLG$_{267}$-8).

FIG. 44A-B. (A) Measured diameter of PVBLG$_{267}$-8/DNA complexes at various polypeptide:DNA weight ratios. (B) Diameter of PVBLG$_{267}$-8/DNA complexes (30:1 polypeptide:DNA ratio) over time in PBS.

FIG. 45A-B. (A) Toxicity of PVBLG$_{267}$-X polymers in COS-7 cells. (B) Toxicity of PVBLG$_{267}$-X polymers in HEK293 cells.

Figure 46:
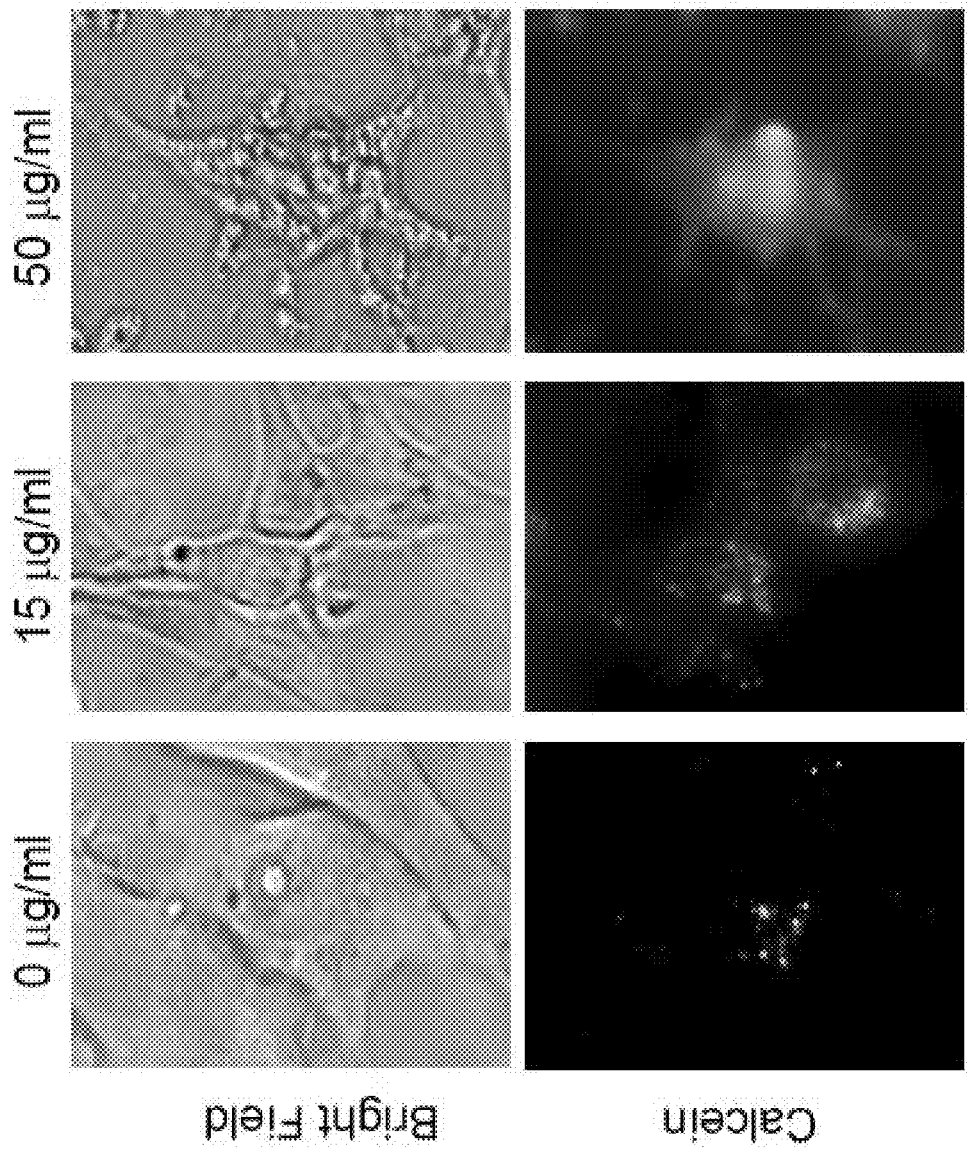

FIG. 46. Calcein uptake in HEK293 cells treated with various concentrations of PVBLG$_{267}$-8. Punctate fluorescence observed in cells incubated with 0 and 15 μg/mL PVBLG$_{267}$-8 indicates pinocytic uptake. Diffuse fluorescence observed in cells treated with 50 μg/mL PVBLG$_{267}$-8 indicates cell membrane permeation and transmembrane uptake.

Figure 47:
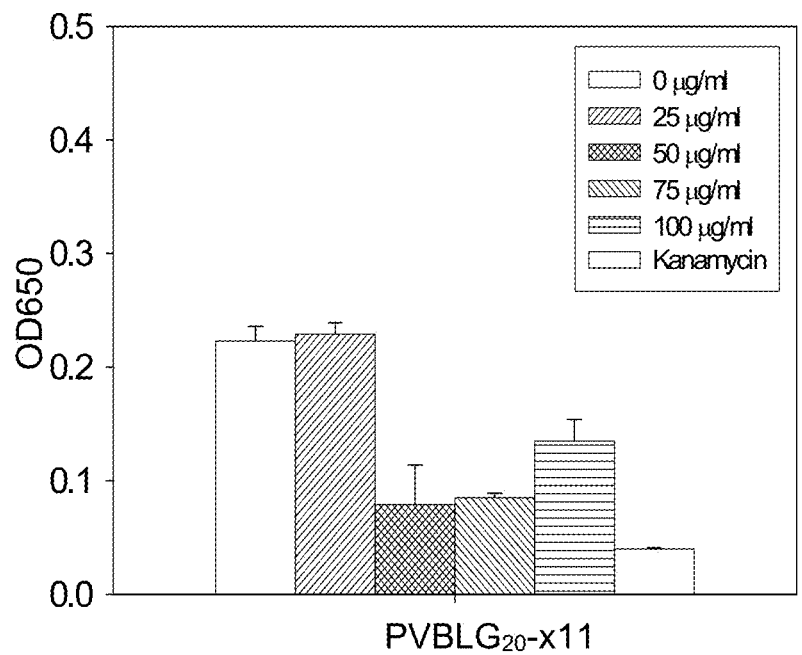

FIG. 47. Antibacterial effects determined by incubating E. coli with PVBLG-x11 at various concentrations for approximately 6 hours at 37° C. The kanamycin concentration used was 50 μg/mL. Samples were assayed for bacteria growth by reading the OD650 (absorbance at 650 nm using a Molecular Devices SpectraMax 340PC Plate Reader).

Figure 48:
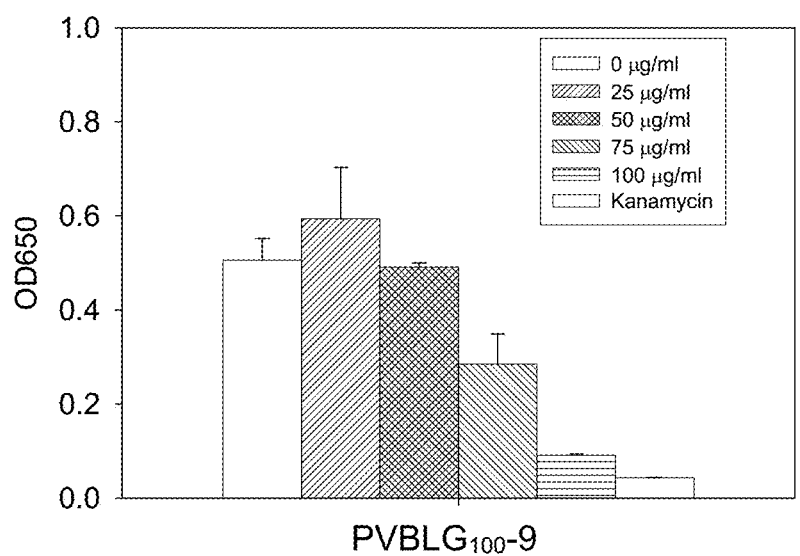

FIG. 48. Antibacterial effects determined by incubating E. coli with PVBLG-11 at various concentrations for approximately 6 hours at 37° C. The kanamycin concentration used was 50 μg/mL. Samples were assayed for bacteria growth by reading absorbance at 650 nm using a Molecular Devices SpectraMax 340PC Plate Reader.

Figure 49:
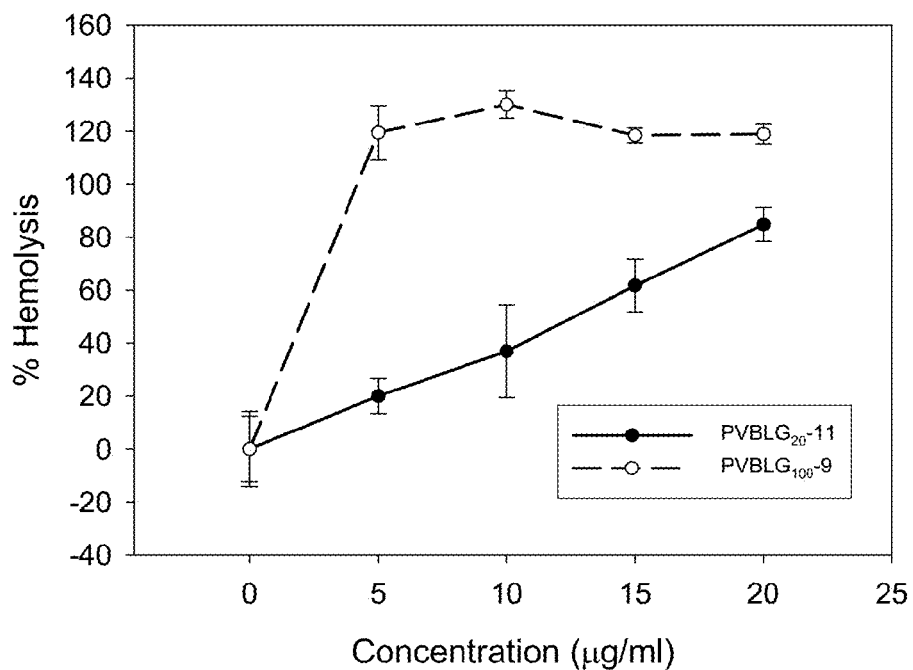

FIG. 49. The hemolytic potential against mammalian cells determined by incubating mouse red blood cells with various concentrations of polymer for 1 hour at 37° C. Cells were centrifuged for 5 minutes at 1000 g to pellet intact blood cells, and absorbance of the supernatant was read at 530 nm using a Perkin Elmer 1420 Multilabel Counter.

Figure 50:
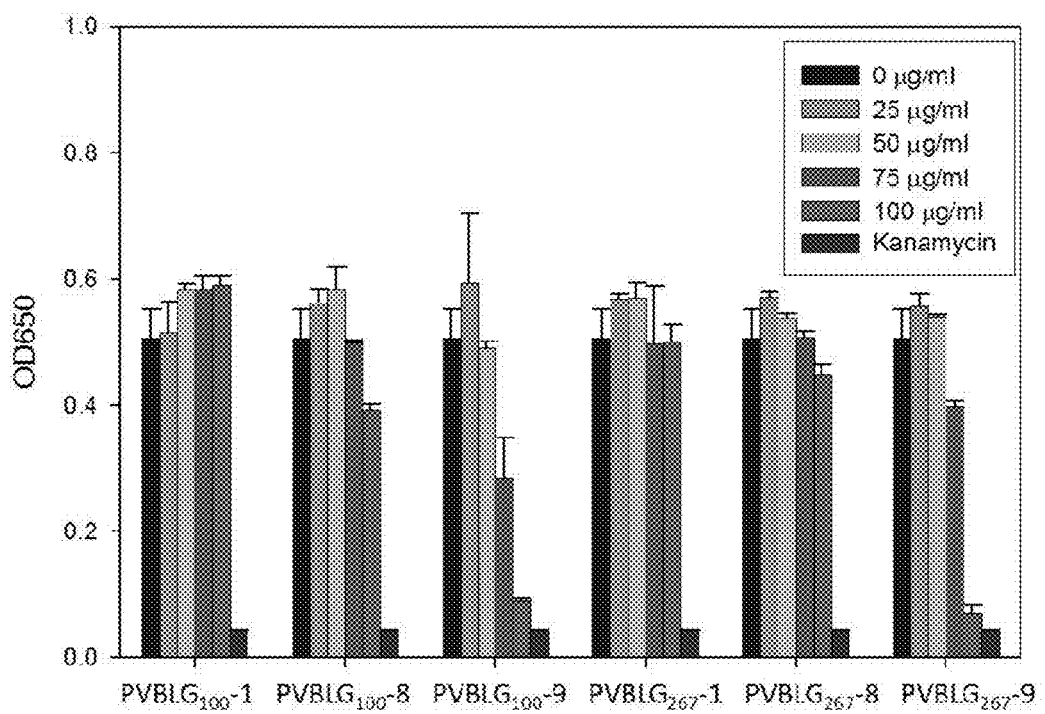

FIG. 50. Inhibition of bacterial growth by PVBLG polymers.

Figure 51:
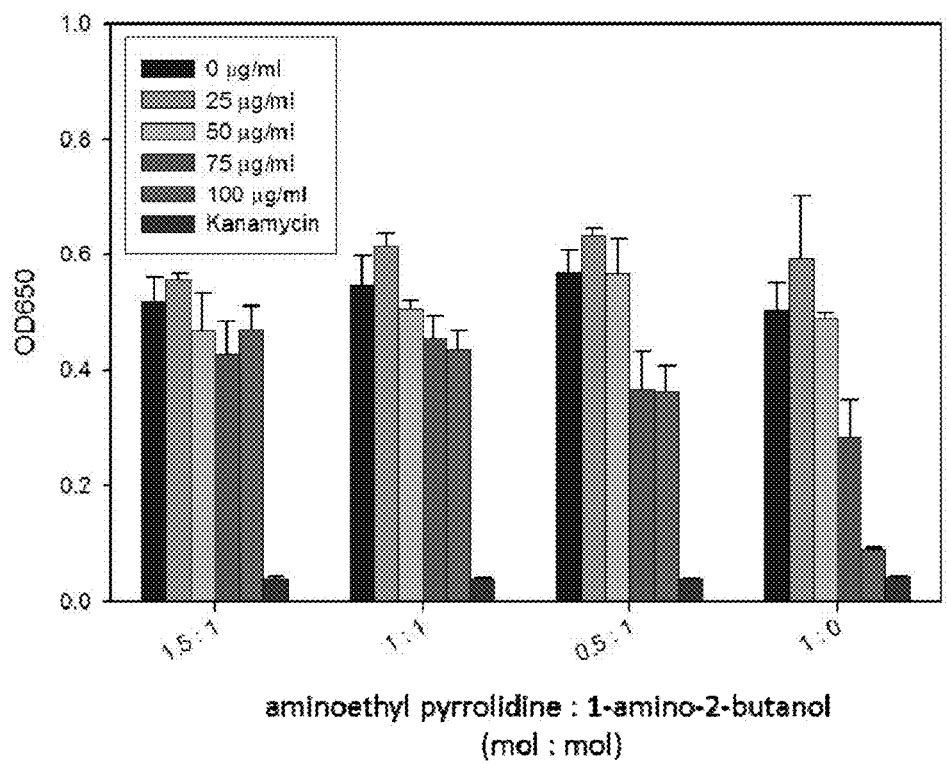

FIG. 51. Inhibition of bacterial growth by PVBLG copolymers.

Figure 52:
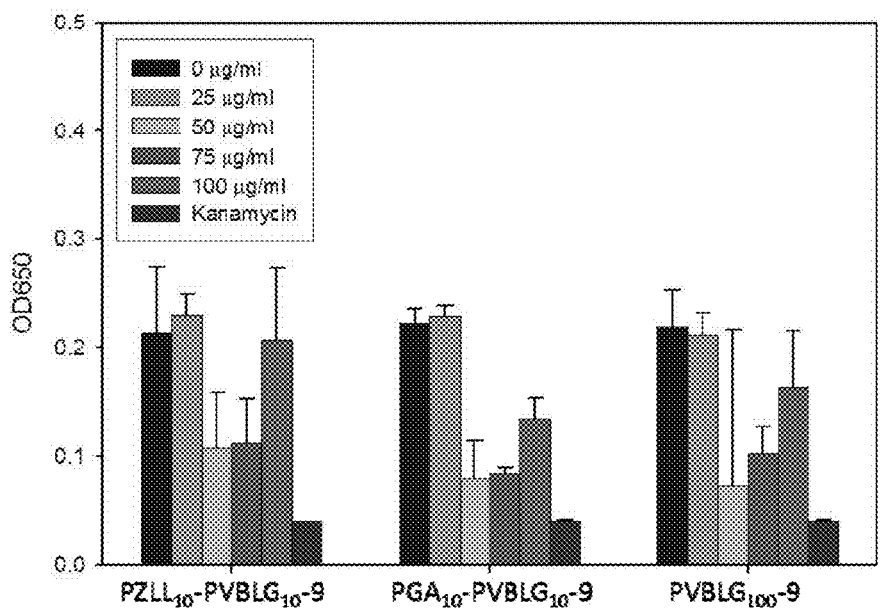

FIG. 52. Inhibition of bacterial growth by PVBLG block co-polymers.

Figure 53:
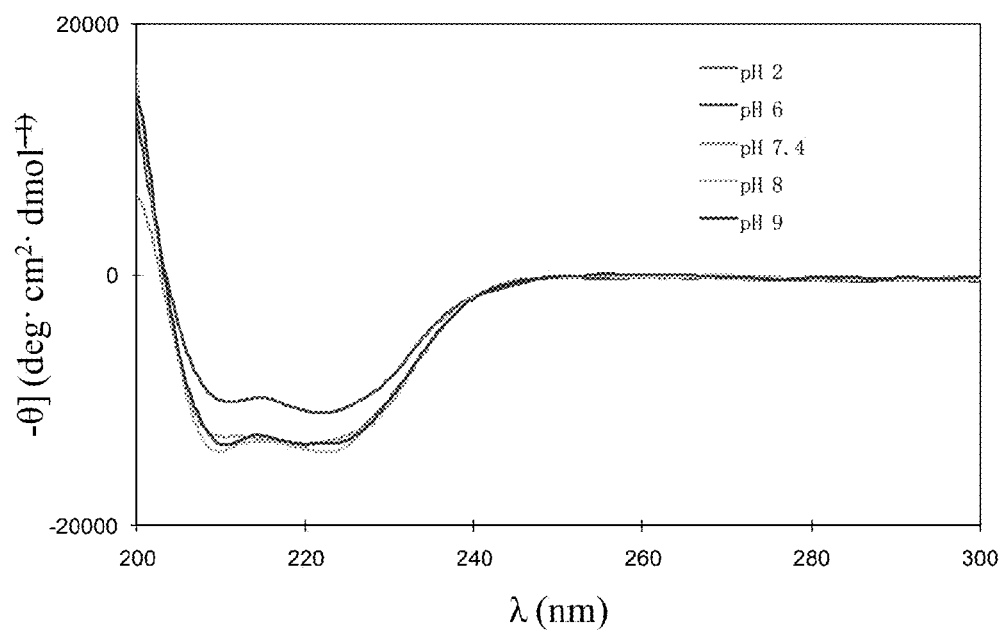

FIG. 53. Stabilized helices can be extended to negative charged polymers where the side chain charges are far away enough from the backbone to promote stable helix formation. Poly(γ-(4-carboxylic acid benzyl) glutamate) was prepared from cleavage oxidation of PVBLG. CD analysis of the polymer in various pH buffer (20 mM) revealed that the polymer can maintain its helical conformation traversing each pH tested (pH=2-9).

Figure 54:
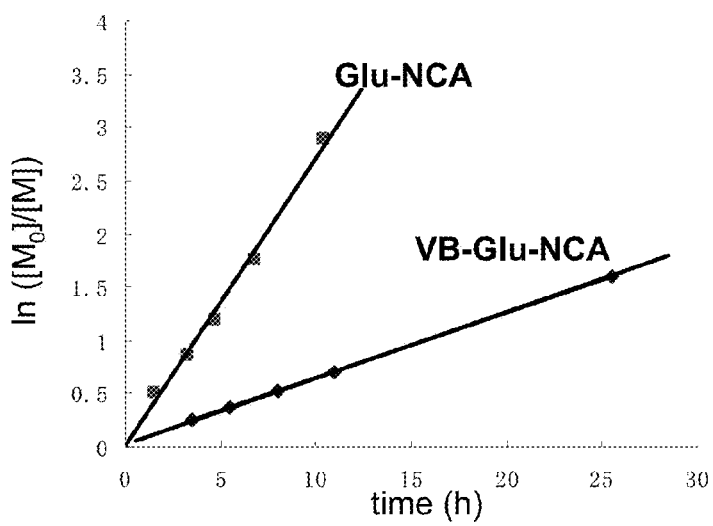

FIG. 54. Kinetic study comparison of Glu-NCA and VB-Glu-NCA initiated HMDS in DMF at rt. The initial NCA concentration was 0.2 mmol/mL. The conversion of the NCA was measured by FT-IR.

Figure 55:
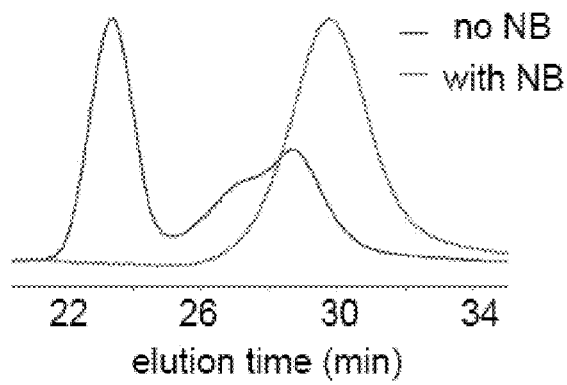

FIG. 55. GPC (MALS detector) curves overlay of HMDS mediated VB-Glu-NCA polymerizations at M/I ratio of 50/1 with (right peak) and without (left peak) addition of NB.

Figure 56:
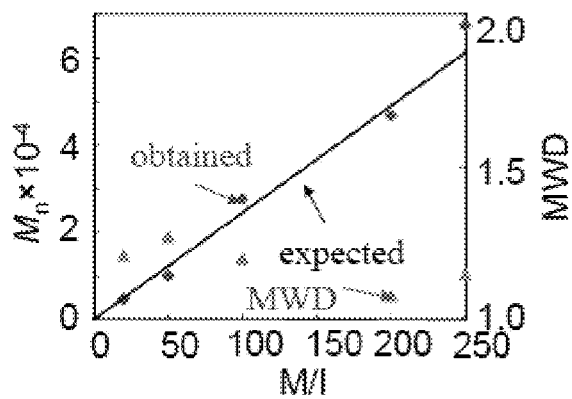

FIG. 56. Plot of MW and MWD versus M/I in the HMDS/C2 initiated VB-Glu-NCA polymerization.

Figure 57:
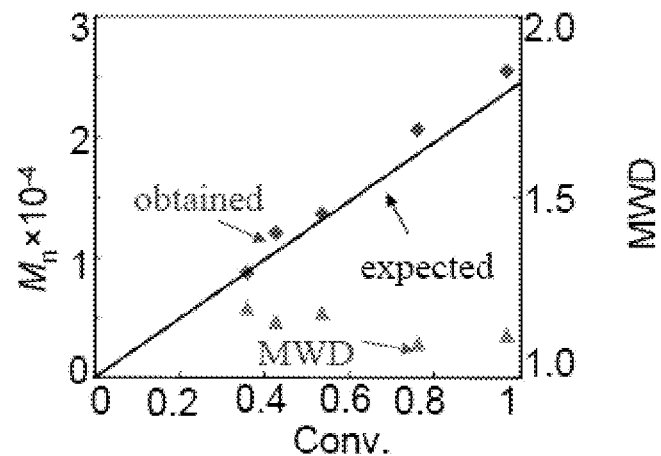

FIG. 57. Plot of MW and MWD versus conversion in the HMDS/C2 initiated VB-Glu-NCA polymerization.

Figure 58:
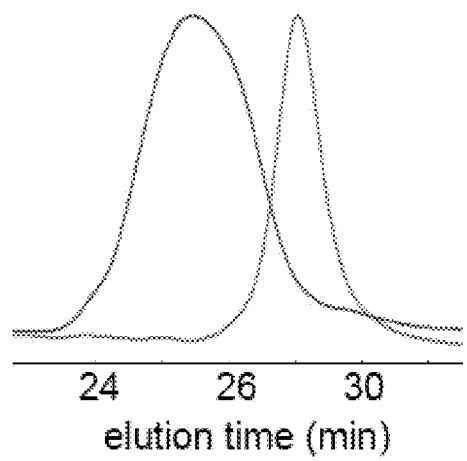

FIG. 58. GPC curves overlay of PZLL20 (right peak) and block polymer PZLL20-b-PVBLG50 (left peak).

Figure 59:
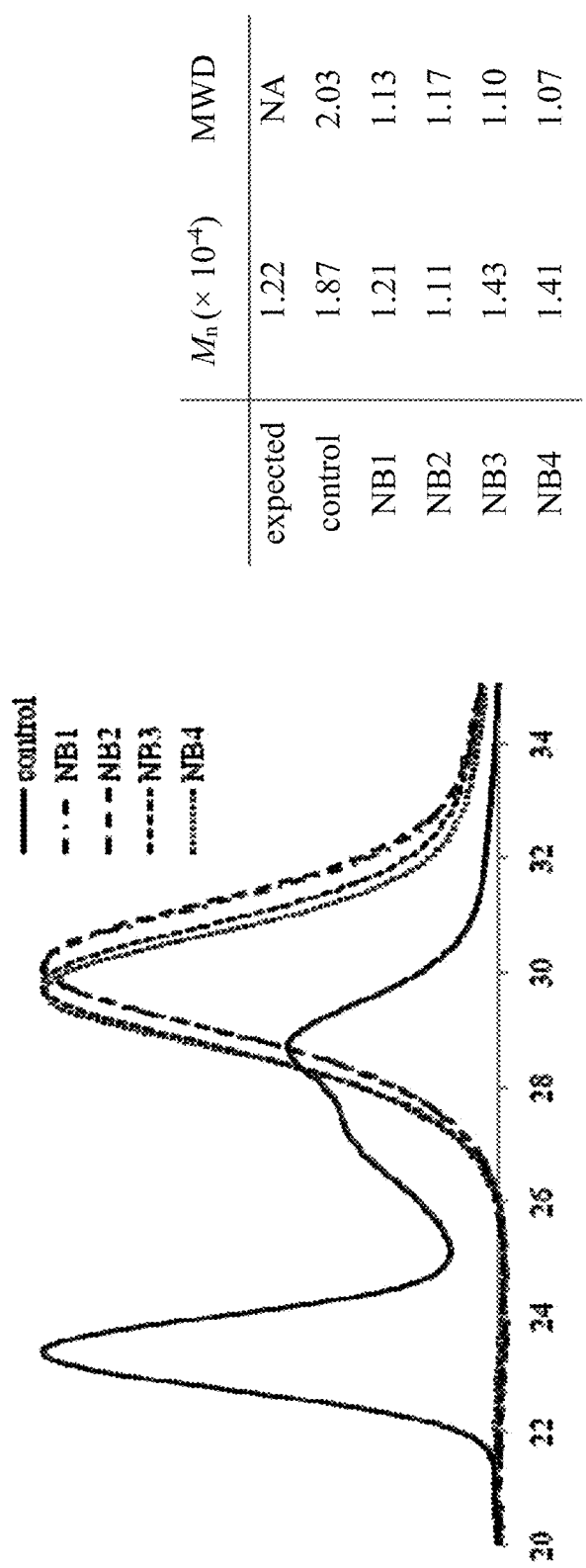

FIG. 59. GPC (MALS detector) curves overlay of HMDS mediated VB-Glu-NCA polymerizations at M/I ratio of 50/1. Various amount of NB (control: 0 μL; NB1: 10 μL; NB2: 20 μL; NB3: 30 μL; NB4: 40 μL) were added as the co-solvent of the polymerizations. The MW and MWD were summarized in the table to the right.

Figure 60:
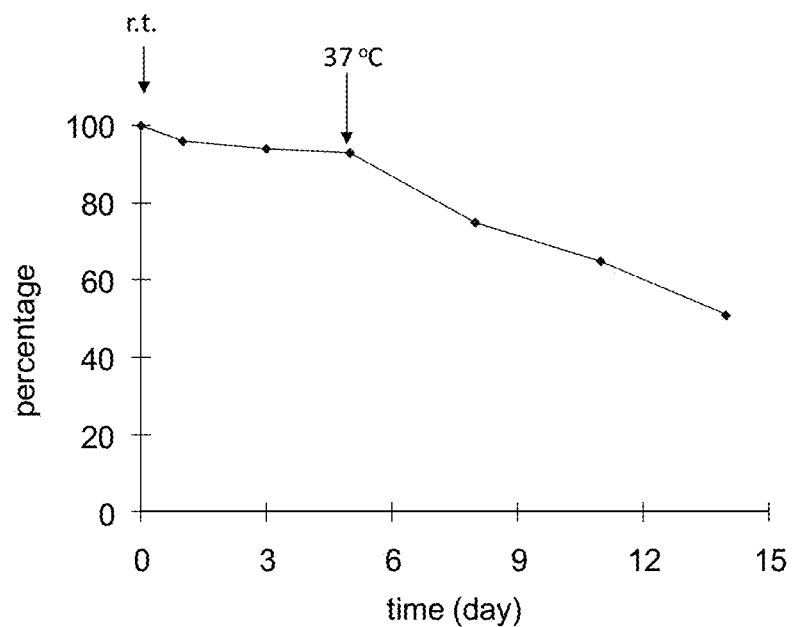

FIG. 60. Hydrolysis kinetics of (PVBLG-1)$_{40}$ in 1×PBS at room temperature (~23° C.) for the first 5 days and 37° C. for the remaining time.

Figure 61:
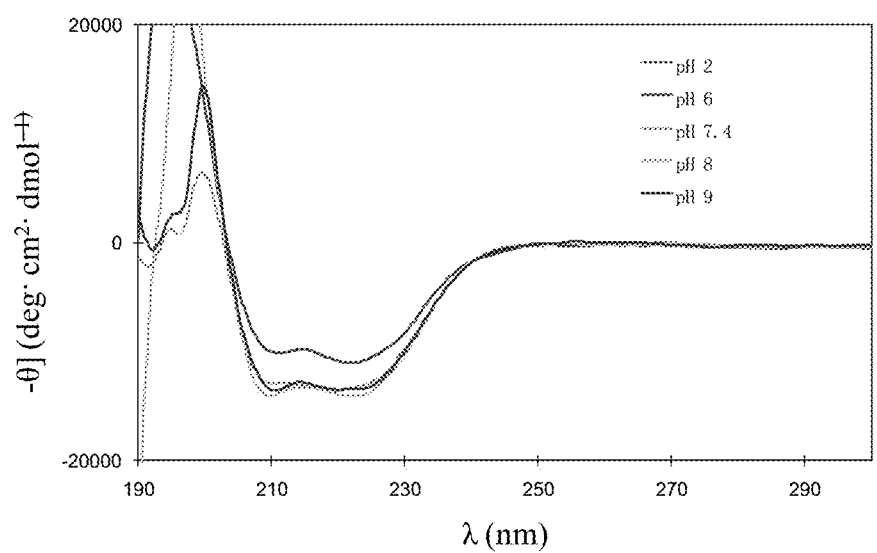

FIG. 61. CD analysis of (PLG-1)$_{60}$ at various pH values.

Figure 62:
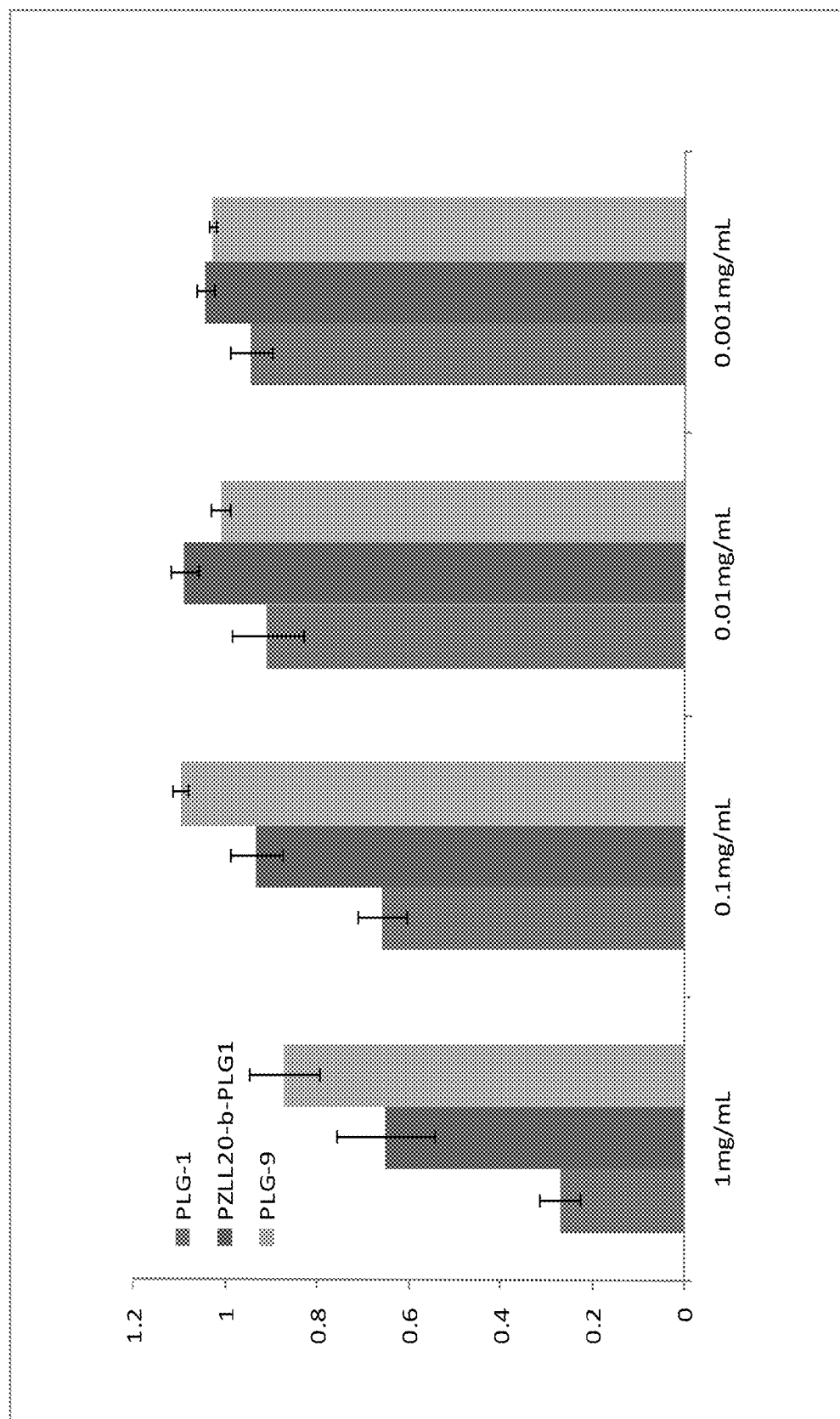

FIG. 62. MTT study using (PLG-1)$_{60}$ (left bar), PZLL20-b-(PLG-1)$_{40}$ (middle bar) and (PLG-7)$_{44}$ (right bar). HeLa was the MTT cell line. Cells were counted at 10,000 cells per well and incubated for one day to let cells adhere to the plate. Cells were incubated for 72 hours in the presence of the polymers.

Figure 63:
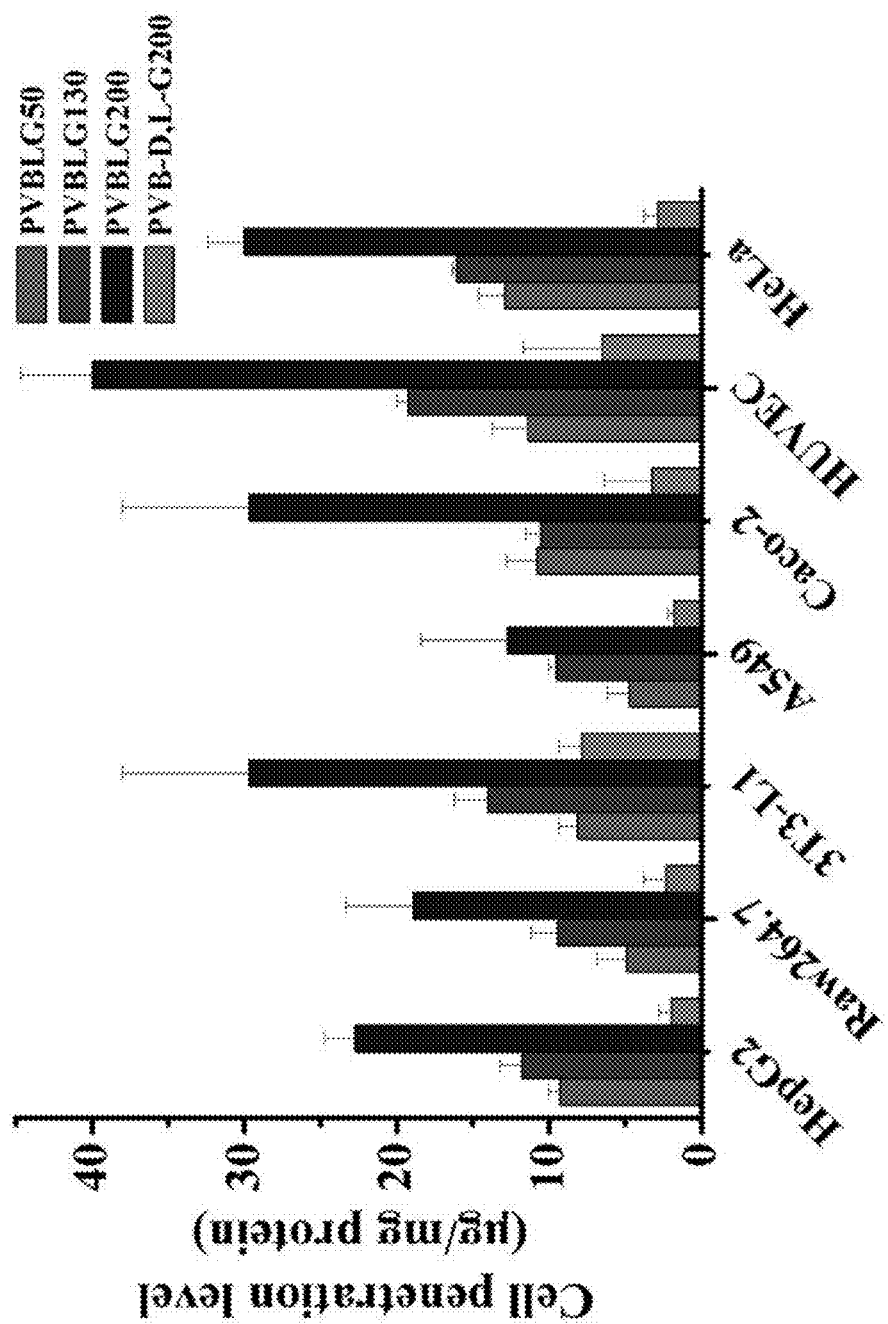

FIG. 63. Penetration of polypeptides in various mammalian cells. Uptake of RhB-PVBLG-8 in HeLa, HepG-2, Raw264.7, A549, HUVEC, Caco-2, and 3T3-L1 cells. Results were expressed as μg of the Rhodamine-polypeptide associated with 1 mg of cellular protein.

Figure 64:
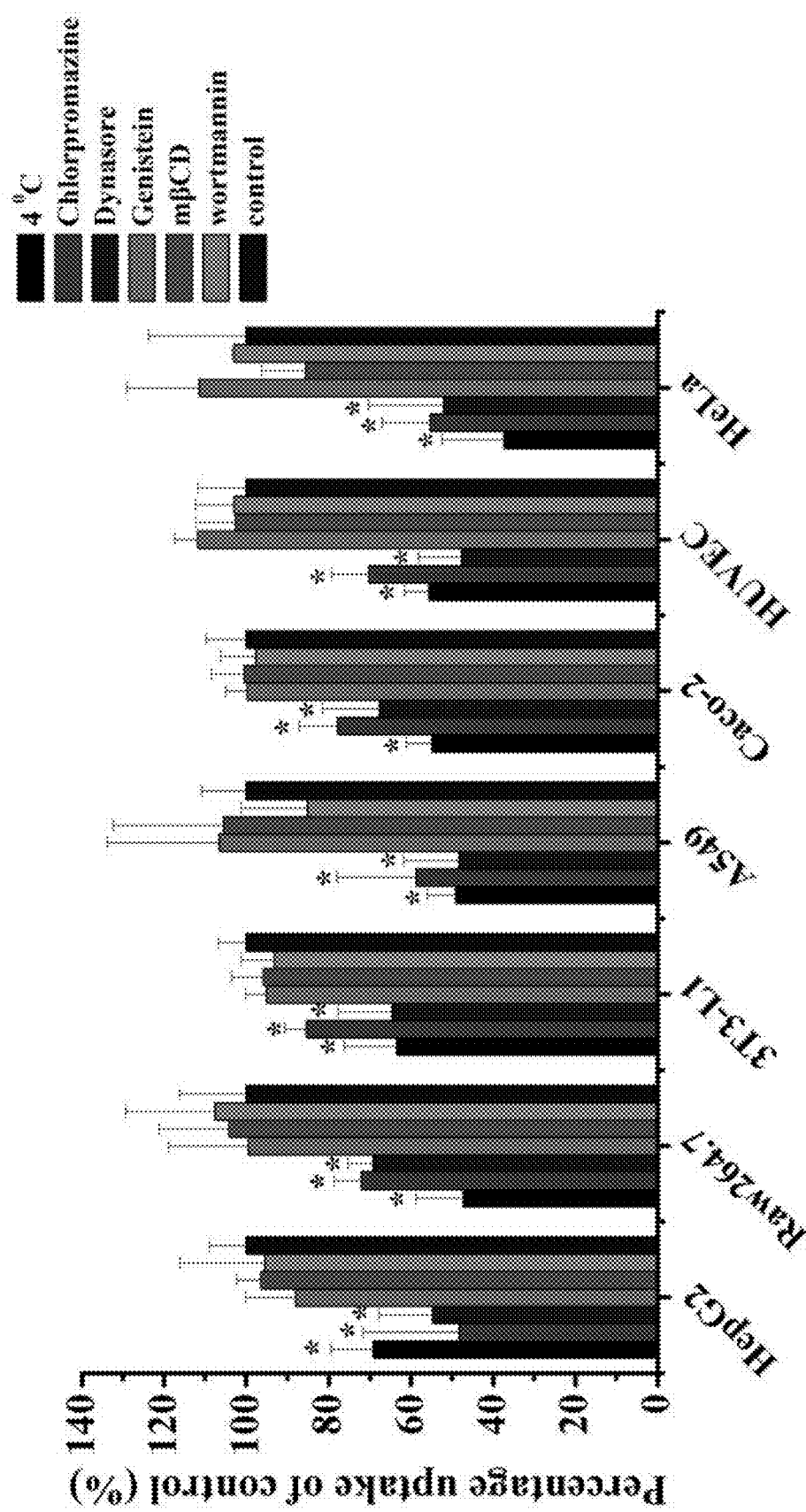

FIG. 64. CLSM images showing penetration and transduction of RhB-PVBLG-8 in HeLa cells. Bar represents 10 μm.

Figure 65:
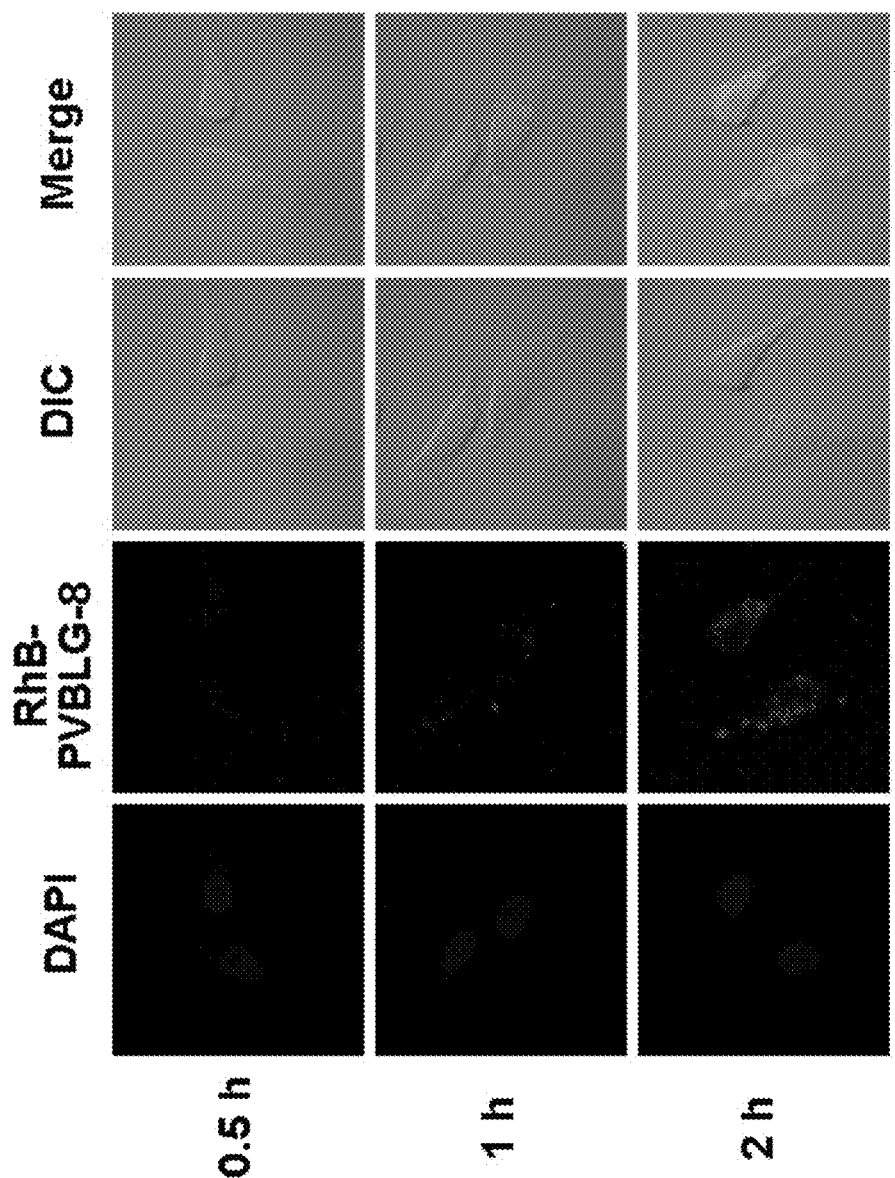

FIG. 65. Elucidation of the mechanism underlying cell uptake of RhB-PVBLG-8 in a variety of cell lines. The uptake study was performed at 4° C. or in the presence of endocytic inhibitors, and results were expressed as percentage uptake (%) of control wherein cells were incubated with RhB-PVBLG-8 at 37° C.

FIG. 66A-D. Characterization of PVBLG-8/DNA complexes. (A) Gel retardation assay showing condensation of DNA by cationic polypeptide. M refers to naked DNA. (B) Particle size and Zeta potential of PVBLG-8/DNA complexes. (C) Stability of PVBLG-8/DNA complexes in terms of particle size alteration upon dilution with PBS. (D) Improved stability of DNA against DNase I degradation following condensation by cationic polypeptides.

FIG. 67A-D. Internalization of PVBLG/DNA complexes (10:1) in a variety of cell lines. (A) Uptake level of PVBLG/DNA complexes after incubation for 2 h at 0.1 μg YOYO-1-DNA/well. Results were expressed as ng YOYO-1-DNA associated with 1 mg of cellular protein. (B) Time-course uptake of PVBLG/DNA complexes at 0.1 µg YOYO-1-DNA/well. (C) CLSM images showing uptake and distribution of RhB-PVBLG-8/YOYO-1-DNA complexes in HeLa cells. Each image is an overlay of four channels: blue (DAPI stain), red (RhB-PVBLG-8), green (YOYO-1), and DIC (cell morphology). Yellow indicates the co-localization of red and green. Bar represented 10 µm. (D) Mechanistic probes of complex internalization through incubation at 4° C. that completely blocks endocytosis or adoption of distinct endocytic inhibitors.

Figure 68A:
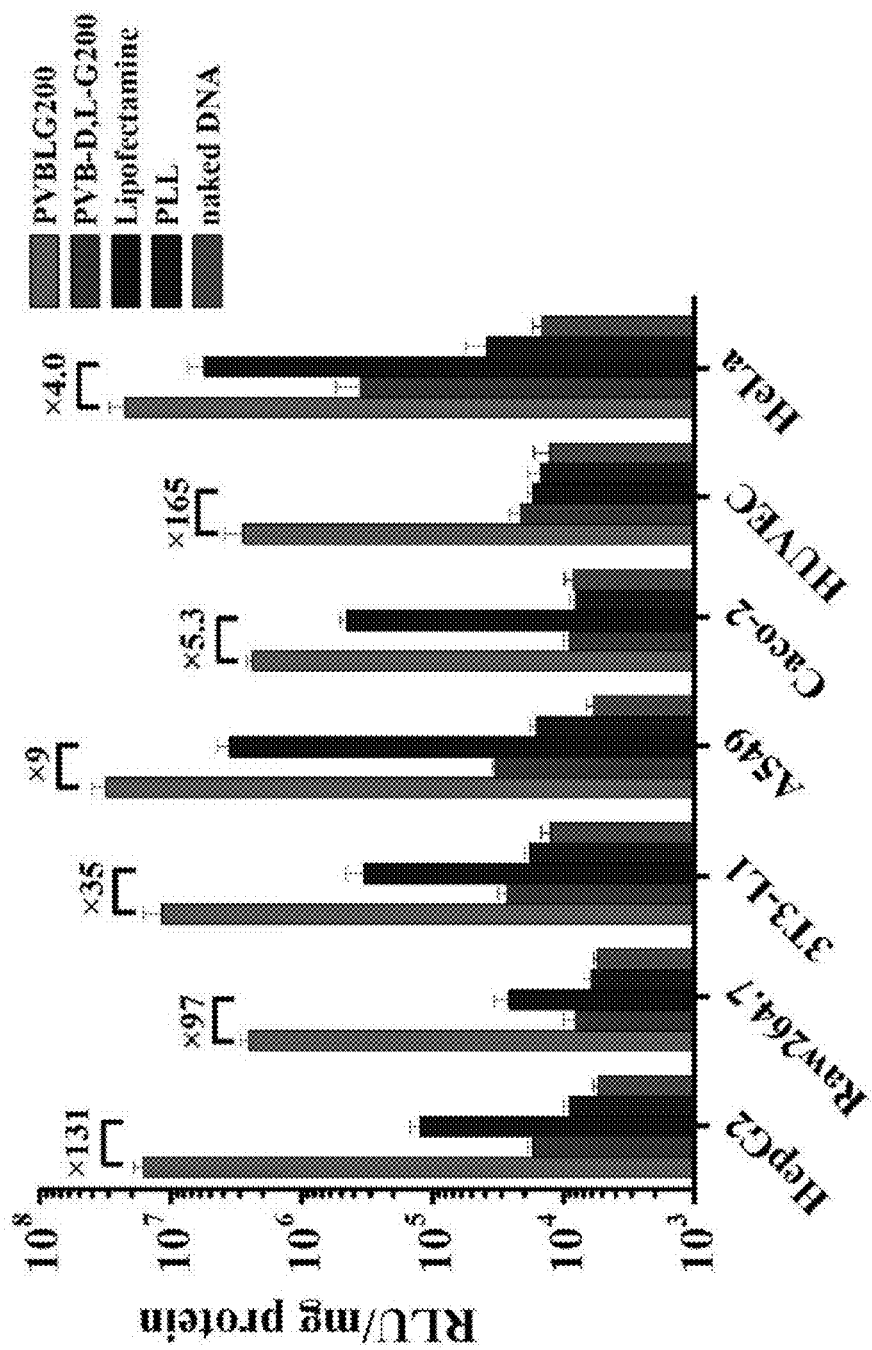
Figure 68B:
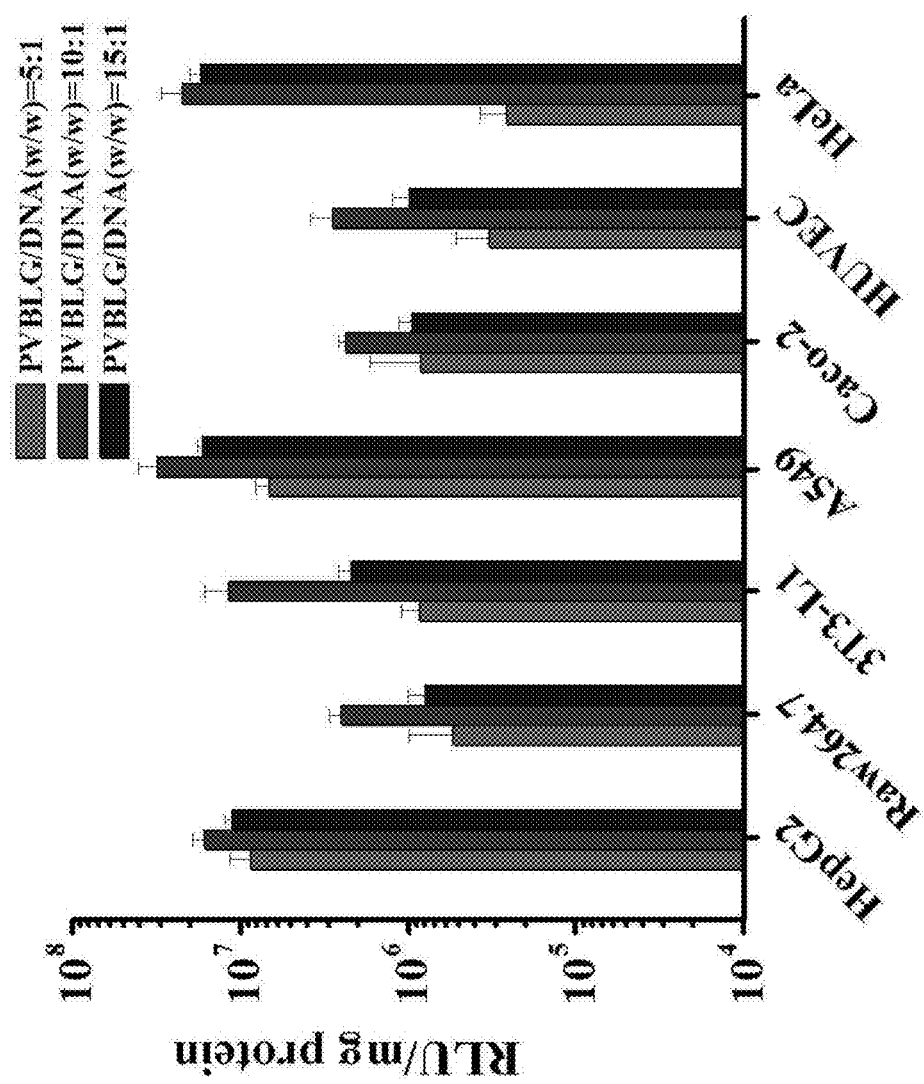
Figure 68C:
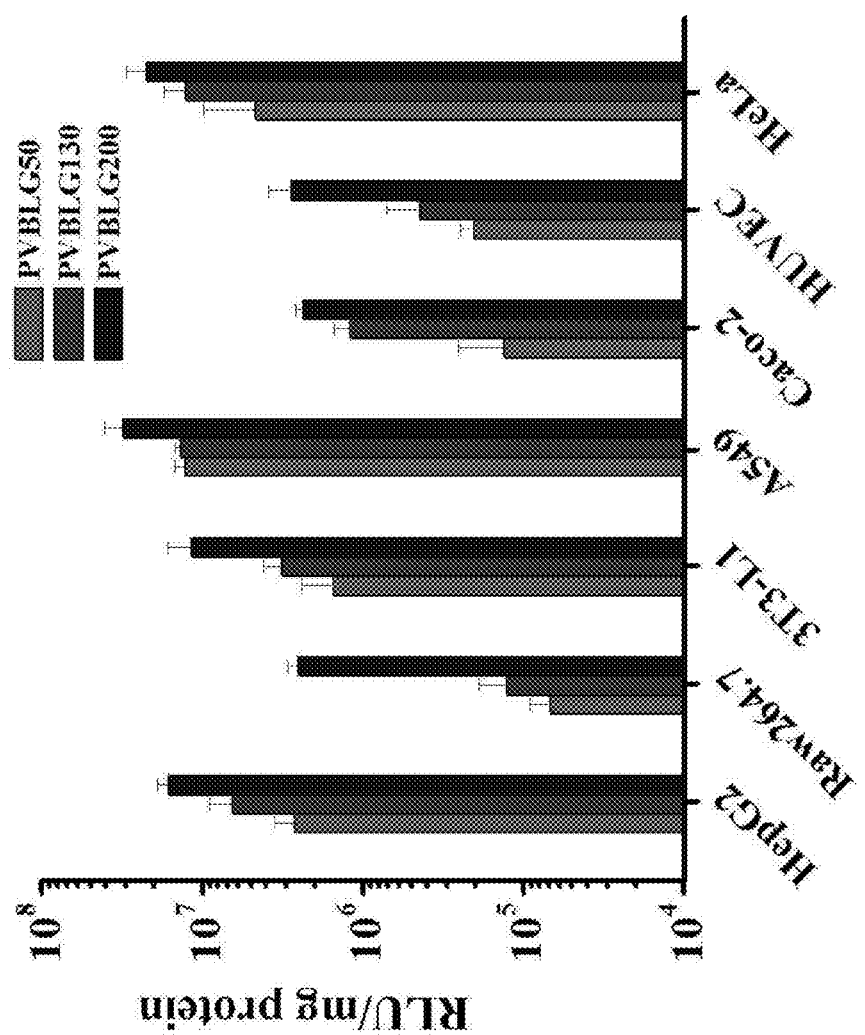
Figure 69G:
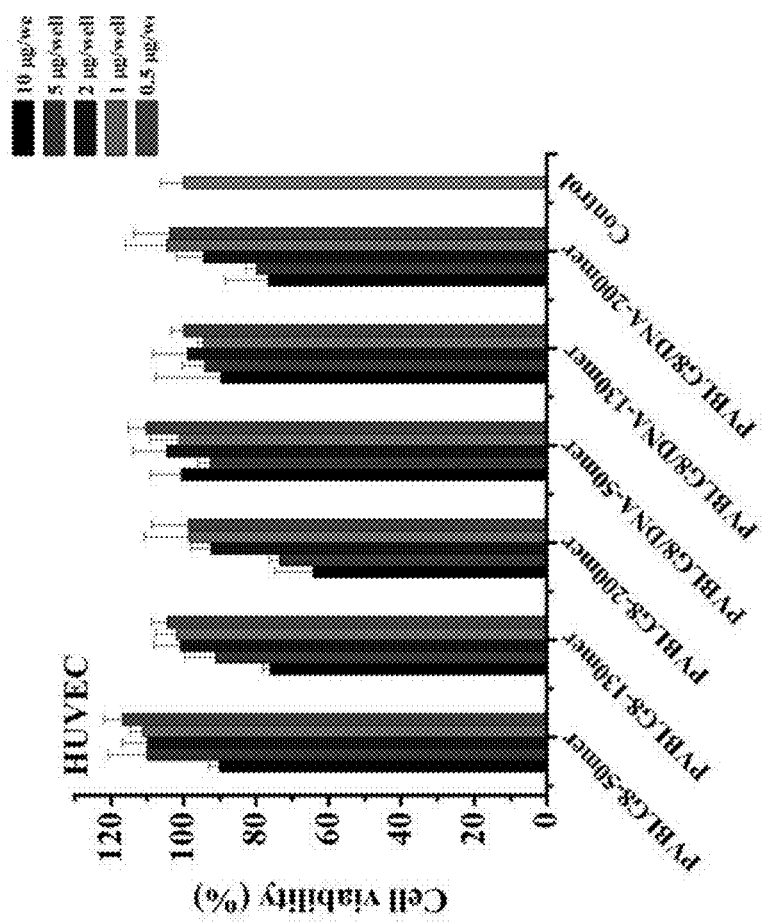

FIG. 68A-C. Polypeptide-mediated plasmid DNA transfection in HeLa, HepG-2, Raw264.7, A549, HUVEC, Caco-2, and 3T3-L1 cells. Cells in 96-well plate were treated with polypeptide/DNA complexes (0.1 µg DNA/well) for 4 h in serum-free media and further cultured in serum-containing media for 20 h before luciferase quantification using the Bright-Glo kit and cellular protein quantification using the BCA kit. Results were expressed as relative luminescence unit (RLU) associated with 1 mg of cellular protein. Values represented mean±SD of three experiments. (A) Transfection efficiencies of PVBLG200/DNA (10:1) complexes in the seven cell lines. (B) Transfection efficiencies of PVBLG200/DNA complexes with different polypeptide/DNA weight ratios. (C) Transfection efficiencies of complexes formed by PVBLG weight various chain length and DNA (10:1).

FIG. 69A-G. Cytotoxicity of PVBLG-8 and PVBLG-8/DNA complexes (10:1) in (A) HepG-2, (B) Raw264.7, (C) 3T3-L1, (D) Caco-2, (E) A549, (F) HeLa, and (G) HUVEC cells. PVBLG-8 or PVBLG/DNA complexes at determined polypeptide amounts were incubated with cells in serum-free DMEM for 4 h, and the media were replaced by serum-containing media followed by further incubation for 24 h. Cell viability was then evaluated using the MTT assay.

FIG. 70A-D. (A) The pH dependence, (B) concentration dependence (pH=3), (C) the urea concentration dependence (pH=3) and (D) salt concentration dependence (pH=3) of the residue molar ellipticity at 222 nm for PDMNBLG-co-PVBLG-8 with different PDMNBLG content: 10% (-■-), 20% (-●-), 30% (-▲-), 40% (-▼-), 60% (-◀-).

FIG. 71A-D. CD spectra PDMNBLG-co-PVBLG-8 with different PDMNBLG content: 10% (-■-), 20% (-●-), 30% (-▲-), 40% (-▼-), 60% (-◀-) at pH=3 before (A) and after (B) UV irradiation (600 s). (C) The helicity of PDMNBLG-co-PVBLG-8 before and after UV irradiation (600 s) at various PDMNBLG contents. (D) Schematic of PDMNBLG-co-PVBLG-8 before and after UV irradiation.

FIG. 72A-B. A) UV/Vis spectral changes of polypeptide upon irradiation with UV light (λ=350 nm). B) CD spectra of polypeptide showing disappearance of α-helicity in response to UV irradiation.

Figure 73A:
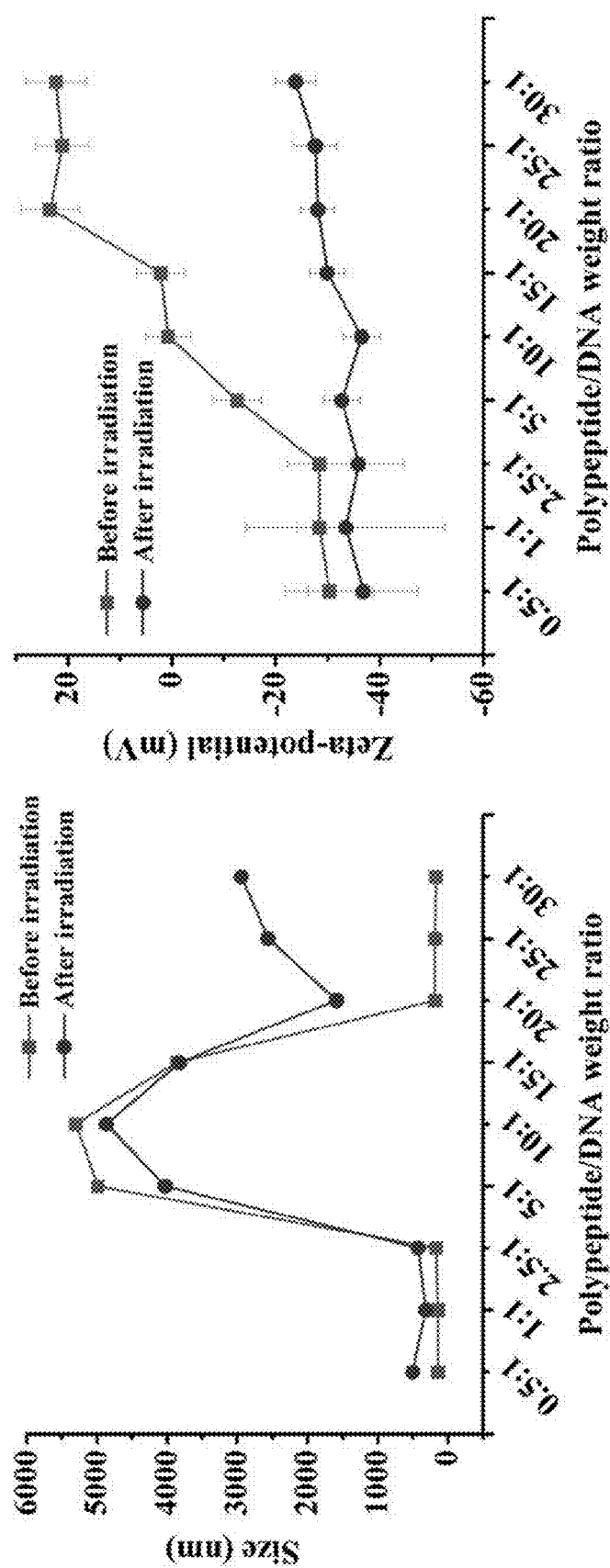
Figure 73B:
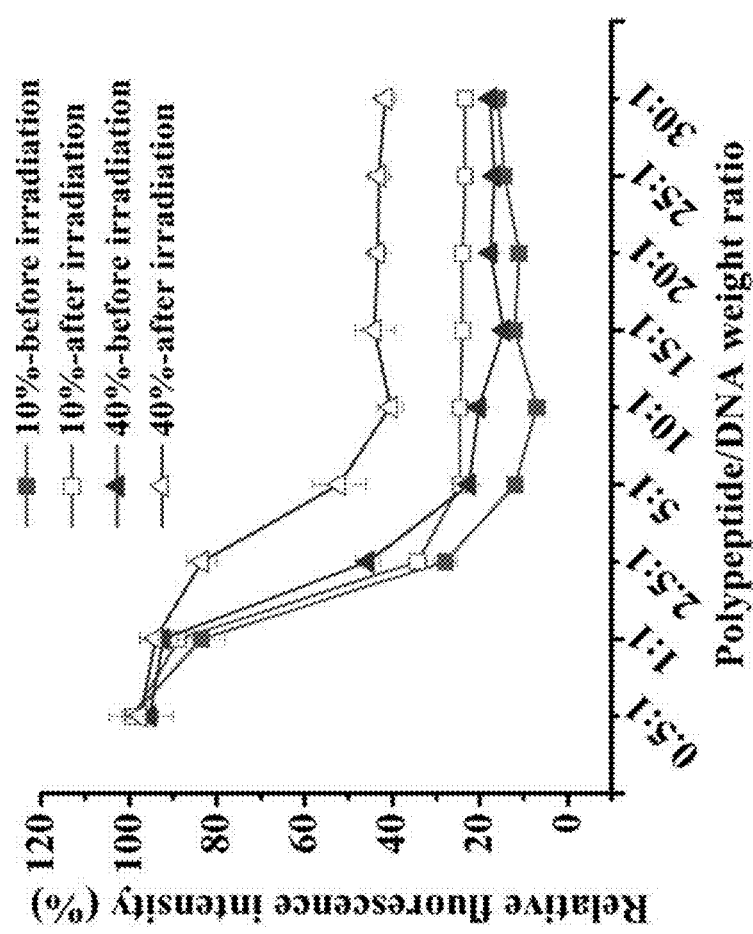

FIG. 73A-B. A) Alteration in complex size (left graph) and Zeta-potential (right graph) following UV irradiation for 5 min. B) EB exclusion assay demonstrating DNA release from complexes upon UV irradiation for 5 min.

Figure 74C:
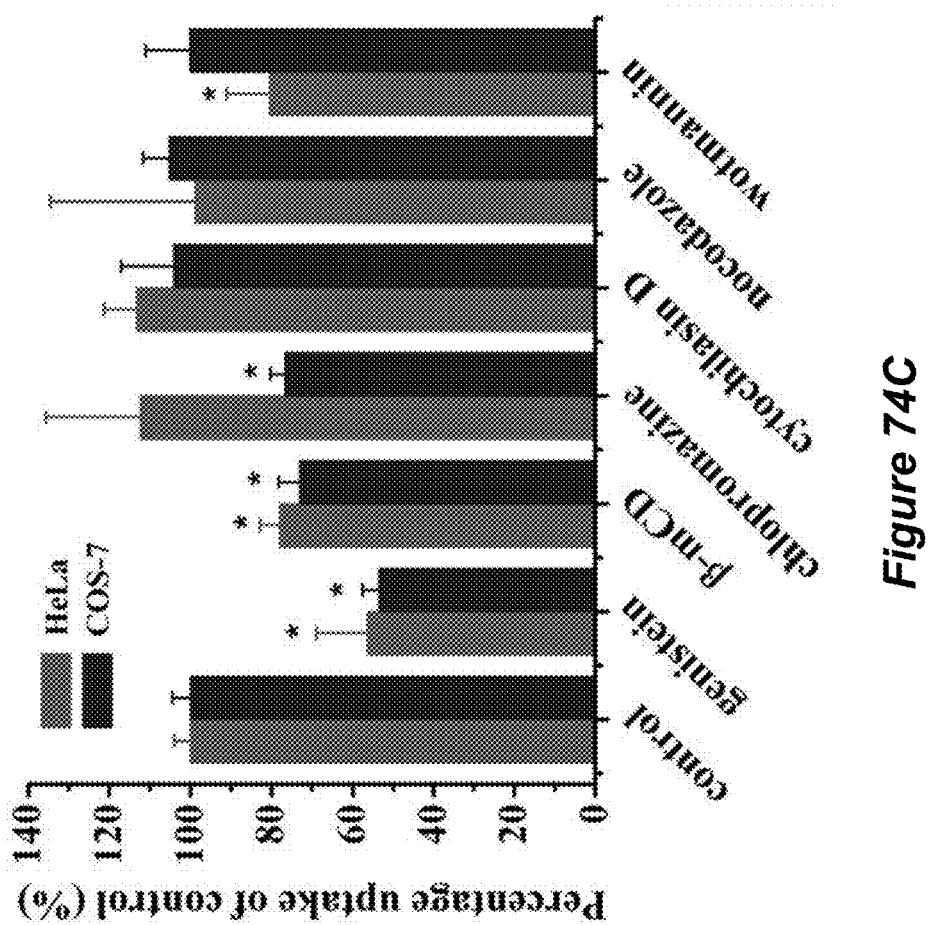

FIG. 74A-C. Internalization of polypeptide/DNA complexes in HeLa and COS-7 cells. (A) Uptake level of complexes after incubation for 2 h at 0.1 µg YOYO-1-DNA/well. Results were expressed as ng YOYO-1-DNA associated with 1 mg of cellular protein. (B) Time-course uptake of polypeptide/DNA complexes at 0.1 µg YOYO-1-DNA/well. (C) Mechanistic probes of complex internalization through incubation with distinct endocytic inhibitors.

Figure 75:
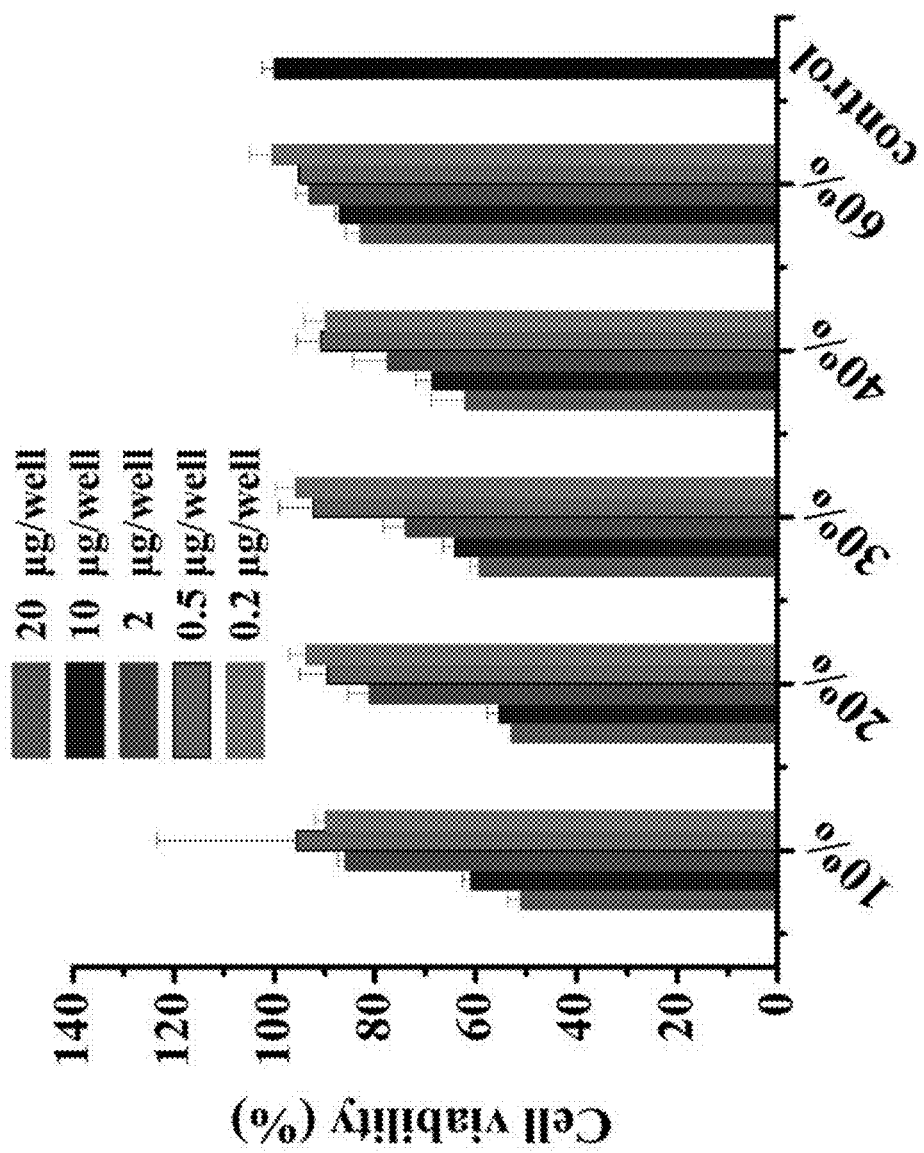

FIG. 75. Cytotoxicity of polypeptide in HeLa cells following 4 h treatment. Cell viability was evaluated by the MTT assay, and was expressed as percentage of control (untreated cells).

Figure 76A:
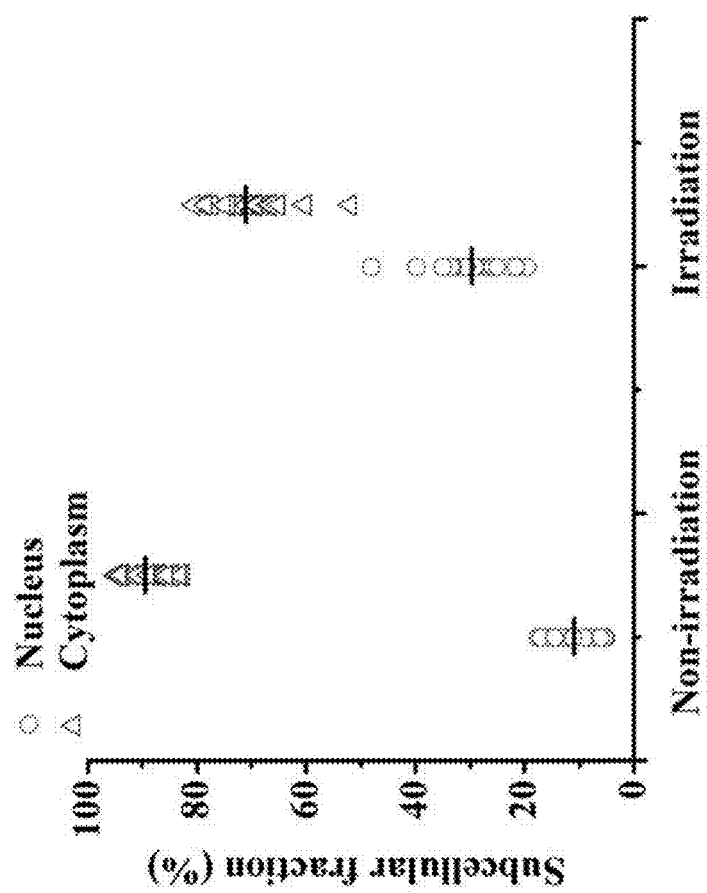

FIG. 76A-B. NIR irradiation facilitated intracellular dissociation of polypeptide/DNA complexes, promoted DNA trafficking into the nuclei, and consequently improved gene transfection in vitro. Rhodamine-polypeptide/YOYO-1-DNA complexes (15:1) in HeLa cells. A) Quantitative CLSM analyses on the nucleic and cytoplasmic distribution of YOYO-1-DNA. B) In vitro transfection in HeLa (left graph) and COS-7 (right graph) cells in terms of luciferase expression.

FIG. 77A-D. CD spectra PDMNBLG-co-PVBLG-8 (PDMNBLG: 40%) with different UV irradiation time (0-600 s) (A) and tested within various time (2-48 h) after UV irradiation for 600 s (C). The residue molar ellipticity at 222 nm of PDMNBLG-co-PVBLG-8 with different irradiation time (0-600 s) (B) and tested within various time (2-48 h) after UV irradiation for 600 s (D).

Figure 78C:
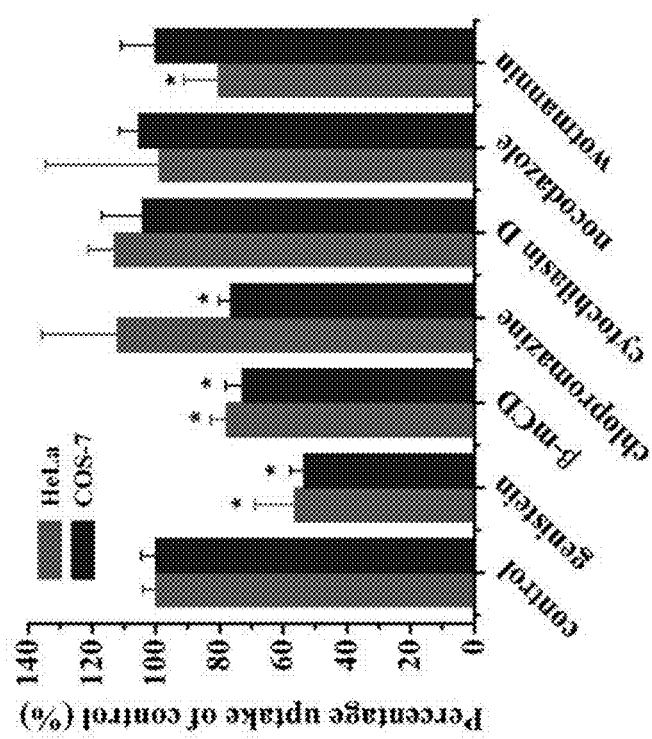

FIG. 78A-C. Internalization of polypeptide/DNA complexes in HeLa and COS-7 cells. (A) Uptake level of complexes after incubation for 2 h at 0.1 µg YOYO-1-DNA/well. Results were expressed as ng YOYO-1-DNA associated with 1 mg of cellular protein. (B) Time-course uptake of polypeptide/DNA complexes at 0.1 µg YOYO-1-DNA/well. (C) Mechanistic probes of complex internalization through incubation with distinct endocytic inhibitors.

Figure 79:
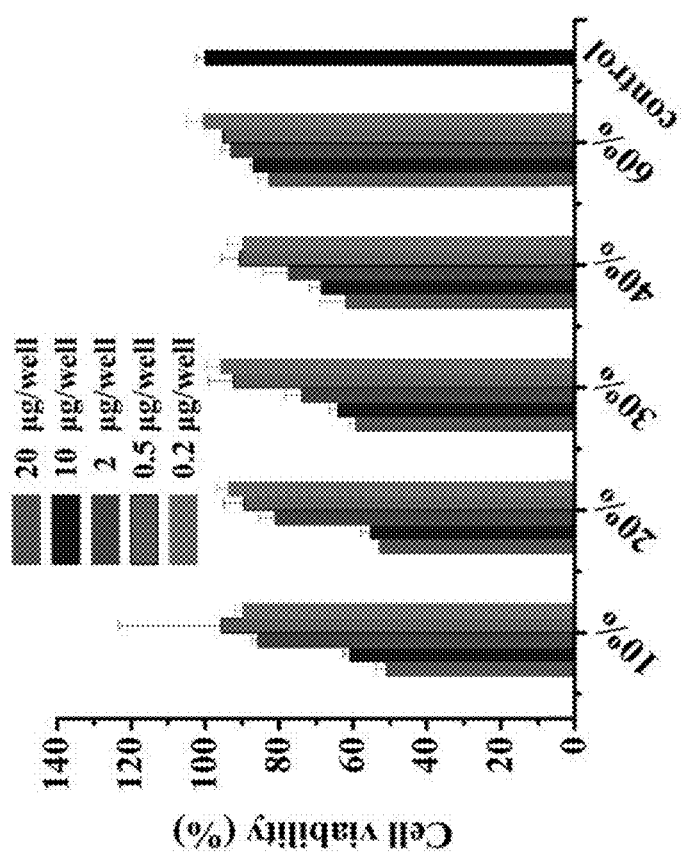

FIG. 79. Cytotoxicity of polypeptide in HeLa cells following 4 h treatment. Cell viability was evaluated by the MTT assay, and was expressed as percentage of control (untreated cells).

Figure 80:
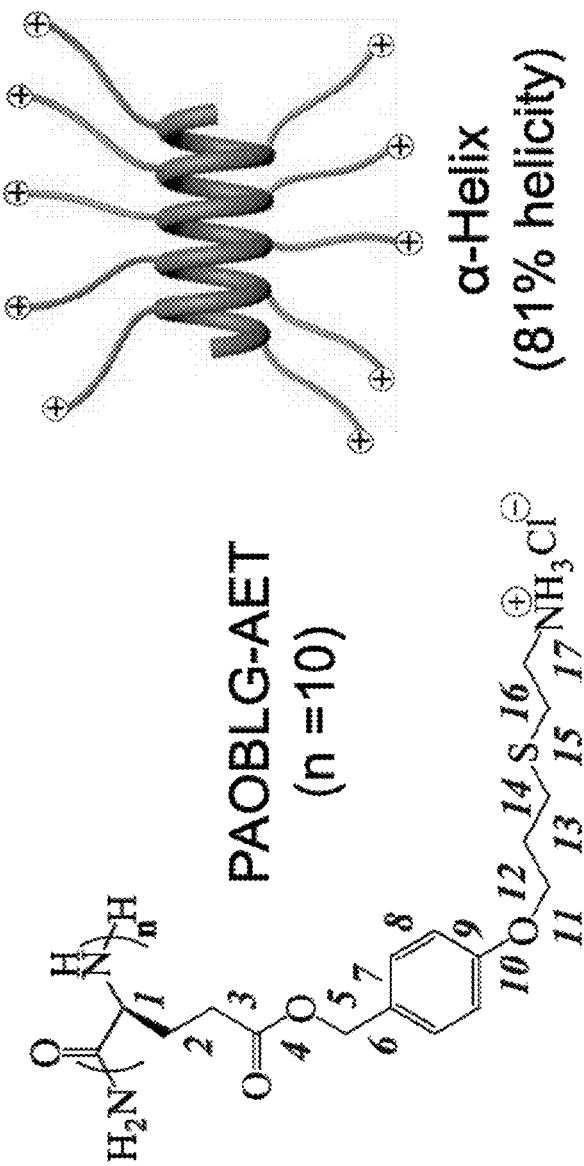

FIG. 80. PAOBLG-AET (n=10) forms a highly stable α-helix.

FIG. 81A-D. (a) Polypeptide with charged side chains and the postulated helix-coil transition in response to the length of the side chains. Chemical structures of (b) PVBLG-1 and (c) PAOBLG-AET. (d) Synthesis of PAOBLG-AET and PAOBLG-MPA.

FIG. 82A-B. (a) CD spectra of various polypeptides bearing charged side chains ((PLL)$_{60}$, (PVBLG-1)$_{10}$ and (PAOBLG-AET)$_{10,20,50}$ at in aqueous solution at pH 2 and (PAOBLG-MPA)$_{10}$) in aqueous solution at pH 10; (b) Fourier-transform infrared spectra (FTIR) of (PVBLG-1)$_{10}$ and (PAOBLG-AET)$_{10}$ and (PAOBLG-AET)$_{50}$.

FIG. 83A-D. (a) The pH dependence of residue molar ellipticity at 222 nm for (PAOBLG-AET)$_{10}$, (PAOBLG-AET)$_{50}$, (PAOBLG-MPA)$_{10}$ and (PLL)$_{60}$ at 0.05 mg·mL$^{-1}$. (b) Temperature dependence of residue molar ellipticity at 222 nm for (PAOBLG-AET)$_{10}$ and (PAOBLG-AET)$_{50}$ at pH 2 and 0.05 mg·mL$^{-1}$. (c) The salt-concentration dependence of residue ellipticity at 222 nm for (PAOBLG-AET)$_{10}$ and (PAOBLG-AET)$_{50}$ at pH 2 and (PAOBLG-MPA)$_{10}$ and (PLL)$_{60}$ at pH 10 (c=0.05 mg/mL). (d) The helical stabilities of (PAOBLG-AET)$_{10}$ and (PAOBLG-AET)$_{50}$ at pH 2, and (PAOBLG-MPA)$_{10}$ and (PLL)$_{60}$ at pH 10 in the presence of urea (c=0.05 mg/mL).

Figure 84:
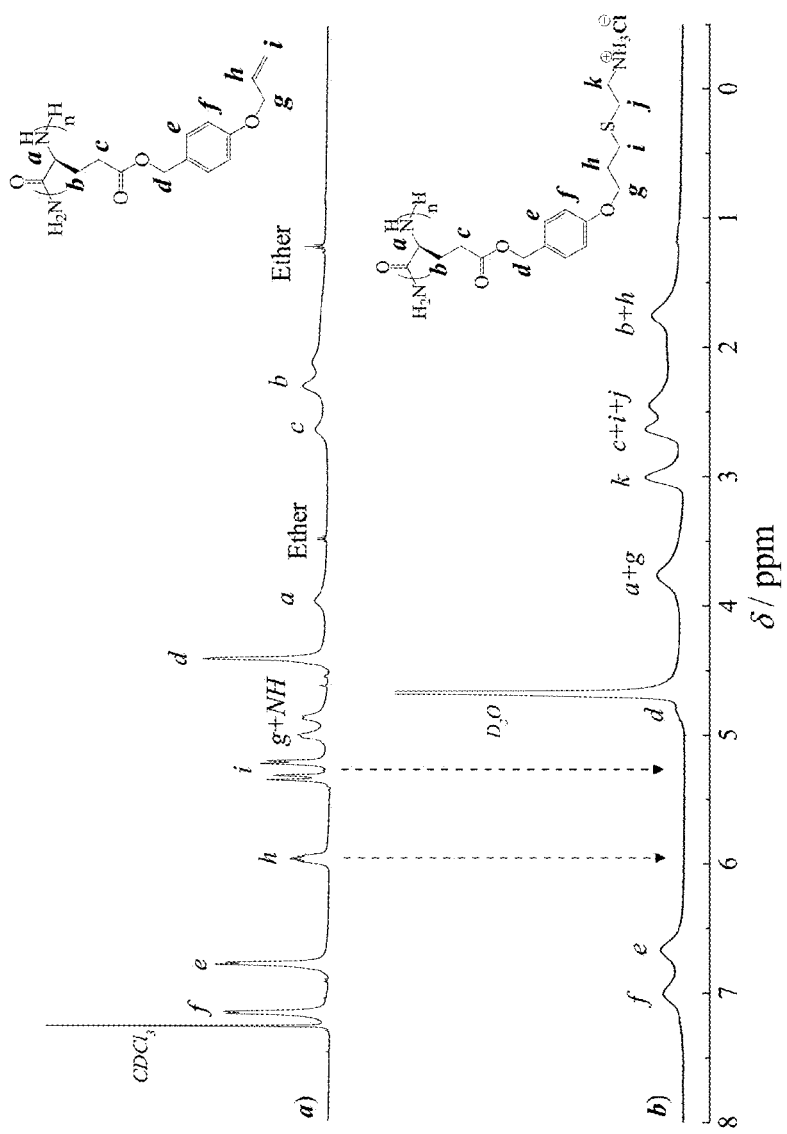

FIG. 84. $^1$H-NMR spectra of PAOBLG and PAOBLG-AET$_{50}$.

FIG. 85A-B. CD spectra guanidine-rich polypeptides with different side chain length, configurations (A) and hydrophobic domains (B).

FIG. 86A-D. (A) The pH dependence, (B) concentration dependence, (C) the urea concentration dependence and (D) salt concentration dependence of the molar ellipticity at 222 nm for guanidine-rich polypeptides with different side-chain length and configurations.

FIG. 87A-D. Uptake level of Rhodamine-labeled polypeptides in different cell lines: (A) HeLa, (B) Raw264.7, (C) 3T3-L1, and (D) HeLa.

FIG. 88A-B. MTT assay in (A) HeLa and (B) Raw264.7 cells.

Figure 89:
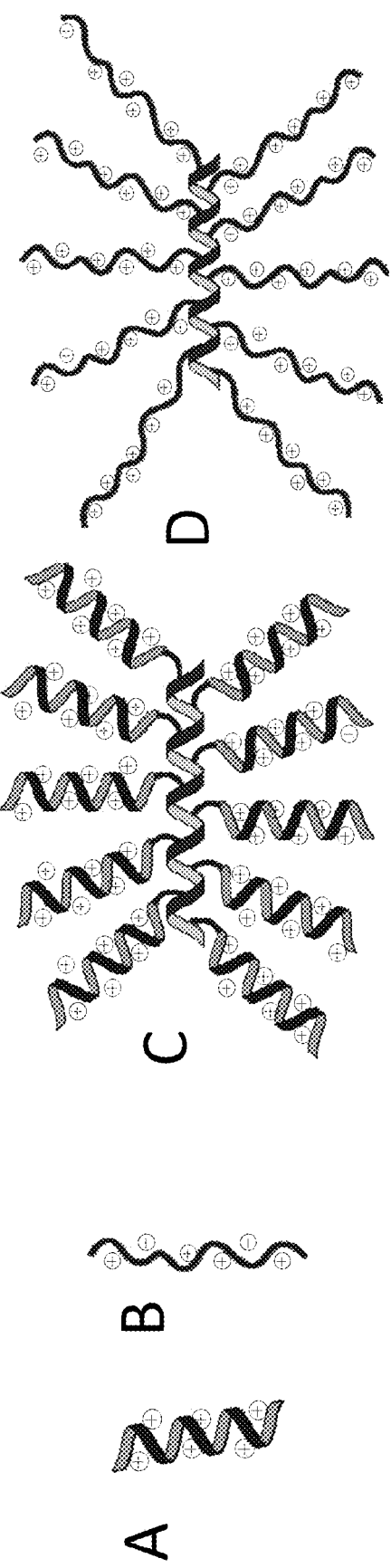

FIG. 89 A-D. Molecular design of guanidine-rich polypeptides with variable configuration and architectures.

FIG. 90A-B. CD spectra ionic polypeptides with different molecular architectures, configurations (A) and charges (B).

FIG. 91A-D. (A) The concentration dependence, (B) pH dependence, (C) salt concentration dependence and (D) the urea concentration dependence of the molar ellipticity at 222 nm for the resulting ionic polypeptides with different molecular architectures and terminal charges.

Figure 92:
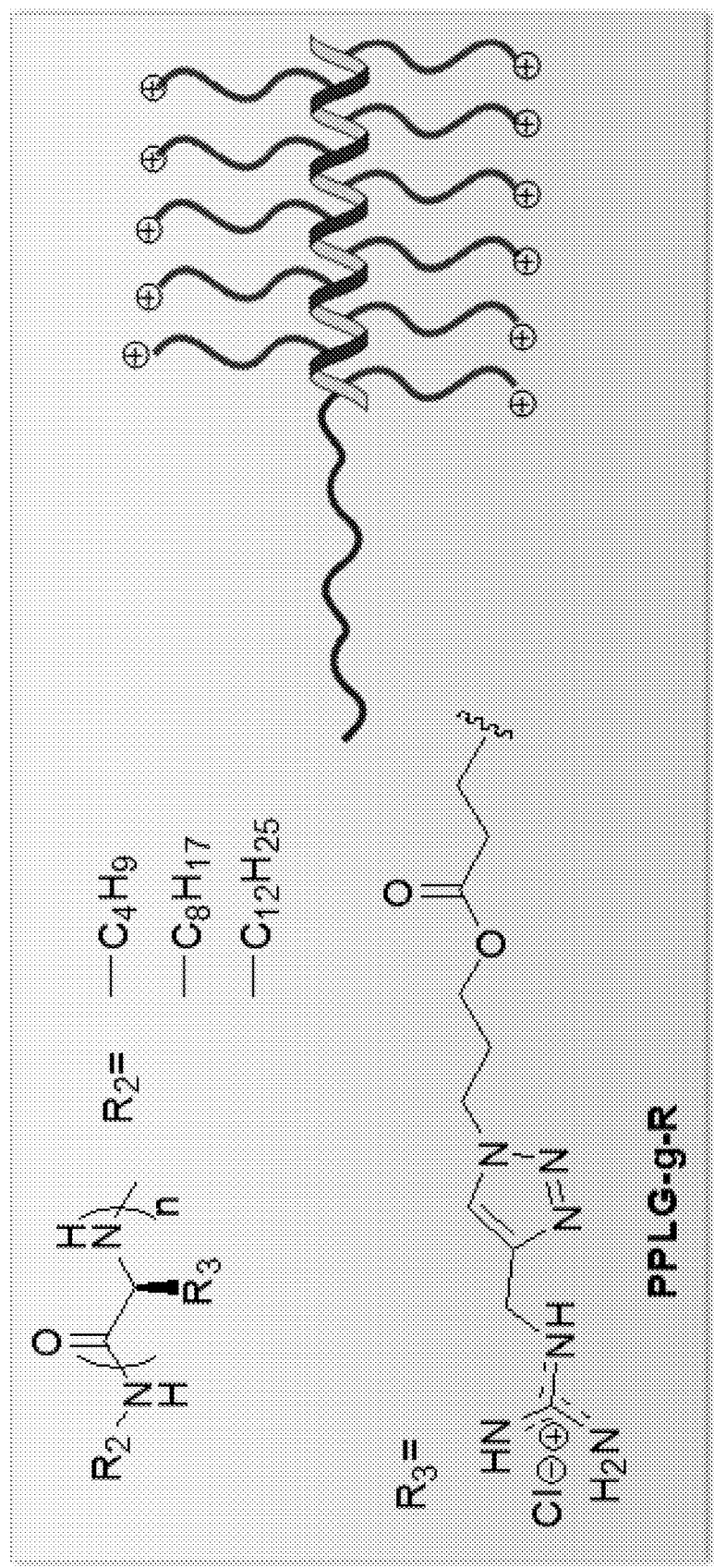

FIG. 92. Molecular design of guanidine-rich polypeptides with variable alkyl-tails.

DETAILED DESCRIPTION

This disclosure shows for the first time that water-soluble, stable α-helical polypeptides can be accessed by elongating charged amino acid side chains to allow for charges to be situated distally from the polypeptide backbone. For example, poly((6-aminohexyl)-L-glutamate)), a water-soluble polypeptide bearing amine-terminated long side chains, adopts a highly stable α-helix conformation. This strategy has been successfully applied to the design and synthesis of several water-soluble polypeptides and polyesters bearing long, charged side chains and various functional moieties to provide polymers that possess unusual helical stability against changing environmental conditions, including changes in the pH and temperature and the presence of denaturing reagents.

Definitions

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a polymer" includes a plurality of such polymers, so that a polymer X includes a plurality of polymers X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percentages, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible subranges and combinations of subranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to," "at least," "greater than," "less than," "more than," "or more," and the like, include the number recited and such terms refer to ranges that can be subsequently broken down into subranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an amount effective can be an amount effective to reduce the progression or severity of the condition or symptoms being treated. Determination of a therapeutically effective amount is well within the capacity of persons skilled in the art. The term "effective amount" is intended to include an amount of a polymer described herein, or an amount of a combination of polymers described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" extend to prophylaxis and include prevent, prevention, preventing, lowering, stopping or reversing the progression or severity of the condition or symptoms being treated. As such, the term "treatment" includes medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

Stable Helical Polypeptides.

In the past, interest in α-helical applications has been largely focused on the design and synthesis of water-soluble α-helical polypeptides or peptide motifs that typically contain a handful of charged amino acids (e.g., Glu or Lys). Yet, the incorporation of charged residues into polypeptides often results in increased side-chain electrostatic repulsion and reduced side-chain hydrophobicity (see for example, Dobson, *Nature* 426, 884-890 (2003)), both of which tend to destabilise helical conformations. In the extreme context in which the polypeptides are made exclusively of amino acids bearing charged side chains, such as poly(L-glutamate) (PLG) or poly(L-lysine) (PLL), the polypeptides adopt completely random coil conformations in aqueous solutions.

Increasing the water solubility and enhancing the helical stability of polypeptides often require incorporating conflicting and opposing properties to the polypeptide. One strategy has been to integrate both water-soluble and helix-stabilising motifs into a peptide structure with the intent to design water-soluble helical peptides. Often, peptides are designed to have the charged amino acid residues placed on one side of the helix surface and residues responsible for stabilizing the helix through side-chain hydrophobic interactions (Dill, *Biochemistry* 29, 7133-7155 (1990)), salt bridges (Marqusee and Baldwin, *Proc. Natl. Acad. Sci. U.S.A.* 84, 8898-8902 (1987)), or tethering (Blackwell and Grubbs, *Angew. Chem., Int. Ed.* 37, 3281-3284 (1998)) placed on the opposite side of the helix surface. These strategies require the design of peptides with specific sequences and/or involve laborious synthesis of polypeptide side chains that are typically difficult to control. For polypeptides made by polymerization rather than through step-wise synthesis, the above-mentioned helix-stabilisation strategies cannot be applied. Readily implementable, robust methods for producing water-soluble polypeptides that adopt stable α-helical conformations have long been sought, but with only limited success (Lotan et al., *Biopolymers* 4, 365-368 (1966)) or success in only restricted systems (Yu et al., *J. Am. Chem. Soc.* 121, 12210-12211 (1999)).

When analysing helical-forming amino acids, it is notable that Ala and its three analogues, α-aminobutyric acid, norvaline and norleucine, have identical helix-forming propensities, indicating that the linear elongation of an amino acid side chain with hydrocarbons does not affect its helix-forming capability.

| n | Amino Acid |
|---|---|
| 0 | Ala |
| 1 | α-Aminobutyric acid |
| 2 | Norvaline |
| 3 | Norleucine |

Figure 1:
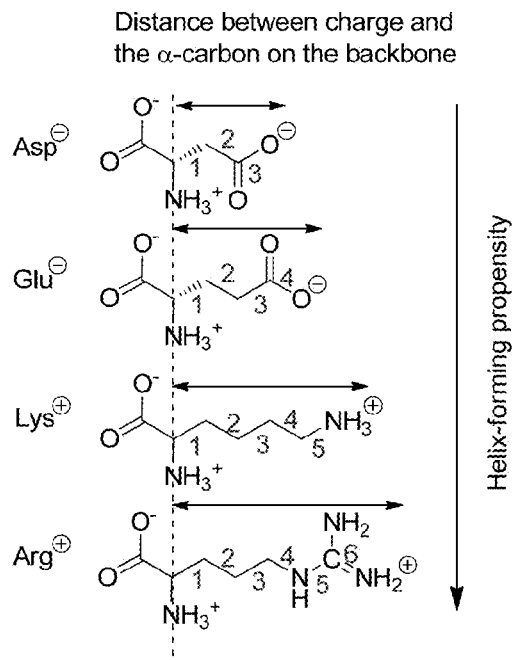
FIG. 1. Amino acids and their helix-forming properties. Illustration of four amino acids with charged side chains (Asp, Glu, Lys and Arg) and the correlation of their helix-forming propensity with the distance between the side-chain charge and the α-carbon.

When a charged group (e.g., $COO^-$ or $NH_3^+$) is placed at the termini of the hydrocarbon side chains of these amino acids, however, substantially reduced amino acid helix propensity scales are noted (Pace et al., *Biophys. J.* 75, 422-427 (1998)). Interestingly, the helix propensity of $Asp^-$, $Glu^-$, $Lys^+$ and $Arg^+$, the four charged natural amino acids with straight side chains (FIG. 1), is strongly correlated with the length of the side chain. The further away the charge is from the backbone, the higher the helix-forming propensity. Their helical propensities are in the order of $Arg^+>Lys^+>Glu^->Asp^-$, where the charge is 6, 5, 4 or 3 σ-bonds away from the peptide backbone, respectively (FIG. 1).

Figure 2:
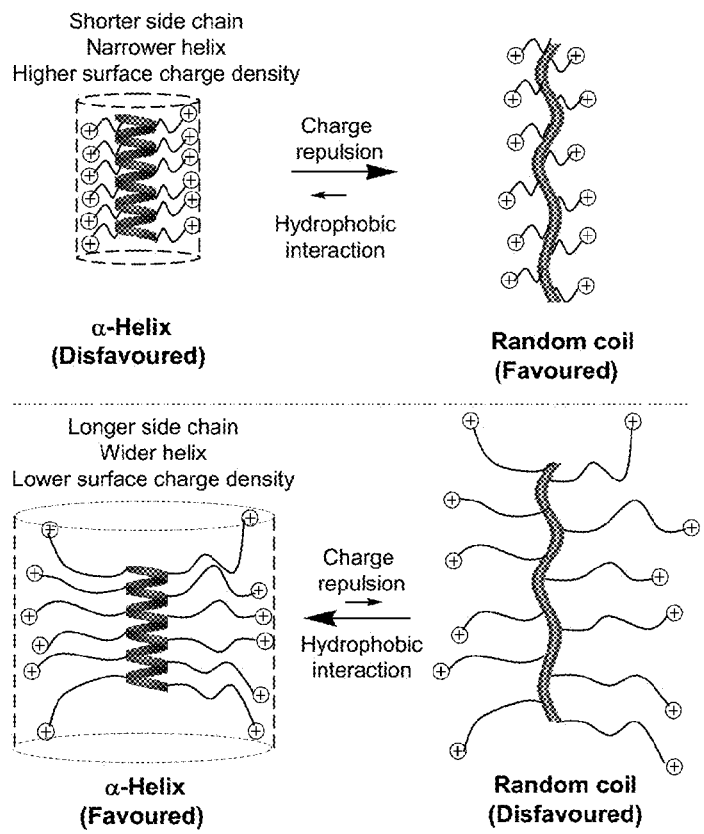
FIG. 2. Amino acids and their helix-forming properties. Illustration of polypeptides with charged side chains and the helix-random coil transition in response to the length of the side chains.
Figure 6:
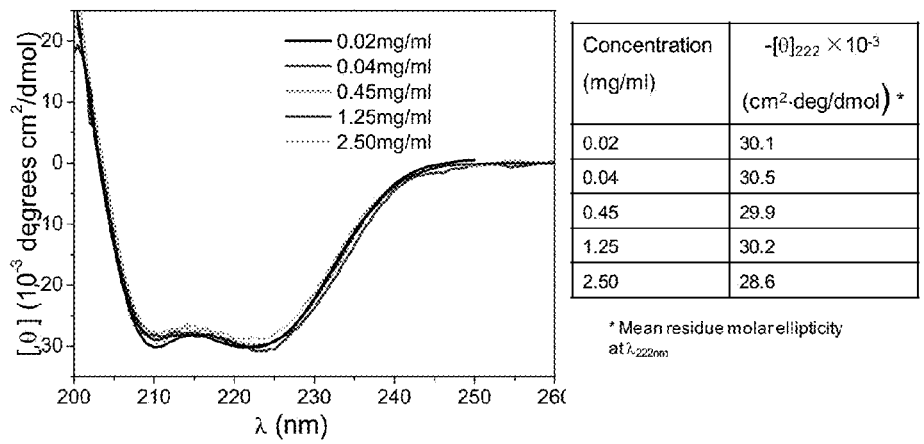
Figure 7:
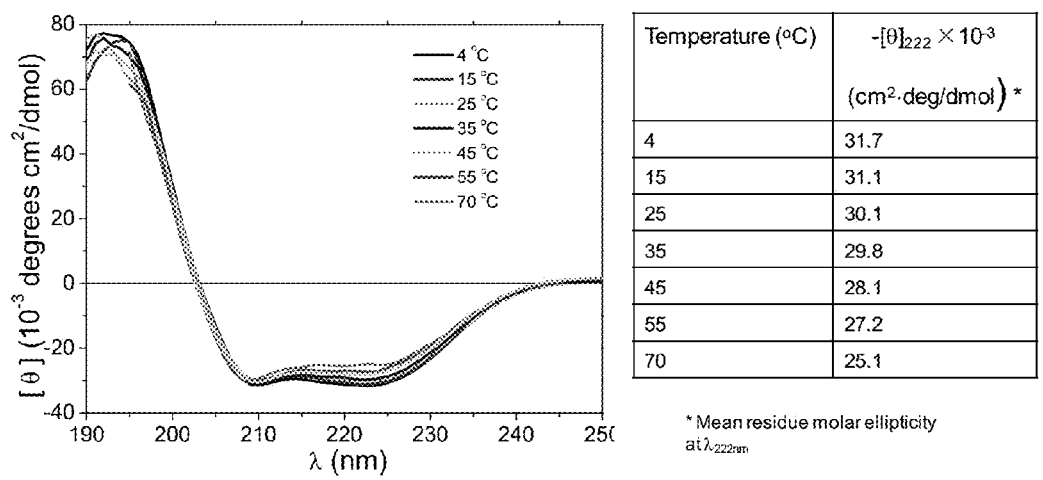
Figure 8:
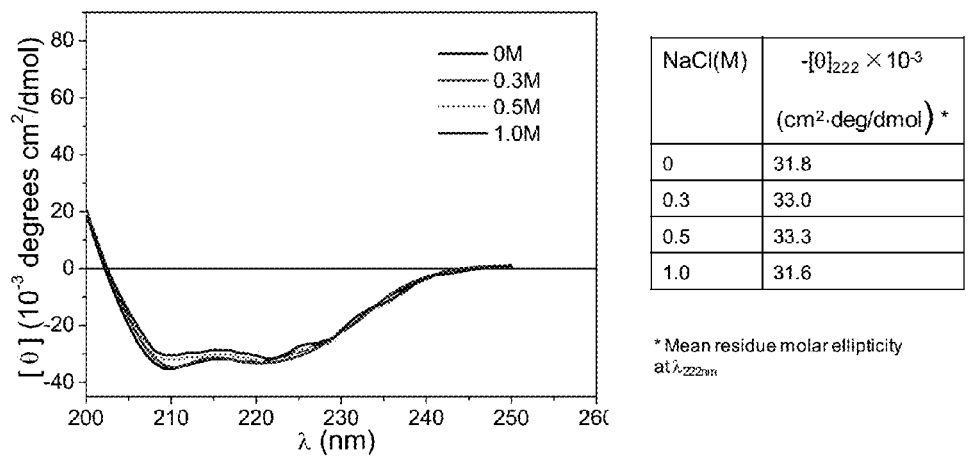
Figure 9:
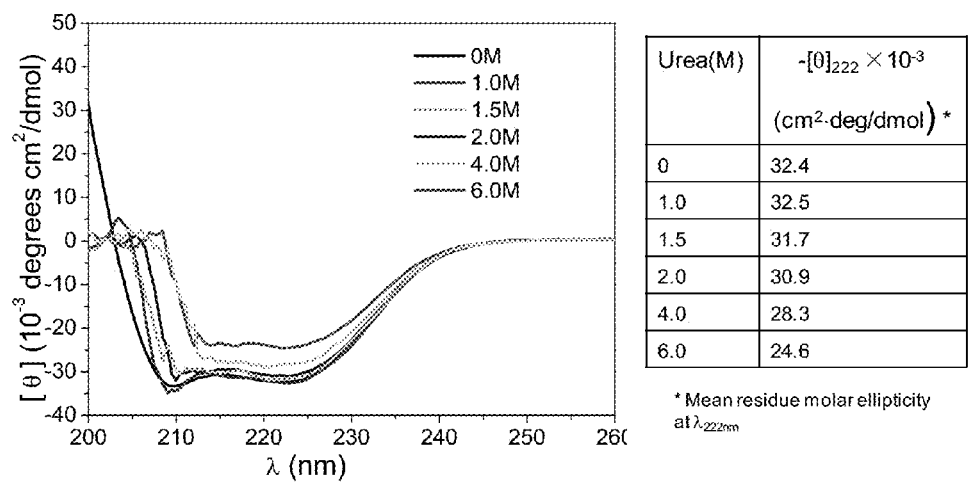
Figure 10:
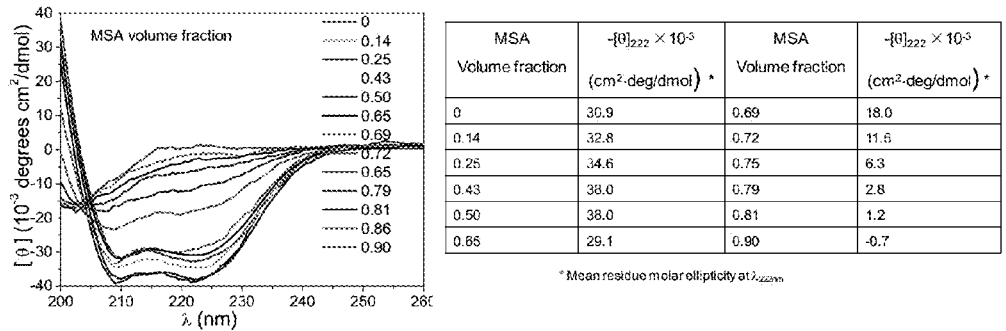
Figure 11:
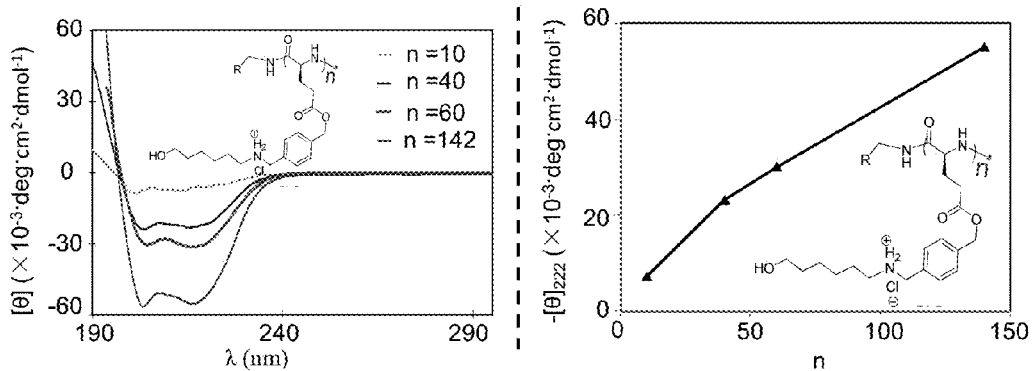
Figure 12:
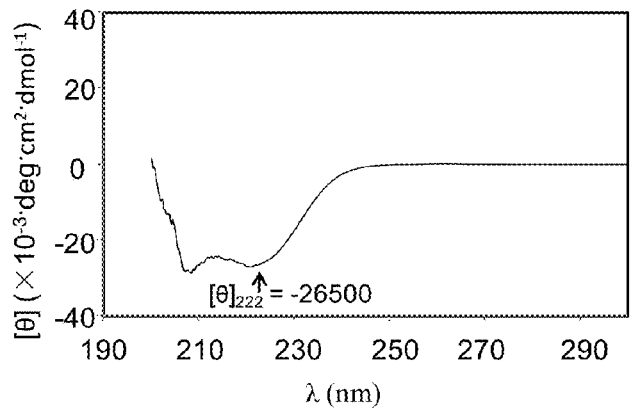
Figure 13:
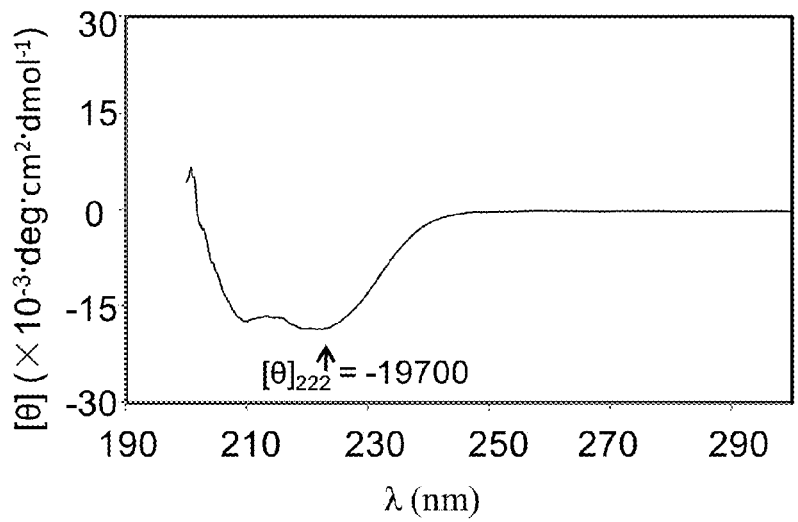
Figure 14:
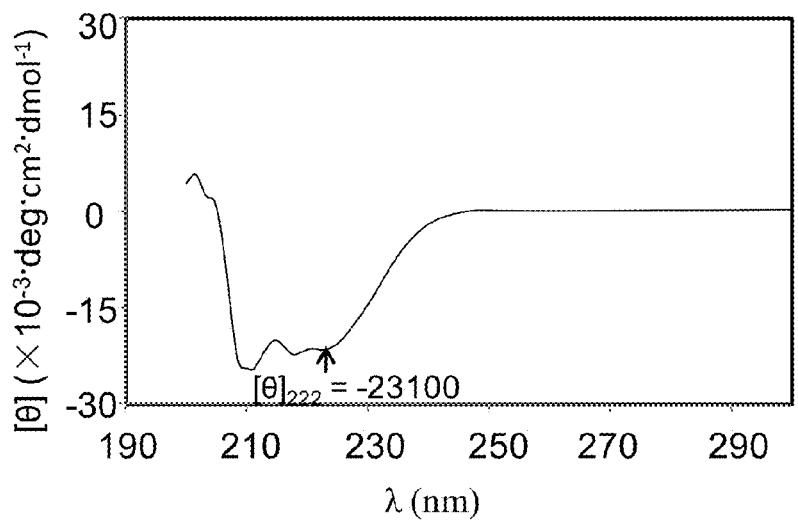
Figure 15:
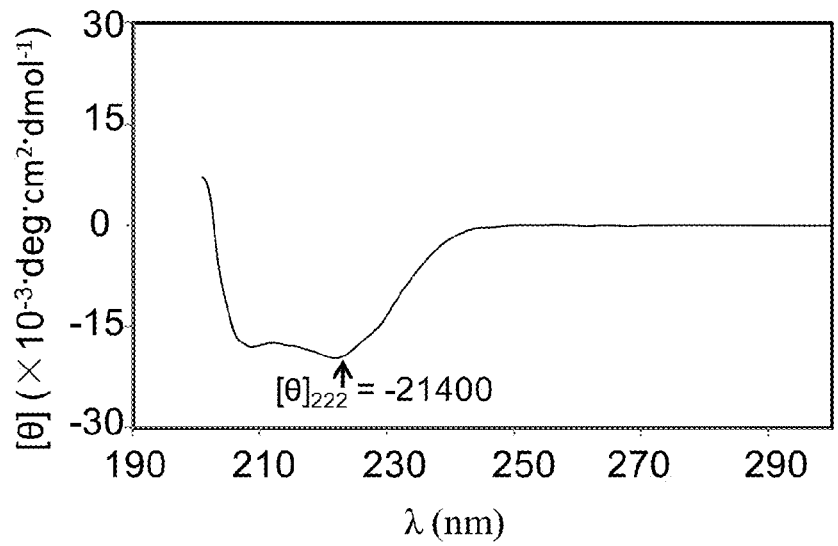
Figure 16:
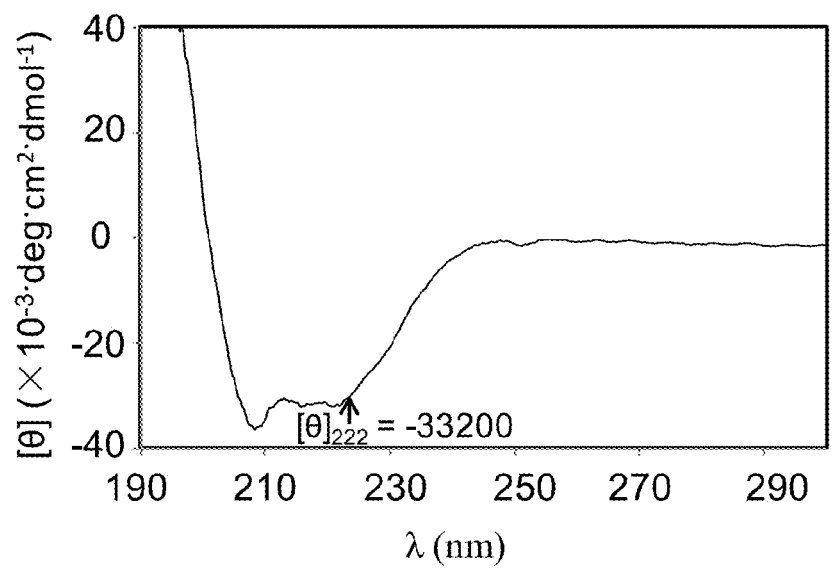

The differences in these helix-forming propensities could be due, at least in part, to the differences in charge density on the helical surfaces, with the poly($Arg^+$) helix being the lowest (the widest helix, the weakest electrostatic repulsion) and poly($Asp^-$) being the highest (the narrowest helix, the strongest electrostatic repulsion) if they are both formed. It was thus postulated that when the charge is moved further away from the peptide backbone to reduce the overall charge density on the helical surface and charge repulsion, at some point the charge may have a negligible effect on the helical propensity of amino acids with long, straight side chains. As a result, polypeptides with charges that are distally situated from the peptide backbone will simultaneously maintain water solubility and stable helical structures (FIG. 2).

Poly(γ-(6-aminohexyl)-L-glutamate)) (PAHG) was prepared through ring-opening polymerisation (ROP) of γ-benzyl-L-glutamate N-carboxyanhydride (Glu-NCA) using the method recently established by Cheng and coworkers (see Lu and Cheng, *J. Am. Chem. Soc.* 130, 12562-12563 (2008); Lu et al., *J. Am. Chem. Soc.* 131, 13582-13583 (2009); and Lu and Cheng, *J. Am. Chem. Soc.* 129, 14114-14115 (2007)). Deprotection of the side-chain benzyl group of the resulting poly(γ-benzyl-L-glutamate) (PBLG), N-capping with CBZ-Cl, conjugation of the side-chain carboxylate groups with N-tert-butoxycarbonyl-6-amino-1-hexanol (Boc-AH) and deprotection of the Boc group provided the desired products, PAHG or PAPG (Scheme 1).

Scheme 1.
Synthesis of polypeptides with charged side chains: PAHG and PAPG.

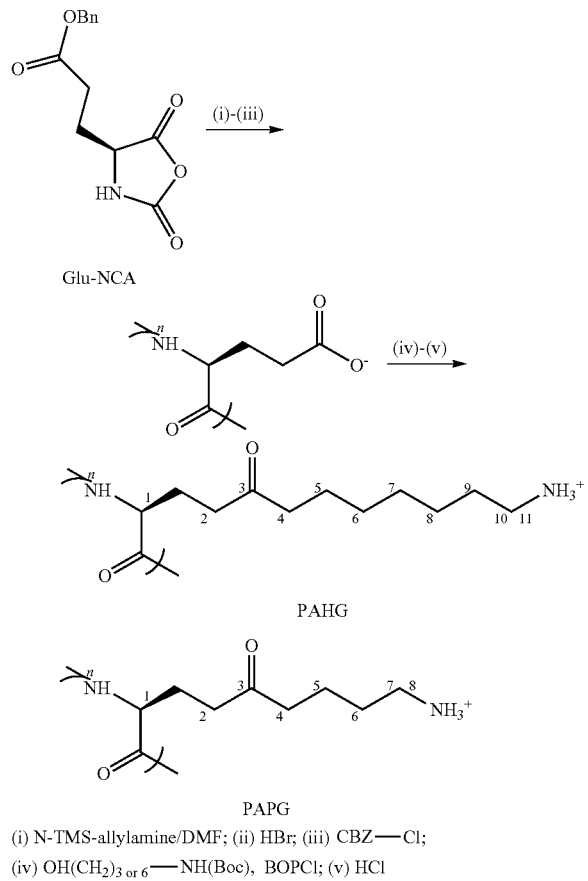

(i) N-TMS-allylamine/DMF; (ii) HBr; (iii) CBZ—Cl;
(iv) OH(CH$_2$)$_{3\ or\ 6}$—NH(Boc), BOPCl; (v) HCl The resulting polymer, denoted as PAHG$_n$ where "n" is the degree of NCA polymerisation, has a positive charge located 11 σ-bonds away from the backbone. Polypeptides of a variety of lengths have been prepared, such as n=50 or 57, but the number of monomers can be about 6 to about 600, or about 10 to about 500.

Circular dichroism (CD) was used to examine its conformation in an aqueous solution. As shown in FIG. 3a, PAHG$_{57}$ adopts an α-helical conformation at pH 1 with characteristic double minima at 208 nm and 222 nm and has excellent water solubility (>50 mg/mL). In comparison, a 75mer of poly(L-lysine) (PLL$_{75}$) at pH 1 adopts the expected, completely random coil conformation due to side-chain charge repulsion (FIG. 3a). When a 57mer of poly(γ-(3-aminopropyl)-L-glutamate)) (PAPG$_{57}$) (Scheme 1), an analogue of PAHG$_{57}$ with a short —(CH$_2$)$_3$— chain rather than a —(CH$_2$)$_6$— chain (positive charge placed 8 σ-bonds away from the backbone), was prepared and analysed by CD at pH 1, it was noted that the PAPG$_{57}$ adopts a distorted conformation rather than a helical conformation (FIG. 3a). These experiments show the importance of the distance between the charge of the side chain and the peptide backbone for helical stability, and they affirm the hypothesis that reducing the polypeptide surface charge density by elongating the side chains with distal or terminal charged groups indeed gives rise to water-soluble α-helical polypeptide electrolytes (αHPEs), as shown in FIG. 2.

PAHG$_{57}$ showed remarkable pH-independent helical stability at pH values ranging from 1 to 10, with –[θ]$_{222}$ at 14,000 cm$^2$·deg·dmol$^{-1}$ for pH 1 and at 14,200 cm$^2$·deg·dmol$^{-1}$ for pH 10 (FIG. 3b). Further increases in pH (pH>11) resulted in deprotonation of the positively charged amino group on the side chain and a decreased solubility of PAHG$_{57}$. PAHG$_{57}$ also showed a lack of concentration dependence of its –[θ]$_{222}$ values in helix-forming conditions, indicating that it remains monomeric in solution (FIG. 3c). PAHG$_{57}$ also showed temperature-dependent helical stability as its –[θ]$_{222}$ value decreased 45% from 15,900 cm$^2$·deg·dmol$^{-1}$ at 4° C. to 8,700 cm$^2$·deg·dmol$^{-1}$ at 70° C. (FIG. 3d).

PAHG$_{57}$ exhibited remarkable stability against changes in the NaCl concentration and remained nearly unchanged in its –[θ]$_{222}$ value when the NaCl concentration was increased from 0 to 4.68 M at pH 3 at 25° C., a concentration for which all of the charges should have been screened, which is distinctly different from PLL$_{75}$ (FIG. 3e). These experiments further demonstrate that the surface charges of PAHG$_{50}$ have minimal effects on its helical stability. The helical conformation of PAHG$_{57}$ was gradually disrupted at increased concentrations of strong denaturing reagents such as urea (FIG. 3f) and methanesulphonic acid (MSA) (FIG. 3g).

Motivated by this discovery, this helix-stabilisation strategy was tested to determine whether it could be generally applied to designing water-soluble αHPEs that contain charged secondary amines with various functional moieties attached to the amine. To avoid deprotection chemistry and low conjugation activity (Scheme 1), a highly efficient conjugation strategy was developed that involves the ring-opening polymerisation of γ-(4-vinylbenzyl)-L-glutamate NCA (VB-Glu-NCA) to yield poly(γ-(4-vinylbenzyl)-L-glutamate) (PVBLG) followed by the formation of poly(γ-(4-aldehydebenzyl-L-glutamate) (PABLG) through the ozonation of PVBLG, hydroamination of the PABLG with 6-amino-1-hexanol (1), and reduction of imines to give the desired products (PVBLG-1)$_m$, where "m" corresponds to the degree of VB-Glu-NCA polymerisation. The positive charge of (PVBLG-1)$_m$ was placed exactly 11 σ-bonds away from its backbone, analogous to PAHG (Scheme 2).

Scheme 2.
Synthesis of polypeptides with charged side chains: PVBLG-X (X = 1-7).

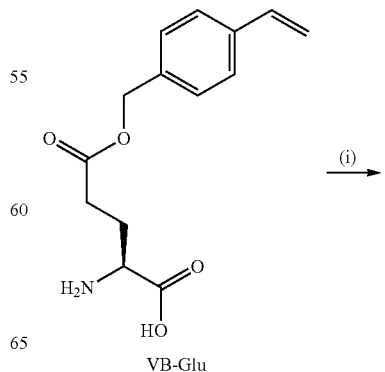

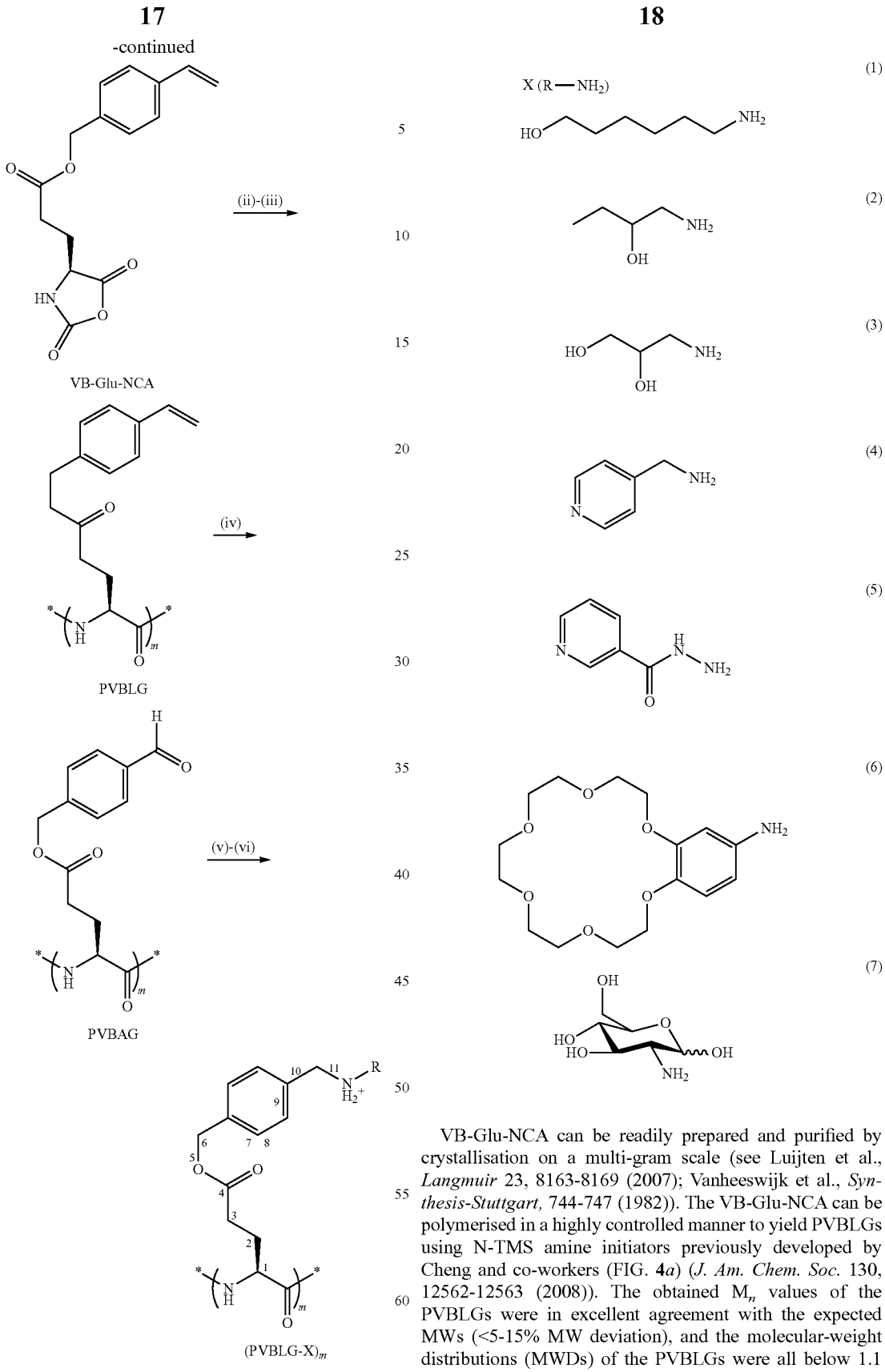

(i) phosgene; (ii) NH(TMS)₂/DMF (with 5% nitrobenzene); (iii) CBZ—Cl; (iv) O₃/CHCl₃/−78° C.; (v) X (══R—NH₂)/[H]; (vi) HCl VB-Glu-NCA can be readily prepared and purified by crystallisation on a multi-gram scale (see Luijten et al., *Langmuir* 23, 8163-8169 (2007); Vanheeswijk et al., *Synthesis-Stuttgart*, 744-747 (1982)). The VB-Glu-NCA can be polymerised in a highly controlled manner to yield PVBLGs using N-TMS amine initiators previously developed by Cheng and co-workers (FIG. 4a) (*J. Am. Chem. Soc.* 130, 12562-12563 (2008)). The obtained $M_n$ values of the PVBLGs were in excellent agreement with the expected MWs (<5-15% MW deviation), and the molecular-weight distributions (MWDs) of the PVBLGs were all below 1.1 (FIG. 4b). PVBLGs are very soluble in common organic solvents (e.g., THF, CHCl₃ and DMF), which facilitates their side-chain modification to yield (PVBLG-1)$_m$ with over 95% grafting efficiency (entries 1-4, Table 1).

TABLE 1

Synthesis and Conformation Analysis of PVBLG-X (X = 1~7).

| entry | PABLG | X (molar eq.) | Reducing Reagent (molar equiv.)/ Rec. Time (h)/ Temp (° C.) | Product (PVBLG-X) | Grafting Eff. (%) | $-[\theta]_{222} \times 10^{-3}$ $(cm^2 \cdot deg \cdot dmol^{-1})$ |
|---|---|---|---|---|---|---|
| 1 | $PABLG_{10}$ | 1 (3) | $NaBH(OAc)_3$ (5)/24/50 | $(PVBLG-1)_{10}$ | >95 | 7.2 |
| 2 | $PABLG_{40}$ | 1 (3) | $NaBH(OAc)_3$ (5)/24/50 | $(PVBLG-1)_{40}$ | >95 | 23.1 |
| 3 | $PABLG_{60}$ | 1 (3) | $NaBH(OAc)_3$ (5)/24/50 | $(PVBLG-1)_{60}$ | >95 | 30.1 |
| 4 | $PABLG_{142}$ | 1 (5) | $NaBH(OAc)_3$ (10)/48/60 | $(PVBLG-1)_{142}$ | >95 | 55.0 |
| 5 | $PABLG_{45}$ | 2 (3) | $NaBH(OAc)_3$ (5)/24/50 | $(PVBLG-2)_{45}$ | >95 | 26.5 |
| 6 | $PABLG_{45}$ | 3 (3) | $NaBH(OAc)_3$ (5)/24/50 | $(PVBLG-3)_{45}$ | >95 | 19.7 |
| 7 | $PABLG_{40}$ | 4 (5) | $NaBH(OAc)_3$ (7)/36/50 | $(PVBLG-4)_{40}$ | >95 | 23.1 |
| 8 | $PABLG_{40}$ | 5 (3) | $NaBH(OAc)_3$ (5)/24/50 | $(PVBLG-5)_{40}$ | >95 | 21.4 |
| 9 | $PABLG_{20}$ | 6 (5) | $NaBH_4$ (5)/72(60-40)$^a$ | $(PVBLG-6)_{20}$ | >95 | 25.3 |
| 10 | $PABLG_{44}$ | 6 (5) | $NaBH_4$ (5)/72(60-40)$^a$ | $(PVBLG-6)_{44}$ | >95 | 33.2 |
| 11 | $PABLG_{40}$ | 7 (10) | $NaBH_4$ (5)/72(60-40)$^a$ | $(PVBLG-7)_{40}$ | 70 | 27.2 |

$^a$PABLG was first condensed with the corresponding amine at 60° C. for 48 hours followed by addition of $NaBH_4$ without separation. Reductive reaction was stirred at 40° C. for 24 hours.

$(PVBLG-1)_{60}$ is highly water-soluble at pH 1-10 (>40 mg/kg) and adopts an α-helical conformation with a $-[\theta]_{222}$ value at 32,600 $cm^2 \cdot deg \cdot dmol^{-1}$ for pH values as low as 1 (FIG. 3a). The high helical content of $(PVBLG-1)_{60}$ as compared to $PAHG_{57}$ is presumably due to its increased side-chain hydrophobic interactions. Its $-[\theta]_{222}$ value remained unchanged when the solution's pH was increased from 1 to 10 (FIG. 3b). At further increased pH values, $(PVBLG-1)_{60}$ became less soluble due to deprotonation of its charged secondary amine group. As with $PAHG_{57}$, $(PVBLG-1)_{60}$ showed a lack of concentration dependence of its $-[\theta]_{222}$ values in helix-forming conditions, suggesting that it remains monomeric in solution (FIG. 3c). It has excellent helical stability against elevated temperatures, with its $-[\theta]_{222}$ value decreasing 21% from 31,700 $cm^2 \cdot deg \cdot dmol^{-1}$ at 4° C. to 25,100 $cm^2 \cdot deg \cdot dmol^{-1}$ at 70° C. (FIG. 3d), and against helix-destabilising conditions such as high concentrations of salt (FIG. 3e), urea (FIG. 3f) and MSA (FIG. 3h).

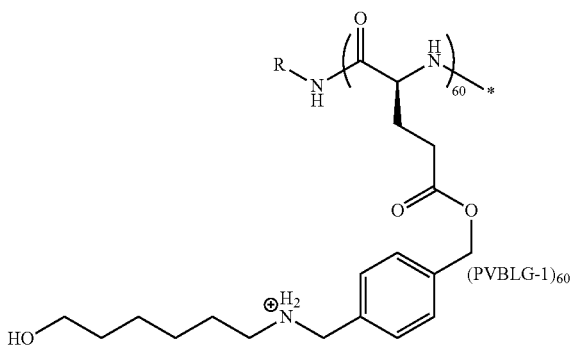

$(PVBLG-1)_{60}$

PVBLG-1 has unprecedented helical stability compared to any known α-peptides and can maintain 76% and 58% of its original helical contents in 6 M urea and 69% MSA, respectively. The helical content of PVBLG-1 is strongly correlated with the length of the polymer, with $-[\theta]_{222}$ values of 55,000, 23,100 and 7,200 $cm^2 \cdot deg \cdot dmol^{-1}$ for $(PVBLG-1)_{142}$, $(PVBLG-1)_{40}$, and $(PVBLG-1)_{10}$, respectively (Table 1). $(PVBLG-1)_{142}$ predominantly adopts a helical conformation, while $(PVBLG-1)_{10}$ has mixed conformations containing both α-helices and β-sheets (FIG. 3i).

This strategy was then used for the synthesis of PVBLG αHPEs with various other motifs on the helix surface. Amine-containing alcohols (1-amino-2-butanol (2) and 3-amino-1,2-dipropanol (3)), pyridines (4-(aminomethyl) pyridine (4) and nicotinic hydrazide (5)), a crown ether (4-aminobenzo-18-crown-6 (6)) and a carbohydrate (D-glucosamine (7)) were selected to make the corresponding PVBLG-X (X=2-7) αHPEs. The grafting efficiencies for all of the PVBLG-Xs are excellent (>95%), except for $(PVBLG-7)_{40}$, which has a grafting efficiency of 70% presumably due to the increased steric bulk of the carbohydrate molecules (Table 1). The PVBLG-Xs are water-soluble and adopt α-helical conformations with minima at 208 and 222 nm for their CD spectra (FIGS. 3a and 5-17).

Figure 17:
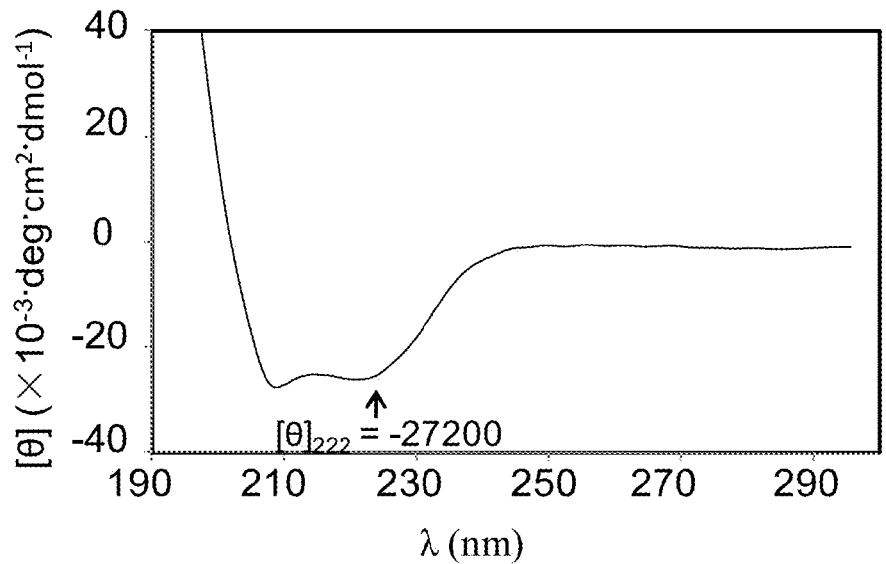

Interestingly, $(PVBLG-4)_{40}$, $(PVBLG-6)_{44}$ and $(PVBLG-7)_{40}$ showed comparable or even larger $-[\theta]_{222}$ values as compared to $(PVBLG-1)_{40}$, confirming the hypothesis that the physicochemical properties and size of the moieties attached to the amine situated distally from the polypeptide backbone have negligible effects on the helical stability of the αHPEs. PVBLG αHPEs containing pyridine, crown ether or sugar on the side chain all adopt very stable helical structures in water, demonstrating the robustness of this strategy in generating water-soluble rod-like αHPEs. PVBLG-2-7 also showed a helical stability similar to that of PVBLG-1 against changes in the pH, temperature and salt and in the presence of denaturing reagents, as exemplified by $(PVBLG-7)_{40}$, which showed remarkable stability at various pH values and temperatures (FIG. 17).

Thus, it was discovered that the length of the charged polypeptide side chains plays a pivotal role in the stability of the α-helical structures of polypeptide electrolytes. When the side chains become sufficiently long and the charge groups are placed distally from the polypeptide backbone (e.g., greater than 6, 7, 8, 9, or 10 σ-bonds away from the backbone), the substantially reduced charge density on the helix surface causes the charge repulsion force to no longer be dominating and helix-disrupting. Therefore, side-chain hydrophobic interactions dominate to drive the formation of stable helical structures, while the charges make the helix hydrated and water-soluble. In addition, the elongation of the hydrophobic side chains makes it more difficult for the polypeptide backbone to be hydrated, which may otherwise weaken the helical structure by competing with the intramolecular hydrogen-bonding formed by the backbone CO and NH groups.

Furthermore, the charged helix surfaces of αHPEs not only render the polypeptides water-soluble but may also function, in conjugation with the increased side-chain hydrophobic interactions, as shields against the access of water (Vila et al., *Proc. Natl. Acad. Sci. U.S.A.* 97, 13075-13079 (2000)). Collectively, the charges situated distally from the backbone (reduced helical surface charge density), long hydrophobic side chains and reduced hydration of the polypeptide backbone facilitate the formation of αHPEs with unprecedented, remarkable helical stability despite changes in the pH or temperature and against various strong denaturing reagents. This discovery may also explain why nature has not evolved to use amino acids with long charged side chains as the building blocks for constructing proteins. Because the reversibility of α-helix folding/unfolding is critical to many important biological processes, the incorporation of amino acid residues bearing long charged side chains would have made the α-helix structure too stable to unfold. The simple method described herein for producing helical water-soluble polypeptides bearing various moieties will find broad applications in basic science, medicine and bio- and nanotechnologies.

Polymers of the Disclosure.

Disclosed herein are polymers comprising Formula I:

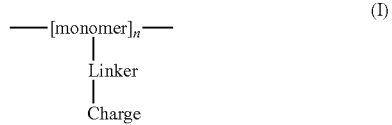

wherein monomer is a repeating unit comprising 2, 3, 4, 5, 6, or 7 linear carbon atoms, often 2 or 3 carbon atoms, and the monomers are linked together through amide or ester bonds to form a backbone chain of a polyamide or polyester polymer;

n is about 6 to about 600;

Linker is an optionally substituted carbon chain that is optionally interrupted by oxygen, nitrogen, phenyl, heterocycle, or heteroaryl; and Charge is a moiety having a positive or negative charge on a heteroatom, wherein the heteroatom is nitrogen, oxygen, phosphorus, or sulfur;

wherein the Linker separates the monomer and the Charge by at least six linear atoms.

The polymer can be in the form of an α-helix. The α-helix form can be highly stable, for example, at pH 1 to about pH 11 in an aqueous solution, or at pH 2 to about pH 10 in an aqueous solution. The α-helix form can also be stable in an aqueous solution containing up to a 2 M concentration of NaCl, or up to a 4 M concentration of NaCl. Additionally, the polymer can form a stable α-helix in aqueous solution wherein the helix is stable temperatures up to about 90° C., up to about 80° C., or up to about 70° C.

The monomers can be linked together by amide linkages. In other embodiments, the monomers are linked together by ester linkages. Thus, the monomers can be amino acid residues including non-natural amino acids, such as β-amino acids, γ-amino acids, δ-amino acids, or other known non-natural amino acids. In some embodiments, the monomers can be ester residues, such as esters of glycolic acid, lactic acid, or other ($C_2$-$C_7$)hydroxyalkanoates, to form polyesters. In some embodiments, the monomers include glutamic acid residues or aspartic acid residues.

Linker can be any organic chain that separates a charge on a side chain of the monomers from the polymer backbone by at least 6 linear atoms. In some embodiments, the linker separates the charged moiety from the backbone by 6, 7, 8, 9, 10, 11, 12, 13, 14, 15, 16, 17, 18, 19, or 20 linear atoms.

Linker can be, for example, a carbon chain of about 4 to about 20 atoms in length, where the chain is optionally interrupted by phenyl, benzyl, ester, amide, —C═C—, —C≡C—, phosphoester, phosphoamide, or oxyethylene groups, the chain can be linear or branched, and the chain can be optionally substituted, for example, with halides, oxo groups (═O), or hydroxyl groups, or by other groups described herein as substituents.

In various embodiments, Linker can be a divalent radical of the formula —W-A-W— wherein each W is independently —N(R')C(═O)—, —C(═O)N(R')—, —OC(═O)—, —C(═O)O—, —O—, —S—, —S(O)—, —S(O)$_2$—, —N(R')—, —C(═O)—, —(CH$_2$)$_n$— where n is 1-10, or a direct bond; wherein each R' is independently H, ($C_1$-$C_6$)alkyl, or a nitrogen protecting group; and A is ($C_1$-$C_{20}$)alkyl, ($C_2$-$C_{16}$)alkenyl, ($C_2$-$C_{16}$)alkynyl, ($C_3$-$C_8$)cycloalkyl, ($C_6$-$C_{10}$)aryl, —(OCH$_2$—CH$_2$)$_n$— where n is 1 to about 20, —C(O)NH(CH$_2$)$_n$ wherein n is 1 to about 6, —(CH$_2$)$_n$—N(Me)(CH$_2$)$_n$ wherein each n is 1 to about 6; or ($C_1$-$C_{20}$)alkyl, ($C_2$-$C_{16}$)alkenyl, ($C_2$-$C_{16}$)alkynyl, or —(OCH$_2$—CH$_2$)$_n$— optionally interrupted between two carbons, or between a carbon and an oxygen, with a ($C_3$-$C_8$)cycloalkyl, heterocycle, or ($C_6$-$C_{10}$)aryl group; wherein the Linker is optionally substituted by one, two, three, four, or five oxo groups, hydroxy groups, ($C_1$-$C_4$)alkyl groups, pyridine groups, piperidine groups, pyrrolidine groups, monosaccharide groups, or a combination thereof. For example, Linker can be a ($C_6$-$C_{20}$)alkyl group optionally interrupted by one, two, three, or four nitrogen atoms, oxygen atoms, phenyl groups, or a combination thereof, and wherein the ($C_6$-$C_{20}$)alkyl group is optionally substituted by one, two, three, four, or five oxo groups, hydroxy groups, ($C_1$-$C_4$)alkyl groups, pyridine groups, piperidine groups, pyrrolidine groups, monosaccharide groups, or a combination thereof.

The group "Charge" can be any moiety that includes a cation or an anion, for example, at a pH of about 2 to about 12, or at a particular range of integers between 2 and 12. For example, the Charge group can be a moiety having a positive or negative charge on a heteroatom, where the heteroatom is nitrogen, oxygen, sulfur, or the like. Examples of Charge groups include a moiety having a cationic nitrogen atom, a carboxylate anion, a phosphate anion, a phosphonate anion, a phosphate heterocycle, or a sulfate anion. The cationic nitrogen atoms can be a group such as protonated nitrogen non-heterocycles (e.g., primary amines, secondary amines, tertiary amines, quaternary ammonium groups, guanidinium groups, hydrazones, hydrazides, hydrazines), or protonated nitrogen heterocycles (e.g., aniline, indole, piperidine, pyridine, pyrimidine, pyrrolidine, pyrrole, or imidazole).

In various embodiments, the Charge moiety can be any protonated primary, secondary, or tertiary amine, where the secondary and tertiary amines are substituted by, for example, ($C_1$-$C_4$)alkyl groups or benzyl groups. The moiety can also be a group that includes a quaternary ammonium cation, such as a protonated nitrogen heteroaryl group. Examples of nitrogen heteroaryl groups that can be protonated include pyridine, imidazole, triazole, and the like (e.g., to form pyridinium cations, imidazolium cations, and triazolium cations). The moiety can also be a group that includes a phosphonate anion, such as the anion derived from a phosphonic acid group. Other examples include sulfur-containing moieties, such as sulfate anions and sulfite anions. Further examples of Charge groups include borate anions, sulfonylamide anions, phosphonylamide anions, and phenol anions.

In various embodiments, the Charge moiety can include one to ten carbon atoms and at least one N, S, or P heteroatom, and/or two or more oxygen atoms, for example, as necessary to form a moiety with an ammonium cation, a guanidinium cation, a carboxylate anion, an amidate anion, or a phosphonate anion.

A polymer of Formula I can be a polymer comprising Formula I-A:

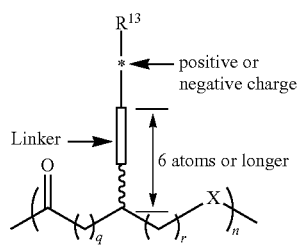

(I-A)

wherein $R^{13}$ is H, absent, an aromatic group, or an aliphatic group, wherein the aromatic group or aliphatic group is optionally substituted;

n is about 6 to about 1000;

q is 0 to about 5;

r is 0 to about 5;

X is O, NH, NH—R where R can be an aliphatic or aromatic group;

Linker is a chain of atoms that is 6 atoms or longer; and

* is a positively or negatively charged atom. The side chain groups (-Linker-*-$R^{13}$) on the polymer backbone can be R, S, or combinations thereof.

Additional examples of polymers of Formula I-A include polymers comprising Formulas I-A1, I-A2, and I-A3:

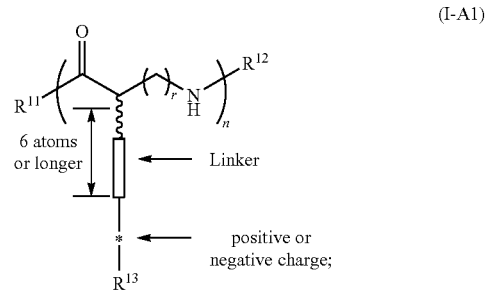

(I-A1)

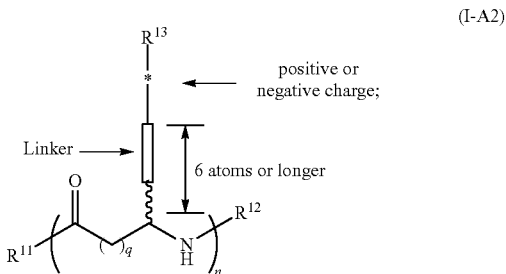

(I-A2)

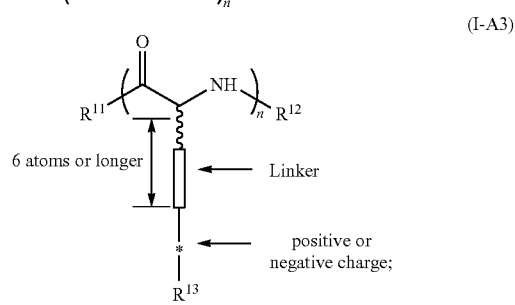

(I-A3)

wherein $R^{11}$ is H, an aromatic terminal group, or an aliphatic terminal group;

$R^{12}$ is H, an aromatic terminal group, or an aliphatic terminal group;

$R^{13}$ is H, absent, an aromatic group, or an aliphatic group, wherein the aromatic group or aliphatic group is optionally substituted;

n is about 6 to about 600;

q is 0 to about 5;

r is 0 to about 5;

Linker is a chain of atoms that is 6 atoms or longer (e.g., ($C_6$-$C_{20}$)alkyl); and

* is a positively or negatively charged atom (e.g., Charge), as described herein. The side chain groups on the polymer backbone can be R, S, or combinations thereof.

Embodiments of Formula I also include Formulas I-B, I-C, and I-D:

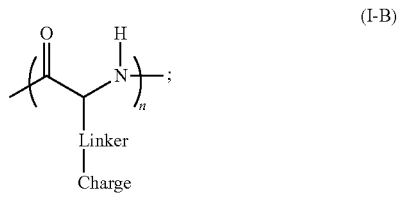

(I-B)

-continued

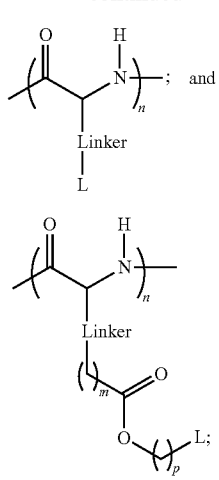

(I-C)

(I-D)

where n, Linker, and Charge are defined as in Formula I, and the definitions of L, m, and p are as defined below. The polymers of the formulas described herein can terminate in carboxy groups at their C terminus (e.g., where Formulas I-B, I-C, and I-D are substituted at the carbonyl of the polymer backbone chain with —OH), and the polymers can terminate in amino groups or nitrogen protecting groups at their N terminus (e.g., where Formulas I-B, I-C, and I-D are substituted at the amine of the polymer backbone chain with —H or -Cbz). Other embodiments include polymers of Formula I where the —NH— of Formulas I-B, I-C, or 1-D is replaced with an oxygen (—O—) to form a polyester.

As would be readily recognized by one skilled in the art, the C termini and N termini (groups at the end of the bond at each end of the polyamides of Formulas I-B, I-C, and I-D) can also be suitable carboxy or amino protecting groups, respectively. Examples of such groups include the various R groups and protection strategies described by Greene and Wuts (*Protective Groups in Organic Synthesis*, 3rd Ed., John Wiley & Sons, Inc., 1999, which is incorporated herein by reference in its entirety), as well as the carboxy or amino protecting groups described by Kocienski (*Protecting Groups*, Georg Thieme Verlag Stuttgart, New York, 1994, which is incorporated herein by reference in its entirety).

Additional embodiments include a polymer of Formula I wherein the monomers comprise natural or non-natural amino acids of Formula I-E or I-F:

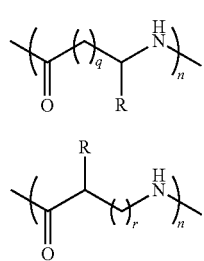

(I-E)

(I-F)

wherein n is about 6 to about 600; q is 0-5; r is 0-5; and each R is independently -Linker-Charge as defined for Formula I. The variable q can be 0, 1, 2, 3, 4, or 5, and each R independently can include a side chain of glutamic acid, aspartic acid, lysine, ornithine, serine, cysteine, tyrosine, or histidine, for example, modified to include a charged atom at least six linear atoms from the polymer backbone, for example, using the techniques described herein.

In some embodiments, the polymer of Formula I comprises a polymer of Formula II-X or II-Y:

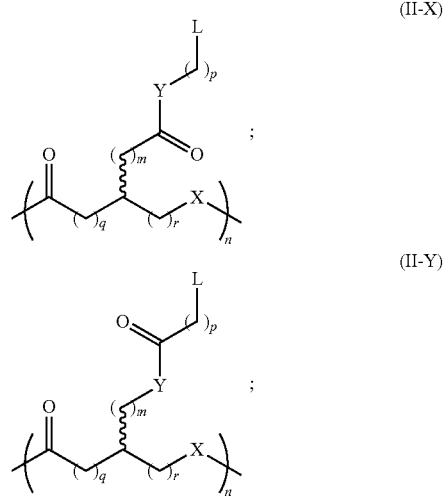

(II-X)

(II-Y)

wherein
n is about 6 to about 1000;
m is 1 to about 20;
p is 0 to about 20;
q is 0 to about 5;
r is 0 to about 5;
X is O, NH, or NH—R where R is an aliphatic or aromatic group;
Y is O or NH;
L is a Charge group as defined herein, such as a carboxylate, a protonated nitrogen non-heterocycle, a protonated nitrogen heterocycle, phosphate, phosphate heterocycle, phosphonate, or sulfate. Terminal groups on the polymers described herein can be $R^{11}$ or $R^{12}$ groups as defined above, and any $R^{11}$ or $R^{12}$ groups in any formula can also be a Charge group (e.g., a cationic nitrogen atom, a carboxylate anion, or a phosphonate anion), or a polymer, or combinations thereof. Any embodiment can also include various salt forms.

In some embodiments, the polymer of Formula I, Formula II-X, or Formula II-Y can be a polymer of Formula IIa:

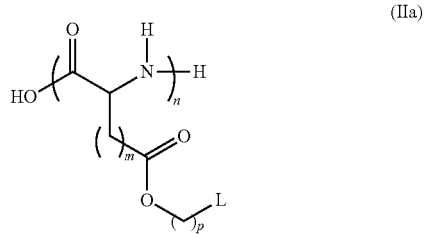

(IIa)

wherein
n is about 6 to about 600;
m is 1 to about 10;
p is 1 to about 16;
L is —$R^1$, or —NH—$R^2$, -Ph-CH$_2$—NH—$R^2$;

$R^1$ is a moiety having a positive or negative charge on a heteroatom, wherein the heteroatom is nitrogen, oxygen, phosphorus, or sulfur;

$R^2$ is —C(=O)-pyridine, sugar, phenyl, phenyl meta para substituted with a crown ether moiety; or $(C_2-C_{10})$alkyl optionally substituted with one or more hydroxy, pyridine, piperidine, or pyrrolidine groups;

or a salt thereof.

In another embodiment, the invention provides a polymer of Formula IIb, IIc, IId, or IIe:

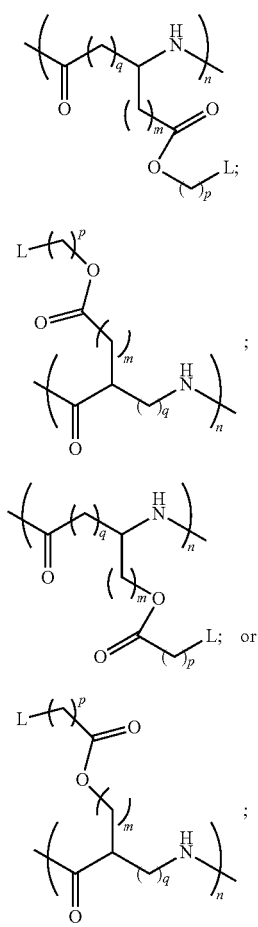

(IIb)

(IIc)

(IId)

(IIe)

wherein n, m, p, and L are as defined for Formula IIa, and q is 0 to about 5; or a salt thereof.

Further embodiments provide a polymer of Formula IIb, IIc, IId, and IIe that are polymers of Formula IIIa, IIIb, IIId, and IIIe, respectively:

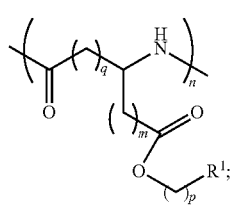

(IIIa)

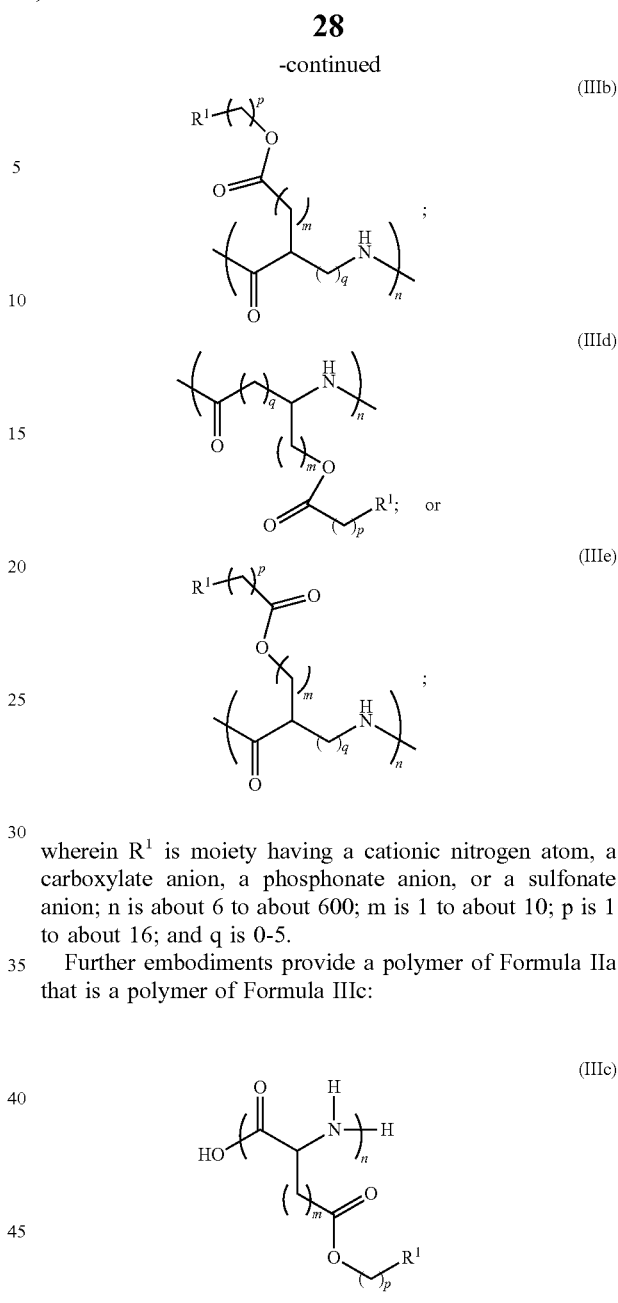

(IIIb)

(IIId)

(IIIe)

wherein $R^1$ is moiety having a cationic nitrogen atom, a carboxylate anion, a phosphonate anion, or a sulfonate anion; n is about 6 to about 600; m is 1 to about 10; p is 1 to about 16; and q is 0-5.

Further embodiments provide a polymer of Formula IIa that is a polymer of Formula IIIc:

(IIIc)

wherein $R^1$ is a moiety having a positive or negative charge on a heteroatom, wherein the heteroatom is nitrogen, oxygen, phosphorus, or sulfur; n is about 10 to about 500; m is 1 to about 10; and p is 1 to about 16. The terminal groups, such as —OH and —H on such formulas can also be a group remaining on the polymer from an initiator molecule, or the terminal groups can be $R^{11}$ or $R^{12}$ as defined herein.

Examples of $R^1$ groups of Formulas II and III include moieties that include a cationic nitrogen atom, a carboxylate anion, a phosphonate anion, or a sulfonate anion, such as an ammonium cation, a guanidinium cation, a carboxylate anion, a phosphonate anion, or a sulfonate anion, or groups that include such charged groups (e.g., a Charge group as defined herein).

The invention further provides copolymers comprising a polyamide or polyester described herein in combination with other polymers, such as polyolefins, polyethers, polyesters, polycarbonates, or polyamides, including poly(ethylene glycol) (PEG), poly(glycolic acid), or poly(lactic acid), to form block copolymers, for example, di-block polymers and tri-block polymers. The polymers can also be random copolymers. Copolymers can be polymers having side chains that include polymers on the side chains.

Methods are also provided for delivering DNA or RNA to a cell comprising: contacting a cell with a composition comprising a polymer disclosed herein and DNA or RNA; wherein the polymer is in the form of an α-helix; under conditions sufficient to transfect the cell with the DNA or RNA.

Further provided are methods for inhibiting bacterial growth comprising: contacting bacteria with a composition comprising a polymer described herein, wherein the polymer is in the form of a stable α-helix; under conditions sufficient to inhibit the growth of the bacteria.

Additionally, the disclosure provides methods for causing pore formation in a cell comprising: contacting the cell with a composition comprising a polymer described herein, wherein the polymer is in the form of a stable α-helix; under conditions sufficient contact the cell with the polymer, whereby the polymer causes pore formation in the cell.

Other methods provided herein include methods of preparing a polypeptide or polyester having charged side chains. The methods can include initiating ring-opening polymerization of a compound of Formula X:

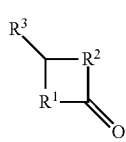

(X)

wherein
$R^1$ is O or NH;
$R^2$ is $CH_2$ or —C(=O)—O— so as to form an anhydride moiety; and
$R^3$ is a carbon linked to an olefin or a protecting group; to form a polypeptide or polyester, and oxidizing the olefin or deprotecting the protecting group to provide a polypeptide or polyester having charged side chains. The charge of the side chain can be separated from the polypeptide or polyester backbone by at least 6 linear atoms, and/or as otherwise described herein. The polymerization initiator can be any suitable strong base, such as an anionic nitrogen, anionic carbon or deprotonated alcohol anion, or their derivatives/complexes with suitable transition metals. When the charged side chain includes a cationic nitrogen, the charge can typically be present at a pH of about 1-9. Above about 9, the charge will typically be quenched. Guanidine moieties can maintain a charge at a pH of about 1-13. Carboxylic acids can maintain a charge at a pH of about 7-14; phosphates at a pH of about 3-14, and sulfates at a pH of about 1-14.

Pharmaceutical Formulations

The polymers described herein can be used to prepare therapeutic pharmaceutical compositions. The polymers may be added to the compositions in the form of a salt or solvate. For example, in cases where polymers are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The polymers of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The polymers described herein may be systemically administered in combination with a pharmaceutically acceptable vehicle, such as an inert diluent or an assimilable edible carrier. For oral administration, polymers can be enclosed in hard or soft shell gelatin capsules, compressed into tablets, or incorporated directly into the food of a patient's diet. Polymers may also be combined with one or more excipients and used in the form of ingestible tablets, buccal tablets, troches, capsules, elixirs, suspensions, syrups, wafers, and the like. Such compositions and preparations typically contain at least 0.1% of active polymer. The percentage of the compositions and preparations can vary and may conveniently be from about 2% to about 60% of the weight of a given unit dosage form. The amount of active polymer or agent in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active polymers or composition may be incorporated into sustained-release preparations and devices.

The active polymers or composition may be administered intravenously or intraperitoneally by infusion or injection. Solutions of the active polymers, composition, or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as antimicrobial agents can be added to optimize the properties for a given use.

Useful dosages of the polymers described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a polymers, or an active salt or derivative thereof, required for use in treatment will vary not only with the particular polymers or salt selected but also with the route of administration, the nature of the condition being treated, and the age and condition of the patient, and will be ultimately at the discretion of an attendant physician or clinician.

The polymers can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention provides therapeutic methods of treating a bacterial infection in a mammal, which involve administering to a mammal having a bacterial infection an effective amount of a polymer or composition described herein. A mammal includes a primate, human, rodent, canine, feline, bovine, ovine, equine, swine, caprine, bovine and the like.

The ability of a compound of the invention to treat a bacterial infection may be determined by using assays well known to the art. For example, the design of treatment protocols, toxicity evaluation, data analysis, quantification of tumor cell kill, and the biological significance of the use of these screens are known. In addition, ability of a polymer to treat a bacterial infection may be determined using the tests described in the examples below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Preparation and Characterization of Stable Polypeptide Helices

Materials.

Chemicals were purchased from Sigma-Aldrich (St. Louis, Mo.) and used as received unless otherwise specified. Anhydrous dimethylformamide (DMF) was dried by a column packed with 4 Å molecular sieves and stored in a glove box. Tetrahydrofuran (THF) and hexane were dried by a column packed with alumina and stored in a glove box. Anhydrous CDCl$_3$ was prepared by treating commercial CDCl$_3$ (Sigma-Aldrich, St. Louis, Mo.) with CaSO$_4$ overnight, followed by distillation under nitrogen. The purified CDCl$_3$ was stored in the presence of 4 Å MS. Dry nitrobenzene and DMSO-d$_6$ were prepared by treating regular nitrobenzene and DMSO-d$_6$ by CaH$_2$ followed by distillation under reduced pressure.

H-Lys(Z)—OH and H-Glu(OBn)-OH were purchased from Chem-Impex International (Des Plaines, Ill.) and used as received. Glu-NCA and Lys-NCA were prepared by following previously reported procedures (Lu, H.; Cheng, J. J. Am. Chem. Soc. 2007, 129, 14114-14115).

Instrumentation.

NMR spectra were recorded on a Varian UI400 MHz, a UI500NB MHz or a VXR-500 MHz spectrometer. Tandem gel permeation chromatography (GPC) experiments were performed on a system equipped with an isocratic pump (Model 1100, Agilent Technology, Santa Clara, Calif.), a DAWN HELEOS 18-angle laser light scattering detector (also known as multi-angle laser light scattering (MALLS) detector, Wyatt Technology, Santa Barbara, Calif.) and an Optilab rEX refractive index detector (Wyatt Technology, Santa Barbara, Calif.). The detection wavelength of HELEOS was set at 658 nm.

Separations were performed using serially connected size exclusion columns (100 Å, 500 Å, 10$^3$ Å and 10$^4$ Å Phenogel columns, 5 μm, 300×7.8 mm, Phenomenex, Torrance, Calif.) at 60° C. using DMF containing 0.1 M LiBr as the mobile phase. The MALLS detector was calibrated using pure toluene with no need for external polymer standards and was used for the determination of absolute molecular weights. The molecular weights (MWs) of all polymers were determined based on the dn/dc value of each sample calculated offline by using the internal calibration system processed by the ASTRA V software (version 5.1.7.3, Wyatt Technology, Santa Barbara, Calif.).

Infrared spectra were recorded on a Perkin Elmer 100 serial FTIR spectrophotometer calibrated with polystyrene film. Circular dichroism (CD) measurements were carried out on a JASCO J-700 or a JASCO 720 CD Spectrometer. Ozone was produced by an OZV-8S ozone generator manufactured by Ozone Solutions Inc. (Hull, Iowa). Lyophilization was performed on a FreeZone lyophilizer (Labconco, Kansas City, Mo.).

Methods

Synthesis of Poly(L-Glutamic Acid) PLG$_{57}$

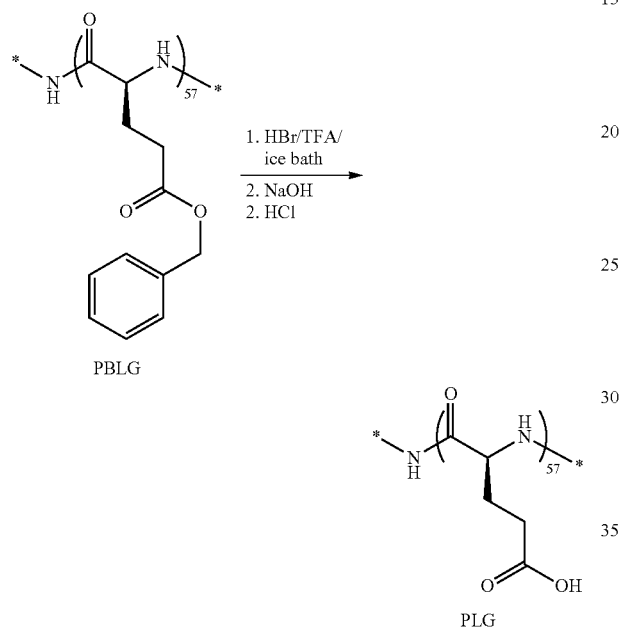

Poly(γ-benzyl-L-glutamate) (PBLG) with a degree of polymerization of 57 (PBLG$_{57}$) was synthesized according to the procedure previously reported (Lu, H.; Cheng, J. *J. Am. Chem. Soc.* 2007, 129, 14114-14115). The $M_n$ was 12,500 g/mol and MWD ($M_w/M_n$) was 1.15 as characterized by GPC. The deprotection of PBLG$_{57}$ was performed by following a procedure modified from the literature (see Wang and Chang, *Macromolecules* 2003, 36, 6511-6518; Blout and Idelson, *J. Am. Chem. Soc.* 1956, 78, 497-498; Li et al., *Biomacromolecules* 2008, 9, 2670-2676) (0° C. as opposed to room temperature) to give PLG$_{57}$ in quantitative yield. The polymer (500 mg) was treated with 2 M NaOH (10 mL) and then with CBZ-Cl (0.1 mL) for 16 hours to cap the N-terminus of PLG. The PLG was acidified by 3 M HCl and the precipitates was purified subsequently by dialysis against DI water and lyophilized. $^1$H NMR (TFA-d, 500 MHz): δ 4.86 (1H), 2.68 (2H), 2.34 (1H) and 2.19 (1H).

General Procedure for the Synthesis of PAHG and PAPG.

PLG$_{57}$ (0.20 mmol Glu repeating unit), BOP—Cl (1.37 mmol), DMAP (0.14 mmol), triethylamine (1.4 mmol) and 6-(N-Boc amino)-1-hexanol (0.2 mmol) were mixed in anhydrous NMP (4 mL) under nitrogen and stirred at 40-50° C. for three to four days. Ethyl acetate (30 mL) and brine (20 mL) were added. The organic phase was washed in water (2×15 mL), dried with Na$_2$SO$_4$, and concentrated under vacuum. The residue was dissolved in TFA/chloroform (2/2 mL), stirred overnight, concentrated under vacuum, dissolved in 3 M HCl, dialysed in DI water and lyophilised to yield the (PAHG)$_{57}$ (43% yield). PAPG was prepared in a similar manner using the corresponding N-Boc amino-alcohol.

Synthesis of 6-(N-Boc-amino)-1-hexanol

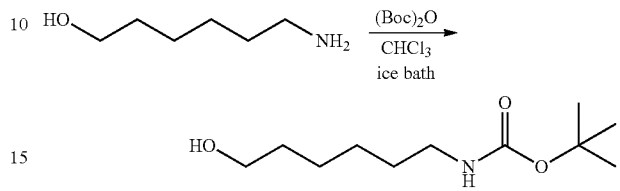

6-Amino-1-hexanol (1.17 g, 10 mmol) was dissolved in chloroform (15 mL) and stirred in an ice bath. (Boc)$_2$O (2.25 g, 10.8 mmol) was added to the mixture in a small portion at a time for about 5 min. The reaction mixture was stirred in the ice bath for another 2 h before the solvent was removed under vacuum. The crude product was recrystallized with hexane to give pure 6-(N-Boc amino)-1-hexanol (1.95 g, 90% yield). $^1$H NMR (CDCl$_3$, 500 MHz): δ 4.58 (s, 1H, NH), 3.62 (t, 2H, J=8.0 Hz, —CH$_2$CH$_2$CH$_2$CH$_2$OH), 3.15 (t, 2H, J=7.5 Hz, BocNHCH$_2$CH$_2$), 1.77 (S, 1H, —CH$_2$CH$_2$CH$_2$CH$_2$OH), 1.60-1.30 (m, 17H, (CH$_3$)$_3$C(CO)NHCH$_2$CH$_2$CH$_2$CH$_2$CH$_2$CH$_2$OH). $^{13}$C NMR (CDCl$_3$, 500 MHz): δ 156.0, 79.0, 62.6, 40.3, 32.5, 30.2, 28.4, 26.3, 25.2.

Synthesis of poly(γ-(6-aminohexyl)-L-glutamate)) (PAHG)

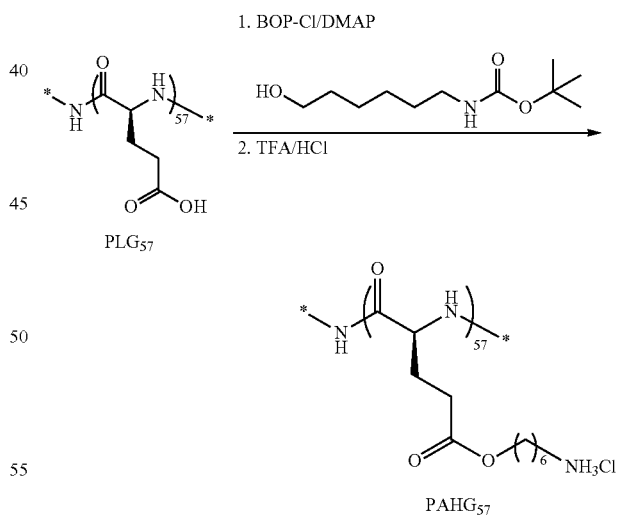

PLG$_{57}$ (25 mg, 0.20 mmol Glu repeating unit), BOP-Cl (350 mg, 1.37 mmol), DMAP (17 mg, 0.14 mmol), anhydrous triethylamine (0.2 mL, 1.4 mmol) and 6-(N-Boc amino)-1-hexanol (440 mg, 2 mmol) were added in anhydrous NMP (4 mL) under nitrogen. The conjugation reaction was allowed to proceed at 40-50° C. for 3 days. Ethyl acetate (30 mL) and a brine (20 mL) were added to the reaction mixture. The organic phase was washed by NaHCO$_3$ (1M, 10 mL) and DI water (2×15 mL), dried with Na$_2$SO$_4$, and concentrated under vacuum to provide an oily residue, which was washed by ether (3×10 mL) to remove the excess 6-(N-Boc)-1-hexanol. The residue was dissolved in chloroform and TFA was added to the solution at r.t. (~23° C.). The mixture was stirred overnight and concentrated under vacuum to yield the deprotected product. The residue oil was dissolved in 3M HCl, dialyzed in DI water and lyophilized to yield (PAHG)$_{57}$ (22 mg, 43% overall yield). The grafting efficiency was 95%, calculated by analysis of $^1$H NMR spectra.

Synthesis of poly(γ-(3-aminopropyl)-L-glutamate)) (PAPG)

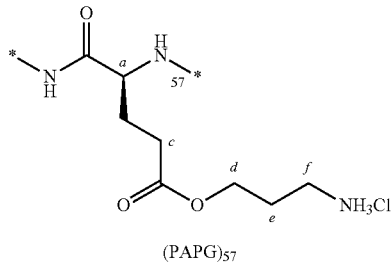

(PAPG)$_{57}$

PAPG$_{57}$ was synthesized via the same protocol as PAHG. PAPG$_{57}$ (18 mg) was obtained after purification. The overall yield was 48%. The grafting efficiency was above 95%, as calculated by analysis of $^1$H NMR spectra.

Synthesis of a 75mer of Poly(L-Lys) (PLL)$_{75}$

Poly(ε-CBZ-L-Lysine) (PZLL) was prepared at a monomer/initiator ratio of 75 by following the literature reported procedure. The $M_n$ of PZLL and MWD of the PZLL were 20.7 kg/mol and 1.05, respectively. The deprotection of PZLL was performed using the standard procedure of Holowka et al. (*Nat. Mater.* 2007, 6, 52-57) to provide the desired PLL$_{75}$.

Synthesis of γ-(4-vinylbenzyl)-L-glutamate NCA (VB-Glu-NCA)

γ-(4-Vinylbenzyl)-L-glutamate (VB-Glu) was synthesized through a modified procedure (Vanheeswijk et al., *Synthesis-Stuttgart* 1982, 744-747). VB (2.45 g, 10 mmol) was dried under vacuum for 2 hours. This solid was suspended in anhydrous THF (30 mL). Phosgene (20% in toluene, 7 mL) was added under nitrogen to solution dropwise for duration of 5 minutes. The suspension was stirred at 50° C. for 2-3 hours. The solvent was removed under vacuum.

The residue was dissolved in anhydrous THF in a glove box and centrifuged to remove the unreacted amino acid. The supernatant was combined and the solvent was removed under vacuum. The residue (containing a mixture of NCA and some dark colored impurity) was dissolved in THF (10 mL) followed by addition of anhydrous ether (100 mL). The solution was cooled at −30° C. in the box. A dark oily residue was removed. The clear solution containing NCA was combined and concentrated. VB-Glu-NCA in white crystalline form (3.4 mmol, 1.0 g, 34%) was obtained through recrystallization three times using THF/Hexane. $^1$H NMR (CDCl$_3$, 500 MHz): δ 7.40 (d, 2H, J=8.0 Hz, ArH), 7.30 (d, 2H, J=8 Hz, ArH), 6.73-6.67 (m, 2H, NH and C$_6$H$_4$CH=CH$_2$), 5.76 (d, 1H, J=17.5 Hz, C$_6$H$_4$CH=CH$_2$), 5.27 (d, 1H, J=11 Hz, C$_6$H$_4$CH=CH$_2$), 5.11 (s, 2H, ArCH$_2$), 4.38 (t, 1H, J=6.0 Hz, CHCH$_2$CH$_2$COOCH$_2$), 2.58 (t, 2H, CH$_2$CH$_2$COOCH$_2$), 2.26 (m, 1H, CH$_2$CH$_2$COOCH$_2$), 2.12 (m, 1H, CH$_2$CH$_2$COOCH$_2$). $^{13}$C NMR (CDCl$_3$, 500 MHz): δ 172.4, 169.3, 151.9, 137.8, 136.1, 134.6, 128.6, 126.4, 114.6, 66.8, 56.9, 29.8, 26.8. ESI MS analysis (with NaCl) Calcd: m/z 289.2 (M). found: m/z 312.3 (M+Na). Anal. Calcd. For C$_{15}$H$_{15}$NO$_5$: 62.29%; C, 5.21%; H, 4.84%; N. found: 62.06%; C, 5.12%; H, 4.83% N.

General Procedure for the Polymerization of VB-Glu-NCA.

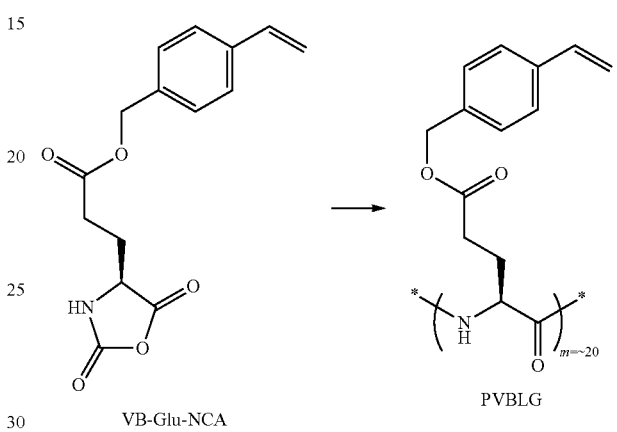

VB-Glu-NCA    PVBLG

In a glove box, VB-Glu-NCA (29 mg, 0.1 mmol) was dissolved in the mixture of DMF (1 mL) and nitrobenzene (50 µL) (nitrobenzene was used to inhibit potential radical reactions on vinyl group). The VB-Glu-NCA solution was added to a DMF solution of hexamethyldisilazane (20 µL, 0.1 mmol/mL). The reaction mixture was stirred for 15 hours at room temperature (~23° C.). An aliquot of the polymerization solution was diluted to 10 mg PVBLG/mL using DMF (containing 0.1 M LiBr), and then analyzed by GPC. The $M_n$ and MWD were assessed by GPC ($M_n$=26,200 g/mol; MWD=1.03). The remaining PVBLG was precipitated with ether (15 mL). The obtained PVBLG was sonicated for 5 min in ether and centrifuged to remove the solvent. After the sonication-centrifugation procedure was repeated two more times, PVBLG was collected and dried under vacuum (>95% yield). $^1$H NMR (TFA-d, 500 MHz): δ 7.53 (d, 2H, J=7.0 Hz, ArH), 7.39 (d, 2H, J=7.0 Hz, ArH), 6.84 (dd, 1H, J$_1$=11.0 Hz, J$_2$=18.0 Hz C$_6$H$_4$CH=CH$_2$), 5.91 (d, 1H, J=18.0 Hz, C$_6$H$_4$CH=CH$_2$), 5.43 (d, 1H, J=11.0 Hz, C$_6$H$_4$CH=CH$_2$), 5.26 (m, 2H, ArCH$_2$), 4.80 (m, 1H, CHCH$_2$CH$_2$COOCH$_2$), 2.68 (m, 2H, CHCH$_2$CH$_2$COO), 2.30 (m, 1H, CHCH$_2$CH$_2$COO), 2.12 (m, 1H, CHCH$_2$CH$_2$COO).

Kinetic Study of the Polymerization of VB-Glu-NCA.

Figure 18:
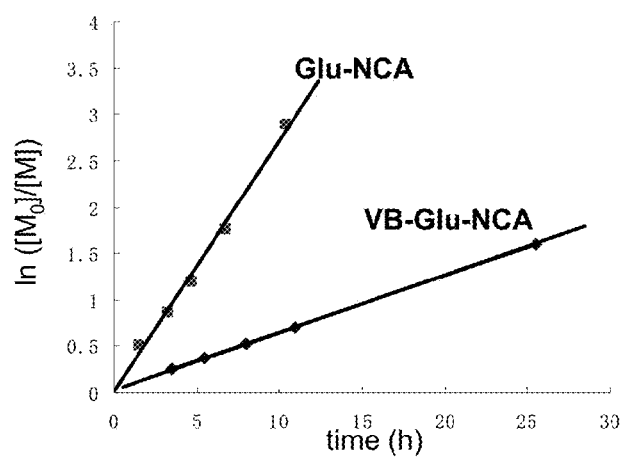
FIG. 18. Kinetic study of Glu-NCA and VB-Glu-NCA initiated by N-TMS allylamine in DMF at room temperature. The initial NCA concentration was 0.2 mM. The conversion of the NCA was determined by FT-IR.

In a glove box, VB-Glu-NCA (172 mg, 0.6 mmol) was dissolved in DMF (3.0 mL). A stock solution of N-TMS allylamine (0.1 M, 0.06 mL) was added to the solution in one portion under stirring. The real-time concentration of NCA was quantified by measuring the intensity of the anhydride band at 1784 cm$^{-1}$ by FT-IR. The conversion of NCA was determined by comparing the NCA concentration in the polymerization solution versus the initial NCA concentration (FIG. 18).

General Procedure for the Synthesis of PVBLG-1.

PABLG (20 mg), 6-amino-1-hexanol (3 M equiv. relative to the Glu repeating unit) and NaBH(OAc)$_3$ (5 M equiv.)

were mixed in THF (3 mL), stirred at 50-60° C. for 24 hours, poured into 3 M HCl (3 mL), dialysed and lyophilised.

Synthesis of poly(γ-(4-aldehydebenzyl)-L-glutamate) (PABLG)

PVBLG (10 mg) was dissolved in chloroform (10 mL) at −78° C. $O_2$ was bubbled into the solution for 1 min followed by bubbling of $O_3$ until the solution became blue. $O_3$ was then replaced by $O_2$, which was bubbled into the solution for another 2 min until the solution became colorless. The solution was then degassed and back filled with nitrogen. $Ph_3P$ (26 mg) was then added to the mixture. The solution was stirred at room temperature for 2-3 h. The solvent was removed under vacuum. The resulting poly(γ-(4-aldehydebenzyl)-L-glutamate) (PABLG) was purified by adding methanol followed by sonication (3×15 mL) to remove unreacted $Ph_3P$ and other impurities. $^1$H NMR (TFA-d, 500 MHz): δ 10.31 (1H, C$\underline{H}$OC$_6$H$_4$), 8.40 (d, 2H, J=7.0 Hz, ArH), 7.96 (d, 2H, J=7.0 Hz, ArH), 5.71 (2H, CHOC$_6$H$_4$ C$\underline{H}_2$), 5.21 (1H, C$\underline{H}$CH$_2$CH$_2$CO$_2$CH$_2$), 3.12 (2H, CHCH$_2$ C$\underline{H}_2$), 2.75 (1H, CHC$\underline{H}_2$CH$_2$), 2.56 (1H, CHC$\underline{H}_2$CH$_2$).

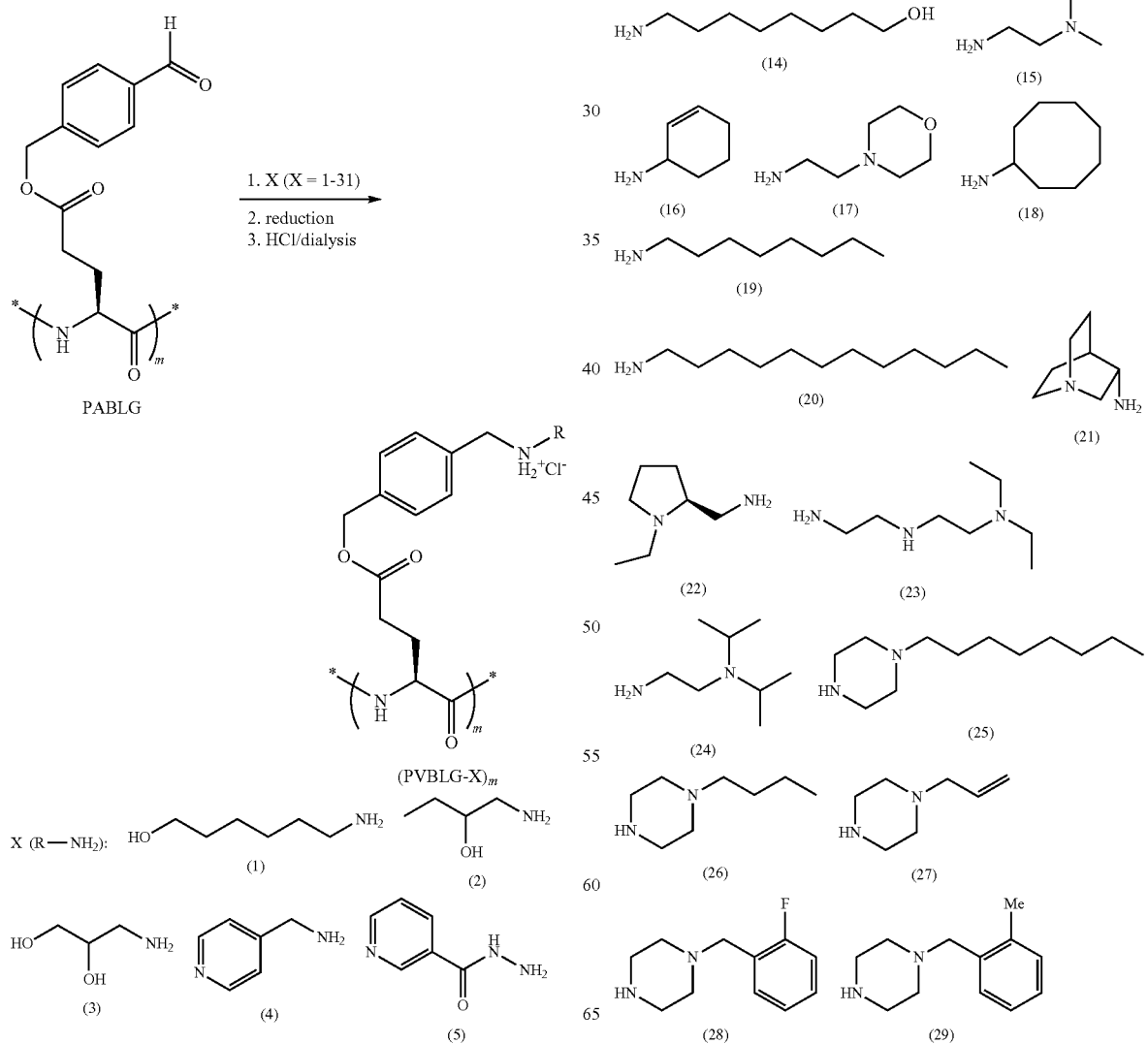

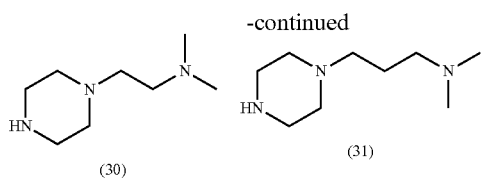

(30)  (31)

Synthesis of PVBLG-X (X=1-7)

The poly(γ-(4-aldehydebenzyl-L-glutamate) (20 mg), amine (3-5 molar equiv. relative to the Glu repeating unit) and the reduction reagent (5-10 molar equiv.) (Table 1) were mixed in THF (3 mL) (except for 7 with DMF was used as the solvent). The reaction mixtures were stirred at 50-60° C. for 24-72 hours. The mixture was then poured into 3 M HCl (3 mL) followed by dialysis against water and was freeze dried. The yields of the products PVBLG-X (X=1-7) were 50-75% after dialysis. Grafting efficiencies were analyzed by $^1$H NMR.

Two suitable procedures to conjugate amines 1-31 to the PABLG structure include methods A and B: A) i) RNHR', NaBH(OAc)$_3$, DMF/HOAc, 60° C., 24 h, ii) HCl; and B) i) RNHR', DMF/HOAc, 60° C., 16 h, ii) BH$_3$ pyridine complex, 8 h, iii) HCl; where RNHR' is a primary or secondary amine, such as amines 1-31 in Scheme 1-1. Other condensation techniques known in the art may also be employed (see for example, G. T. Hermanson, *Bioconjugation Techniques*, 2$^{nd}$ Ed., Academic Press, New York 2008).

Hydrolysis Kinetics of the Benzyl Ester of PVBLG-1.

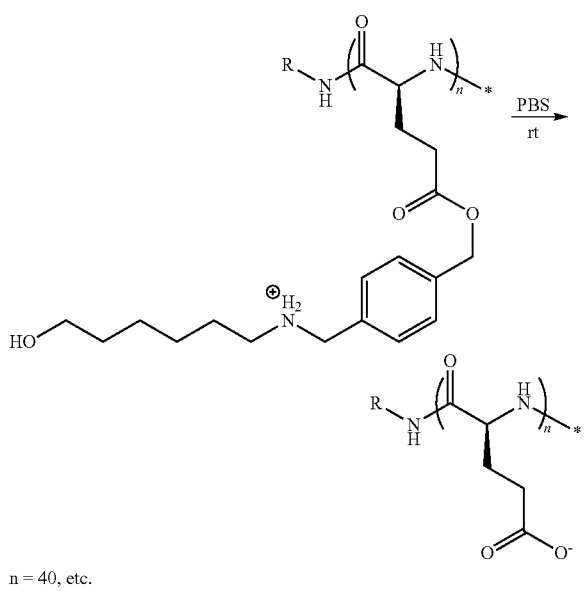

n = 40, etc.

Figure 19:
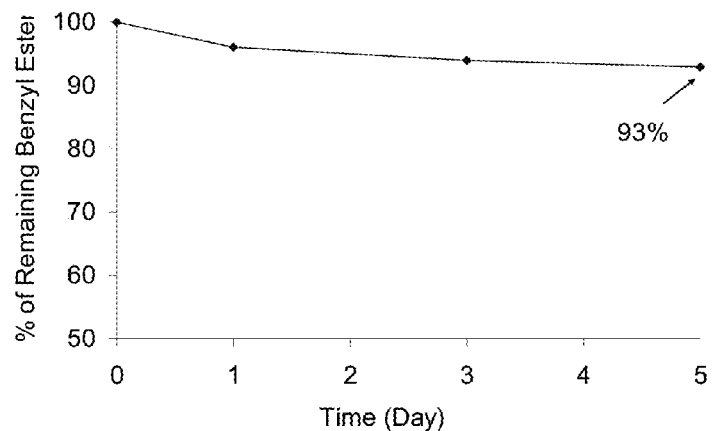
FIG. 19. Hydrolysis kinetic of (PVBLG-1)$_{40}$ in PBS (1×) at room temperature.

PBS (100 μL, 10×) was lyophilized following addition of 1 mL D$_2$O to prepare PBS/D$_2$O (1×). (PVBLG-1)$_{40}$ (10 mg) was dissolved in the PBS/D$_2$O (1×) and incubated at room temperature. The extent of cleavage of the benzyl ester was monitored by $^1$H NMR (FIG. 19).

Characterisation of PAHG, PAPG and PVBLG-1 using Circular Dichroism (CD).

CD measurements were carried out on a JASCO J-700 CD spectrometer in a quartz disc with a light path length of 1 cm at 0.01-0.1 mg/mL in DI water at room temperature or under conditions otherwise indicated.

General Procedure for the Analysis of Polymer by Circular Dichroism (CD).

The CD study was performed on a JASCO J-700 or on a J-720 CD spectrometer. Polymer samples were prepared at concentrations of 0.01-0.1 mg/mL at pH 3 unless otherwise specified. The solution was placed in a quartz cell with light path of 0.2 cm. The mean residue molar ellipticity of each polymer was calculated based on the measured apparent ellipticity, the molar concentration of polymer and the m.w. of the repeating unit. The CD experiments were carried out at room temperature unless otherwise specified. For temperature-dependency study, the temperature of the sample chamber which hosts the quartz cell was controlled by a water bath (from 4° C. to 70° C.).

The samples were equilibrated at corresponding temperature for at least 10 min before the CD measurements. For the sample preparations, the polymers were dissolved in DI water or in a solution containing NaCl, urea or methanesulfonic acid (MSA). For the pH-dependency study, the pH of the polymer solution was tuned by the addition of a concentrated HCl or NaOH solution. See FIGS. 5-17 for the CD analysis of (PVBLG-1)$_{60}$ and FIGS. 20-25 for the CD analysis of (PAHG)$_{57}$ under various conditions.

Wide-Angle X-Ray Diffraction of PVBLG-1

Two-dimensional (2D) wide-angle X-ray diffraction (WAXD) experiments were performed on an Oxford Xcalibur diffractometer with an ONYX CCD area detector. The X-ray wavelength was 0.1542 nm for Cu Kα. One-dimensional (1D) profiles were obtained by integration from corresponding 2D WAXD images. The d-spacing was calibrated using silver behenate which has the first-order reflection (d$_{001}$=58.380 Å) at q=1.076 nm$^{-1}$ (scattering vector q=(4π sin θ)/λ with θ being half of the scattering angle).

Discussion.

The MW dependence of the secondary conformation of PVBLG-1 was evaluated. As shown in the figure top-left of FIG. 11, (PVBLG-1)$_{10}$, with a $-[\theta]_{222}$ of 7170 deg·cm$^2$·dmol$^{-1}$, has low helical content. The FTIR analysis (FIG. 3*i*) confirmed its low helical content (1651 cm$^{-1}$ and 1545 cm$^{-1}$). Instead, the predominant conformation of (PVBLG-1)$_{10}$ is β-sheet as indicated in its FTIR spectrum (1627 cm$^{-1}$ and 1520 cm$^{-1}$, FIG. 3*i*), which agrees well with the conformation of short PBLG (20 mer) previously reported (Klok et al., *Macromolecules* 2000, 33, 7819-7826). The $-[\theta]_{222}$ of (PVBLG-1)$_{DP}$ shows the linear correlation with the polymer chain length (DP) with $-[\theta]_{222}$'s of (PVBLG-1)$_{40}$, (PVBLG-1)$_{60}$ and (PVBLG-1)$_{142}$ being 23,200, 30,100 and 55,000 deg·cm$^2$·dmol$^{-1}$, respectively.

Preliminary X-ray scattering experiments showed that PAHG$_{57}$ and (PVBLG-1)$_{180}$ directly cast from water have ordered structures with well-defined packing of the helical chains (FIG. 26). The ordering of helical cylinders is more pronounced in PVBLG-1 than in PAHG, evidenced by the numerous reflections in FIG. 26(*b*). A broad and intense scattering, comprising the reflections associated with the pitch length of the α-helix, appears at 5.2~5.4 Å d-spacing in both figures. The accurate assignment of different layer lines and the calculation of chain-spacing for the helical polymers were difficult because of overlapping of the reflections due to lack of orientation, as well as the limited q-range. X-ray diffraction studies on the orientated fibers of these helical polymers are under way and the results will provide detailed structural information of these novel polypeptides.

Example 2. Cationic α-Helical Polypeptides Template for Non-Viral Gene Delivery Poly(γ-(4-vinylbenzyl)-L-glutamate) (PVBLG) was used as a reactive template for the generation of a library of cationic α-helical polypeptides for gene delivery. PVBLG compounds can bind and condense anionic material such as plasmid DNA and transfect cells. $PVBLG_{267}$-8 significantly outperformed 25-kDa PEI by 12-fold (FIG. 27). Preliminary data indicates that these cationic α-helical polypeptides are capable of enhanced membrane disruption, which properties provide improved performance as delivery agents.

Proteins and peptides have long been considered as potential non-viral gene delivery vectors. Poly-L-lysine (PLL) was one of the earliest materials used for gene delivery. However, on its own, PLL is a poor gene transfer agent and provides low transfection efficiency. Currently, proteins and peptides are more commonly used as supplementary components in gene delivery systems where they function as cell targeting ligands, membrane destabilization moieties or nuclear localization signals. In terms of membrane destabilization, the fusogenic peptides KALA and GALA are two of the more well-studied additives (Wyman et al., *Biochemistry* 1997, 36, 3008). Both KALA and GALA are positively charged and water soluble due to their arginine and lysine residues. However, their hydrophobic leucine residues impart the peptides with a propensity to adopt an α-helical structure in aqueous solution. In their helical conformation, KALA and GALA are amphipathic with a hydrophobic and hydrophilic face. The hydrophilic face induces binding with negatively charged membranes while the hydrophobic face is believed to cause pore formation and membrane disruption.

Recently, there has been success in applying a semi-rational approach to the design of non-viral gene delivery vectors using a combinatorial/parallel synthesis approach to construct libraries of polymers with unique molecular structures (see Anderson et al., *Angew Chem* 2003, 42, 3153; Barua et al., *Mol. Pharm.* 2009, 6, 86; and Sun et al., *Chem. Comm.* 2010, 46, 2016). Often, the only rational design strategy in the library approach is the inclusion of amines to impart a net positive charge that facilitates DNA binding and condensation. Other concerns, such as DNA binding strength and endosomal escape, are not explicitly addressed. As described herein, the incorporation of various structurally unique domains in the library can yield molecules with the appropriate balance of hydrophilicity (i.e. DNA binding strength) and hydrophobicity (i.e. endosomolysis) to yield efficient gene delivery.

A library of cationic α-helical polypeptides for gene delivery is described herein. Much like the helical peptides KALA and GALA destabilize membranes by balancing hydrophilic and hydrophobic amino acid residues, a similar balance was struck in the libraries of α-helical polypeptides described herein by varying the hydrophilic and hydrophobic balance in the polymer side chains. The ring-opening polymerization of γ-(4-vinylbenzyl)-L-glutamate N-carboxyanhydride (VB-Glu-NCA) was used to form poly(γ-(4-vinylbenzyl)-L-glutamate) (PVBLG) (Lu and Cheng, *J Am Chem Soc* 2008, 130, 12562-12563). PVBLG served as a reactive template that, through subsequent ozonation, hydroamination and reduction, allowed for the creation of a library of cationic polypeptides ($PVBLG_n$-X, where n is the degree of polymerization and X refers to a grafted amine side chain, Scheme 2-1; see also Scheme 1-1 for additional amines).

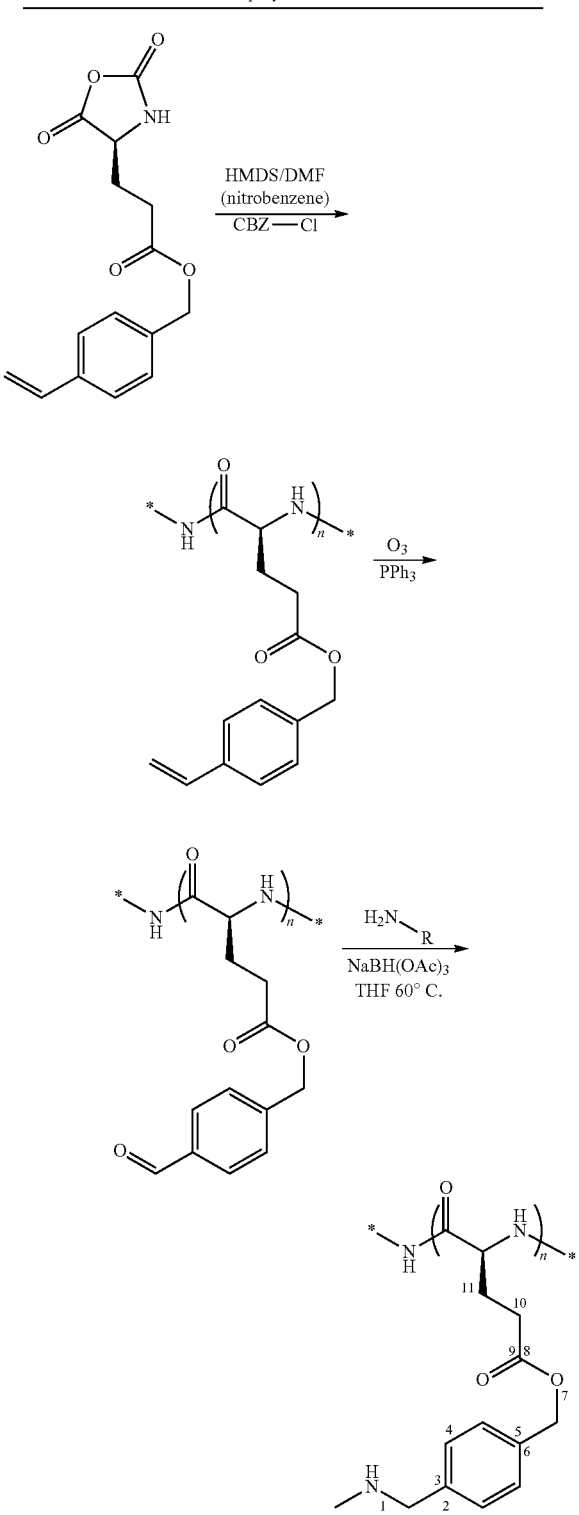

Scheme 2-1.
Preparation of PVBLG-X polypeptides and examples of PVBLG-X polymers where R is H or an optionally substituted alkyl, aryl, heteroaryl, heterocycle, or saccharide, or a moiety illustrated below. Additional examples of amines for the R group are illustrated in Scheme 1-1 above.

PVBLG-1
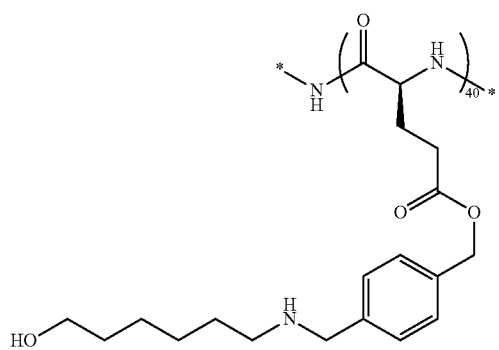
PVBLG-2
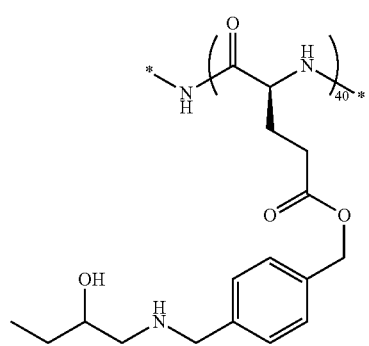
PVBLG-3
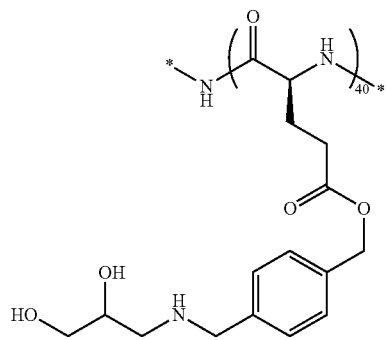
PVBLG-4
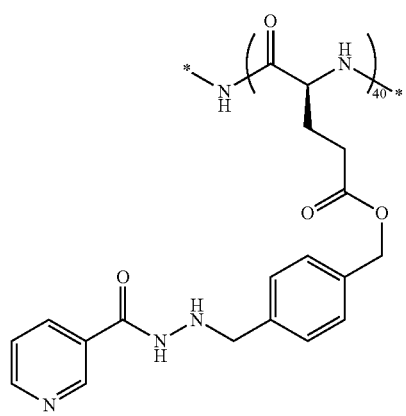
-continued
PVBLG-5
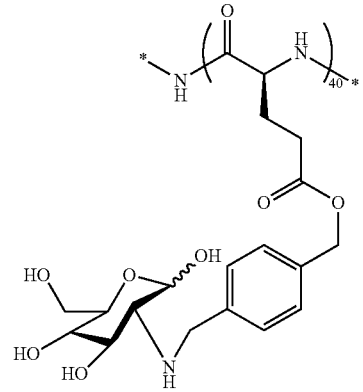
PVBLG-6
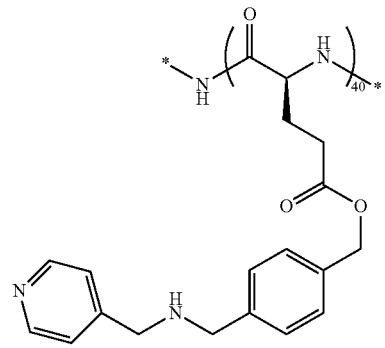
PVBLG-7
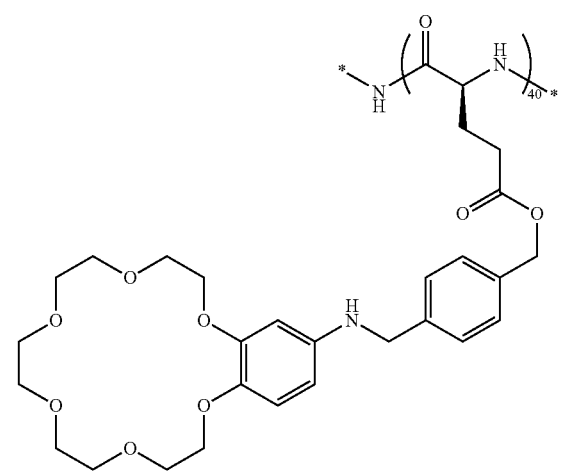
PVBLG-8
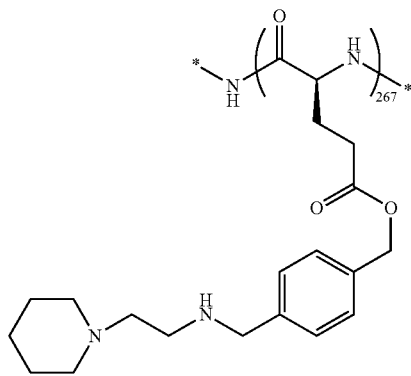

-continued

PVBLG-9

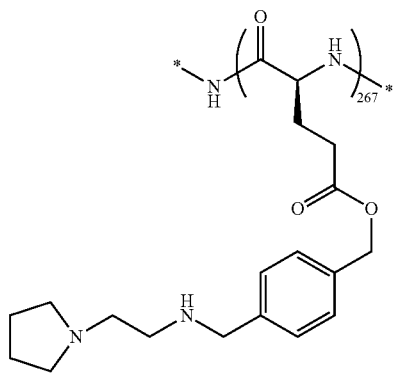

Due to its glutamate residues, PVBLG has a propensity to adopt an α-helical secondary structure. Typically, cationic polypeptides such as PLL are unable to adopt helical conformations at physiological pH due to side chain charge disruption. However, it was recently discovered that the helical structure of cationic polypeptides such as PVBLG can be stabilized by lengthening the distance between the side chain charge group and the backbone of polypeptide, thus minimizing the effect of side chain charge repulsion by reducing the helix surface charge density (FIG. 2). Stable helical structure with very high helical content (>90%) can be achieved by maintaining a minimum separation distance of about 8, 9, 10, or 11 σ-bonds between the peptide backbone and the side chain charge for a polypeptide with charged side chains and reasonable length (degree of polymerization of 6-600, for example, 60). Such polypeptides result in a helix structure that is stable over a broad range of pH values and salt concentrations (see FIG. 28). By following this general strategy, polypeptide materials can be generated that are sufficiently large and positively charged to bind and condense DNA yet also retain the helical structure seen in many cell penetrating peptides (CPPs). The unique combination of material properties allows the examination of helicity as a functional motif in the backbone of gene delivery vectors and the evaluation of its impact on transfection efficiency.

Thirty-one different $PVBLG_n$-X polymers ($PVBLG_{40}$-1 to $PVBLG_{40}$-31) were synthesized. The degree of polymerization was varied between 10 and 300 for the top-performing amines. In preliminary experiments, $PVBLG_{40}$-1 with an aminohexanol side chain, showed transfection efficiencies on par with 25-kDa branched polyethylenimine (PEI) in COS-7 cells (FIG. 29). Keeping the aminohexanol side chain, $PVBLG_n$-1 with other degrees of polymerization was prepared (DP=10-300). Generally, increased molecular weight corresponded to increased transfection efficiency, and $PVBLG_{267}$-1, outperforming 25-kDa branched PEI by more than 4-fold (FIG. 30). Two additional polymers, $PVBLG_{267}$-8 and $PVBLG_{267}$-9, were prepared and tested. $PVBLG_{267}$-8 with an aminoethyl piperidine side chain resulted in a high transfection efficiency, a 12-fold improvement over 25 kDa PEI (FIG. 31). The superior performance of $PVBLG_{267}$-8 was confirmed in three additional cell lines (HEK293, MDA-MB-231, and HeLa) (see FIG. 33 and the Materials and Methods section below). To test the breadth of its applicability, $PVBLG_{267}$-8 was also used to deliver siRNA specific for the GL3 luciferase gene in a light producing cell line derived from HeLa cells (HeLa-Luc). The results shown in FIG. 32 reveal that $PVBLG_{267}$-8 outperforms both 25-kDa PEI and the commercial agent lipofectamine 2000 (LFA) for siRNA delivery.

Of the various side chains, 15 showed improved performance relative to 22-kDa PLL and two (X=1 and 8) showed improved performance relative to 25-kDa branched polyethyleneimine (PEI) in COS-7 cells (FIG. 34a). $PVBLG_{267}$-8 resulted in the highest transfection efficiency and showed low toxicity in COS-7 cells, in sharp contrast to PEI that is known for its high toxicity (FIG. 34b). Circular dichroism analysis (CD) confirmed that $PVBLG_{267}$-8 maintained its helical conformation at physiological pH as well as the acidic pH encountered within endosomes and lysosomes (FIG. 34c).

Because the $PVBLG_n$-X polymers were designed to have an α-helical architecture similar to that found in peptides capable of disrupting membranes such as CPPs, the ability of the polymers to cause pore formation in cell membranes was also examined. COS-7 cells were incubated with 250 μM calcein, a fluorescent dye, in the presence of various concentrations of $PVBLG_{267}$-8. Calcein is unable to cross intact membranes. Thus, in the absence of an agent capable of pore formation, calcein is taken up by cells in a pinocytic fashion, resulting in the appearance of small punctuate intracellular fluorescent spots (FIG. 35, 0 μg/mL). However, as the amount of $PVBLG_{267}$-8 in the extracellular medium is increased, the intracellular fluorescent signal becomes more diffuse, indicating membrane permeation and non-electrolyte calcein uptake (FIG. 35, 50 μg/mL).

The 15 μg/mL calcein concentration corresponds to the concentration of $PVBLG_{267}$-8 used in one optimum transfection formulation. As indicated by the punctate fluorescent signal, 50 μg/mL of $PVBLG_{267}$-8 is unable to cause cell membrane pore formation. Thus, the complexes formed between $PVBLG_{267}$-8 and plasmid DNA enter cells via endocytosis and not through direct membrane penetration. This is supported by flow cytometry data showing reduced complex uptake in the presence of an inhibitor of caveolae-mediated endocytosis. Similar results for calcein and complex uptake were observed for analogous experiments conducted in HEK293 cells (see Materials and Methods section below).

Because $PVBLG_{267}$-8 complexes appear to enter cells via endocytosis and not direct membrane transduction, they likely escape endocytic vesicles to mediate transfection. $PVBLG_{267}$-8 possesses secondary and tertiary amines which can act as buffering agents to aid endosomal escape via the proton sponge effect. To investigate if this mechanism contributed to the gene delivery observed with $PVBLG_{267}$-8, transfections were performed in the presence of bafilomycin A1, an ATPase inhibitor that prevents endosome acidification and thus disrupts the proton sponge effect (Bowman et al., Proc Nat Acad Sci 1988, 85, 7972).

FIG. 36 shows that bafilomycin A1 dramatically reduces the gene delivery efficiency of PEI vectors, known proton sponges, but has no negative effect on cells transfected with $PVBLG_{267}$-8 vectors. This indicates that $PVBLG_{267}$-8 escapes from endosomes via membrane disruption, a mechanism more commonly associated with lipid-based transfection agents like lipofectamine 2000 (LFA). To explore this further, transfection was performed in the presence of nocodazole. Nocodazole depolymerizes microtubules, thus preventing the active transport of endosomes along their normal progression from early endosomes to late endosomes to lysosomes (Bayer et al., J. Virol. 1998, 72, 9645). As a result, endocytosed material accumulates in early endosomes. In agreement with the data indicating that the membrane disruption capabilities of $PVBLG_{267}$-8 increases with increasing polymer concentration (FIG. 37), nocodazole causes a greater than 2-fold increase in the transfection efficiency of $PVBLG_{267}$-8 vectors in COS-7 cells and HEK293 cells (FIG. 33b for HEK293 cells). Flow cytometry revealed that this increase was not due to increased complex uptake in drug-treated cells. Rather, the enhanced transfection in the presence of nocodazole is likely due to the accumulation of PVBLG$_{267}$-8 complexes in endocytic vesicles. As more complexes accumulate, the effective polymer concentration becomes large enough to cause enhanced vesicle lysis. This phenomenon was also observed in nocodazole-treated HEK293 cells (see Materials and Methods section below).

These results indicate that secondary structure has a dramatic impact on the intracellular performance of polymer-based non-viral gene delivery vehicles. Specifically, the incorporation of helical architecture, a trait shared by many peptides capable of membrane disruption, into the gene delivery vector library described herein yielded polypeptides that possess the ability to disrupt endosomes. Ultimately, this results in improved transfection performance of the polypeptides relative to branched 25-kDa PEI in a variety of cell lines.

To directly demonstrate the importance of secondary structure, a random coil of the top performing PVBLG$_n$-8 polymer was synthesized using D- and L-VB-Glu-NCA monomers. The racemic configuration of amino acids (1:1 ratio) was confirmed to prevent the formation of secondary structure in the resulting PVB-D,L-G$_{150}$-8 polymer by circular dichroism. For comparison, helical PVB-L-G$_{100}$-8 was also synthesized. Both polymers were used to transfect COS-7 cells over a variety of polymer:DNA weight ratios (FIG. 37). Confirming the understanding from cell penetration and drug inhibition data, the random coil PVB-D,L-G$_{150}$-8 polypeptide was unable to mediate effective transfection while helical PVB-L-G$_{100}$-8 was. As previous results have shown that transfection increases with polymer molecular weight, enhanced performance by the shorter PVB-L-G$_{100}$-8 polypeptide relative to the longer PVB-D,L-G$_{150}$-8 polypeptide cannot be attributed to molecular weight. This stands as direct evidence that polymer secondary structure impacts overall polypeptide performance.

To test the breadth of applicability of the helical polypeptides as gene delivery vehicles, PVBLG$_{267}$-8 was used to transfect the H9 human embryonic stem cell (hESC) line. hESCs are traditionally hard to transfect, with commercial agents often successfully delivering the transgene to less than 10% of the treated cells. To explore if the enhanced membrane disruptive properties of PVBLG$_{267}$-8 aided transfection in hard-to-transfect cells in addition to cells more amenable to gene delivery (i.e. COS-7 and HEK293 cells), H9 hESCs were transfected with a plasmid coding for green fluorescent protein (pEGFP-N1) and assayed for gene expression 48 hours post-transfection by flow cytometry. As nocodozole treatment was observed to aid transfection with PVBLG$_{267}$-8, hESCs were also transfected in the presence and absence of nocodazole. In addition to PVBLG$_{267}$-8, the commercial transfection agent lipofectamine 2000 (LFA) was also evaluated. Without the addition of nocodazole, PVBLG$_{267}$-8 at a 20:1 PVBLG$_{267}$-8:DNA weight ratio outperforms LFA by 50% and results in approximately 1.5% of all hESCs expressing the transgene. The addition of 10 μM nocodazole to the transfection media increases the percentage of cells successfully transfected with PVBLG$_{267}$-8 to roughly 4.5%. This is approximately a 3-fold enhancement over the transfection efficiency of LFA.

The study reported herein demonstrates the successful application of a library screening approach to the development of α-helical cationic peptides for gene and siRNA delivery. To our knowledge, this is the first time a library approach has been combined with a reactive template bearing a well-defined and bioactive secondary structure. The data reported herein indicate that certain library members retain the membrane destabilization properties commonly associated with helical peptides, yet can also mediate effective gene delivery in a variety of cell lines, including immortalized cancer cells and hESCs. Vector helicity appears to be an essential component in the successful use of polypeptides for gene delivery. In view of the interesting properties of the reported class of helical cationic polypeptides, these polymers can be used to develop high throughput strategies to further expand the library as well as to mediate in vivo gene and siRNA delivery.

Materials and Methods.

Materials.

Chemicals were purchased from Sigma-Aldrich (St. Louis, Mo.) and used as received unless otherwise specified. Anhydrous dimethylformamide (DMF) was dried by a column packed with 4 Å molecular sieves and stored in a glove box. Tetrahydrofuran (THF) and hexane were dried by a column packed with alumina and stored in a glove box. Anhydrous CDCl$_3$ was prepared by treating commercial CDCl$_3$ (Sigma-Aldrich, St. Louis, Mo.) with CaSO$_4$ overnight, followed by distillation under nitrogen. The purified CDCl$_3$ was stored in the presence of 4 Å molecular sieves. Dry nitrobenzene and DMSO-d$_6$ were prepared by treating regular nitrobenzene and DMSO-d$_6$ by CaH$_2$ followed by distillation under reduced pressure.

H-Lys(Z)—OH and H-Glu(OBn)-OH were purchased from Chem-Impex Int. (Des Plaines, Ill.) and used as received. Glu-NCA and Lys-NCA were prepared by following previously reported procedures (see Lu, H.; Cheng, J. J. Am. Chem. Soc. 2007, 129, 14114-14115). Pierce BCA assay kits were purchased from ThermoFisher Scientific (Rockford, Ill.). Luciferase assay reagent and Fugene HD was purchased from Promega (Madison, Wis.). Lipofectamine 2000 (LFA) and the fluorescent dyes YOYO-1 and TAMRA-SE were purchased from Invitrogen (Carlsbad, Calif.).

Instrumentation.

NMR spectra were recorded on a Varian UI400 MHz, a UI500NB MHz or a VXR-500 MHz spectrometer. Tandem gel permeation chromatography (GPC) experiments were performed on a system equipped with an isocratic pump (Model 1100, Agilent Technology, Santa Clara, Calif.), a DAWN HELEOS 18-angle laser light scattering detector (also known as multi-angle laser light scattering (MALLS) detector, Wyatt Technology, Santa Barbara, Calif.) and an Optilab rEX refractive index detector (Wyatt Technology, Santa Barbara, Calif.). The detection wavelength of HELEOS was set at 658 nm. Separations were performed using serially connected size exclusion columns (100 Å, 500 Å, 10$^3$ Å and 10$^4$ Å Phenogel columns, 5 μm, 300×7.8 mm, Phenomenex, Torrance, Calif.) at 60° C. using DMF containing 0.1 M LiBr as the mobile phase. The MALLS detector was calibrated using pure toluene with no need for external polymer standards and was used for the determination of the absolute molecular weights.

The molecular weights (MWs) of all polymers were determined based on the do/dc value of each sample calculated offline by using the internal calibration system processed by the ASTRA V software (version 5.1.7.3, Wyatt Technology, Santa Barbara, Calif.). Circular dichroism (CD) measurements were carried out on a JASCO J-700 or a JASCO 720 CD Spectrometer. Ozone was produced by an OZV-8S ozone generator manufactured by Ozone Solutions Inc (Hull, Iowa). Lyophilization was performed on a FreeZone lyophilizer (Labconco, Kansas City, Mo.).

Cells, Plasmids and siRNA.

COS-7, HEK293, MDA-MB-231, and HeLa cells were obtained from ATCC. HeLa-Luc cells, which stably produce the GL3 luciferase gene, were a gift of the Davis Lab (Caltech). All cells were cultured according to their ATCC protocols at 37° C. and 5% CO2 in Dulbecco's modified Eagle's medium (DMEM). The growth medium was supplemented with 10% fetal bovine serum and 1% penicillin-streptomycin. The expression vector pCMV-Luc, coding for the luciferase gene, was obtained from Elim Biopharmaceuticals (Hayward, Calif.). siRNA specific to the GL3 luciferase gene was purchased from Dharmacon (Lafayette, Colo.).

VB-Glu-NCA was prepared and polymerized as described above in Example 1.

Synthesis of PVBLG-X (X=1-31; See Also Example 1)

Method 1:
Poly(γ-(4-aldehydebenzyl-L-glutamate) (20 mg), amine (3-5 molar equivalents relative to the Glu repeating unit) and the reducing agent $NaBH(OAc)_3$ (5-10 molar equivalents) were mixed in DMF (2 mL). The reaction mixtures were stirred at 50-60° C. for 24-48 h. The solution was then poured into 3 M HCl (3 mL), followed by dialysis against water and lyophilization (X=1-5).

Method 2:
Poly(γ-(4-aldehydebenzyl-L-glutamate) (20 mg) and amine (3-5 molar equivalents relative to the Glu repeating unit) were stirred in DMF (2 mL) at 50-60° C. for 24 h, followed by the addition of the reducing agent $NaBH_4$ (5-10 molar equivalents). The resulting solutions were stirred at room temperature for another 24 h. The mixture were then poured into 3 M HCl (3 mL), followed by dialysis against water and lyophilization (X=6-7).

Method 3:
Poly(γ-(4-aldehydebenzyl-L-glutamate) (20 mg) and amine (3-5 molar equivalents relative to the Glu repeating unit) were stirred in DMF (2 mL) at 50-60° C. for 24 h, followed by the addition of the reducing agent borane pyridine (5-10 molar equivalents). The resulting solutions were stirred at 50-60° C. for another 24 h. The mixtures were then poured into 3 M HCl (3 mL), followed by dialysis against water and lyophilization (X=8-31).

The yields of the products PVBLG-X (X=1-31) were around 50-75% after dialysis. Grafting efficiencies were analyzed by $^1$H-NMR integration and all of the polymers have grafting efficient around 90% except for PVBLG-7 (70% grafting density).

General procedure for the analysis of polymer by circular dichroism (CD).

Circular dichroism experiments were performed as described in Example 1. See FIGS. 12-17 and 38-39.

Gel Retardation Studies (DNA).

A solution of DNA (1 μg/10 μL) was prepared in doubled distilled water. Appropriate amounts of PVBLG-X dissolved in double distilled water were added to the DNA solution (10 μl) to achieve the desired PVBLG-X:DNA weight ratio. Complexes were incubated at room temperature for 15 min, after which loading dye was added and the solution (10 μl) was run on a 1% agarose gel (70 V, 70 min). DNA was stained with ethidium bromide and visualized on a Gel Doc imaging system (Biorad, Herclues, Calif.). See FIG. 40.

Complex Formation and Transfection (DNA).

DNA/polymer complexes were prepared at room temperature by dissolving DNA (0.35 μg) in 150 mM NaCl, 20 mM HEPES (175 μL). An equal volume of 25-kDa branched PEI, lipofectamine 2000 or $PVBLG_n$-X in 150 mM NaCl, 20 mM HEPES was added to achieve the desired weight ratio. The final complexes were incubated at room temperature for 15 min before further use. Cells (COS7, HEK293, MDA-MB-231 or HeLa) were cultured in DMEM supplemented with 10% horse serum and 1% penicillin-streptomycin according to ATCC protocols and plated in 96-well plates at $1\times10^4$ cells/well 24 h prior to transfection. Immediately before transfection, the growth medium was replaced with fresh serum-free DMEM and polyplex solution (50 μL) was added to each well (0.05 μg DNA/well). The transfection medium was replaced with fresh serum-supplemented growth medium 4 h post-transfection.

For studies involving drug treatment (methyl-β-cyclodextrin at 10 mg/mL, chlorpromazine at 5 μg/mL, bafilomycin at 5 nM, nocodazole at 20 μM), cells were incubated with serum-free DMEM containing the drug 30 min prior to transfection. Luciferase expression was quantified 24 h post-transfection using the Promega Bright-Glo luciferase assay system (Promega, Madison, Wis.). Luciferase activity was measured in relative light units (RLU) using a PerkinElmer plate reader with luminescence capabilities (Waltham, Mass.). Results were normalized to total cell protein using the Pierce BCA protein assay kit (Rockford, Ill.). See FIG. 41. Transfections were performed in triplicate.

Complex Formation and Transfection (siRNA).

siRNA/polymer complexes were prepared at room temperature by dissolving siRNA in 150 mM NaCl, 20 mM HEPES (100 μL) and adding an equal volume of $PVBLG_{100}$-8 in 150 mM NaCl, 20 mM HEPES to achieve the desired weight ratio. The final complexes were incubated at room temperature for 15 min before further use. HeLa-Luc were cultured in DMEM supplemented with 10% horse serum and 1% penicillin-streptomycin according to ATCC protocols and plated in 96-well plates at $1\times10^4$ cells/well 24 h prior to transfection. Immediately before transfection, the growth medium was replaced with fresh serum-free DMEM and siRNA/polymer solution was added to each well to achieve final siRNA concentrations between 25 nM and 100 nM. The transfection medium was replaced with fresh serum-supplemented growth medium 4 h post-transfection. Luciferase expression was quantified 24 h post-transfection using the Promega Bright-Glo luciferase assay system (Promega, Madison, Wis.). Luciferase activity was measured in relative light units (RLU) using a PerkinElmer plate reader with luminescence capabilities (Waltham, Mass.). Results were normalized to untreated HeLa-Luc cells prepared in parallel. Transfections were performed in triplicate.

Uptake (DNA).

DNA complexes were formed at their respective optimum transfection weight ratios as described above. The intercalating dye YOYO-1 was added at the ratio 15 nL YOYO-1 per 1 μg of DNA. Cells (COS7 or HEK293) were cultured in DMEM supplemented with 10% horse serum and 1% penicillin-streptomycin according to ATCC protocols and plated in 24-well plates at $5\times10^4$ cells/well 24 h prior to transfection. Immediately before transfection, the growth medium was replaced with fresh serum-free medium and polyplex solution (50 μL) was added to each well (0.25 μg DNA/well).

For studies involving drug treatment (methyl-β-cyclodextrin at 10 mg/mL, chlorpromazine at 5 μg/mL, bafilomycin at 5 nM or nocodazole at 20 μM), cells were incubated with DMEM containing the drug 30 min prior to transfection. Four hours post-transfection, the cells were rinsed with PBS (0.5 mL×2) to remove surface-bound complexes. Next, trypsin in PBS (0.05%, 100 μL) was added to each well. The cells and trypsin were incubated for approximately ten minutes before formaldehyde (4%, 400 μl) was added to each well. The cells were then collected and FACS analyses were performed on a BD Biosciences LSR II flow cytometer (Franklin Lakes, N.J.). Data were analyzed using the FCS Express software package (De Novo Software, Los Angeles, Calif.). See FIGS. 42 and 43. Transfections and uptake measurements were performed in triplicate.

Dynamic Light Scattering (DNA).

DNA complexes were formed in double distilled water at various PVBLG$_{267}$-X to DNA weight ratios as indicated above. Following incubation at room temperature for 15 minutes, the complexes were diluted in water or PBS (1.8 mL) and subjected to size measurement on a Brookhaven Instruments Corporation 90 Plus Particle Size Analyzer (Holtsville, N.Y.). Five sets of measurements were performed for each sample. See FIG. 44.

Cytotoxicity Measurements.

The cytotoxicity of the PVBLG-X polymers was characterized using the MTT cell viability assay (Sigma-Aldrich, St. Louis, Mo.). Cells (COS7 or HEK293) were seeded in 96-wells plates at $1 \times 10^4$ cells/well and grown overnight at 37° C., 5% $CO_2$ in medium containing 10% horse serum and 1% penicillin-streptomycin. Approximately 24 h after seeding the medium was replaced with serum-supplemented DMEM and the uncomplexed material was added to the cells at final concentrations between 0 and 50 µg/ml. After four hours of incubation, the medium was replaced with serum-containing medium and grown for another 20 h, after which reconstituted 3-[4,5-dimethylthiazol-2-yl]-2,5-diphenyltetrazolium bromide (MTT, 10 µL) was added. The plates were then incubated for another four hours and MTT solubilization solution (100 µL, Sigma-Aldrich, St. Louis, Mo.) was added and the absorbance at 570 nm was read using a PerkinElmer plate reader (Waltham, Mass.). The background absorbance of cells killed with ethanol was subtracted from the viable cell absorbance and normalized to cells grown in DMEM. Each experiment was repeated four times at each concentration. See FIG. 45.

Large Unilamellar Vesicle (LUV) Disruption Assay.

Dioleoyl phosphatidylethanolamine (DOPE) and dioleoyl phosphatidylglycerol (DOPG) were purchased from Enzo Life Sciences. LUVs containing 60 mM calcein were prepared by the lipid film hydration method. Briefly, lipid films were made by dissolving 2 mg total lipid (8:2 DOPE:DOPG molar ratio) in 2 mL methanol followed by solvent evaporation under reduced pressure to deposit the lipid as a film on the walls of a round bottom flask. Films were hydrated with a 60 mM solution of calcein in PBS. LUVs were obtained by subjecting the solution to five freeze-thaw cycles and five passes through a 0.45 µm syringe filter. To remove unencapsulated calcein, the LUVs were passed through a size exclusion column (PD-10, GE Healthcare, Piscataway, N.J.). LUVs were stored at 4° C. and used for leakage assays within a few hours of preparation. To assay for vesicle leakage, LUVs were mixed with known concentrations of PVBLG$_{267}$-1, 8 or 9 in wells of an opaque 96-well plate and the fluorescence was recorded ($\lambda_{ex}$=485 nm, $\lambda_{em}$=535 nm). Fluorescence values were normalized to LUVs complete disrupted by incubation with 10% triton X-100.

Fluorescence Microscopy (DNA).

DNA complexes were formed at the previously determined optimum transfection weight ratio as described above. COS-7 and HEK293 cells were cultured in DMEM supplemented with 10% horse serum and 1% penicillin-streptomycin according to ATCC protocols and plated in 6-well plates containing coverslips at $20 \times 10^4$ cells/well 24 h prior to transfection. Immediately before transfection, the growth medium was replaced with fresh serum-free medium containing 250 nM calcein. PVBLG$_{267}$-8 was added to cells at 0, 15 or 50 µg/mL. Sixty minutes post-transfection, the cells were rinsed with PBS (2 mL×2) to remove surface-bound complexes and formaldehyde (4%, 1 mL) was added to each well. Following a 10 min incubation, the cells were rinsed with PBS (2 mL×2) and mounted on glass slides. Cells were visualized with a Zeiss Axiovert 40 CFL fluorescence microscope equipped with a 40× objective. See FIG. 46.

Transfection and Analysis of H9 hESCs.

DNA complexes were formed at PVBLG$_{267}$-8:DNA weight ratios between 15:1 and 30:1 as described above save for the use of pEGFP-N1 instead of pCMV-Luc. DNA complexes with Lipofectamine 2000 were prepared according to manufacturer recommendations. H9 hESCs were cultured in DMEM/F12 with 20% knockout serum replacement (KSR), 1 mM glutamine, 1% non-essential amino acid, 0.1 mM mercaptoethanol, and 4 ng/mL bFGF and plated in 24-well plates at $5 \times 10^4$ cells/well 24 h prior to transfection. Immediately before transfection, the growth medium was replaced with fresh serum-free medium and polyplex solution (50 µL) was added to each well (0.25 µg DNA/well). For studies involving nocodazole treatment (10 µM), drug was added immediately prior to transfection. Four hours post-transfection, the cells were rinsed with PBS (0.5 mL) to remove surface-bound complexes and the media was replaced with growth media and incubated for 48 hours. Prior to analysis by flow cytometry, trypsin in PBS (0.05%, 100 µL) was added to each well. The cells and trypsin were incubated for approximately ten minutes before formaldehyde (4%, 400 µL) was added to each well. The cells were then collected and FACS analyses were performed on a BD Biosciences LSR II flow cytometer (Franklin Lakes, N.J., USA). Data were analyzed using the FCS Express software package (De Novo Software, Los Angeles, Calif., USA). Transfections and uptake measurements were performed in triplicate.

Example 3. Antimicrobial Activity of Helical Polypeptides

The helical polypeptides described herein possess antibacterial properties. For example, *E. coli* cells were incubated with PVBLG-9 (shown below) at the concentrations indicated in FIG. 48 for approximately 6 hours at 37° C. The samples were then assayed for bacteria growth by reading absorbance at 650 nm, the results of which are shown in FIG. 48.

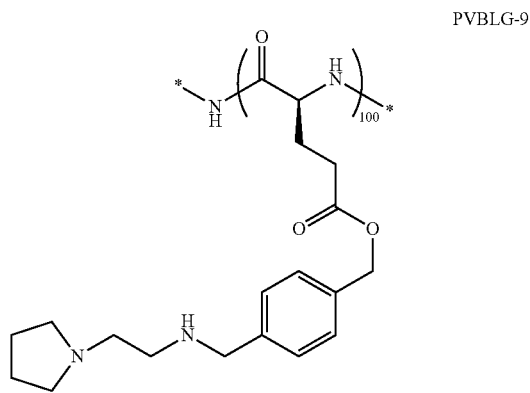

PVBLG-9

Similarly, antibacterial effects were determined by incubating E. coli with PVBLG-x11 (shown below) at the concentrations indicated in FIG. 47 for approximately 6 hours at 37° C. The samples were assayed for bacteria growth by reading absorbance at 650 nm.

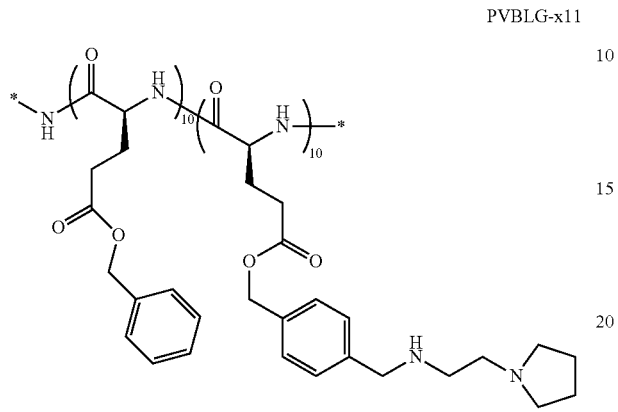

PVBLG-x11

The hemolytic potential against mammalian cells was determined by incubating mouse red blood cells with various concentrations of polymer for 1 hour at 37° C. The cells were centrifuged for 5 minutes at 1000 g to pellet intact blood cells. The absorbance of the supernatant was read at 530 nm. Results obtained from this analysis are shown in FIG. 49.

Activity of PVBLG Homopolymers.

Helical PVBLG polymers retain their α-helical structure over a wide variety of temperatures, pH and salt concentrations. α-Helical motifs are seen in many host defense peptides, therefore the potential for PVBLG-polymers to act as synthetic mimics of natural antimicrobial peptides was explored. A series of polypeptides with degrees of polymerization (n) of 100 and 267 were synthesized bearing aminohexanol (PVBLG$_n$-1), aminoethyl piperidine (PVBLG$_n$-8) or aminoethyl pyrrolidine (PVBLG$_n$-9) side chains. The R group on any PVBLG polymer can be any aliphatic or aromatic small molecule motif (e.g., allyl or benzyl), a polymer (e.g., methoxy-poly(ethylene glycol), or HMDS derivatives (e.g., H or TMS).

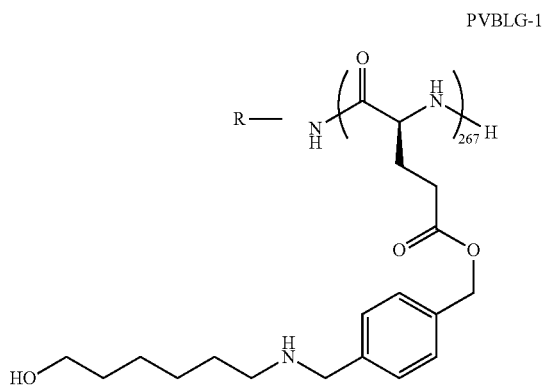

PVBLG-1

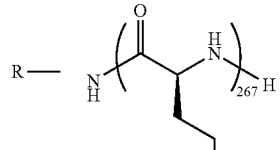

PVBLG-8

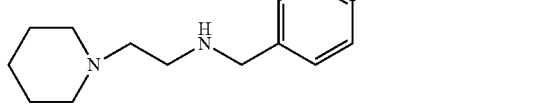

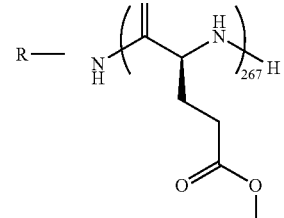

PVBLG-9

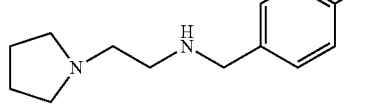

Luria broth (1×) was prepared containing known concentrations of the three polymers between 0 µg/mL and 100 µg/mL and dispensed (200 µL aliquots) in triplicate into the wells of a clear polystyrene 96-well plate. Separate wells containing the antibiotic kanamycin at 50 µg/mL were also prepared as a control. The wells were then inoculated with DHSα E. coli and left to grow at 37° C. with agitation. After seven hours, the plate was removed and the absorbance of 650 nm light was measured for each well (OD650). In general, as bacterial growth was inhibited, the resulting OD650 decreased. The average OD650 was then plotted for each sample (FIG. 50).

Neither PVBLG$_n$-1 nor PVBLG$_n$-8 displayed antimicrobial properties at concentrations up to 100 µg/mL. However, both PVBLG$_{100}$-9 and PVBLG$_{267}$-9 showed antimicrobial behavior comparable to kanamycin when added to the culture at 100 µg/mL. Moreover, the response appeared to be dose dependent, with 75 µg/ml of PVBLG$_n$-9 showing between 25-50% of the activity of a 100 µg/mL dose.

Activity of Random Copolymers.

A random PVBLG-based copolymer was made containing the aminoethyl pyrrolidine side chain shown to be effective in PVBLG$_n$-9 and 1-amino-2-butanol (copolymer 3.1, where R can be any aliphatic or aromatic small molecule motif (e.g., allyl or benzyl), a polymer (e.g., methoxy-poly(ethylene glycol), or HMDS derivatives (e.g., H or TMS); x can be about 5 to about 1000; and y can be about 5 to about 1000). Copolymers were prepared with molar ratios of aminoethyl pyrrolidine to 1-amino-2-butanol of 1.5:1, 1:1, and 0.5:1.

(3.1)

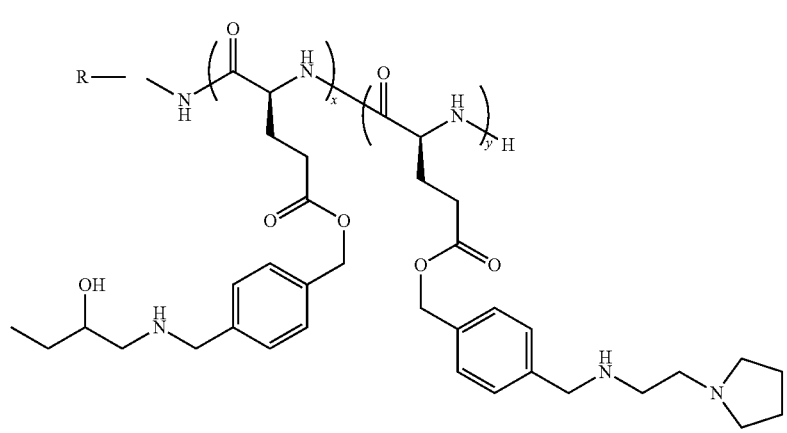

When subjected to the same antimicrobial evaluation described for the PVBLG Homopolymers above, the random copolymer was less efficient at preventing *E. coli* growth than the homopolymer PVBLG-9 (FIG. 51). Interestingly, as less 1-amino-2-butanol was incorporated into the copolymer, the more effective the resulting material was at preventing bacteria growth. This suggests that long uninterrupted blocks of aminoethyl pyrrolidine may be necessary for antimicrobial activity.

Activity of Block Copolymers.

The antimicrobial properties block copolymer derivatives of PVBLG-9 were also tested. The block copolymers synthesized contained the aminoethyl pyrrolidine proven to be effective in the PVBLG-9 homopolymer and either benzyloxy-carbonyl protected polylysine (PZLL) or polyglutamic acid (PGA), where R can be any aliphatic or aromatic small molecule motif (e.g., allyl or benzyl), a polymer (e.g., methoxy-poly(ethylene glycol), or HMDS derivatives (e.g., H or TMS).

PZLL-PVBLG-9

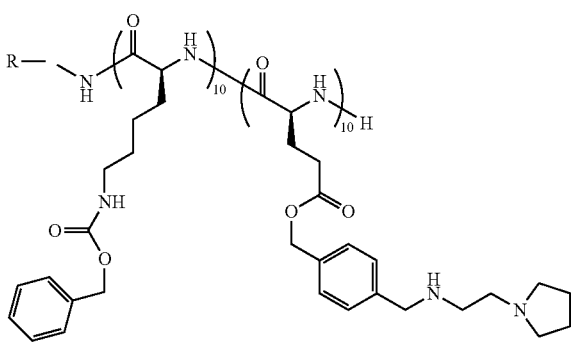

-continued

PGA-PVBLG-9

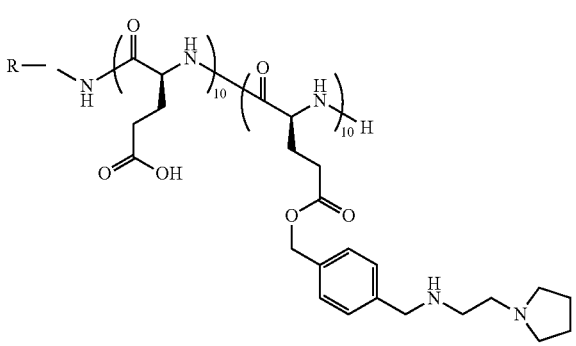

In studies to evaluate antimicrobial performance, both block copolymers displayed the ability to prevent bacteria growth (FIG. 52). Antimicrobial behavior was observed even though the total degree of polymerization in the block copolymers was 20, as compared to 100 in the PVBLG-9 homopolymer used for comparison. The ability of the block copolymer to retain its antimicrobial function indicates that PVBLG-9 based block copolymers can be functionalized and modified in a number of ways while still retaining their ability to inhibit bacterial growth.

Example 4. Stable Helical Negatively Charged Polypeptides

Stabilized helices can be extended to negatively charged polymers having side chain charges a sufficient distance (e.g., number of linear atoms or sigma bonds) from the polymer backbone. Poly(γ-(4-carboxylic acid benzyl) glutamate) was prepared from oxidative cleavage of PVBLG (m=10-100, about 50 to about 90, or about 70 in various embodiments).

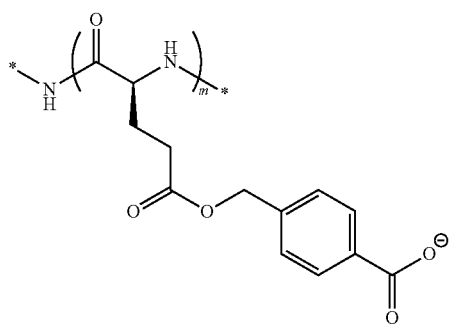

poly(γ-(4-carboxylic acid benzyl) glutamate)

In one embodiment, m=70. CD analysis of the polymer in various pH buffers (20 mM) (FIG. 53) revealed that the polymer maintains its helical conformation at each pH tested (pH=2-9).

Example 5. Additional Stable Helical Ionic Polymers of the Disclosure

In addition to the polypeptides derived from glutamic acid described above, other stable helical polymers, such as polypeptides and polyesters, can be prepared as described below.

Various Natural Amino Acid Polypeptides.

Helical ionic polypeptides can be prepared from a variety of natural amino acids such as serine and aspartic acid, as shown below in Schemes 5-1 and 5-2.

Scheme 5-1. Preparation of Poly-L-Serine Polypeptides.

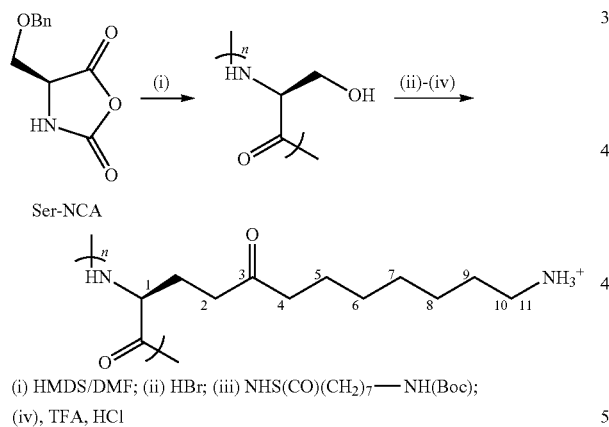

(i) HMDS/DMF; (ii) HBr; (iii) NHS(CO)(CH$_2$)$_7$—NH(Boc); (iv), TFA, HCl

Scheme 5-2. Preparation of Poly-L-Aspartate Polypeptides.

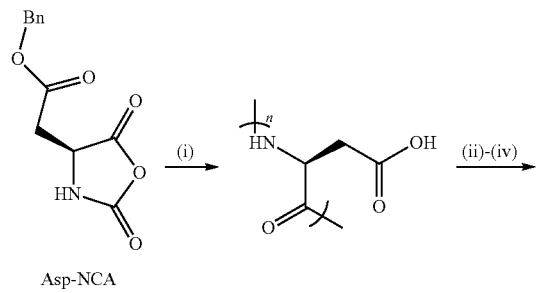

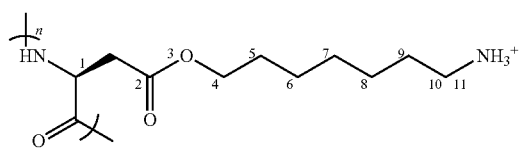

(i) HMDS/DMF; (ii) HBr; (iii) OH(CH$_2$)$_7$—NH(Boc); BOP—Cl, DMAP, (iv), TFA, HCl Unnatural amino acids can also be used to prepare helical peptides, as shown below in Scheme 5-3.

Scheme 5-3. Preparation of Non-natural Amino Acid Polypeptides.

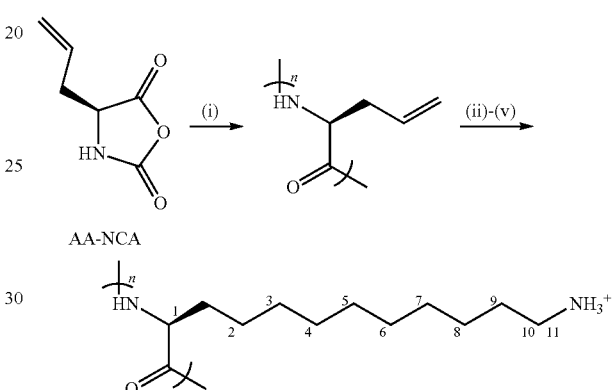

(i) HMDS/DMF; (ii) CBZ—Cl; (iii) 9-BBN; (iv) PD(PPh$_3$)$_4$, B(OMe)$_2$(CH$_2$)$_7$—NH(Boc); (v) HCl Beta-amino acids can be used to prepare helical peptides, as shown below in Scheme 5-4.

Scheme 5-4. Preparation of Beta-Amino Acid Polypeptides.

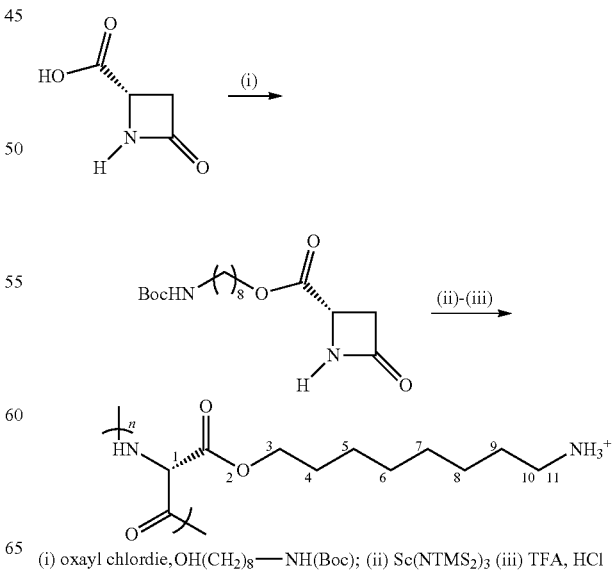

(i) oxayl chlordie, OH(CH$_2$)$_8$—NH(Boc); (ii) Sc(NTMS$_2$)$_3$ (iii) TFA, HCl Stable helical polymers can also be prepared from appropriately designed polyesters, for example, as shown below in Scheme 5-5.

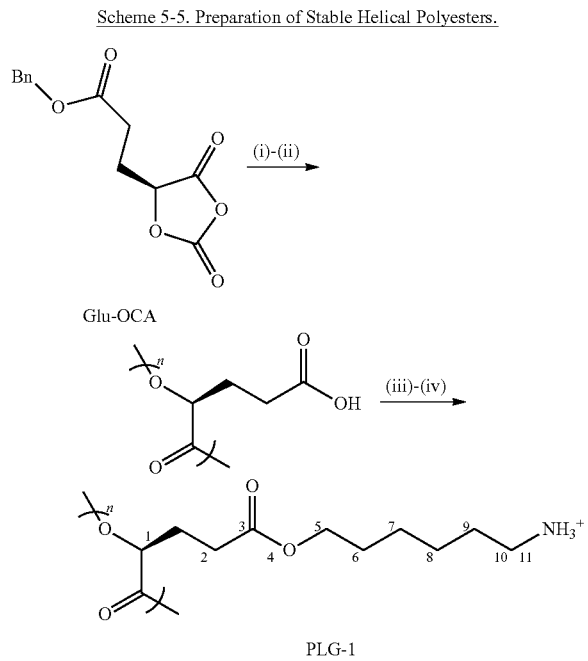

Scheme 5-5. Preparation of Stable Helical Polyesters.

Glu-OCA

PLG-1

(i) Zn(BDI)(N(TMS)$_2$), isopropanol, HMDS; (ii) hydrogen, palladium-carbon; (iii) BOP—Cl, DMAP, OH(CO)(CH$_2$)$_7$—NH(Boc); (Iv) TFA, HCl The specific side-chain lengths shown in Schemes 5-1 to 5-5 are merely representative of the various lengths of side chains that can be used to prepare stable helical polymers. Other length side chains where the charge is located at least about six atoms to about 20 atoms from the polymer backbone can be used to prepare the stable helical polymers.

Example 6. Polymer Preparation Techniques Including Controlled Ring-Opening Polymerization of γ-(4-Vinylbenzyl)-L-Glutamate N-Carboxyanhydrides Synthetic polypeptides are a class of emerging biomaterials receiving increasing interests for various applications including drug delivery, gene therapy, antimicrobial and tissue engineering (Deming, *Progress in Polymer Science* 2007, 32, 858). The ring-opening polymerization (ROP) of α-amino acid N-carboxyanhydrides (NCAs) has long been demonstrated as a powerful technique for preparation of high molecular weight (MW) synthetic polypeptides in gram scale. A number of controlled NCA polymerization system, e.g. organometallic (nickel and cobalt) catalysts developed by Deming (*Nature* 1997, 390, 386), high vacuum technique developed by Hadjichristidis (*Biomacromolecules* 2004, 5, 1653), ammonium salt initiator discovered by Schlaad (*Chemical Communications* 2003, 2944) and N-TMS amine initiators developed by Cheng (*J. Amer. Chem. Soc.* 2007, 129, 14114; 2008, 130, 12562), have been reported during the last decade. Both controlled MW and narrow molecular weight distributions (MWDs) can be achieved by these methodologies.

Although theoretically all 20 amino acids can be used for the synthesis of polypeptides via NCA polymerization, only very few polypeptides have been synthesized and extensively studied because the poor solubility of most polypeptides and the difficulty of preparing NCA monomers with satisfactory purity and yield. One successful example includes poly(γ-benzyl-L-glutamate) (PBLG) because γ-benzyl-L-glutamate NCA (Glu-NCA) is relatively easy to scale up and purify by crystallization, both Glu-NCA and PBLG are soluble in common organic solvents such as THF, chloroform and DMF, and PBLG tends to adopt helical structures and therefore shows remarkable liquid crystalline property in solution or in bulk.

To expand the library of poly(glutamates), modifying the side chain of PBLG by removing the benzyl ester and conjugating the desired side chain to the poly(glutamic acid) has been routinely practiced. However, this strategy involves the use of harsh deprotection chemistry (e.g., 33% HBr) and is nearly impossible to give rise to materials with quantitative conjugation efficiency, especially when handling high molecular-weight (MW) PBLG. An alternative method is via the synthesis and polymerization of new Glu-NCA monomers bearing the desired side chains. However, this strategy is rarely pursued due to the level of difficulty of synthesizing, purifying and handling corresponding new Glu-NCA monomers. Controlling their polymerization may vary case by case and a general strategy for preparing a large library of poly(glutamate)-like polypeptide materials has not been achieved.

An emerging approach is to develop new Glu-NCA monomers bearing high-efficiency, conjugation-amenable functional groups that can stay intact during polymerization. The moieties of interest can then be grafted to the resulting polymer via these conjugation-amenable functional groups. To date, there have been a limited set of such Glu-NCA monomers being prepared and their polymerization and utility of side chain modification being explored, exemplified by γ-propargyl-L-glutamate NCA (PP-Glu-NCA) (*Angew Chem Int Ed Engl* 2009, 48, 9334) and γ-3-chloropropanyl-L-glutamate (CP-Glu-NCA) (*Biomacromolecules* 2010, 11, 1585) functional group bearing NCAs derived from other amino acids, DL-allylglycine NCA (DL-AG-NCA) (*Macromolecules* 2010, 43, 4445) and DL-propargylglycine NCA (DL-PG-NCA) (*Synthesis-Stuttgart* 1982, 744; *Langmuir* 2007, 23, 8163) for example, are less interesting due to their racemic configuration.

As demonstrated herein, polymerization of VB-Glu-NCA is now believed to be the most versatile approaches to achieve a large number of polypeptide materials with various functionalities given the ease of handling of monomer and versatility of vinyl chemistry. The synthesis and controlled polymerization of γ-(4-vinylbenzyl)-L-glutamate N-carboxyanhydrides (VB-Glu-NCA) and use of the resulting poly(γ-(4-vinylbenzyl)-L-glutamate) (PVBLG) to prepare a variety of PBLG analogues is described below (Scheme 6-1).

Scheme 6-1. Preparation of PVBLG Polymers.

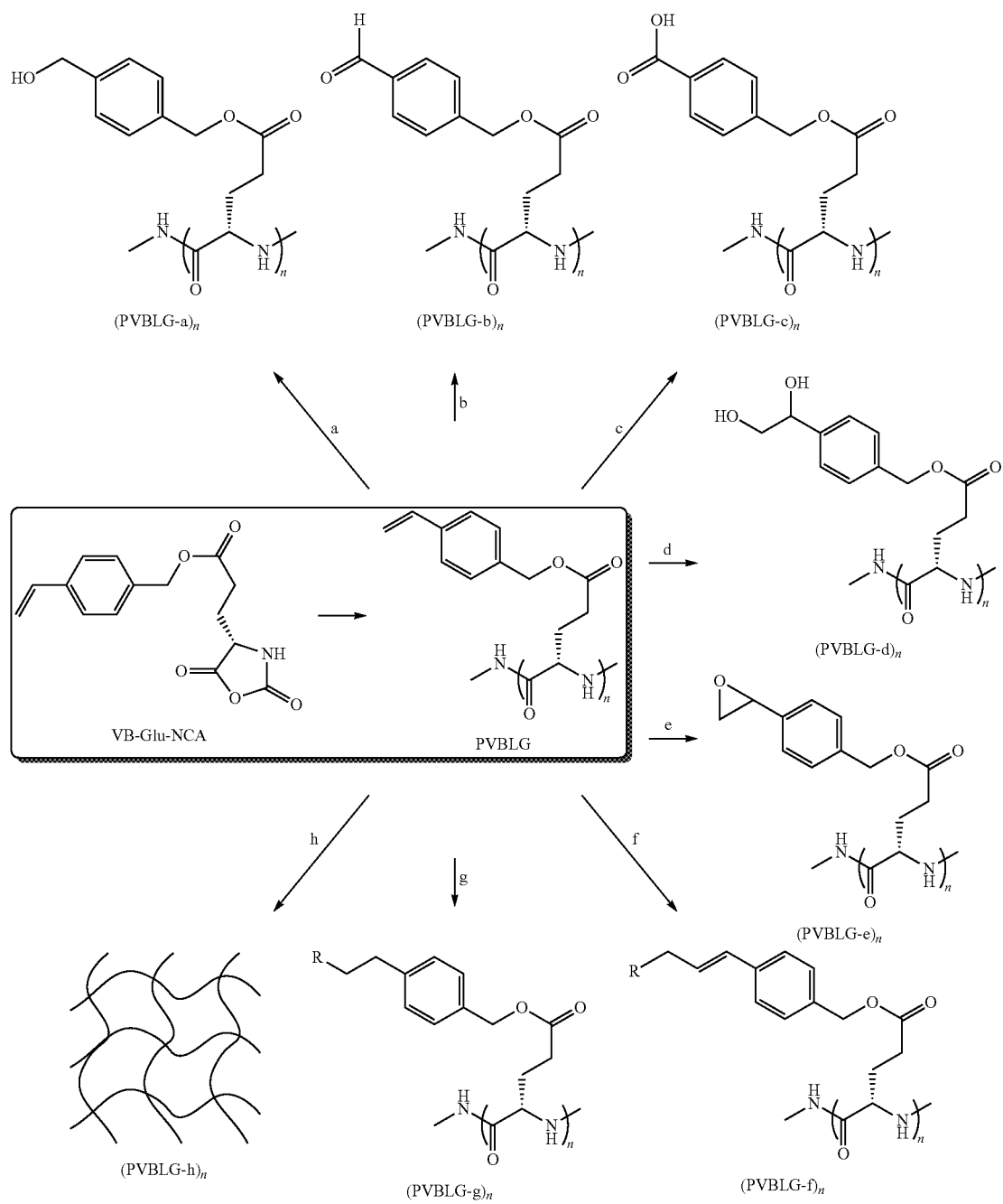

a) i. $O_3$, −78° C., 1-5 min; ii. $NaBH_4$, rt, overnight; b) i. $O_3$, −78° C., 1-5 min; ii. $P(Ph)_3$, rt, 2-3 h; c) $OsO_4$, oxone, rt, 2d; d) $OsO_4$, NMO, rt, 20 h; e) dimethyl dioxirane (in situ), rt, 1d; f) Grubbs catalyst $2^{nd}$, cis-$RCH_2$=$CH_2R$, rt, 1d; g) i. 9-BBN, rt, overnight; ii. R—Br, $Pd(PPh_3)_4$, $NaHCO_3$(aq), $N_2$, 70° C., 20 h; h) UV.

Scheme 6-1 illustrates reactions that allow conversion of a vinyl group to other useful functional groups (e.g., alcohol (route a), aldehyde (route b) and carboxylic acid (route c), 1,2-dihydroxyl (route d) and epoxy (route e)) and the use of vinyl group for metathesis (route f), Suzuki reaction via 9-BBN induced formation of reactive alkylborane species (route g) and UV crosslinking reactions (h).

VB-Glu-NCA can be readily prepared in multi-gram scales in white crystalline form. Similar to Glu-NCA, VB-Glu-NCA can be stored in glove-box at −30° C. for months with well maintained properties. At first, hexamethyldisilazane (HMDS), an initiator that gives controlled polymerization of Glu-NCA, was used for the polymerization of VB-Glu-NCA. At monomer/initiator (M/I) ratio of 50 with expected $M_n$ of $1.22 \times 10^4$ g/mol, the resulting PVBLG has an $M_n$ of $1.87 \times 10^4$ g/mol with a very broad MWD of 2.03 (Table 6-1, entry 1).

TABLE 6-1

| | | | | | | | |
|---|---|---|---|---|---|---|---|
| HMDS mediated VB-Glu-NCA polymerization. | | | | | | | |
| entry | monomer | M/HMDS/C | Cata. | NB[a] (μL) | time (h) | conv. (%) | Mn (Mn*) (×10–4)[b] | MWD |
| 1 | VB-Glu-NCA | 50/1/0 | NA | 0 | 30 | >98 | 1.87 (1.22) | 2.03 |
| 2 | Glu-NCA | 50/1/0 | NA | 30 | 8 | >98 | 1.17 (1.09) | 1.15 |
| 3 | VB-Glu-NCA | 50/1/0 | NA | 30 | 30 | >98 | 1.43 (1.22) | 1.10 |
| 4 | VB-Glu-NCA | 200/1/0.1 | NA | 30 | 40 | 67 | 3.30 (4.9) | 1.08 |
| 5 | VB-Glu-NCA | 200/1/0.1 | C1 | 30 | 20 | >98 | 3.92 (4.9) | 1.21 |
| 6 | VB-Glu-NCA | 200/1/0.1 | C2 | 30 | 24 | >98 | 4.68 (4.9) | 1.08 |
| 7 | VB-Glu-NCA | 200/1/0.5 | C3 | 30 | 40 | 90 | 4.96 (4.9) | 1.10 |
| 8 | Lys-NCA/ VB-Glu-NCA | (20/1 + 50/1)/0.02[c] | C2 | 30 | 8 + 12[d] | >98 | 0.61/2.10 (0.52/1.74)[e] | 1.05/ 1.18[f] |

[a]NB = nitrobenzene;
[b]the MW obtained (MW expected);
[c](the feeding ration of Lys-NCA/HMDS + VB-Glu-NCA/HMDS)/C;
[d]Lys-NCA reaction time + VB-Glu-NCA reaction time;
[e]the obtained MW of PZLL/PZLL-b-PVBLG (the expected MW of PZLL/PZLL-b-PVBLG);
[f]the MWD of PZLL/PZLL-b-PVBLG.

This polymerization is distinctly different from HMDS-mediated Glu-NCA polymerization under similar condition that gives PBLG with nearly perfect agreement of the expected and obtained $M_n$'s and much narrower MWD (Table 6-1, entry 2).

Next, the kinetic study of HMDS-mediated polymerizations of VB-Glu-NCA and Glu-NCA was carried out (FIG. 54). Both polymerizations showed first-order propagation rate against monomer concentration in DMF, indicating that HMDS-mediated VB-Glu-NCA has a level of control for the polymerization of VB-Glu-NCA. From the obtained bimodal gel permeation chromatography (GPC) curve (FIG. 55, larger left peak and smaller right peak), it was noted that the higher MW GPC peak only has light scattering signal but has no refractive index signal (data not shown), which indicates the existence of a small portion of very high-MW PVBLG in the solution.

Because the PVBLG is soluble in DMF and is unlikely to form physical aggregates, the formation of the high-MW PVBLG may be due to inter-chain crosslinking of vinyl groups. To confirm this view, nitrobenzene (NB), a well-known radical polymerization retarder, was added to HMDS-mediated VB-Glu-NCA polymerization solution. The initial monomer concentration in 0.5 mL solvent and the M/I ratio were fixed at 0.2 M and 50:1, while 30 μL of NB was added. The reaction was monitored by FT-IR until all the VB-Glu-NCA was consumed. As expected, crosslinking side reaction was completely inhibited. The resulting PVBLG had much narrower MWDs (1.10; Table 6-1, entry 3), as evidenced by the monomodal GPC curve (right peak) shown in FIG. 55. FIGS. 56 and 57 show plots of MW and MWD versus M/I in the HMDS/C2 initiated VB-Glu-NCA polymerization, and plots of MW and MWD versus conversion in the HMDS/C2 initiated VB-Glu-NCA polymerization, respectively. FIG. 58 shows a GPC curves overlay of PZLL20 (right peak) and block polymer PZLL20-b-PVBLG50 (left peak).

The control over the MWs of PVBLG in the presence of NB was also improved as compared to the PVBLG obtained from the polymerization without addition of NB (Table 6-1, entry 3). Polymerizations with different amount of NB gave similar MWs and narrow MWDs (FIG. 59), which demonstrates that NB primarily functions as the free radical inhibitor and has no obvious effect on the polymerization. The initial VB-Glu-NCA concentrations were evaluated and do not affect polymerization.

The polymerization of VB-Glu-NCA was then tested at selected M/I ratios (20/1, 40/1, 50/1, 70/1 and 100/1) using HMDS as the initiator. All the polymerizations were allowed to remain stirring at room temperature in a dry box until quantitative conversions were reached. Linear MW increase was obtained when the M/I was gradually elevated from 20/1 to 100/1. For example, at M/I ratio of 20/1, of the polymer was $5.33 \times 10^3$ g/mol, which is 8.8% deviation from the MW expected ($4.9 \times 10^3$ g/mol). The obtained MW grew to $1.11 \times 10^4$ g/mol, $1.43 \times 10^4$ g/mol, $1.88 \times 10^4$ g/mol and $2.55 \times 10^4$ g/mol when the feeding M/I ratios was 40/1, 50/1, 70/1 and 100/1, respectively. All the MWs obtained only slightly deviated from the MW expected. All the polymers had narrow MWD below 1.20. The Linear increase of the MW of PVLG against the increase of M/I ratio and the narrow MWD demonstrated that the polymerization in the mixture of DMF/nitrobenzene is a living polymerization.

PVBLGs with controlled MWs and narrow MWDs were achieved using HMDS/NB. However, the relatively low reactivity of VB-Glu-NCA rendered the HMDS mediated polymerization to proceed at a rate approximately 4 times lower than that of Glu-NCA polymerization. The apparent propagation constant ($k_p'$) of VB-Glu-NCA was determined to be 0.062 h$^{-1}$ from the kinetic study, as compared to the $k_p'$ of 0.272 h$^{-1}$ of Glu-NCA under similar polymerization condition. It is therefore inefficient to prepare high MW PVBLG using HMDS/NB mediated polymerization. To address this problem, the use of a co-catalyst in conjunction with HMDS/NB was attempted (Scheme 6-2).

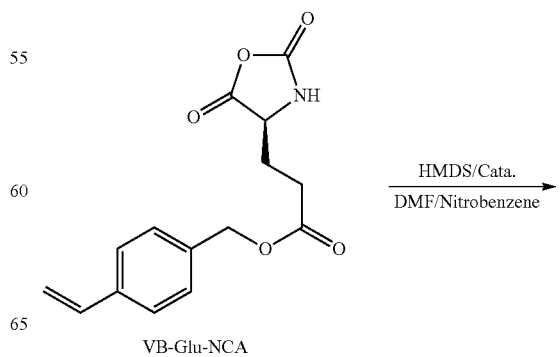

Scheme 6-2.

VB-Glu-NCA

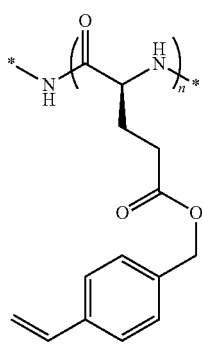

PVBLG

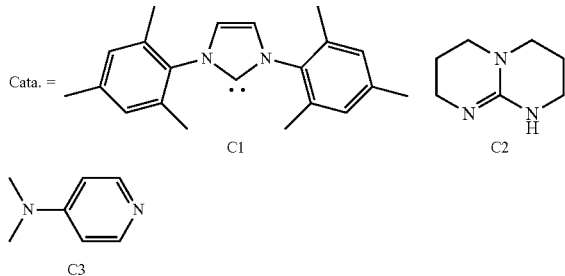

Data obtained indicated that HMDS mediated Glu-NCA polymerization proceeds via a trimethylsilyl carbamate (TMS-CBM) terminal group. Polypeptide chains were propagated through the transfer of the TMS group from the terminal TMS-CBM to the incoming monomer to form a new TMS-CBM terminal propagating group. The co-catalysts was used to promote the chain propagation by either activating the chain propagation center, which is the TMS-CBM, or by activating the VB-Glu-NCA monomer. Three co-catalysts were used: 1,3-bis(2,4,6-trimethylphenyl)imidazol-2-ylidene (NHC, C1), 1,5,7-triazabicyclo[4.4.0]dec-5-ene (TBD, C2), and 4-(dimethylamino)pyridine (DMAP, C3). These three co-catalysts are strong acylation nucleophiles and have been previously used as effective organocatalysts for lactide (LA) polymerization (Kamber et al., *Chemical Reviews* 2007, 107, 5813).

Herein, the three co-catalysts were primarily used to accelerate chain propagation by either facilitating the TMS transfer to the incoming NCA monomer by attacking the TMS-CBM carbonyl group or by activating the incoming NCA monomer. At an M/I ratio of 200/1, HMDS/NB mediated VB-Glu-NCA polymerization only gave PVBLG in 67% yield (Table 6-1, entry 4). In the presence of co-catalyst C1, C2 or C3, each polymerization was noticeably faster. HMDS/NB/C1 gave the fastest polymerization among the three tested HMDS/NB/co-catalyst mediated polymerizations. At HMDS/C1 molar ratio of 1/0.1, the reaction completed within 20 hours with quantitative monomer conversion.

GPC analysis of the reaction mixture in situ revealed that the resulting PVBLG has an $M_n$ of $3.92 \times 10^4$ g/mol and an MWD of 1.21 (Table 6-1, entry 5). The addition of C2 also promoted the reaction rate dramatically. At the HMDS/C2 molar ratio of 1/0.1, the reaction completed within 24 hours. C2 catalyzed polymerization gave excellent controlled polymerization outperforming HMDS/NB/C1 mediated VB-Glu-NCA polymerization. The PVBLG has an obtained $M_n$ of $4.68 \times 10^4$ g/mol, which is in excellent agreement with the expected $M_n$ ($4.88 \times 10^4$ g/mol), and has very narrow MWD (1.08).

HMDS/NB/C3 gave the slowest polymerization among the three tested co-catalysts. Addition of 0.5 equivalent of C3 to HMDS/NB resulted in 90% conversion of VB-Glu-NCA in 40 hours (Table 6-1, entry 6). Although HMDS/NB/C3 mediated polymerization is slower than C2 and C3, the polymerization still showed remarkable control over the MW and yielded PVBLG with very narrow MWD (Table 6-1, entry 7).

Given that the HMDS/NB/C2 gave highly effective controlled polymerization with respect to polymerization rates, control over PVBLG MW, and MWD, the polymerization of VB-Glu-NCA was performed at different M/I ratios. As shown in FIG. 1c, the obtained $M_n$'s agree nearly perfectly with the expected $M_n$'s and the resulting PVBLGs all have very narrow MWDs (1.08-1.27). The MWs of PVBLG showed linear correlation with the conversions of VB-Glu-NCA and agreed well with the expected MWs (FIG. 56), demonstrating that PBLG chains were propagated through living chain ends. Block co-polypeptides such as poly(ε-Cbz-L-Lysine)-block-PVBLG (PZLL-b-PVBLG), can be readily prepared with predictable MWs and narrow MWDs (Table 6-1, entry 8). C1 and C3 also gave the results of linear MW growth traversing the tested VB-Glu-NCA/HMDS ratio from 20/1 to 250/1, indicating that the dual-catalyst systems (HMDS/NB/C1-C3) mediate well controlled, living polymerization of VB-Glu-NCA. Data obtained using various catalysts are provided below in Tables 6-2 to 6-6.

TABLE 6-2

HMDS and C1 mediated VB-Glu-NCA polymerization.

C1

| entry | NCA/HMDS/C | time (h) | conv. (%) | Mn (Mn*) (×10-3)$^a$ | MWD |
|---|---|---|---|---|---|
| 1 | 20/1/0.04 | 8 | >98 | 6.25 (4.9) | 1.45 |
| 2 | 20/1/0.01 | 10 | >98 | 5.51 (4.9) | 1.30 |
| 3 | 50/1/0.1 | 10 | >98 | 15.5 (12.2) | 1.48 |
| 4 | 50/1/0.025 | 10 | >98 | 11.9 (12.2) | 1.37 |
| 5 | 100/1/0.1 | 12 | >98 | 22.9 (24.5) | 1.31 |
| 6 | 150/1/0.1 | 18 | >98 | 31.7 (36.8) | 1.23 |
| 7 | 200/1/0.1 | 20 | >98 | 39.2 (49) | 1.21 |

$^a$Mn = MW obtained and Mn* = MW expected.

TABLE 6-3

HMDS and C2 mediated VB-Glu-NCA polymerization.

C2

| entry | NCA/HMDS/C | time (h) | conv. (%) | Mn (Mn*) (×10-3)$^a$ | MWD |
|---|---|---|---|---|---|
| 1 | 20/1/0.04 | 10 | >98 | 7.03 (4.9) | 1.60 |
| 2 | 20/1/0.01 | 10 | >98 | 4.76 (4.9) | 1.21 |
| 3 | 50/1/0.1 | 12 | >98 | 16.1 (12.2) | 1.41 |
| 4 | 50/1/0.05 | 15 | 95 | 15.1 (12.2) | 1.31 |
| 5 | 50/1/0.025 | 20 | >98 | 10.1 (12.2) | 1.27 |
| 6 | 100/1/0.1 | 18 | >98 | 27.8 (24.5) | 1.20 |
| 7 | 200/1/0.1 | 24 | >98 | 46.8 (49) | 1.08 |
| 8 | 250/1/0.05 | 32 | >98 | 67.5 (61.2) | 1.15 |

$^a$Mn = MW obtained and Mn* = MW expected.

TABLE 6-4

HMDS and C3 mediated VB-Glu-NCA polymerization.

C3: (structure of 4-dimethylaminopyridine-like compound)

| entry | NCA/HMDS/C | time (h) | conv. (%) | Mn (Mn*) (×10−3)[a] | MWD |
|---|---|---|---|---|---|
| 1 | 20/1/0.04 | 12 | >98 | 5.33 (4.9) | 1.21 |
| 2 | 50/1/0.1 | 12 | >98 | 15.5 (12.2) | 1.25 |
| 3 | 100/1/0.1 | 24 | 90 | 22.5 (24.5) | 1.03 |
| 4 | 150/1/0.1 | 36 | 88 | 33.1 (36.8) | 1.06 |
| 5 | 200/1/0.5 | 40 | 90 | 49.6 (49) | 1.10 |

[a]Mn = MW obtained and Mn* = MW expected.

TABLE 6-5

HMDS and C4 mediated VB-Glu-NCA polymerization.

C4: tetrabutylammonium iodide (Bu$_4$N$^+$ I$^-$)

| entry | NCA/HMDS/C | time (h) | conv. (%) | Mn (Mn*) (×10−3)[a] | MWD |
|---|---|---|---|---|---|
| 1 | 20/1/0.4 | 10 | >98 | 5.89 (4.9) | 1.19 |
| 2 | 50/1/0.5 | 12 | >98 | 15.3 (12.2) | 1.09 |
| 3 | 100/1/1 | 20 | 92 | 20.2 (24.5) | 1.07 |
| 4 | 150/1/0.5 | 24 | 80 | 28.5 (36.8) | 1.06 |
| 5 | 200/1/0.6 | 40 | 78 | 45.1 (49) | 1.06 |

[a]Mn = MW obtained and Mn* = MW expected.

TABLE 6-6

HMDS and C5 mediated VB-Glu-NCA polymerization.

C5: (3,5-bis(trifluoromethyl)phenyl thiourea)

| entry | NCA/HMDS/C | time (h) | conv. (%) | Mn (Mn*) (×10−3)[a] | MWD |
|---|---|---|---|---|---|
| 1 | 20/1/0.4 | 10 | >98 | 6.58 (4.9) | 1.17 |
| 2 | 50/1/0.5 | 12 | >98 | 15.6 (12.2) | 1.09 |
| 3 | 100/1/1 | 20 | 88 | 22.5 (24.5) | 1.06 |
| 4 | 150/1/0.5 | 24 | 77 | 29.2 (36.8) | 1.05 |
| 5 | 200/1/0.6 | 40 | 75 | 40.6 (49) | 1.05 |

[a]Mn = MW obtained and Mn* = MW expected.

Each reaction illustrated in Scheme 6-1 was then carried out, to further explore the scope and versatility of the vinyl group chemistry of PVBLG. The N-terminus of the PVBLG was capped by a CBZ group immediately after the polymerization to prevent possible side reactions. The PVBLG polymer reacted smoothly in an ozonolysis reaction. After the polymer was treated by ozone, the vinyl group was converted to an alcohol (route a) and an aldehyde (route b), when sodium borohydride or triphenylphosphine was used as the reducing reagent, respectively. The vinyl group on the PVBLG was converted to carboxylic acid under mild condition by osmium tetroxide-promoted catalytic oxidative cleavage of the olefin (route c). In this reaction, osmium tetraoxide was added as the catalyst and oxone was used as the oxidative reagent (see J. Amer. Chem. Soc. 2002, 124, 3824).

1,2-Bishydroxylation of the olefin was performed by following osmium tetraoxide catalyzed oxidative addition in the presence of morpholine N-oxide (route d), resulting in a water-soluble PBLG analogue because of the large quantity of hydroxyl groups on the side chain. To introduce an expoxy group to the polymer, a PVBLG solution was treated with in situ generated dimethyl dioxirane under mild condition (route e). Olefin metathesis reaction of PVBLG was also carried out (route f). By mixing the polymer solution in dichloromethane with excessive cis-1,4-dichlorobutene in the presence of the secondary generation Grubbs catalyst, allyl chloride functionalized polypeptide was exclusively generated. The reaction completed within 2 days with nearly quantitative grafting density.

Carbon-carbon bond formation has long been an intriguing topic in synthetic chemistry. Organometallic catalysts can promote C—C bond coupling reactions, such as the Heck reaction, the Suzuki reaction, and the Sonogashira reaction, each of which have been utilized in small molecule synthesis. However, those reactions are rarely employed in polymer modification. By taking advantage of the vinyl group on PVBLG, those reactions can be used to modify polypeptides polymers. For instance, reaction of 9-borabicyclo[3.3.1]nonane (9-BBN) with PVBLG double bond was observed to quantitatively convert the vinyl group to borane species, which can be subsequently coupled with 4'-bromoacetophenone in situ through palladium catalyzed Suzuki coupling reaction (route g). This two-step reaction not only gives reasonably high yield but also a complete transfunctionalization as confirmed by $^1$H NMR. Given the broad availability of commercial aromatic halides, route e can be used as a general method for grafting aromatic compounds to the PBLG.

The polymer can also undergo UV initiated crosslinking to form an organogel or hydrogel (route h), which can be useful in many research areas involving the use of network polypeptides such as energy transfer, solar cell and light harvesting (Chem. Soc. Rev. 2008, 37, 109). Moderate to high yields were received for all the reactions above and the efficiencies of transfunctionalization were all above 90%, as confirmed by $^1$H NMR (Table 6-7).

TABLE 6-7

VB-Glu-NCA polymerization mediated by (bpy)Ni(COD) in the presence of NB at various M/I ratios.

| entry | M/I | time (h) | conv. (%) | solvent | Mn (Mn*) (×10−3)[a] | MWD |
|---|---|---|---|---|---|---|
| 1 | 20 | 3 | >98 | DMF/NB | 12.2 (4.9) | 1.11 |
| 2 | 50 | 4 | >98 | DMF/NB | 29.9 (12.2) | 1.22 |
| 3 | 100 | 16 | >98 | DMF/NB | 38.6 (24.5) | 1.23 |
| 4 | 150 | 16 | >98 | DMF/NB | 60.8 (36.7) | 1.21 |
| 5 | 200 | 18 | 95 | DMF/NB | 71.6 (49.0) | 1.18 |
| 6 | 20 | 3 | >98 | THF/NB | 15.0 (4.9) | 1.36 |
| 7 | 50 | 4 | >98 | THF/NB | 24.5 (12.2) | 1.29 |
| 8 | 100 | 6 | >98 | THF/NB | 34.7 (24.5) | 1.15 |
| 9 | 150 | 16 | >98 | THF/NB | 42.2 (36.7) | 1.11 |
| 10 | 200 | 20 | >98 | THF/NB | 68.0 (49.0) | 1.06 |

[a]Mn = MW obtained and Mn* = MW expected.

The purifications of the polymers were also generally straightforward as described in the experimental sections below. Small molecular reactants can be removed by washing with ether or methanol, or dialysis against water for water-soluble PBLG analogues such as compound 3.

Materials.

Chemicals were purchased from Sigma-Aldrich (St. Louis, Mo.) and used as received unless otherwise specified.

Anhydrous dimethylformamide (DMF) was dried by a column packed with 4 Å molecular sieves and stored in a glove box. Tetrahydrofuran (THF) and hexane were dried by a column packed with alumina and stored in a glove box. Dry nitrobenzene was prepared by treating regular nitrobenzene by $CaH_2$ followed by distillation under reduced pressure. H-Lys(Z)—OH and H-Glu(OBn)-OH were purchased from Chem-Impex International (Des Plaines, Ill.) and used as received. Glu-NCA and Lys-NCA were prepared by following previously reported procedures (Lu and Cheng, *J. Amer. Chem. Soc.* 2007, 129, 14114). $Ni(COD)_2$ was purchased from Strem Chemical Inc. (Newburyport, Mass.). 2,2'-Bipyridine was purified by sublimation under vacuum.

Instrumentation.

NMR spectra were recorded on a Varian UI400 MHz, a UI500NB MHz or a VXR-500 MHz spectrometer. Tandem gel permeation chromatography (GPC) experiments were performed on a system equipped with an isocratic pump (Model 1100, Agilent Technology, Santa Clara, Calif.), a DAWN HELEOS 18-angle laser light scattering detector (also known as multi-angle laser light scattering (MALLS) detector, Wyatt Technology, Santa Barbara, Calif.) and an Optilab rEX refractive index detector (Wyatt Technology, Santa Barbara, Calif.). The detection wavelength of HELEOS was set at 658 nm.

Separations were performed using serially connected size exclusion columns (100 Å, 500 Å, $10^3$ Å and $10^4$ Å Phenogel columns, 5 μm, 300×7.8 mm, Phenomenex, Torrance, Calif.) at 60° C. using DMF containing 0.1 M LiBr as the mobile phase. The MALLS detector was calibrated using pure toluene with no need for external polymer standards and can be used for the determination of the absolute molecular weights. The molecular weights (MWs) of polymers were determined based on the dn/dc value of each sample calculated offline by using the internal calibration system processed by the ASTRA V software (version 5.1.7.3, Wyatt Technology, Santa Barbara, Calif.).

Infrared spectra were recorded on a Perkin Elmer 100 serial FTIR spectrophotometer calibrated with polystyrene film. Circular dichroism (CD) measurements were carried out on a JASCO J-700 or a JASCO 720 CD Spectrometer. Ozone was produced by an OZV-8S ozone generator manufactured by Ozone Solutions Inc. (Hull, Iowa). Lyophilization was performed on a FreeZone lyophilizer (Labconco, Kansas City, Mo.). UV light was generated from an OmiCure S 1000 UV lamp (EXFO, Mississauga, Canada).

Compound Preparation.

The synthesis of γ-(4-vinylbenzyl)-L-glutamate NCA (VB-Glu-NCA) and the general procedure for the VB-Glu-NCA polymerization were carried out as described in Example 1 above.

PVBLG Reactions (Scheme 6-1).

Protocol of Route a:

PVBLG (45 mg, 0.18 mmol) was dissolved in chloroform (15 mL) at −78° C. Oxygen ($O_2$) was bubbled into the solution for 1 min followed by bubbling of $O_3$ until the solution became blue indicating the reaction was completed. Ozone ($O_3$) was then replaced by $O_2$, which was bubbled into the solution for another 2 min until the solution became colorless. The solution was then degassed and back filled with nitrogen. $NaBH_4$ (95 mg, 2.5 mmol) was then added to the mixture. The solution was stirred at room temperature overnight and solvent was removed under vacuum. The residue oil was treated by cold water (10 mL) and stirred at rt for 1 h. The polymer was collected by filtration and washed twice by DI water (5 mL×2). The resulting product was freeze dried to give 33 mg white solid, yield 72%.

Protocol of Route b:

PVBLG (49 mg, 0.2 mmol) was dissolved in chloroform (15 mL) at −78° C. $O_2$ was bubbled into the solution for 1 min followed by bubbling of $O_3$ until the solution became blue indicating the reaction was completed. $O_3$ was then replaced by $O_2$, which was bubbled into the solution for another 2 min until the solution became colorless. The solution was then degassed and back filled with nitrogen. $Ph_3P$ (131 mg, 0.5 mmol) was then added to the mixture. The solution was stirred at room temperature for 2-3 h and solvent was removed under vacuum. The resulting poly(γ-(4-aldehydebenzyl)-L-glutamate) (PABLG) was purified by adding methanol followed by sonication (3×15 mL) to remove unreacted $Ph_3P$ and other impurities. 39 mg PABLG was successfully obtained after vacuum dry, yield 78%.

Protocol of Route c:

To the solution of $PVBLG_{70}$ (20 mg, 0.08 mmol vinyl) in DMF (1 mL), was added $O_5O_4$ (2.5 wt. % in tert-butanol, 0.1 mL) and oxone (614 mg, 2 mmol). The mixture was stirred at rt for 2 days. The excess oxone was quenched by $Na_2SO_3$ (200 mg, 1.6 mmol in 5 mL water). The solution was tuned to slightly basic by 2M $NaHCO_3$ solution and purified by dialysis against water and dried by lyophilize to give 17 mg of white solid (yield 81%). Informative techniques are reported by Travis et al., *J. Amer. Chem. Soc.* 2002, 124, 3824-3825.

Protocol of Route d:

$PVBLG_{70}$ (25 mg, 0.1 mmol vinyl) and $OsO_4$ (2.5 wt. % in tert-butanol, 0.1 mL), morpholine N-oxide (NMO) (57 mg, 0.49 mmol) was stirred in acetone/$H_2O$ (v/v:10/1, 1.5 mL total) mixture for 20 h. The excess NMO was treated by $Na_2SO_3$ solution (126 mg, 1 mmol in 5 mL water). The solution was purified by dialysis against water and dried by lyophilize to give 22 mg of white solid (yield 79%).

Protocol of Route e:

In an ice bath, to the mixture of vigorously stirred acetone (1.0 mL) and aqueous $NaHCO_3$ solution (1.0 g in 2.0 mL water) in a 20 mL capped vial, was added the solid oxone (1.1 g, 3.6 mmol) during a time period of 3 min. The vial was opened only when oxone was added. The mixture was stirred for another 5 min followed by addition of $PVBLG_{70}$ (25 mg, 0.1 mmol vinyl) in DCM (2 mL). The mixture was vigorously stirred for 24 h. another portion of DCM (2 mL) and DI water (5 mL) were added to dilute the mixture. The organic phase was collected and washed by brine (3 mL) once. The DCM solution was dried in $Na_2SO_4$ and concentrated under vacuum. 18 mg of white solid was obtained, yield 69%.

Protocol of Route f:

Grubbs catalyst ($2^{nd}$ generation, 2 mg, ca. 0.0025 mmol) and cis-1,4-dichloro-2-butene (0.2 mL, 1.9 mmol) was dissolved in 2 mL dry DCM in glove box. $PVBLG_{70}$ (25 mg, 0.1 mmol vinyl group) was added to the mixture via syringe. The solution was stirred at rt for 24 h. After the reaction was completed, solvent was removed under vacuum. The residue was washed by ether (10 mL) twice and dried under vacuum to give light yellow oil 23 mg (yield 78%).

Protocol of Route g:

$PVBLG_{70}$ (25 mg, 0.1 mmol vinyl) and 9-BBN (1 mL×0.5 M in THF) were mixed in dry THF (1 mL) under nitrogen. The solution was stirred at rt overnight. Under protection of nitrogen, to the solution was added $Pd(PPh_3)_4$ (2 mg, ca. 0.0017 mmol), 4'-bromoacetophenone (100 mg, 0.5 mmol) and 3 M aqueous $NaHCO_3$ solution (1 mL). The mixture was stirred in a 70° C. oil bath for 20 h. The organic phase was collected, washed by brine solution (10 mL), dried by $Na_2SO_4$, and concentrated under vacuum. The resulting product was washed by ether twice (10 mL) to remove small organic molecules. The residue was dried under vacuum to give 22 mg of oil, 2 step yield 60%.

Protocol of Route h:

$PVBLG_{70}$ (25 mg, 0.1 mmol vinyl) was dissolved in THF (0.5 mL) containing 0.1% 12959 in a 7 mL glass vial. The solution was exposed to UV (365 nm, 10% intensity of the source power) for 10 min and an organogel was formed.

General Procedure for Synthesis of PZLL-b-PVBLG (PVLG$_{20}$-b-PVBLG$_{50}$).

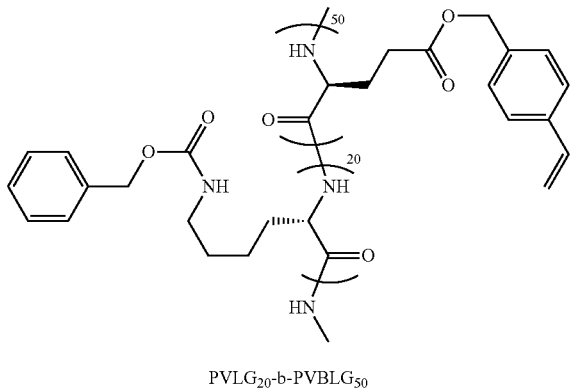

PVLG$_{20}$-b-PVBLG$_{50}$

In a glove box, Lys-NCA (61 mg, 0.2 mmol) was dissolved in dry DMF (1.0 mL). HMDS stock solution in DMF (0.1M×100 μL) was added to the solution under stirring. The reaction was let stirred overnight and an aliquot of the solution was taken out for GPC analysis. VB-Glu-NCA (145 mg, 0.5 mmol) dissolved in DMF/NB (1 M×100 μL) was added to the rest of the PZLL polymer solution. C2 (0.01 M×20 μL) was then added to the mixture. The mixture was monitored by FT-IR and taken out of box until all the VB-Glu-NCA was consumed. An aliquot of the solution was injected into GPC for MW and MWD analysis. The rest solution was treated by TBAF (0.1M×50 μL), diisopropylethylamine (10 μL) and benzyl chloroformate (20 μL) to cap the N-terminus. The solution was allowed to stir at room temperature for 2-3 h followed by removing majority of the solvent under vacuum. The residue was precipitated with ether (30 mL). The obtained PZLL-b-PVBLG was sonicated for 5 min in ether and centrifuged to remove the solvent. After the sonication-centrifugation procedure was repeated two more times, PVBLG was collected and dried under vacuum. 108 mg polymer was obtained; yield 62%.

General Procedure for Synthesis of PZLL-b-PABLG.

The ozonolysis of poly(ε-Cbz-L-lysine)-block-poly(γ-(4-vinylbenzyl-L-glutamate) (PZLL-b-PABLG) to generate poly(ε-Cbz-L-lysine)-block-poly(γ-(4-aldehydebenzyl-L-glutamate) (PZLL-b-PABLG) was performed by following the same protocol as ozonolysis of PVBLG homopolymer.

Hydrolysis Kinetic Study of PVBLG-1.

PBS (100 μL, 10×) was freeze dried followed by dissolving in 1 mL D$_2$O to prepare PBS/D$_2$O (1×). (PVBLG-1)$_{40}$ (10 mg) was dissolved by PBS/D$_2$O (1×) and incubated at room temperature. The hydrolysis was monitored by $^1$H NMR. See FIG. 60.

General Procedure for the Analysis of Polymers by Circular Dichroism (CD).

The CD study was performed on a JASCO J-700 and J-720 CD spectrometer. Polymer samples were prepared at a concentration of 0.05 mg/mL in general unless otherwise specified. The solution was placed in a quartz disc with light path of 0.5 cm. Mean residue molar ellipticity was calculated based on the ellipticity obtained, concentration of polymer and the molar weight of the repeating unit. See FIG. 61.

MTT Assay:

HeLa was used as the cell line for MTT assay. Cells were counted and seeded (10,000 cells/well) in a 96-well-plate and incubated for 24 h before adding the polymers. Cells were further incubated for 72 h after treating with polymer solutions at different concentrations. Polymer solutions were removed and cells were washed by PBS. MTT reagent was then added and incubated at 37° C. for 4 h. MTT solubilizer solution was then added to the plate and shaken for 10 min. Cell viability was examined by a Perkin Elmer 1420 multilable counter. See FIG. 62.

Example 7. Mammalian Cell Penetration and DNA Transfection by Cationic α-Helical Polypeptides Gene therapy has emerged as a promising approach for the treatment or prevention of acquired and genetic diseases. Development of safe and efficient gene transfer methods/vectors is the most crucial demand in achieving clinical success for gene therapy. Described above is a strategy for the facile generation of cationic and helical polypeptides. The helical structure was stabilized by increasing the hydrophobic interaction of the side chains. Based on this strategy, a library of cationic polypeptides with different amine-containing groups on the side chains were screened for gene transfer, and the top-performing PVBLG-8 demonstrated distinguished potentials for non-viral gene delivery. Motivated by these findings, the penetration and DNA transfection efficiency of the PVBLG-8 were evaluated in a variety of mammalian cell lines that are resistant to cationic lipid-mediated transfection.

Polypeptides penetrate cell membranes via clathrin-mediated endocytosis as well as non-endocytosis. After condensing the oppositely charged DNA into ~150 nm complexes, they extend the stability of the nucleic acid against DNase hydrolysis and deliver it into intracellular compartments including the nuclei in a more effective manner than Lipofectamine. Accordingly, polypeptide/DNA complexes demonstrate a 4-165-fold elevation in transfection efficiencies compared to Lipofectamine/DNA complexes in all test cell lines. Furthermore, the polypeptide exhibited desired cytotoxicity as assessed by the MTT assay. These findings indicate that the α-helical cationic polypeptide can overcome some of the key limitations of currently used transfection agents and shows great potentials for further application.

Introduction.

Non-viral vectors have significant potential for gene delivery due to their desired biocompatibility, low immunogenicity, and amenability to scale-up compared to viral vectors. Commercially available cationic lipid reagents serve as a representative example that are widely used to transfect nucleic acids in mammalian cell culture. However, the effectiveness of these reagents demonstrates great cell line dependence, and a number of cell lines including some carcinoma cell, neuron, T cell, fibroblast, epithelia, and endothelia have shown resistance to them in terms of transfection. Additionally, unpredictable cytotoxicity raises another limit for these cationic lipids. Various problems still remain for suitable and effective gene delivery including the generality, cytotoxicity, stability, simplicity as well as reproducibility in preparation, and liability to scale-up. Therefore, the development of novel gene transfection reagents that are easily prepared, stable, non-toxic, and widely applicable to a variety of cell lines is needed.

A library of cationic and helical polypeptides based on controlled polymerization of NCA monomers and side chain functionalization was described above. The helical structure can be stabilized by increasing the hydrophobic interaction of the side chains, which was achieved by maintaining a minimum separation distance of 11 σ-bonds between the polypeptide backbone and the side chain charge. Considering their cationic properties that can condense DNA, the library of polypeptides was screened for non-viral gene transfer. PVBLG-8 displayed desired efficacy in COS-7 cells, which was presumably attributed to its capacity in inducing membrane disruption. In light of its potentials in gene delivery, the generality of this polypeptide was evaluated in terms of cell penetration and gene transfection, aiming at developing an effective and biocompatible gene transfer vector.

The cell-penetrating and DNA transfection efficiencies of cationic α-helical polypeptide in a variety of cell lines is described herein, including several cell lines known to be resistant to cationic lipid-mediated transfection. Plasmid DNA encoding luciferase was used as the model gene to evaluate the in vitro transfection efficiency, and the capacity of the polypeptide in condensing DNA and improving the DNA stability was investigated. Furthermore, a detailed mechanistic assessment was also performed to elucidate the internalization pathway of the polypeptide and polypeptide/DNA complexes.

Materials and Cell Lines.

All chemicals were purchased from Sigma-Aldrich (St. Louis, Mo.) and used as received unless otherwise specified. VB-L-Glu-NCA and VB-D-Glu-NCA was prepared and polymerized according to procedures described above. Pierce BCA assay kits were purchased from ThermoFisher Scientific (Rockford, Ill.). Plasmid DNA encoding luciferase (pCMV-Luc) was purchased from Elim Biopharm (USA), and Bright-Glo Luciferase assay reagent was from Promega (Madison, Wis.). Lipofectamine 2000 (LFA) and YOYO-1 were purchased from Invitrogen (Carlsbad, Calif.).

HepG-2 (human hepatocellular carcinoma), Raw264.7 (mouse monocyte macrophage), 3T3-L1 (mouse embryonic fibroblast), Caco-2 (human colon carcinoma), and HeLa (human cervix adenocarcinoma), A549 (human lung carcinoma), and HUVEC (human umbilical vein endothelial cell) were purchased from the American Type Culture Collection (Rockville, Md., USA). HepG-2, Raw264.7, 3T3-L1, Caco-2, and HeLa cells were cultured in Dulbecco's Modified Eagle Medium (DMEM) (Gibco, Grand Island, N.Y., USA) containing 10% fetal bovine serum (FBS). A549 cells were cultured in Nutrient Mixture F-12 Ham's Kaighn's Modification (F12-K) containing 10% fetal bovine serum (FBS). HUVEC cells were cultured in F12-K media containing 0.1 mg/ml heparin; 0.05 mg/ml endothelial cell growth supplement (ECGS, Sigma), and 10% FBS.

Synthesis and Characterization of PVBLG-8

A representative polymerization of VB-L-Glu-NCA is as follows. Inside a glove-box, VB-L-Glu-NCA (100 mg, 0.167 mmol) was dissolved in 2 mL DMF (2.0 mL), followed by addition of nitrobenzene (60 μL) and HMDS solution (0.1 M, dissolved in DMF). FTIR was used to monitor the polymerization until the conversion was above 99% (~48 h). Tetrabutylammonium fluoride solution (0.2 mL, 1.0 M) and benzyl chloroformate (0.4 mL, 2.8 mmol) was added to cleavage the N—Si bond and protect the amino end groups. The resulting polymer (Poly(γ-(4-aldehydebenzyl-L-glutamate)) was precipitated from cold methanol and collected by centrifuge.

Poly(γ-(4-aldehydebenzyl-L-glutamate) (50 mg) was dissolved in 2 mL DMF, and 1-(2-Aminoethyl)piperidine (10 molar equivalents relative to the Glu repeating unit) was added and stirred at 50° C. for 24 h. Borane pyridine as the reducing agent (5-10 molar equivalents) was added, and the resulting solutions was further stirred at 50° C. for 24 h. 3 M HCl (3 mL) was then added to protonate the amine groups, and the soluble polypeptide was dialyzed against water before lyophilization.

PVB-D,L-G-8 with random coil structure was copolymerized from VB-L-Glu-NCA and VB-D-Glu-NCA at a molar ratio of 1:1 via the same approach as described for PVBLG-8.

Polymerization degree of the obtained polypeptide was calculated according the molecular weight (MW) of the Poly(γ-(4-aldehydebenzyl-L-glutamate) determined by gel permeation chromatography (GPC). The system was equipped with an isocratic pump (Model 1100, Agilent Technology, Santa Clara, Calif., USA), a DAWN HELEOS multi-angle laser light scattering detector (MALLS) detector, Wyatt Technology, Santa Barbara, Calif., USA) and an Optilab rEX refractive index detector (Wyatt Technology, Santa Barbara, Calif., USA). The detection wavelength of HELEOS was set at 658 nm. Separations were performed using serially connected size exclusion columns (100 Å, 500 Å, $10^3$ Å and $10^4$ Å Phenogel columns, 5 μm, 300×7.8 mm, Phenomenex, Torrance, Calif., USA) at 60° C. using DMF containing 0.1 M LiBr as the mobile phase. The MALLS detector is calibrated using pure toluene with no need for calibration using polymer standards and can be used for the determination of the absolute molecular weights (MWs). The MWs of polymers were determined based on the do/dc value of each polymer sample calculated offline by using the internal calibration system processed by the ASTRA V software (version 5.1.7.3, Wyatt Technology, Santa Barbara, Calif., USA).

Scheme 7-1. Polymerization scheme of PVBLG-8 from VB-L-Glu-NCA.

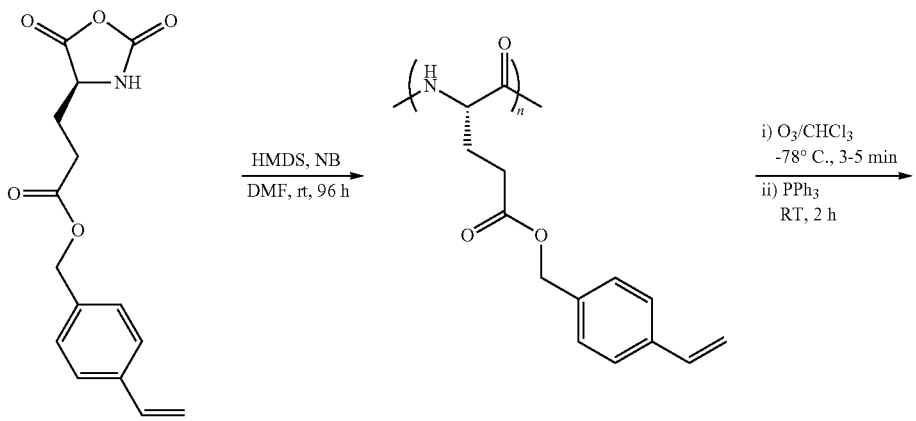

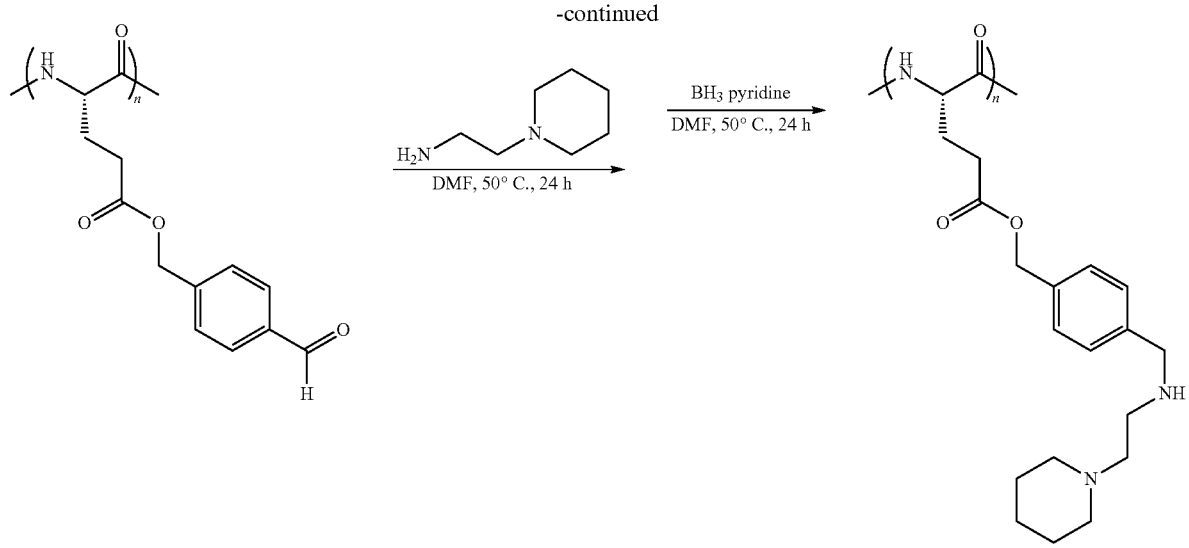

TABLE 7-1

Polymerization and characterization of polypeptides.

| Entry | monomer | M/HMDS | time (d) | DP | Mn ($\times 10^4$)$^a$ | MWD |
|---|---|---|---|---|---|---|
| 1 | VB-$_L$-Glu-NCA | 50 | 2 | 50 | 1.23 | 1.05 |
| 2 | VB-$_L$-Glu-NCA | 130 | 2 | 164 | 40.2 | 1.10 |
| 3 | VB-$_L$-Glu-NCA | 200 | 2 | 195 | 4.77 | 1.05 |
| 4 | VB-$_L$-Glu-NCA VB-$_D$-Glu-NCA | 50 | 2 | 53 | 1.30 | 1.33 |
| 5 | VB-$_L$-Glu-NCA VB-$_D$-Glu-NCA | 130 | 2 | 139 | 3.40 | 1.08 |
| 6 | VB-$_L$-Glu-NCA VB-$_D$-Glu-NCA | 200 | 2 | 214 | 5.25 | 1.08 |

Synthesis of Rhodamine Labeled PVBLG-8 (RhB-PVBLG-8)

Rhodamine isothiocyanate and ethylenediamine were dissolved in DMF at the molar ratio of 1:20. TEA was added (5 molar equivalents to the amine group), and the reaction was allowed to proceed at RT for 24 h from light. Residual ethylenediamine and DMF were removed by vacuum-drying, and the polymer was washed 3 times with ether to completely get rid of residual ethylenediamine, thus achieving the RhB—NH$_2$.

Poly(γ-(4-aldehydebenzyl-L-glutamate) (50 mg) was dissolved in 2 mL DMF, into which a mixture of RhB—NH$_2$ and 1-(2-Aminoethyl)piperidine (molar ratio 1:20) was added. The reaction was allowed at 50° C. for 24 h, borane pyridine as the reducing agent (5-10 molar equivalents) was added, and the resulting solutions was further stirred at 50° C. for 24 h. 3 M HCl (3 mL) was then added to protonate the amine groups, and the soluble RhB-PVBLG-8 was dialyzed against water before lyophilization.

Cell Uptake of RhB-PVBLG-8.

Cells were seeded on 96-well plates at 1×10$^4$ cells/well and cultured for 24 h or 48 h before they reached confluence. The medium was refreshed with serum-free DMEM, and RhB-PVBLG-8 was added at 2 μg/well. Rhodamine-labeled PLL and TAMRA-Arg9 were used as internal control. After incubation at 37° C. for determined time, the cells were washed with cold PBS containing 20 U/mL heparin for 3 times, which could completely remove surface-bound cationic proteins from cells (McNaughton et al. (2009) Mammalian cell penetration, siRNA transfection, and DNA transfection by supercharged proteins. Proc. Natl. Acad. Sci. USA 106:6111-6116). Cells were then lysed with RIPA lysis buffer at RT for 20 min before assessment of RhB-PVBLG-8 content by spectrofluorometry and protein level using the BCA kit. Uptake level was expressed as μg RhB-PVBLG-8 associated with 1 mg of cellular protein.

To explore the mechanism involved in polypeptide-mediated penetration, cells were pre-incubated with endocytosis inhibitor chlorpromazine (10 μg/mL), dynasore (80 μM), genistein (200 μg/mL), methyl-β-cyclodextran (5 mM), and wortmannin (10 μg/mL) for 30 min prior to polypeptide application and throughout the 2-h uptake experiment at 37° C. To block all energy-dependent endocytosis, uptake study was performed at 4° C. Results were expressed as percentage uptake of the control where cells were incubated with RhB-PVBLG-8 at 37° C. for 2 h.

CLSM Imaging.

HeLa cells were seeded on glass coverslips placed in 6-well plates at 1×10$^5$ cells/well and cultured for 24 h followed by refreshment of the medium with serum-free DMEM and addition of RhB-PVBLG$_{200}$-8 at 20 μg/well. After incubation at 37° C. for 0.5, 1, and 2 h, respectively, the medium was discarded and cells were washed with cold heparin-containing PBS for three times before fixation with 4% PFA, nuclei staining with DAPI, mounting in Prolong Gold, and CLSM visualization.

Stability of PVBLG-8 Against Proteolytic Hydrolysis.

To assess stability of PVBLG-8 against proteinase K, 100 pmol of polypeptide or BSA was treated with 0.6 units of proteinase K (New England Biosciences) at 37° C. The samples were mixed with SDS protein loading buffer, heated to 90° C. for 10 minutes, which were subsequently analyzed by SDS-PAGE on an 18% acrylamide gel (Promega). Following staining with Coomassie Blue and de-staining in water overnight, polypeptide bands were imaged by gel documentation.

Preparation and Characterization of PVBLG-8/DNA Complexes.

PVBLG-8 and pCMV-Luc were separately dissolved in water at 1 mg/mL and mixed at various weight ratios. The mixture was vortexed for 5 s and incubated at 37° C. for 30 min to allow DNA condensation and complex formation. PVBLG-8/pDNA complexes were subjected to electrophoresis in 2% agarose gel at 100 mV for 45 min to evaluate DNA condensation by PVBLG-8 in terms of DNA migration. Freshly prepared complexes were also evaluated for particle size and Zeta potential on a Malvern Zetasizer. To explore the stability of the complexes, they were diluted with PBS (pH 6.5, 7.0, 7.4) for 10 fold and incubated at 37° C. for determined time before particle size and Zeta potential assessment.

Enzymatic Stability of DNA.

Stability of DNA towards degradation by DNase I was evaluated based on the hyperchromic effect. Briefly, polypeptide/DNA complexes (15:1) were mixed with DNase I was added at 1 U/ug DNA, and OD260 of the mixture was monitored continuously at 37° C. Naked DNA treated with DNase I served as a positive control.

Cell Uptake of PVBLG-8/DNA Complexes.

Cells were seeded on 96-well plates at $1 \times 10^4$ cells/well and cultured for 24 h or 48 h before they reached confluence. DNA was labeled with YOYO-1 at one dye molecule per 50 bp DNA (Reitan N K, et al. (2009) Characterizing DNA Condensation by Structurally Different Chitosans of Variable Gene Transfer Efficacy; *Biomacromolecules* 10:1508-1515), which was allowed to form complexes with PVBLG-8 at the optimal weight ratio of 15:1. As controls, PLL/DNA complexes were formed at 15:1 (w/w), and Lipofectamine/DNA complexes were prepared according to the manufacture's protocol. The medium was replaced by serum-free DMEM, and complexes were added at 0.1 µg DNA/well. After incubation at 37° C. for determined time, the cells were washed with cold PBS containing 20 U/mL heparin for 3 times and lysed with RIPA lysis buffer at RT for 20 min. RhB-PVBLG-8 content in the lysate was monitored by spectrofluorometry and protein level was quantified using the BCA kit. Uptake level was expressed as ng YOYO-1-DNA associated with 1 mg of cellular protein.

To explore the mechanism underlying internalization of PVBLG-8/DNA complexes, the uptake study was performed at 4° C. or in the presence of various endocytic inhibitors as described above. Internalization and subcellular distribution of RhB-PVBLG-8/YOYO-1-DNA complexes in HeLa cells were further visualized by CLSM. Cells seeded on coverslips in 6-well plates were treated with complexes at 1 µg DNA/well. Following incubation for 0.5, 1, and 2 h, cells were washed with PBS, fixed in 4% PFA, nuclei-stained with DAPI, and observed by CLSM.

In Vitro Transfection.

Cells were seeded on 96-well plates at $1 \times 10^4$ cells/well and cultured for 24 h or 48 h before they reached confluence. The medium was replaced with serum-free DMEM, into which complexes were added at 0.1 µg pDNA/well. After incubation at 37° C. for 4 h, the medium was replaced by serum-containing media and cells were further incubated for 24 before evaluation of luciferase production using the Bright-Glo Luciferase kit (Promega). Protein content in the cell lysate was quantified using the BCA kit, and results were expressed as relative luminescence unit (RLU) associated with 1 mg cellular protein. PLL/DNA complexes (15:1) and Lipofectamine/DNA complexes were used as controls.

Cytotoxicity.

Cells were seeded on 96-well plates at $1 \times 10^4$ cells/well and cultured for 24 h or 48 h before they reached confluence. The medium was replaced with serum-free DMEM, into which polypeptides or polypeptide/DNA complexes were added at determined polypeptide content (10, 5, 2, 1, 0.5 µg/well). After incubation at 37° C. for 4 h, the medium was aspirated and refreshed with serum-containing media. Cells were further incubated for 24 h before viability assessment using the MTT assay.

Results and Discussion.

Mammalian Cell Penetration by Cationic α-Helical PVBLG-8.

With HMDS as the initiator, a well-controlled polymerization of VB-L-Glu-NCA was allowed to produce soluble PVBLG-8 with well-defined Mw and low PDI (Table 7-1). Notable characteristic negative ellipticity minima at 208 nm and 222 nm in CD spectra clearly confirmed α-helical conformation of the polypeptide. With an attempt to study the effect of polypeptide conformation in terms of cell penetration and transfection, VB-L-Glu-NCA and VB-D-Glu-NCA at a molar ratio of 1:1 were copolymerized to obtain polypeptides with minimized helicity and random-coil structure. By co-grafting Rhodamine-NH$_2$ onto the side chain, evaluation of polypeptide penetration was enabled both qualitatively and quantitatively using spectrofluorometry, flow cytometry, and CLSM.

As illustrated in FIGS. 63 to 65, PVBLG-8 effectively penetrated all the test cell lines which increased with incubation time. An increase in the polymer DP led to notably elevated cell uptake level of the polypeptide, and random-coiled polypeptide demonstrated significantly lower cell penetration level than α-helical peptide.

In a further step, CLSM images were used to visualize the penetration and intracellular distribution of PVBLG$_{200}$ in HeLa cells. Punctated foci with red fluorescence were noted in the cytoplasm and on the nucleus periphery 0.5 h post incubation, which was typical morphology for endocytosis that involved vesicle formation. As incubation was prolonged to 1 h, the punctuated foci migrated towards the interior of the cell and some of them trafficked inside the nuclei, indicating that the polypeptide could not only penetrate the cell membrane but also conquer the nucleus membrane. At 2 h post incubation, higher amount of red fluorescence could be seen inside the cells and some of them formed clusters, indicating that the polypeptide might induce pore formation on cell membranes and thereafter passively permeate via the pores apart from the endocytic route.

Characterization of Complexes.

Figure 66A:
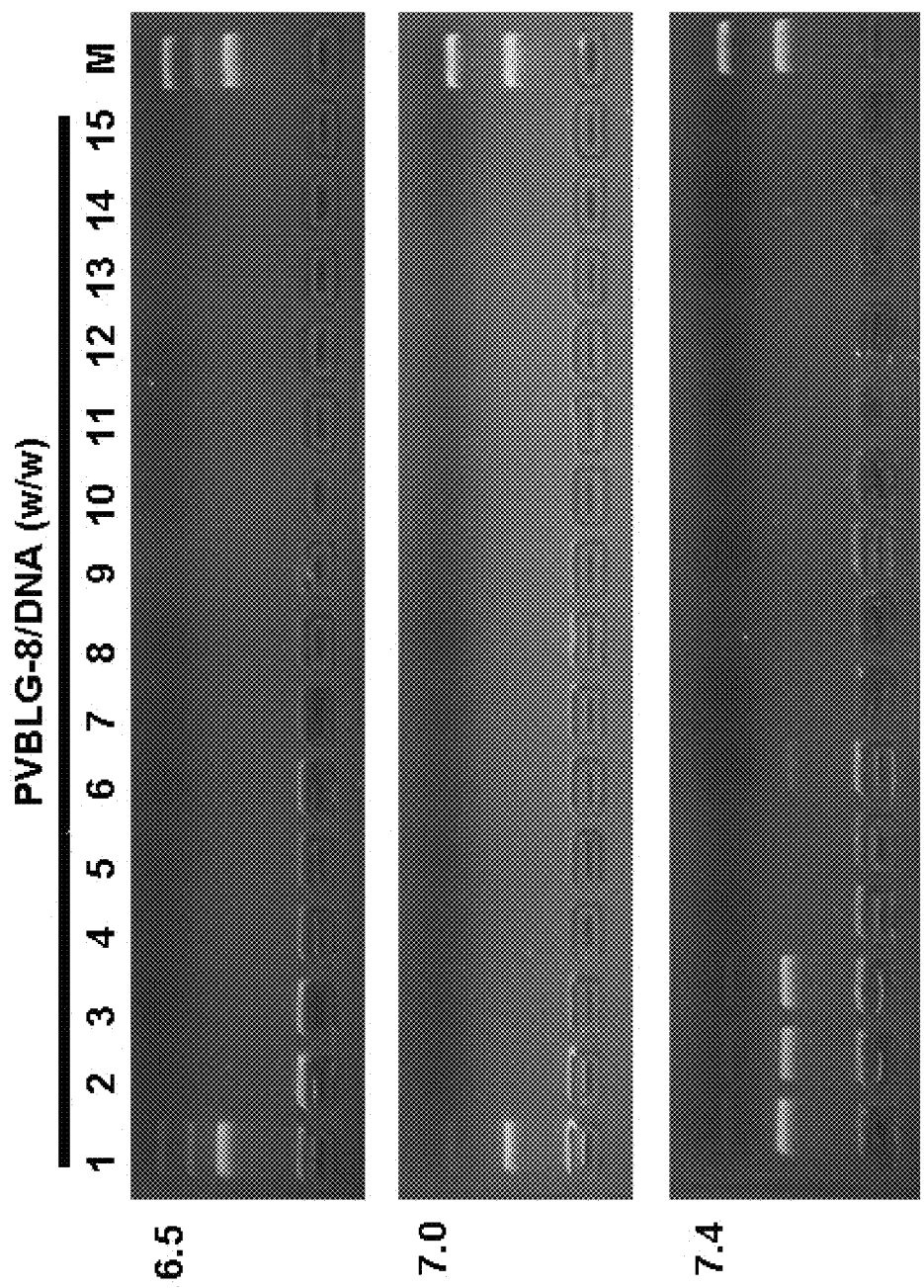
Figure 66B:
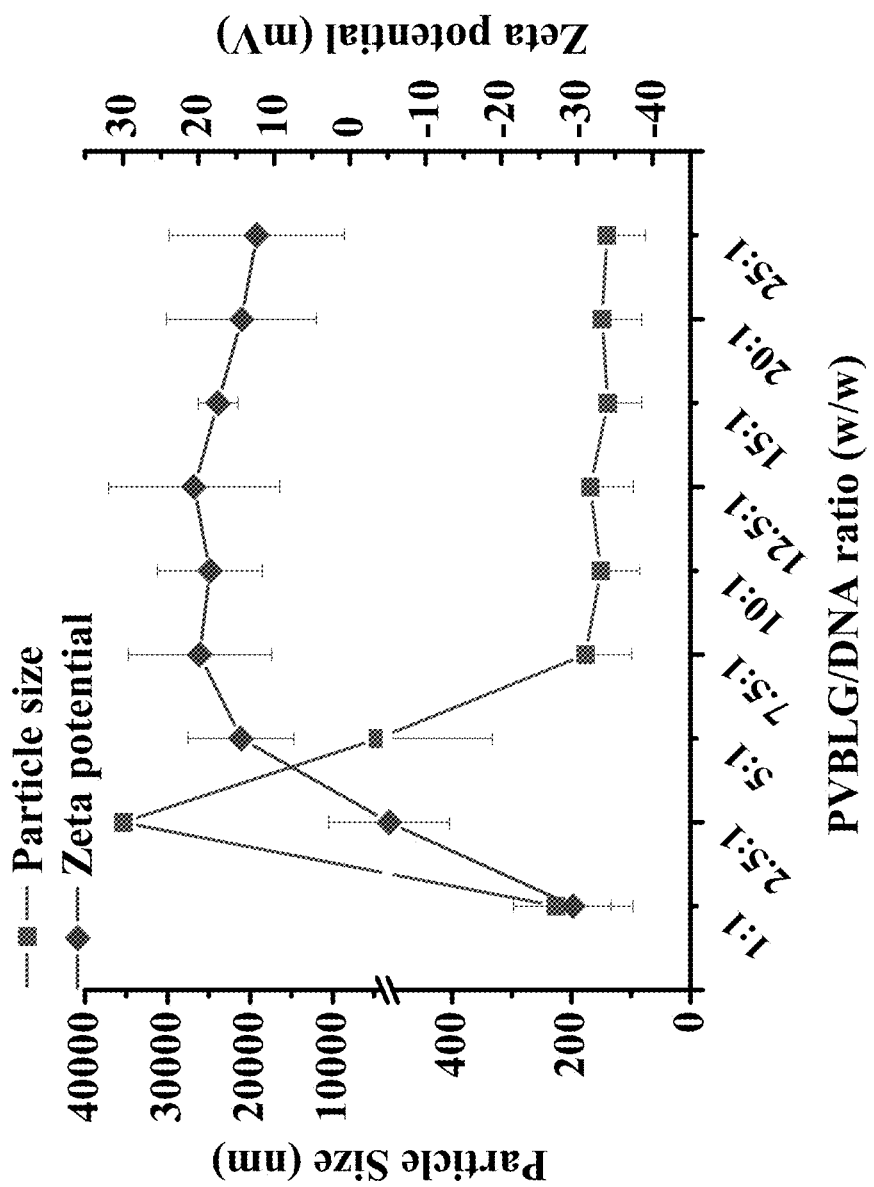

A gel retardation assay was adopted to evaluate DNA condensation by cationic PVBLG-8 (FIG. 66A). At pH 6.5 and 7.0, PVBLG-8 completely retarded DNA migration in 2% agarose gel and restricted it in the loading well at polypeptide/DNA weight ratio higher than 1:1. When the pH was increased to 7.4, higher weight ratio of 3:1 was needed to retard DNA migration, which can be attributed to partial deprotonation of side amine groups that decreased the positive charge density of PVBLG-8. Size and Zeta potential were further measured to characterize the PVBLG-8/DNA complexes (FIG. 66B). As the polypeptide/DNA weight ratio increased from 1:1 to 10:1, particle size remarkable decreased to approximately 150 nm while surface charge increased from negative to positive (~15 mV), which confirmed condensation of DNA and formation of homogenous nano-complexes.

Stability of Complexes.

Figure 66C:
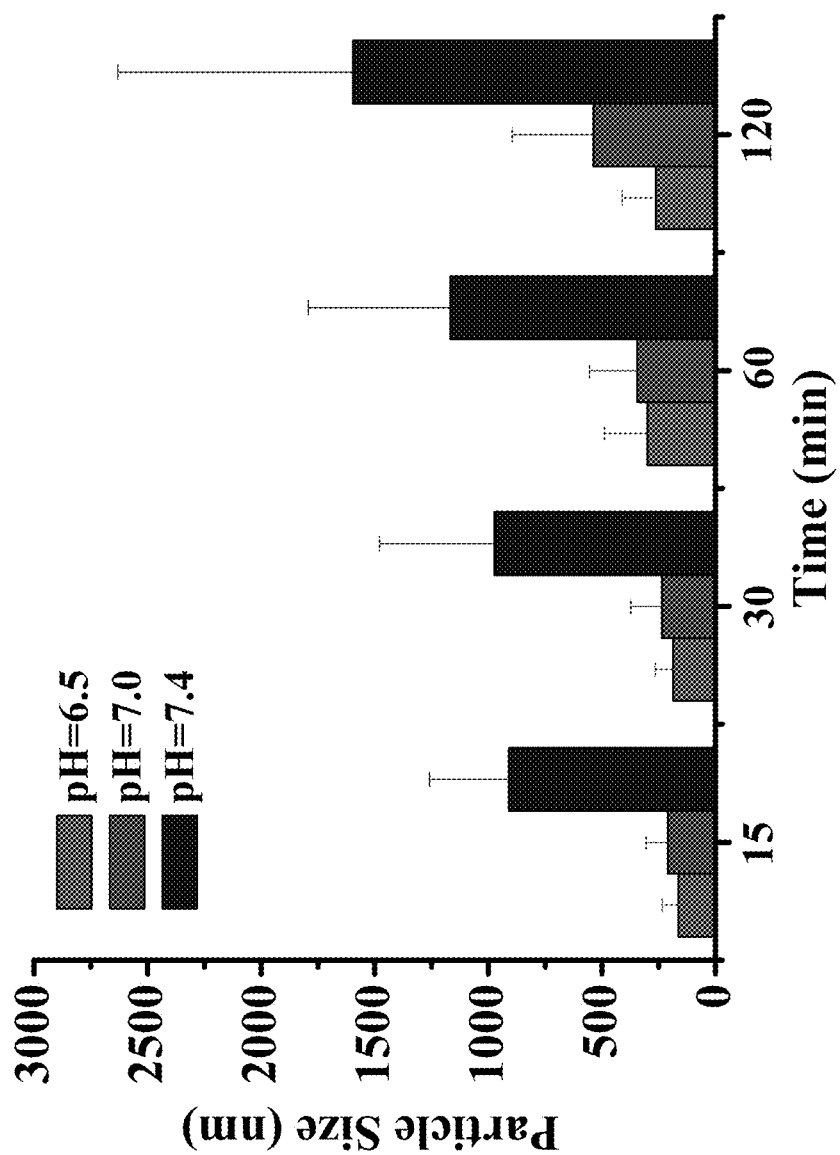
Figure 66D:
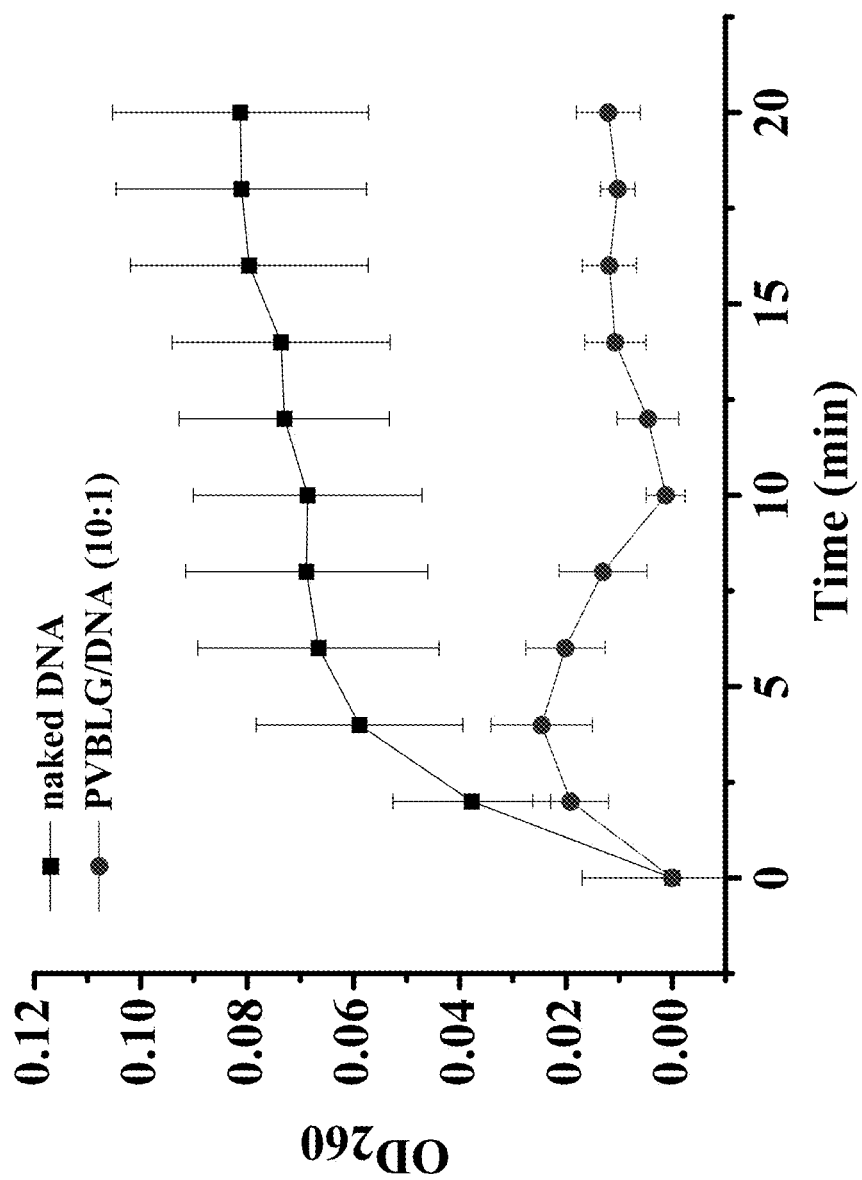

In the context of both in vitro transfection and in vivo gene therapy, complexes would be subject to extensive dilution either by the cell culture media or physiological fluid. Therefore, it necessitated the assessment on the complex stability against dilution with salt-containing solution. From this point of view, PVBLG-8/DNA complexes (10:1) were diluted with DMEM (pH 6.5, 7.0, and 7.4) by 10 fold and the particle size was monitored following incubation for determined time intervals. As shown in FIG. 66C, particle size maintained constant upon dilution with pH 6.5 DMEM and slightly increased in response to pH 7.0 DMEM, indicating good stability of the complex against both ionic strength and dilution. Nevertheless, dilution with pH 7.4 DMEM significantly increased complex diameter to micron-scale, which can be ascribed to heavy loss of the cationic density on the polypeptide and weakened binding towards DNA.

Intracellular Delivery of DNA into a Variety of Mammalian Cell Lines.

Figure 67A:
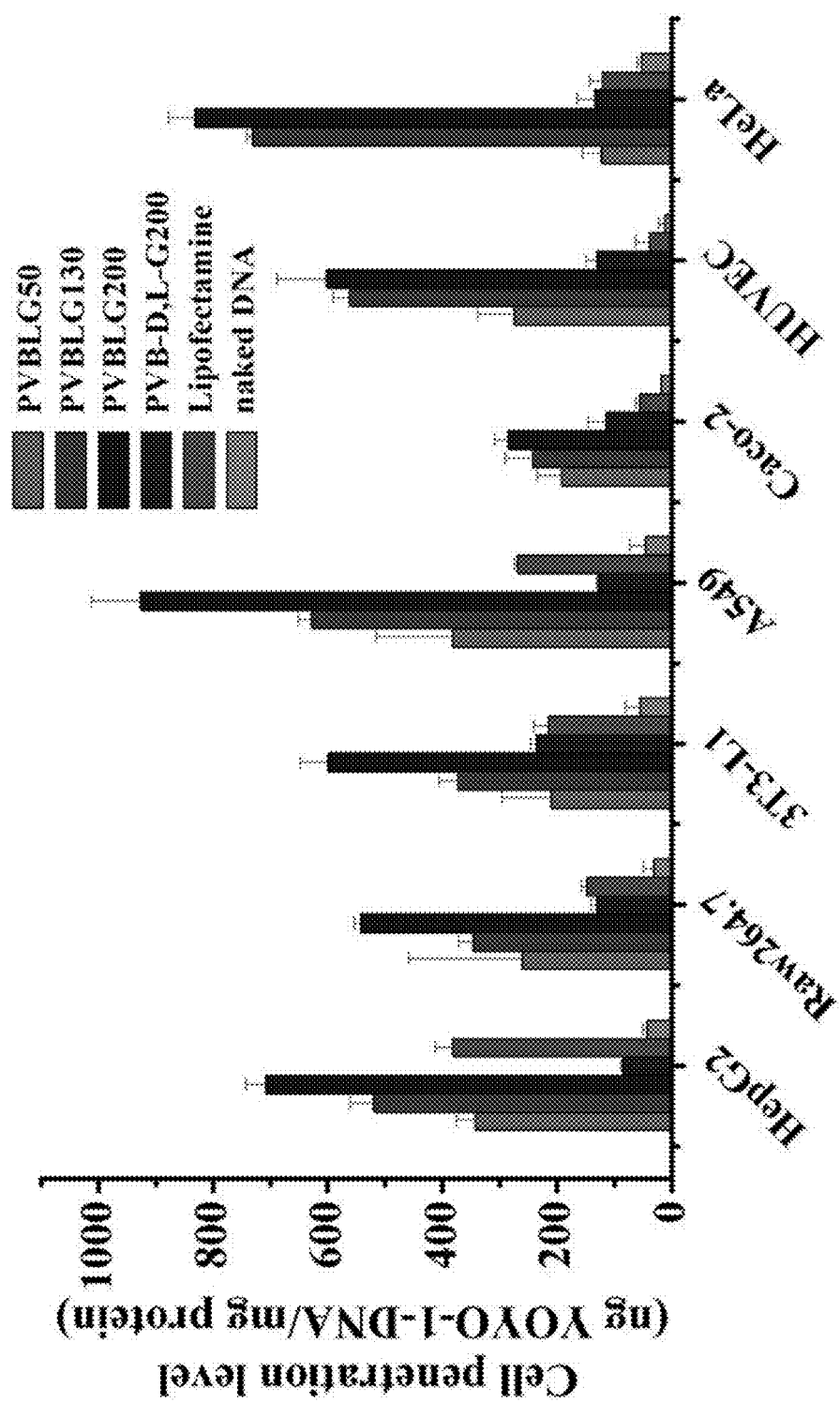
Figure 67B:
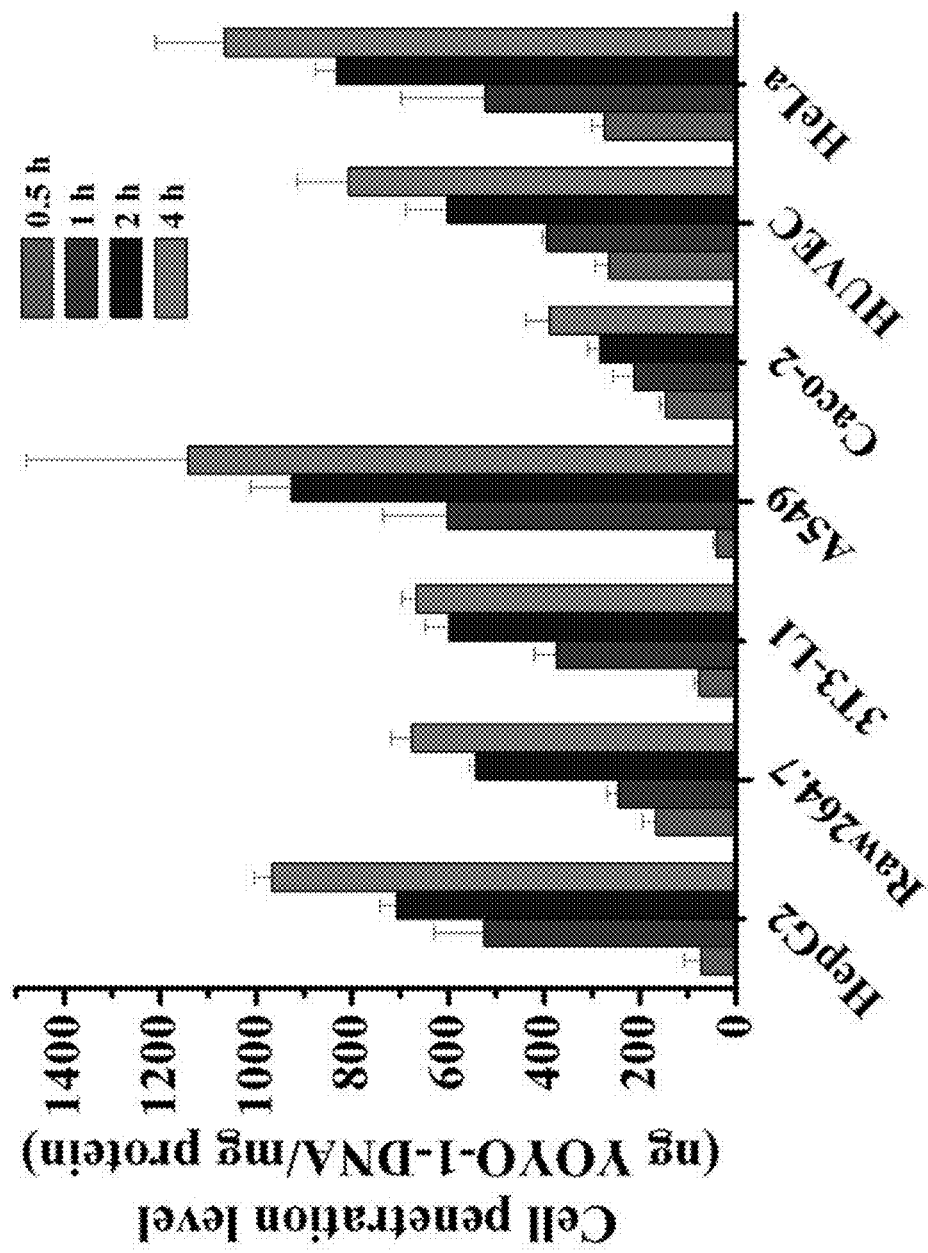
Figure 67C:
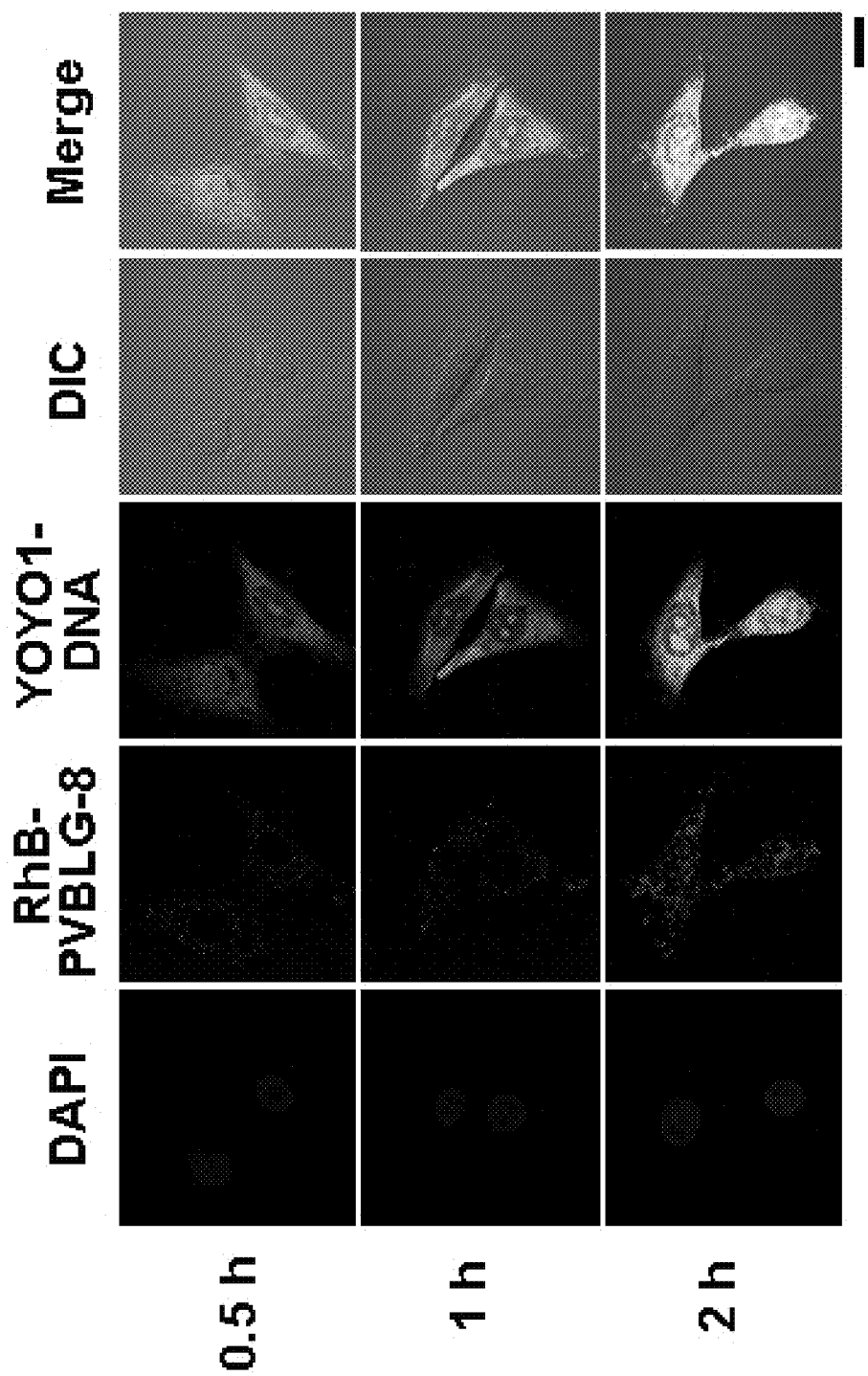

In light of the cell penetration capacity of PVBLG-8 in variety of mammalian cell lines, it was determined that PVBLG-8 can also facilitate the intracellular delivery of DNA after condensing it into nanocomplexes. DNA was labeled with YOYO-1 to allow visualization and quantification of the cell uptake level. As illustrated in FIGS. 67A and B, the cell penetrating PVBLG-8 delivered DNA intracellularly in a more effective manner than Lipofectamine. Consistently, polypeptide with higher PD corresponded to augmented DNA uptake level, and PVBLG with α-helical structure notably outperformed PVBDLG with random-coil structure. Such results again confirmed the essential role of α-helical conformation in overcoming the cell membrane barrier. CLSM images further substantiated uptake of the complexes in HeLa cells (FIG. 67C) as evidenced by distribution of green fluorescence in the entire cells. It was also noted that a large amount of DNA had been delivered to the nuclei 2 h post incubation, indicating that PVBLG-8 were also capable of conquering the nucleus membrane and would thereafter facilitate gene transcription by nucleus-localized DNA polymerase.

Figure 67D:
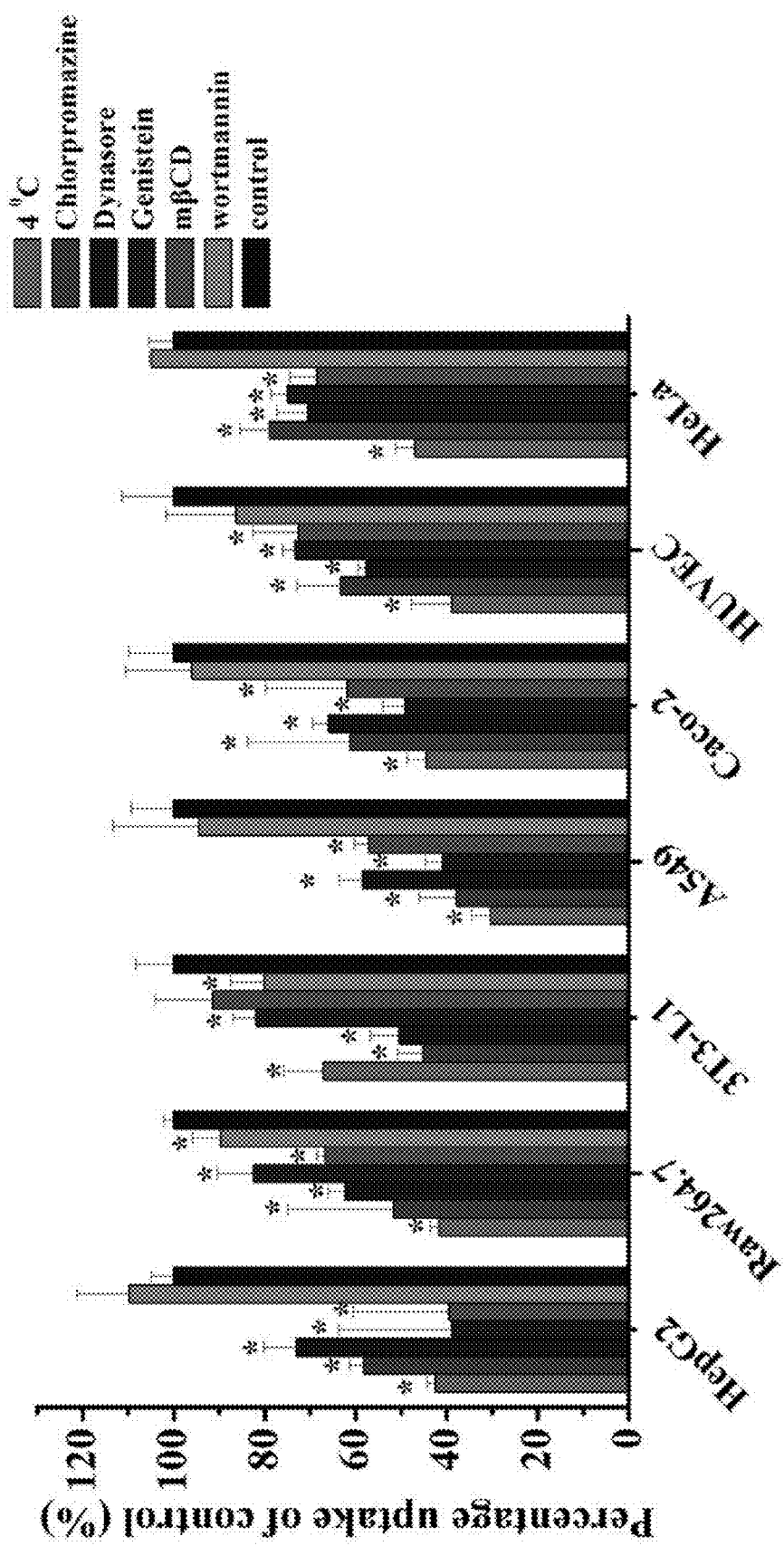

Since the intracellular fate of gene carriers is related to the internalization pathway, the trafficking mechanisms of complexes in a variety of cells was further investigated by utilizing various inhibitors (FIG. 67D). Treatment with chlorpromazine and dynasore significantly decreased DNA uptake in all cells, indicating that complexes enter the cells partly via clathrin-mediated endocytosis. Genistein and methyl-β-cyclodextran also inhibited DNA uptake, indicating caveolae-mediated endocytosis with cholesterol employment. Wortmannin that inhibited macropinocytosis worked only for Raw264.7 and 3T3-L1 cells, indicating cell-line dependence for this pathway. To further clarify the contribution of endocytosis during complex internalization, uptake was performed at 4° C. wherein endocytosis was completely blocked. An uptake level of approximately 40% of the control was noted, which can be attributed to passive permeation of the DNA molecules through the pores on cell membranes that were induced by PVBLG.

PVBLG-8-Mediated pDNA Transfection.

The efficiency of PVBLG-8 to trigger pDNA transfection was evaluated in the above-mentioned cell lines, which have been reported to be poorly transfected by commercial cationic lipid except HeLa and A549. With pCMV-Luc as the model pDNA, transfection efficiency was evaluated in terms of luminescence intensity that correlated to luciferase expression. As shown in FIG. 68A, PVBLG-8 (200 mer) led to a 4-165-fold improvement over Lipofectamine among all test cell lines, which indicates its generality in different types of cell lines including carcinoma, macrophage, fibroblast, epithelia, and endothelia. Maximized transfection efficiency was noted at polypeptide/DNA weight ratio of 10:1, where DNA was fully condensed into stable nanocomplexes. When it was increased to 15:1, a decrease in the transfection efficiency was detected, which can be attributed to the existence of excessive polypeptide that exerted additional cytotoxicity. In consistence with their cell penetration capabilities, polypeptides with longer chain length yielded enhanced transfection efficiencies, and α-helical conformation played an important role in inducing effective gene transfer.

Cytotoxicity of PVBLG-8.

High transfection efficiency and low toxicity are the two dominant requirements for commercial transfection reagent. An MTT assay that sensitively detected early cell injury was adopted to evaluate the cytotoxicity of PVBLG-8 and its complexes with DNA (weight ratio 10:1). In all test cell lines, PVBLG-8 exhibited dose-dependent cytotoxicity, and at the concentration used for transfection studies, they showed unappreciable toxicity except in HeLa and A549 cells (FIG. 69). Polypeptides with longer chain length demonstrated higher cytotoxicity in Raw264.7, A549, Caco-2, and HUVEC cells, which can be attributed to their superiority in inducing pore formation on cell membranes that caused loss of membrane integrity and severe membrane damage. Cytotoxicity of the polypeptide was significantly alleviated after being complexed with DNA, which was due to counteraction of the positive charge density by oppositely charged nucleic acid.

Summary.

Cationic PVBLG-8 with typical α-helical structure effectively penetrated mammalian cell membranes and delivered DNA into intracellular compartments after condensing it to nano-scale complexes. The complexes were stable against ionic strength and dilution, and they increased stability of DNA against hydrolysis by DNase. Consequently, the polypeptide induced remarkably improved DNA transfection efficiency than commercial cationic lipid (Lipofectamine) in a series of mammalian cells. Mechanistic assessment revealed that PVBLG-8 and PVBLG-8/DNA complexes traversed the cell membrane via clathrin-mediated endocytosis and energy-independent non-endocytosis, and the latter pathway was presumably due to pore formation on cell membranes as induced by the cell penetrating polypeptide. The efficacy of the polypeptides was also complemented by their low cytotoxicity, simplicity and precise control in polymerization as well as complex formulation, ease in reproducibility, and liability to scale-up. These attributes collectively define a new non-viral gene delivery vector that effectively addresses problems of currently used vectors.

Example 8. Two-Photon Responsive α-Helical Polypeptides for Promoted Non-Viral Gene Delivery With the rapid progress in biotechnology, there is increased interest in gene therapy, which offers new hope for the treatment or prevention of acquired and genetic diseases, such as cancer, diabetes, cystic fibrosis, and AIDS. To achieve successful gene therapy, tremendous requirements are put forward for effective vectors that can deliver nucleic acids into target cells or specific subcellular organelles to exert biological functions. Non-viral vectors have significant potential for gene delivery due to their desired biocompatibility, low immunogenicity, and amenability to scale-up compared to viral vectors. Cationic polymers define an important category of non-viral vectors, which condense nucleic acids into nanocomplexes and consequently improve cell internalization due to interaction with oppositely charged cell membranes. Nevertheless, low gene transfection efficiency still remains a large hurdle for non-viral vectors, which can be attributed to the difficulty in traversing the cell membrane barrier, intracellular release of the cargo, and transport to the nuclei.

In an attempt to address these challenges, cationic cell penetrating peptides (CPPs) have been developed to promote uptake and transfection efficiency of plasmid DNA (pDNA) due to cell membrane transduction/destabilization. In other approaches, stimuli-sensitive cationic polymers containing amino ketal or disulfide bonds are designed to facilitate intracellular complex dissociation and DNA unpackaging upon pH- or redox-triggered bond cleavage. Optical stimulus is another attractive approach because it can be remotely applied and controlled with high spatial and temporal precision. Near-infrared (NIR) light has wide in vivo applications. NIR penetrates deep into tissues without causing impairment. However, few studies have been reported on light, and especially NIR light, triggered gene delivery.

A photolabile PVBLG-8 (PDMNBLG-co-PVBLG-8) has been developed to construct a highly efficient gene transfer vector in a light triggerable manner. By taking advantage of the original PVBLG, the newly developed polypeptide can initially condense DNA and efficiently deliver it into cells via membrane transduction. Light (UV or NIR) irradiation can cleave the nitrobenzyl linkage, exposing the anionic carboxyl group to counteract the cationic secondary amines. Such reversal in polypeptide electrostatics from positive to neutral or negative leads to efficient release of DNA, facilitated subsequent trafficking to the nuclei, and higher level of recovery in terms of DNA transcription.

PDMNBLG-co-PVBLG-8 with polymerization degree of about 180 and various DMNB contents (10%, 20%, 30%, 40%, and 60%) was synthesized via ring opening copolymerization of DMNB-glu-NCA and VB-glu-NCA as initiated by hexamethyldisilazane (HMDS) followed by multistep side-chain derivatization. VB-glu-NCA was prepared as described herein above while DMNB-glu-NCA was prepared as described below. HMDS ensured a well-controlled polymerization as evidenced by well-defined Mw and low PDI (lower than 1.1). The obtained polypeptides exhibited good solubility in water at pH lower than 9.0, and they adopted α-helical conformations as verified by the characteristic negative ellipticity minima at 208 nm and 222 nm in CD spectra (FIGS. 70 and 71).

PDMNBLG-co-PVBLG-8 aqueous solution was irradiated with UV light (λ=350 nm, 20 mW) or NIR light (λ=750 nm, 2 W), which respectively corresponded to one-photon and two-photon processes, and the course of the photochemical reaction was monitored by UV/Vis spectroscopy to evaluate cleavage of the nitrobenzyl ester linkage (Scheme 8-1).

Scheme 8-1. NIR triggered cleavaged of DMNB groups on polypeptide side chains, which sunsequently leads to charge and conformation conversion of PDMNBLG-co-PVBLG-8.

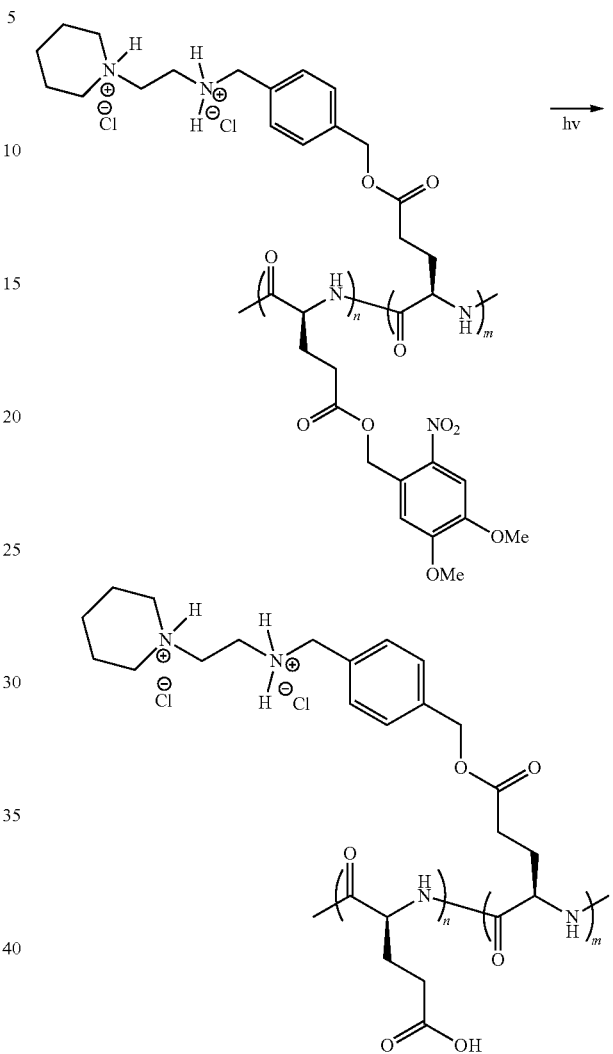

Upon light exposure, absorption at 346 nm decreased while absorption at 400 nm increased (FIG. 72A), which indicated breakage of the photolabile ester bond and generation of nitrobenzaldehyde. By plotting the absorbance at 400 nm against irradiation time, it was demonstrated that the photochemical reaction approached maximum conversion within 10 min and 2 h for UV and NIR irradiation, respectively. Interestingly, it was found that light irradiation significantly attenuated the α-helicity of PDMNBLG-co-PVBLG-8 and promoted transition to random coil structures in comparison to unappreciable alteration for PVBLG-8 (FIGS. 72B and 71). Such transition can be attributed to the intramolecular electronic interactions between carboxyl and secondary amine that led to suppression of the polypeptide backbone and destabilization of the helical structure. The conformation alteration from densely oriented helix to flexible coils can decrease the DNA binding sites in a fixed region and thereby facilitate DNA unpackaging in a synergistic manner.

The polypeptide was then subject to evaluations as delivery carriers for plasmid DNA encoding luciferase (pCMV- Luc). Particle size and Zeta potential assessments illustrated that polypeptide condensed pLuc into stable nanocomplexes with diameters of 130-170 nm (FIG. 73A) at polypeptide/DNA weight ratio higher than 10:1 for 10% and 20%, 15:1 for 30%, and 20:1 for 40%, respectively. Upon irradiation, complex size was remarkably augmented and Zeta potential was drastically decreased, which substantiated charge conversion of the polypeptide and reduced DNA binding capacities. EB exclusion assay was further adopted to evaluate the condensation capacity of polypeptide towards DNA. As shown in FIG. 73B, UV irradiation caused pronounced elevation in the fluorescence intensity of EB-DNA complexes which pointed to DNA unpackaging.

Next, the light-triggered intracellular DNA release and gene transfection was explored to confirm the biological applicability of the polypeptides. Considering potential toxic effects of UV light on living cells and its low penetration capacity, cells and animals were irradiated by NIR light for 2 h to ensure complete photochemical conversion. Prior to irradiation, internalization of polypeptide/DNA complexes was first evaluated in HeLa and COS-7 cells. Polypeptide 10% and 20% showed comparable uptake level to the original PVBLG-8 (FIG. 74), and it was therefore determined that copolymerization of the DMVB constituent did not compromise the cell transduction capacity of the polypeptide. Nevertheless, diminished uptake was noted for polypeptide 30% and 40%, which could be attributed to insufficient positive charges and α-helicity that are important for efficient membrane transduction.

The time-course profile revealed that cell uptake level reached a plateau within 4 h, and therefore in all following assessments, cells were treated with complexes for 4 h before light irradiation. The cell internalization mechanism was also investigated by pretreatment of cells with various endocytosis inhibitors. With genisteine and methyl-β-cyclodextrin exerting significant inhibitory effect in complex internalization, the internalization pathway was determined associated with caveolar-mediated endocytosis (FIG. 75). Since caveolar uptake led to direct transport of genes to the Golgi and/or endoplasmic reticulum and avoided endosomal/lysosomal degradation, the specific internalization pathway of polypeptide/DNA complexes also contributed to their desired transfection. Chlorpromazine also inhibited cell uptake in COS-7 cells while wortmannin inhibited uptake in HeLa cells, indicating additional involvement of clathrin-mediated endocytosis and macropinocytosis in these two cells lines, respectively.

By labeling the polypeptide with rhodamine and DNA with YOYO-1, the intracellular unpackaging of complexes in HeLa cells was visualized using CLSM. Compared to non-irradiated cells wherein red and green fluorescence were largely overlapped, NIR-irradiated cells exhibited notably enhanced separation of green fluorescence from red fluorescence, indicating facilitated intracellular DNA release. In accordance, green fluorescence spread to the entire cell including the nuclei. Since DNA needed to enter the nuclei before it could be transcribed, the nuclear distribution of YOYO-1-DNA was further monitored using an image-based quantification method (Akita et al., *Mol. Ther.* 2004, 9, 443). As illustrated in FIG. 76, following the 4-h uptake experiment and subsequent NIR irradiation (λ=750 nm, 6 W/cm²) for 2 h, ~31% of the internalized DNA was distributed to the nuclei, which was 2.3-fold higher than non-irradiated cells.

Consistent with these results, NIR irradiation of HeLa cells and COS-7 cells transfected with polypeptide/DNA complexes led to an ultimate 2-3 fold increase in luciferase expression. Maximal transfection efficiency was noted for polypeptide 20% after NIR irradiation, which outperformed the original PVBLG and Lipofectamine by ~3 and ~10 folds, respectively. NIR irradiated exerted minimal effect on the transfection efficiency of PVBLG-8, demonstrating that the improved gene expression was not caused by the light irradiation. An MTT assay indicated 97.8±7.2% and 101.3±5.2% (n=3) viability of irradiated HeLa cells and COS-7 cells compared to non-irradiated cells, respectively, indicating that the NIR light did not induce significant cell damage.

Summary.

A photon-sensitive α-helical polypeptide has been developed that provides effective light-regulated control over polypeptide-DNA interactions. The in vitro and in vivo efficacy verifies the strategy to induce promoted gene delivery efficiency by simultaneously taking advantage of PVBLG-8 in terms of membrane destabilization and light-responsiveness that triggered intracellular DNA release. To our knowledge, this is the first development of a photon-responsive polypeptides and application of NIR light irradiation with respect to gene delivery. Such a strategy therefore provides effective non-viral gene transfer and can be used for gene therapy, especially via regional administration. Efficient phototriggers such as coumarin-based groups can be employed in place of the nitrobenzyl group, which can allow for a faster and more potent NIR light responsiveness.

Materials, Cell lines, and Animals.

Chemicals were purchased from Sigma-Aldrich (St. Louis, Mo., USA) and used as received unless otherwise specified. Plasmid DNA encoding luciferase (pLuc) was obtained from Elim Biopharm (Hayward, Calif., USA), and Luciferase assay reagent and BCA protein assay kit were purchased from Promega (Madison, Wis., USA). Lipofectamine2000, YOYO-1 and MTT were purchased from Invitrogen (Carlsbad, Calif., USA).

HeLa cell line (human cervix adenocarcinoma) was obtained from the American Type Culture Collection (ATCC, Rockville, Md., USA) and cultured in Dulbecco's Modified Eagles Medium (DMEM, Grand Island, N.Y., USA) supplemented with 10% (v/v) fetal bovine serum.

Female C57BL/6 mice were obtained from Charles River Laboratory (Wilmington, Mass., USA) and were housed in a clean room four to a cage with access to water ad libitum, a 12:12 h light-dark cycle (7:00 am-7:00 pm), a temperature of 25±1° C. Relevant animal experimental protocols were approved and followed.

Methods.

Scheme 8-2. The synthetic route to γ-4,5-dimethyloxy-2-nitrobenzyl-L-glutamic acid-based N-carboxyanhydride (4).

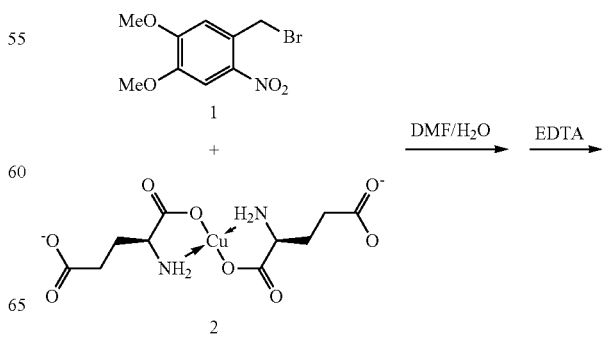

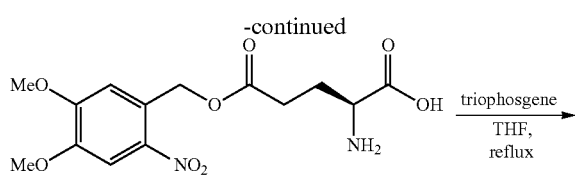

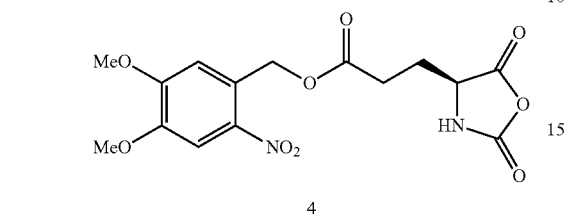

Synthesis of γ-4,5-dimethoxy-2-nitrobenzyl-L-glutamate (3)

In a 300-mL round bottom flask, N,N,N',N'-tetramethylguanidine (1.1 mL, 0.86 mmol) was added slowly to a stirred mixture of L-Glutamic acid (0.64 g, 4.3 mmol) and L-glutamic acid copper(II) complex (1.05 g, 2.14 mmol) in DMF (4 mL) and distilled water (0.6 mL). The mixture turned to dark blue. After the dissolution of all solids (~2 h), an additional DMF (3.1 mL) was added. Then, 4,5-dimethoxy-2-nitro-1-bromomethylbenzene (DMNB, 2.5 g, 9 mmol) was added to the above solution in one portion. The reaction solution became darker and kept at 40° C. for 38 h. After that, acetone (100 mL) was added into the mixture and kept stirring until a fine precipitate was obtained (~1 h). The violet solid was collected by filtration, followed by mixed with freshly prepared EDTA (2 g)/sodium bicarbonate (1 g) aqueous solution (15 mL) and kept stirring for 24 h. The product was collected by filtration and washed with DI water. Further purification can be performed by recrystallizing from $H_2O$/isopropanol. Freeze dry to yield the purified product as a yellow crystalline solid. Obtained 1.51 g (yield: 49%). $^1$H NMR [$D_2O$/DCl (1 wt %), δ, ppm]: 7.52 (s, 1H, ArH), 6.90 (s, 1H, ArH), 5.21 (s, 2H, $ArCH_2$—), 3.95 (t, 1H, —$CHNH_2$), 3.74 (s, 3H, $CH_3O$—), 3.70 (s, 3H, $CH_3O$—), 2.55 (t, 2H, —$COCH_2CH_2$—), 2.08 (m, 2H, —$COCH_2CH_2$—).

Synthesis of γ-4,5-dimethoxy-2-nitrobenzyl-L-glutamic acid-based N-carboxyanhydride (DMNB-glu-NCA, 4)

DMNB-glutamate (1.51 g, 4.4 mmol) and triphosgene (0.66 g, 0.22 mmol) were dispersed in anhydrous THF (30 mL) in a round-bottomed flask. The reaction was heated up to reflux temperature. The reaction was stopped until the mixture became clear. THF was distilled at room temperature under vacuum. The yellow solid residue was purified by recrystallization from THF/Hexane three times. The product was obtained as a yellowish needle-like crystalline solid (obtained 1.0 g, yield: 62%). $^1$H NMR ($CDCl_3$, δ, ppm): 7.69 (s, 1H, ArH), 6.97 (s, 1H, ArH), 6.42 (s, 1H, NH), 5.49 (m, 2H, $ArCH_2$—), 4.46 (t, 1H, —CHNH), 4.00 (s, 3H, $CH_3O$—), 3.96 (s, 3H, $CH_3O$—), 2.65 (t, 2H, —$COCH_2CH_2$—), 2.10-2.35 (m, 2H, —$COCH_2CH_2$—).

$^{13}$C NMR ($CDCl_3$, δ, ppm): 172.13, 169.51, 153.71, 151.72, 148.88, 140.52, 125.81, 111.62, 108.57, 64.43, 56.98, 56.77, 56.67, 29.80, 27.07.

Scheme 8-3. Synthetic route to PDMNBLG-co-PVBLG-8 (8).

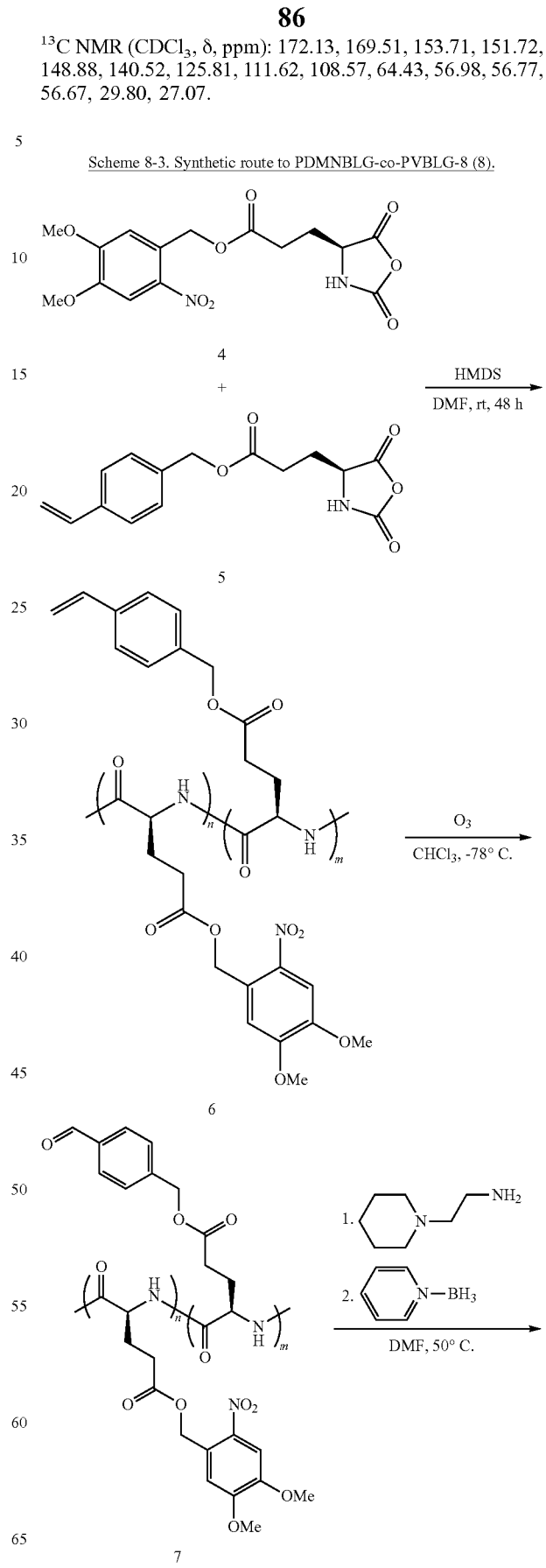

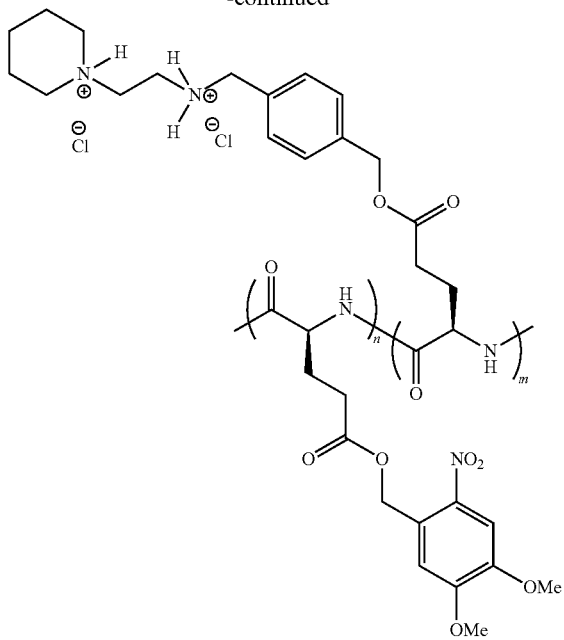

8

Synthesis of poly(γ-4,5-dimethoxy-2-nitrobenzyl-L-glutamate)-co-poly(γ-vinylbenzyl-L-glutamate) (PDMNBLG-co-PVBLG) (6)

A representative copolymerization of VB-Glu-NCA and DMNB-Glu-NCA is as follows. Inside a glove-box, VB-Glu-NCA (60 mg, 0.1 mmol) and DMNB-Glu-NCA (40 mg, 0.05 mmol) were dissolved in the mixture of DMF (2.0 mL) and nitrobenzene (60 µL), followed by adding the HMDS/DMF solution (16.7 µL, 0.1 M). FTIR was used to monitor the polymerization until the conversion was above 99% (~48 h). Tetrabutyl-ammonium fluoride solution (0.2 mL, 1.0 M) and benzyl chloroformate (0.4 mL, 2.8 mmol) was added to cleavage the N—Si bond and protect the amino end groups. The resulting polymer was precipitated from cold methanol and collected by centrifuge. Obtained 68 mg (yield: 80%). $^1$H NMR (CDCl$_3$/TFA-d, v:v=80:20, δ, ppm): 7.31 (s, 2H, ArH), 7.19 (d, 2.7H, ArH), 6.96 (m, 0.7H, ArH), 6.61 (t, 1H, CH$_2$=CH—), 5.69 (d, 1H, CH$_2$=CH—), 5.38 (d, 1.4H, ArCH$_2$—), 5.21 (d, 1H, CH$_2$=CH—), 5.05 (s, 2H, ArCH$_2$—), 4.63 (s, 1.7H, —CHNH), 3.94 (s, 2.1H, CH$_3$O—), 3.92 (s, 2.1H, CH$_3$O—), 2.49 (s, 3.4H, —COCH$_2$CH$_2$—), 1.80-2.30 (d, 3.4H, —COCH$_2$CH$_2$—).

Synthesis of poly(γ-4,5-dimethoxy-2-nitrobenzyl-L-glutamate)-co-poly(γ-adehydobenzyl-L-glutamate) (PDMNBLG-co-PABLG) (7) and PDMNBLG-co-PVBLG-8 (8)

A representative side-chain modification of PDMNBLG-co-PVBLG is as follows. The copolymer (68 mg, 0.17 mmol of vinyl groups) was dissolved in chloroform (60 mL) at −78° C. O$_2$ was bubbled into the solution for 1 min followed by bubbling of O$_3$ until the solution became blue indicating the reaction was completed. O$_3$ was then replaced by O2, which was bubbled into the solution for another 2 min until the solution became colorless. The solution was then degassed and back filled with nitrogen. Ph$_3$P (262 mg, 1.0 mmol) was then added to the mixture. The solution was stirred at room temperature for 2-3 h and solvent was removed under vacuum. The resulting polymer (7) was purified by stirring in methanol (3×20 mL) to remove unreacted Ph$_3$P and other impurities. Obtained 62 mg (yield: 90%). $^1$H NMR (CDCl$_3$/TFA-d, v:v=80:20, δ, ppm): 9.82 (s, 1H, —CHO), 7.87 (d, 2H, ArH), 7.66 (m, 0.7H, ArH), 7.43 (d, 2H, ArH), 6.94 (m, 0.7H, ArH), 5.38 (d, 1.4H, ArCH$_2$—), 5.16 (s, 2H, ArCH$_2$—), 4.63 (s, 1.7H, —CHNH), 3.92 (s, 2.1H, CH$_3$O—), 3.90 (s, 2.1H, CH$_3$O—), 2.56 (s, 3.4H, —COCH$_2$CH$_2$—), 1.80-2.30 (d, 3.4H, —COCH$_2$CH$_2$—).

The resulting polymer (62 mg, 0.15 mmol of aldehyde groups) was reacted with 1-(2-aminoethyl)piperidine (0.20 g, 1.5 mmol, 10 eqv.) in DMF (4 mL) at 50° C. for 24 h. Borane pyridine (0.2 mL, 1.5 mmol 10 eqv.) was added after that. The solution was stirred at 50° C. for another 24 h. 3 M HCl solution was added to the above DMF solution and then dialysis against DI water using a dialysis bag with a cut-off MW=8000. Freeze-dry to yield the solid products. Obtained 30 mg (yield: 45%). $^1$H NMR (D$_2$O, δ, ppm): 6.80-7.45 (br d, 5.4H, ArH), 4.84 (br s, 3.4H, ArCH$_2$O—), 4.32 (br s, 1.7H, —CHNH), 4.13 (br s, 2H, ArCH$_2$NH—), 3.43 (s, 2.1H, CH$_3$O—), 3.38 (s, 2.1H, CH$_3$O—), 3.08 (s, 2H, —HNCH$_2$CH$_2$N—), 2.77 (s, 2H, —HNCH$_2$CH$_2$N—), 1.00-2.50 (br m, 14H, —COCH$_2$CH$_2$— and —NCH$_2$CH$_2$CH$_2$—).

Preparation and Characterization of Polypeptide/DNA Complexes.

Polypeptides and pDNA were dissolved in deionized water at 0.2 mg/mL. Complexes were allowed to form by addition of the polypeptide solution to pDNA at different weight ratios followed by vortex for 30 s and incubation at 37° C. for 30 min. The suspension was subject to assessment of particle size and Zeta potential on a Malvern Zetasizer. To evaluate the light-responsiveness of the polypeptide, complexes produced in the same manner were UV irradiated for 5 min at before assessment of particle size and Zeta potential.

EB Exclusion Assay.

Complexes were formed and UV irradiated as described above. EB solution was added to the complex suspension at DNA/EB ratio of 10:1 (w/w), and the mixture was incubated at RT for 30 min before quantification of fluorescence intensity on a microplate reader ($\lambda_{ex}$=510 nm, $\lambda_{em}$=590 nm). A pure EB solution and the DNA/EB solution without any polypeptide were used as negative and positive controls, respectively. EB exclusion efficiency was defined as:

$$EB \text{ exclusion efficiency}(\%) = \frac{F - F_{EB}}{F_0 - F_{EB}} \times 100$$

Whereas $F_{EB}$ and $F_0$ denote the fluorescence intensity of pure EB solution and the DNA/EB solution without any polypeptide, respectively.

Cell Uptake of Complexes.

DNA (1 mg/mL) was labeled with YOYO-1 (20 mM) at one dye molecule per 50 bp DNA, and the resultant YOYO-1-DNA was allowed to form complexes with the polypeptide at 1:15 (w/w) as described above. Lipofectamine/DNA complexes were formed according to the manufacturer's protocol.

HeLa cells were seeded on 96-well plates at 1×10$^4$ cells/well, and cultured in serum-containing DMEM for 24 h to reach confluence. The media was replaced by fresh serum-free DMEM, and complexes were added at 0.1 µg YOYO-1-DNA/well. After incubation at 37° C. for 4 h, the medium was discarded and cells were washed with PBS for three times before lysis with 100 µL of RIPA lysis buffer. YOYO-1-DNA content in the lysate was quantified by spectrofluorometry ($\lambda_{ex}$=485 nm, $\lambda_{em}$=530 nm) and protein content was measured using the BCA kit. Uptake level was expressed as ng YOYO-1-DNA per µg of protein. To evaluate the time-resolved cell internalization, complexes were incubated with cells for 0.5, 1, 2, 3, 4, 6, 8 h, respectively, before analysis of the uptake level of YOYO-1-DNA. To explore the mechanism involved in cell internalization, cells were pre-incubated with endocytosis inhibitors including chlorpromazine (10 µg/mL), genistein (100 µg/mL), methyl-β-cyclodextrin (mβCD, 5 mM), wortmannin (10 µg/mL), dynasore (80 µM), and sodium azide (10 mM)/deoxyglucose (50 mM) for 30 min prior to complex addition and throughout the 4-h uptake experiment at 37° C. Results were expressed as percentage uptake of the control where cells were incubated with complexes at 37° C. for 4 h.

CLSM Observation on the Intracellular Complex Unpackaging.

To visualize the intracellular unpackaging of polypeptide/DNA complexes, RhB-polypeptide and YOYO-1-DNA were allowed to form complexes at the weight ratio of 15:1 and incubated with HeLa cells as described above. Following incubation for 4 h, the media was refreshed by serum-containing DMEM and cells were irradiated with NIR irradiation (750 nm, 10 fs pulse, 6 W/cm$^2$) at 37° C. for 1.5 h before further incubation for another 2 h. Cells were then washed with cold PBS, fixed with 4% paraformaldehyde, stained with DAPI (1 µg/mL), and subjected to observation using CLSM (LSM700, Zeiss).

Subcellular Distribution of Plasmid DNA.

For further quantitative assessment upon the nucleic and cytoplasmic distribution of DNA, an image-based quantification method was adapted. Briefly, polypeptide/YOYO-1-DNA complexes (weight ratio of 15:1) were incubated with HeLa cells for 4 h, and the media was replaced by serum-containing DMEM. Cells were irradiated with NIR irradiation (750 nm, 10 fs pulse, 6 W/cm$^2$) at 37° C. for 2 h before further incubation for 4 h. They were subsequently visualized by CLSM as described above, and the total pixel area for clusters of YOYO-1-DNA in the nucleus or the cytoplasm in each cell was calculated by XX to determine the subcellular fraction of YOYO-1-DNA.

Cytotoxicity of Complexes.

HeLa cells were seeded on 96-well plate at 1×10$^4$ cells/well and incubated for 24 h. The culture media were replaced by serum-free DMEM into which polypeptide/DNA complexes (weight ratio of 15) were added at 20, 10, 5, 2, and 0.5 µg polypeptide/well. Following incubation for 4 h, cells were further cultured in serum-containing DMEM for 20 h before viability assessment using the MTT assay.

In Vitro Transfection.

HeLa cells were seeded on 96-well plate at 1×10$^4$ cells/well and incubated for 24 h prior to transfection studies. The media were replaced by serum-free DMEM into which polypeptide/DNA complexes (weight ratio of 15:1) were added at 0.1 µg DNA/well. After incubation for 4 h, the media was replaced by serum-containing DMEM and cells were irradiated by NIR laser (750 nm, 10 fs pulse, 6 W/cm$^2$) for 2 h. Subsequently, cells were allowed to be cultured for another 20 h before assessment of luciferase expression and protein content. Results were expressed as relative light unit (RLU) associated with 1 mg of protein.

In Vivo Transfection.

Polypeptide/DNA complexes were injected to the posterior tibialis muscles of C57BL/6 mice at a dose of 10 µg DNA per mouse with naked DNA and Lipo2000/DNA complexes serving as controls. Four hours after administration, mice were anesthetized and the injection site was irradiated with NIR laser (750 nm, 10 fs pulse, 6 W/cm$^2$) for a total time of 1.5 h with 2-min irradiation and 2-min interval during which ice would be applied to the irradiation site to prevent over-heating of the tissue. Mice were euthanized 24 h later, and the tibialis muscles were harvested, homogenized with the lysis buffer (0.1% TritonX-100, 2 mM EDTA, 0.1 M Tris, pH 7.8). After three cycles of freezing and thawing, the homogenate was centrifuged at 10,000 g for 10 min at 4° C., and an aliquot of 20 µL was used to quantify luciferase expression and protein content. Results were expressed as RLU/mg protein.

Results and Discussion.

γ-4,5-Dimethoxy-2-nitrobenzyl-L-glutamic acid-based N-carboxyanhydride (DMNB-glu-NCA) has been synthesized (Scheme 8-2) by a multi-step synthetic route, namely the mono-esterification between L-glutamic acid copper(II) complex and 4,5-dimethoxy-2-nitro-1-bromomethylbenzene, and the cyclization of γ-4,5-Dimethoxy-2-nitrobenzyl-L-glutamic acid in the presence of triphosgene. DMNB-glu-NCA was purified by recrystallization from anhydrous THF/hexane three times to yield a light yellow crystalline product with high purity. The molecular structure of DMNB-glu-NCA was verified by $^1$H NMR and $^{13}$C NMR.

Hexamethyldisilazane (HMDS) has been previously shown to polymerize γ-benzyl-L-glutamic acid based NCAs (BLG-glu-NCA) in a controlled manner. It can also polymerize DMNB-glu-NCA and VB-glu-NCA to yield corresponding copolymers Poly(γ-4,5-dimethoxy-2-nitrobenzyl-L-glutamate)-co-poly(γ-vinylbenzyl-L-glutamate) (PDMNBLG-co-PVBLG) with well-defined structures, including controlled molecular weight (MW) and polydispersity index (PDI) (Scheme 8-3). High MW copolymers (total degree of polymerization, DP>150) was attempted to obtained based on previous results, namely, PVBLG-8 with higher DP has better gene delivery efficiency.

Polymerizations were conducted under a nitrogen atmosphere in room temperature DMF for 48 h at various DMNB-glu-NCA to VB-glu-NCA feeding ratios (10%-60%). An aliquot of the reaction mixture was taken for analysis of conversion by FTIR spectroscopy. The end groups of the copolymers were protected by CBz groups to prevent the cross-linking reaction in the ozone oxidation step. The copolymers were isolated by precipitation with cold methanol and their molecular structures were determined by $^1$H NMR. The absolute polymer MW and PDI were determined by size-exclusion chromatography coupled with multi-angle light scattering and differential refractive index detectors (SEC-MALS-DRI) (Table 8-2).

TABLE 8-2

HMDS-Mediated ROP of NCAs in DMF.[a]

| Entry | (VB-glu-NCA + DMNB-glu-NCA)/ HMDS | $M_n$[b] × 10$^{-3}$ (g mol$^{-1}$) | $M_n$[c] × 10$^{-3}$ (g mol$^{-1}$) | PDI[c] | Conversion[d] (%) |
|---|---|---|---|---|---|
| 1 | (180 + 20)/1 | 50.6 | 47.9 | 1.02 | >99 |
| 2 | (160 + 40)/1 | 52.2 | 62.2 | 1.02 | >99 |
| 3 | (140 + 60)/1 | 53.8 | 55.6 | 1.03 | >99 |
| 4 | (120 + 80)/1 | 55.4 | 52.7 | 1.06 | >99 |
| 5 | (80 + 120)/1 | 58.5 | 63.7 | 1.07 | >99 |

[a] Polymerization ($C_M$ = 0.16-0.17M) were conducted in DMF at room temperature using HMDS as initiator.
[b] Theoretical polymer molecular weight were calculated from the M/I ratio and the conversion.
[c] Absolute polymer molecular weight and molecular weight distribution (PDI).
[d] Conversions were determined form FTIR spectroscopy.

PDMNBLG-co-PVBLG was further derivatized into poly (γ-4,5-dimethoxy-2-nitrobenzyl-L-glutamate)-co-poly(γ-adehydobenzyl-L-glutamate) (PDMNBLG-co-PABLG) by oxidation with the ozone and reduction in the presence of Ph₃P in chloroform at −78° C. ¹H NMR analysis of the resulting polymers revealed a quantitative conversion, as evidenced by the disappearance of the vinyl peak at 6.61 ppm and the appearance of the aldehydo peak at 9.82 ppm. Quantitative aldehydo substitution was observed for the copolymers.

The aldehydo groups on the PDMNBLG-co-PABLG sidechains can be orthogonally derivatized via amine-aldehyde reaction, followed by reduction reaction using borane pyridine to yield a stable product. After acidified with $HCl_{aq}$ and dialysis against DI water for three days, high purity PDMNBLG-co-PVBLG-8 with ionic charge on the side-chains can be obtained. PDMNBLG-co-PVBLG-8s with different PDMNBLG contests (10%-60%) are readily dissolved in DI water. The molecular structure of PDMNBLG-co-PVBLG- was verified by ¹H NMR and the disappearance of the aldehydo groups indicated a high grafting efficiency.

The solution conformation of PDMNBLG-co-PVBLG-8s with different PDMNBLG contests (10%-60%) was characterized by CD spectroscopy (FIGS. 71A and B). All the resulting copolymers adopt α-helical conformations in $H_2O$, as verified by the characteristic negative ellipticity minima at 208 nm and 222 nm. The helicity of the polypeptides were calculated by the following equation: helicity=(−[θ$_{222}$]+3,000)/39,000. Where [θ]$_{222}$ is the mean residue ellipticity at 222 nm. All the copolymers exhibit high helicity (80-100%) in water (FIG. 71C). The helicity decreases with increasing of PDMNBLG content. This can be attributed to the poor solubility of DMNB groups in water, which suppresses the polypeptide backbone and destabilizes the helical structure.

PDMNBLG-co-PVBLG-8s show remarkable pH-independent helical stability at pH values ranging from 1 to 9 (FIG. 70A). High pH (pH>10) conditions were not able to perform due to protonation of the positively charged amino group on the side chain and a decreased solubility. These polymers also showed a lack of concentration dependence (FIG. 70B), indicating that it remains monomeric in solution. Additionally, the resulting copolymers exhibited remarkable stability against the strong denaturing reagent (i.e., urea) (FIG. 70C). All the copolymers show reasonably stable helical structure in the NaCl media and the ellipticity at 222 nm remain nearly unchanged when the NaCl concentration was increased from 0 to 0.4 M at pH 3 at 25° C. The copolymers started to aggregate when further increasing the NaCl concentration and the one with higher PDMNBLG contents aggregates at a lower NaCl concentration (FIG. 70D), which may be due to the hydrophobic property of the PDMNBLG segments.

To demonstrate the cleavage of the ester bond with DMNB groups, UV light (λ=365 nm, 20 mW) was used to irradiate the aqueous solution of DMNB-glu as the model reaction. The reaction was monitored by ¹H NMR. After irradiation for 300 s, a characteristic peak of glutamic acid at δ=2.42 ppm appeared and the cleavage conversion was 43% based on the integration of peaks at 2.54 ppm and 2.42 ppm, which correspond to DMNB-glu and L-glutamic acid respectively.

The aqueous solutions of PDMNBLG-co-PVBLG-8s with different PDMNBLG contents (10%-60%) have also been irradiated by UV light. An interesting phenomenon was observed: the residue molar ellipticity and helicity of the PDMNBLG-co-PVBLG-8s decreased after irradiation for 600 s while the homopolypeptide, i.e., PVBLG-8 shows no change after the same treatment (FIG. 71B). For example, the helicity of PDMNBLG-co-PVBLG-8 with 10% of PDMNBLG segments decreased by 8% after irradiation while the one containing 20% of PDMNBLG shows a 51% decrease of helicity (FIG. 71C). A maximum helicity decrease was observed on the samples with 30% and 40% of PDMNBLG. To the best of our knowledge, this is the first observation of the helix to coil where the transition is triggered by light. The reason for this transition may be that the intermolecular electronic interaction suppressed the polypeptide backbone and destabilized the helical structure (FIG. 71D).

Kinetic studies were performed consequently. Typically, PDMNBLG-co-PVBLG-8 with 40% of PDMNBLG segments was used as the representative. The residue molar ellipticity starts to decrease after irradiation for 120 s and equivalent after 600 s (FIGS. 77A and 77B). The residue molar ellipticity at 222 nm decreased by 23400 deg·cm²·dmol⁻¹ within 2 h after the irradiation. The relaxation of helix to coil transition was also tested to see how fast the transition is after UV irradiation. After UV irradiation, the copolymer was equivalent at room temperature for various times (2 h, 12 h, 24, 36 h and 48 h) before CD measurement. The residue molar ellipticity at 222 nm decreased only by 2300 deg·cm²·dmol⁻¹ after equivalent for 48 h, indicating a fast transition in the first 2 h after irradiation (FIGS. 77C and 77D).

All the tested polypeptide/DNA complexes displayed higher uptake level than naked DNA and Lipofectamine/DNA complexes in HeLa and COS-7 cells (FIGS. 78 and 79). By using various endocytic inhibitors, the uptake pathway of the complexes was different in the two cell lines. In HeLa cells, uptake was inhibited by genistein and mBCD, indicating a caveolar-mediated endocytosis with cholesterol depletion. Wortmattin also exerted inhibitory effect, which indicated involvement of macropinocytosis. For COS-7 cells, chlorpromazine showed some inhibitory effects, which suggested that the cell entry route was partly associated with the clathrin-mediated endocytosis.

Figure 81:
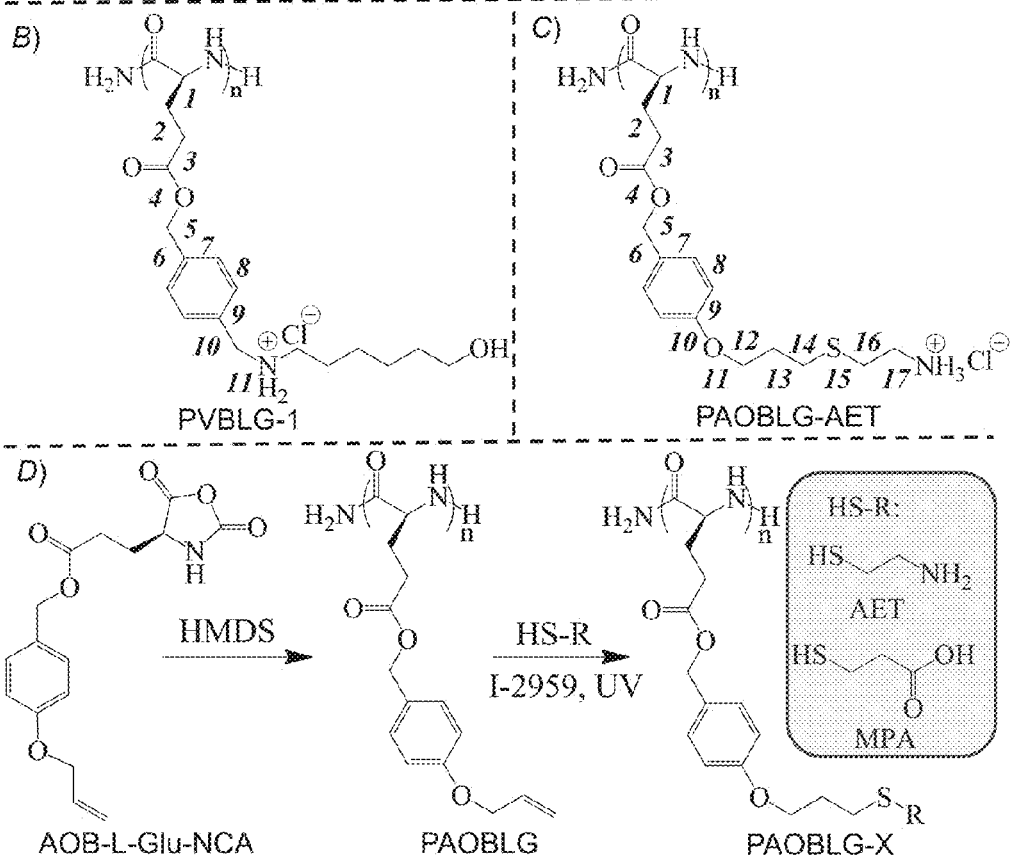

Example 9. Water-Soluble Polypeptides with Elongated, Charged Side Chains Adopt Ultra-Stable Helical Conformations Water-soluble polypeptides adopting α-helical conformations with unprecedented high helicities were obtained by lengthening the charge-containing side chains of the constituent amino acids to allow the terminal charges to be situated distally from the peptide backbone. Poly(γ-(4-aminoethylthiopropoxyl)-benzyl-L-glutamate) (PAOBLG-AET) with a charge-peptide backbone distance of 17 σ-bonds exhibited a remarkably high helical content (81%) at a degree of polymerization as low as 10 (FIGS. 80 and 81). The helical conformations of these short polypeptides were very stable against various harsh, protein-denaturing conditions, such as extreme pH, high temperature, and high salt or urea concentrations.

The α-helix is one of the most important functional domains in polypeptides controlling numerous biological activities and functions. Studies aimed at increasing the overall helicity and stability of helical motifs of proteins and peptides, especially short-chain oligopeptides, have contributed to the fundamental understanding of protein folding/unfolding and have led to improvements in the biological and pharmaceutical activities of peptides. There is often a drawback in the design of water-soluble, bioactive helical peptides: charged amino acid building blocks provide water solublity but decrease helicity because of disruption of helix due to side-chain charge repulsion. Increasing the proportion of hydrophobic amino acids tends to increase helicity by increasing side-chain hydrophobic interactions, but the resulting structures show reduced water solubility, which is undesirable for the design of biologically active peptides. It has been a general strategy to integrate both water-soluble and helix-stabilizing motifs in the peptide structure to design water-soluble, helical peptides. Such peptides are often designed to have charged amino acid residues situated on one side of the helix surface and the residues responsible for stabilizing the helix through side-chain hydrophobic interactions, salt bridges, or tethering situated on the opposite side of the helix surface. These strategies require the design of peptides with specific sequences and usually involve tedious chemistries of polypeptide side chains that are typically difficult to control. For polypeptides prepared by polymerization instead of through step-wise synthesis, such helix-stabilization strategies mentioned above for the synthesis water-soluble, helical peptides cannot be simply applied.

Water-soluble, synthetic polypeptides that can adopt stable α-helical conformations have attracted much attention. Prior efforts have been focused on introducing neutrally charged, hydrophilic functional groups or moieties. Poly(N-hydroxyalkyl-L-glutamine), one of the early design of water-soluble polypeptides derived from aminolysis of poly(L-glutamate) (PLG) with pendant hydroxyl groups, showed excellent water-solubility and fairly high helical contents (up to ~65% helicity) in aqueous solution (Lotan et al., *Biopolymers* 1966, 4, 365-368). Later, Deming designed PLL containing pendant oligoethyleneglycol moieties (Yu et al., *J. Am. Chem. Soc.* 1999, 121, 12210-12211). The resulting oligoethyleneglycol-graft PLL showed excellent water-solubility and remarkably high helcial content (100% helicity in pH 7 water at 25° C.). Recently, Li and coworkers designed thermo-responsive α-helical polypeptide from peglated poly(L-glutamate), highlighting the recent progress of this class of special polypeptides containing non-charged, water-soluble segments on a α-helical structure (Chen et al., *Biomacromolecules* 2011, DOI: 10.1021/bm200849m).

This disclosure describes charged, water-soluble polypeptides that adopt stable α-helical conformations (i.e., α-helical polypeptide electrolytes; αHPEs), by using polypeptide containing charged side chains but elongating the charge-containing amino acid side chains to place the charges distally from the polypeptide backbone (FIG. 81a). When the charges are 11 σ-bonds away from the peptide backbone, as in poly(γ-(4-(1-hexanol-6-aminomethyl))benzyl-L-glutamate) (PVBLG-1; FIG. 81b), the resulting polypeptide with a degree of polymerization (DP) of 60 ((PVBLG-1)$_{60}$) maintains a stable α-helical conformation with 91% helicity. PVBLG-1's with very low DPs, such as (PVBLG-1)$_{10}$ with a DP value of 10, however, have mixed conformations containing both β-sheets and α-helices, with a helicity of only 26% for (PVBLG-1)$_{10}$. Because both the charge-backbone distance and the hydrophobicity of the side chains in αHPEs have significant effect on the stability of α-helix, further elongating the side chain could not only further reduce side chain charge repulsion by increasing the charge-backbone distance but also increase the side-chain hydrophobicity. By doing so, it is possible to obtain a water-soluble αHPE with ultra-stable α-helix and high helicity even at a very low DP. This disclosure reports the design and synthesis of a water-soluble αHPE, (poly(γ-(4-aminoethylthiopropoxyl)benzyl-L-glutamate) (PAOBLG-AET, FIG. 81c), with side chain charges situated 17 σ-bonds away from the peptide backbone, which adopts an unprecedented, remarkably high helicity (81%) with a DP of 10 at pH 2 aqueous solution.

The synthesis of PAOBLG-AET is illustrated in FIG. 81d. γ-(4-Allyloxylbenzyl)-L-glutamate N-carboxyanhydride (AOB-L-Glu-NCA) can be easily prepared in multi-gram scale. The ring-opening polymerization of AOB-L-Glu-NCA initiated by hexamethyldisilazane (HMDS) yielded PAOBLGs with controlled molecular weights (MWs) and narrow molecular-weight distributions (MWDs) that were determined by gel permeation chromatography (GPC) (Table 9-1).

TABLE 9-1

HMDS-Initiated Polymerization of AOB-L-Glu-NCA.

| entry | M/HMDS/TBD$^a$ | time (h) | conv. (%) | $M_n$ ($M_n$*) ($\times 10^{-4}$)$^b$ | MWD |
|---|---|---|---|---|---|
| 1 | 10/1/0 | 8 | >98 | 0.28 (0.30) | 1.22 |
| 2 | 20/1/0 | 12 | >98 | 0.55 (0.56) | 1.12 |
| 3 | 50/1/0.1 | 16 | >98 | 1.42 (1.38) | 1.05 |
| 4 | 100/1/0.1 | 36 | >98 | 2.68 (2.76) | 1.06 |

$^a$Molar ratio of M/HMDS/TBD (M = AOB-l-Glu-NCA, HMDS = hexamethyldisilazane, TBD = 1,5,7-triazabicyclo [4.4.0]dec-5-ene);
$^b$The MW obtained (the MW expected*).

For example, at a monomer/initiator (M/I) ratio of 10 with expected $M_n$ of $3.0\times10^3$ g·mol$^{-1}$, the resulting PAOBLG had an $M_n$ of $2.8\times10^3$ g·mol$^{-1}$ with a narrow MWD of 1.22 (entry 1, Table 9-1). The MW and MWD of PAOBLG$_{10}$ obtained by matrix-assisted laser desorption ionization mass spectrometry (MALDI-TOF MS) agreed well with the values obtained by GPC. To accelerate the polymerization of AOB-L-Glu-NCA and synthesize higher MW PAOBLGs, 1,5,7-triazabicyclo[4.4.0]dec-5-ene (TBD) was used as a co-catalyst, which gave faster yet controlled NCA polymerization. In the presence of a small amount of TBD (HMDS/TBD=1/0.1), the polymerizations yielded corresponding PAOBLGs with the expected MWs and narrow MWDs (entries 3 and 4, Table 9-1).

The PAOBLGs were then treated with 2-aminoethanethiol hydrochloride in a mixture of dimethylformamide and deionized water to effect a UV-triggered thiol-ene "click" reaction. Dialysis of the reaction mixture followed by lyophilization removed all the small-molecule impurities and afforded the desired polymers as a fluffy powder. As expected, the thiol-ene reaction proceeded rapidly and completed in 10 min, yielding PAOBLG-AETs with nearly quantitative grafting efficiency.

TABLE 9-2

Conformation Analysis of Ionic Polypeptides.

| Entry | Polypeptide | DP | $-[\theta]_{222} \times 10^{-3}$ (cm$^2$ · deg · dmol$^{-1}$)$^a$ | Helical content (%)$^b$ |
|---|---|---|---|---|
| 1 | (PLL)$_{60}$ | 60 | — | 0 |
| 2 | (PVBLG-1)$_{10}$ | 10 | 7.2 | 26 |
| 3 | (PAOBLG-AET)$_{10}$ | 10 | 28.5 | 81 |
| 4 | (PAOBLG-AET)$_{20}$ | 20 | 34.0 | 94 |
| 5 | (PAOBLG-AET)$_{50}$ | 50 | 36.8 | 100 |
| 6 | (PAOBLG-MPA)$_{10}$ | 10 | 29.6 | 84 |

$^a$The mean residue molar ellipticity [θ] was determined by following literature-reported formulas: Ellipticity ([θ]$_{222\ nm}$ in cm$^2$ deg dmol$^{-1}$) = (millidegrees × mean residue weight)/(path length in millimetres × concentration of polypeptide in mg · ml$^{-1}$);
$^b$The helical contents of the polypeptides were calculated using the following equation: percentage of α-helix = (−[θ]$_{222}$ + 3000)/39,000.

Figure 82:
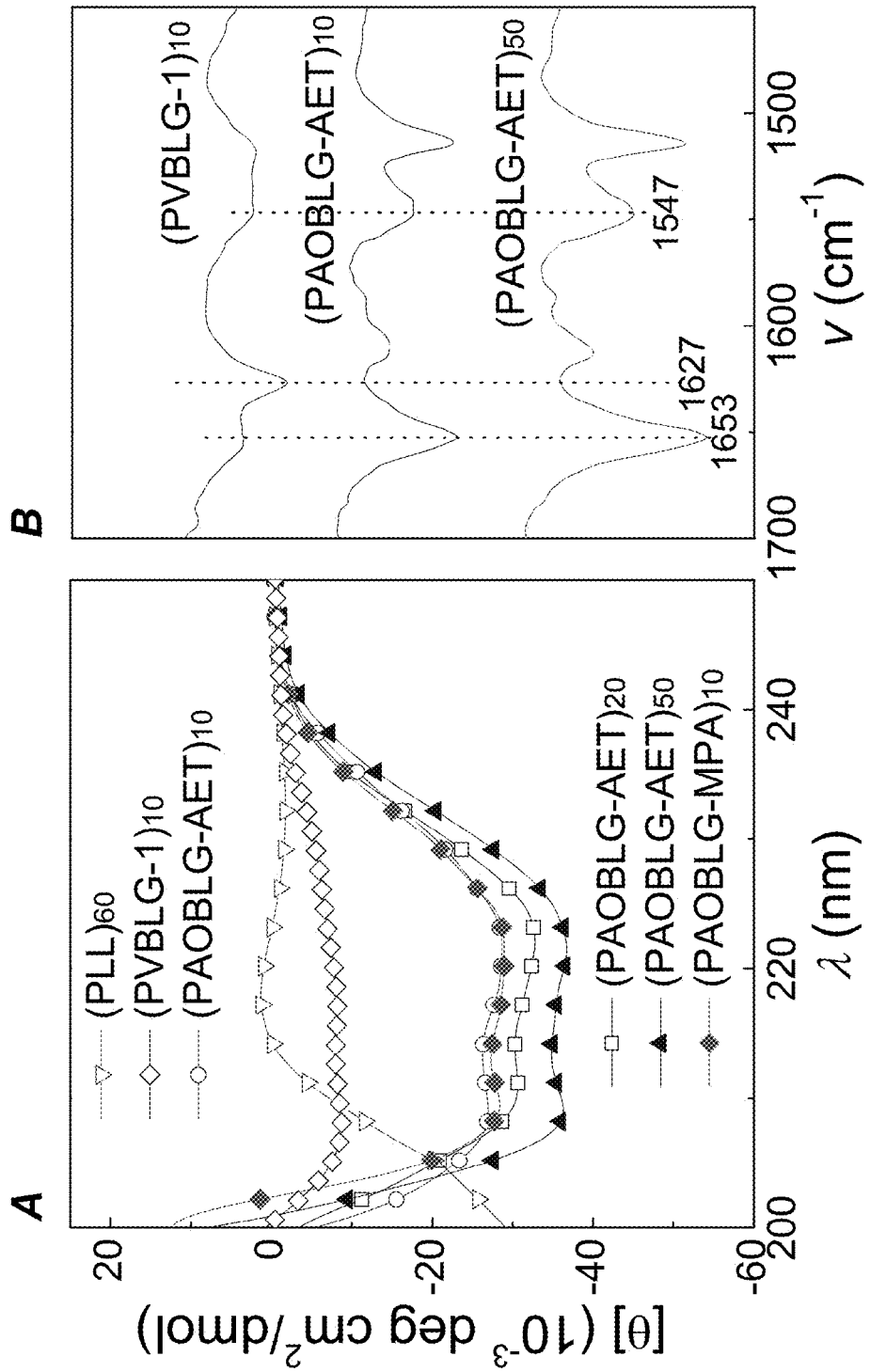

The PAOBLG-AETs are very soluble in water (>20 mg·mL$^{-1}$) because of the terminal ammonium groups on each of their side chains, in sharp contrast to PAOBLG which is insoluble in water. To determine whether the PAOBLG-AETs have the expected high helicity at low DP, circular dichroism (CD) spectroscopy was used to analyze the conformation of the PAOBLG-AETs at pH 2, at which all side-chain amines should be protonated and are charged. All three PAOBLG-AETs ((PAOBLG-AET)$_{10}$, (PAOBLG-AET)$_{20}$ and (PAOBLG-AET)$_{50}$) showed the characteristic CD spectra of α-helix with two minima at 208 and 222 nm (FIG. 82$a$). (PAOBLG-AET)$_{10}$ (charge-backbone distance of 17 σ-bonds, FIG. 1$c$) had a $-[\theta]_{222}$ value of $28.5 \times 10^3$ cm$^2$·deg·dmol$^{-1}$, which corresponds to a helicity of 81% (FIG. 82$a$, Table 9-2), in sharp contrast to a 60-mer poly-L-lysine ((PLL)$_{60}$, charge-backbone distance of 4 σ-bonds) that adopts a random coil conformation and (PVBLG-1)$_{10}$ (charge-backbone distance of 11 σ-bonds, FIG. 81$b$) that has a $-[\theta]_{222}$ value of $7.2 \times 10^3$ cm$^2$·deg·dmol$^{-1}$, which corresponds to a helicity of only 26% (FIG. 81$a$ and Table 9-2). The high helicity of (PAOBLG-AET)$_{10}$ was further verified by FTIR (FIG. 82$b$). (PVBLG-1)$_{10}$ has mixed conformations containing both α-helix (amide I band at 1653 and amide II band 1547 cm$^{-1}$) and β-sheet (amide I band at 1627 cm$^{-1}$) in solid state, while (PAOBLG-AET)$_{10}$ has predominant α-helix (strong amide I band at 1653 and amide II band 1547 cm$^{-1}$) and negligible β-sheet conformation. For PAOBLG-AETs with DP values of 20 and 50, the $-[\theta]_{222}$ values were 34.0 and $36.8 \times 10^3$ cm$^2$·deg·dmol$^{-1}$, corresponding to helicities of 94% and 100%, respectively (FIG. 82$a$, and Table 9-2). (PAOBLG-AET)$_{10}$ and (PAOBLG-AET)$_{50}$ have nearly identical FTIR spectrum (FIG. 82$b$), further validating the high helical content of (PAOBLG-AET)$_{10}$.

Figure 83:
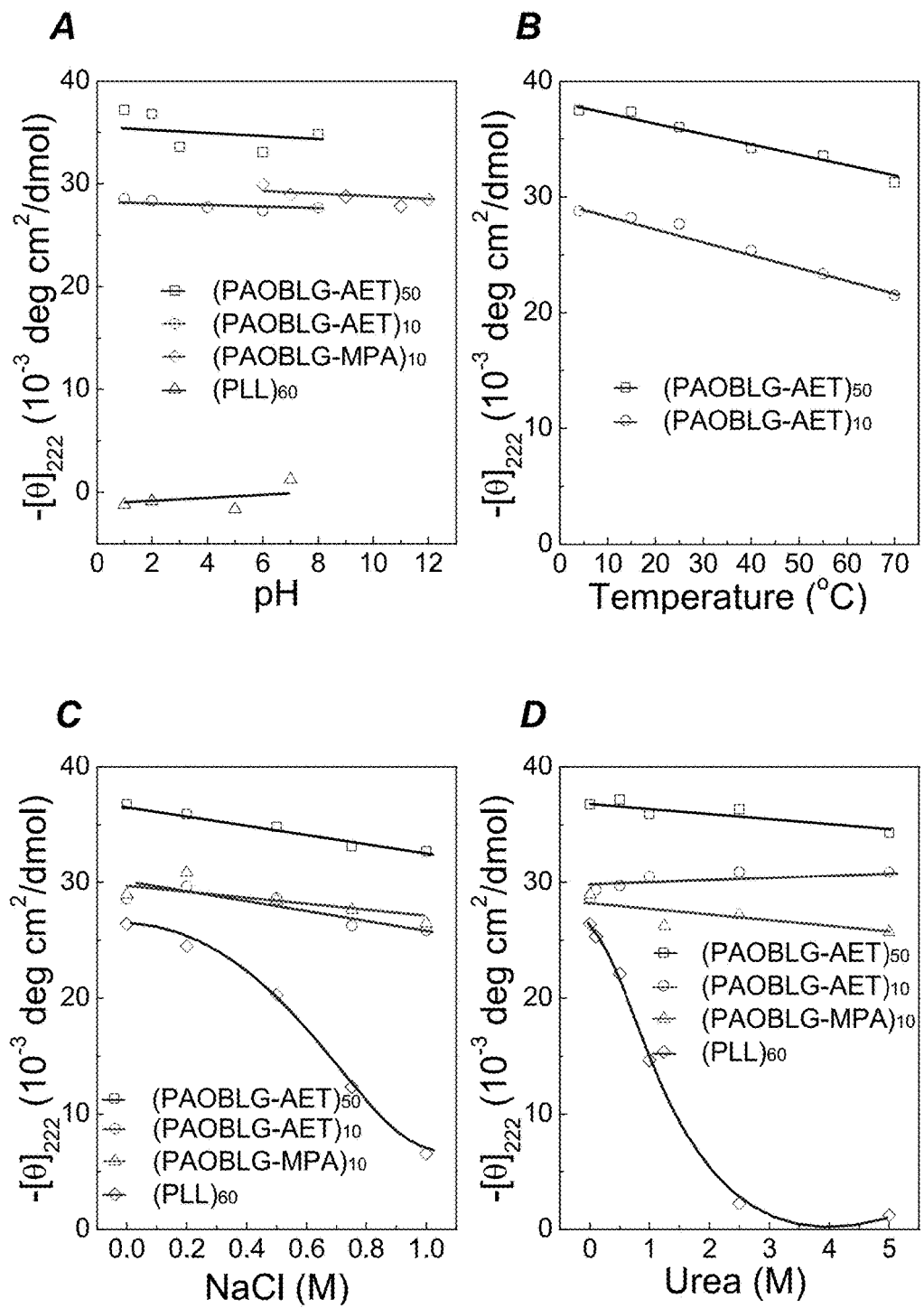

The helical stability of PAOBLG-AETs against changing environmental conditions was then studied, including changes in the pH and temperature and the presence of denaturing reagents. The $-[\theta]_{222}$ value of (PAOBLG-AET)$_{10}$ remained unchanged when the solution's pH was increased from 1 to 8 (FIG. 83$a$). At further increased pH values, (PAOBLG-AET)$_{10}$ became less soluble because of de-protonation of some of its charged ammonium groups. (PAOBLG-AET)$_{10}$ showed a lack of concentration dependence of its $-[\theta]_{222}$ value in helix-forming conditions, indicating that it remained monomeric in aqueous solution. It displayed excellent helical stability against elevated temperature, with its $-[\theta]_{222}$ value decreasing 25% from 28,800 cm$^2$·deg·dmol$^{-1}$ at 4° C. to 21,600 cm$^2$·deg·dmol$^{-1}$ at 70° C. (FIG. 83$b$), and against helix-destabilizing conditions such as high concentrations of NaCl (FIG. 83$c$) and urea (FIG. 83$d$). (PAOBLG-AET)$_{10}$ showed unprecedented helical stability against any known α-peptides and amazingly maintained ~100% of its original helical content in 5M urea. (PAOBLG-AET)$_{50}$ showed very similar helical stability as (PAOBLG-AET)$_{10}$ to those changing environmental conditions; the helical stabilities of both (PAOBLG-AET)$_{10}$ and (PAOBLG-AET)$_{50}$ were drastically different from that of PLL$_{60}$ in high concentrations of NaCl (FIG. 83$c$) and urea solutions (FIG. 83$d$).

This novel strategy of distal charge placement on side chains to maintain both water solubility and high helicity in low MW polypeptide can also be extended to polypeptides bearing negatively charged side chains. (PAOBLG-MPA)$_{10}$, a peptide with similar structure as (PAOBLG-AET)$_{10}$ bearing carboxylate terminated side-chain with charge-backbone distance of 18 σ-bonds, was prepared via thiol-ene reaction of PAOBLG with 3-mercaptopropionic acid (FIG. 81$d$). (PAOBLG-MPA)$_{10}$ had a helicity of 84% in aqueous solution at pH 9, when its carboxylate groups are completely deprotonated. The $-[\theta]_{222}$ value of (PAOBLG-MPA)$_{10}$ remained unchanged when the solution's pH was decreased from 12 to 6 (FIG. 83$a$). At further decreased pH values, (PAOBLG-MPA)$_{10}$ became less soluble because of protonation of some of its charged carboxylate ions. (PAOBLG-MPA)$_{10}$ showed very similar response as (PAOBLG-AET)$_{10}$ against the helix-destabilizing conditions such as high concentrations of NaCl (FIG. 83$c$) and urea (FIG. 83$d$).

In summary, polypeptides with long side chain bearing positive/negative charge groups were synthesized by controlled ROP of AOB-L-Glu-NCA and subsequent thiol-ene reaction. Because of their elongated hydrophobic side chains and distally situated charges, these polypeptides are highly water-soluble and have very high helicity even with a DP value as low as 10. Furthermore, the helical structures of these low MW polypeptide electrolytes were stable to changes in pH, temperature, NaCl, and urea. To our knowledge, PAOBLG-AET(MPA) is the shortest, charged peptide to show such high helicity, remarkable helical stability and water solubility. This study demonstrates that elongating the hydrophobic side chain bearing a terminal charge group can serve as a general strategy for the design of water-soluble polypeptide with high helicity and high helical stability.

Materials.

Chemicals were purchased from Sigma-Aldrich (St. Louis, Mo., USA) and used as received unless otherwise specified. Anhydrous dimethylformamide (DMF) was dried by a column packed with 4 Å molecular sieves and stored in a glove box. Tetrahydrofuran (THF) and hexane were dried by a column packed with alumina and stored in a glove box. 4-Allyloxylbenzyl chloride (Podichetty et al., *J. Med. Chem.* 2009, 52, 3484-3495), L-glutamic acid copper(II) complex copper(II) salt tetrahydrate (Vanheeswijk et al., *Synthesis-Stuttgart* 1982, 744-747), PLL$_{60}$ (Lu and Cheng, *J. Am. Chem. Soc.* 2007, 129, 14114-14115), and (PVBLG-1)$_{10}$ (Lu et al., *Nature Communications* 2011, 2, 206) were prepared as described in the literature procedures.

Instrumentation.

NMR spectra were recorded on a Varian UI400 MHz, a UI500NB MHz or a VXR-500 MHz spectrometer. Tandem gel permeation chromatography (GPC) experiments were performed on a system equipped with an isocratic pump (Model 1100, Agilent Technology, Santa Clara, Calif.), a DAWN HELEOS 18-angle laser light scattering detector (also known as multi-angle laser light scattering (MALLS) detector, Wyatt Technology, Santa Barbara, Calif.) and an Optilab rEX refractive index detector (Wyatt Technology, Santa Barbara, Calif.). The detection wavelength of HELEOS was set at 658 nm. Separations were performed using serially connected size exclusion columns (100 Å, 500 Å, 10$^3$ Å and 10$^4$ Å Phenogel columns, 5 μm, 300×7.8 mm, Phenomenex, Torrance, Calif.) at 60° C. using DMF containing 0.1 M LiBr as the mobile phase.

A MALLS detector was calibrated using pure toluene with no need for external polymer standards and was used for the determination of the absolute molecular weights. The molecular weights (MWs) of all polymers were determined based on the dn/dc value of each sample calculated offline by using the internal calibration processed by the ASTRA V software (version 5.1.7.3, Wyatt Technology, Santa Barbara, Calif.). Infrared spectra were recorded on a Perkin Elmer 100 serial FTIR spectrophotometer equipped with universal attenuated total reflectance (ATR), which enabled the analysis of polymer sample in powder form. Circular dichroism (CD) measurements were carried out on a JASCO J-700 or a JASCO 720 CD Spectrometer. Lyophilization was performed on a FreeZone lyophilizer (Labconco, Kansas City, Mo.). UV light was generated from an OmiCure 51000 UV lamp (EXFO, Mississauga, Canada). Matrix Assisted Laser Desorption/Ionization-Time Of Flight mass spectrometry (MALDI-TOF MS) spectra were collected on a Applied Biosystems Voyager-DE™ STR system using 2,5-dihydroxybenzoic acid as matrix.

Synthesis of γ-(4-allyloxylbenzyl)-L-glutamate (AOB-L-Glu)

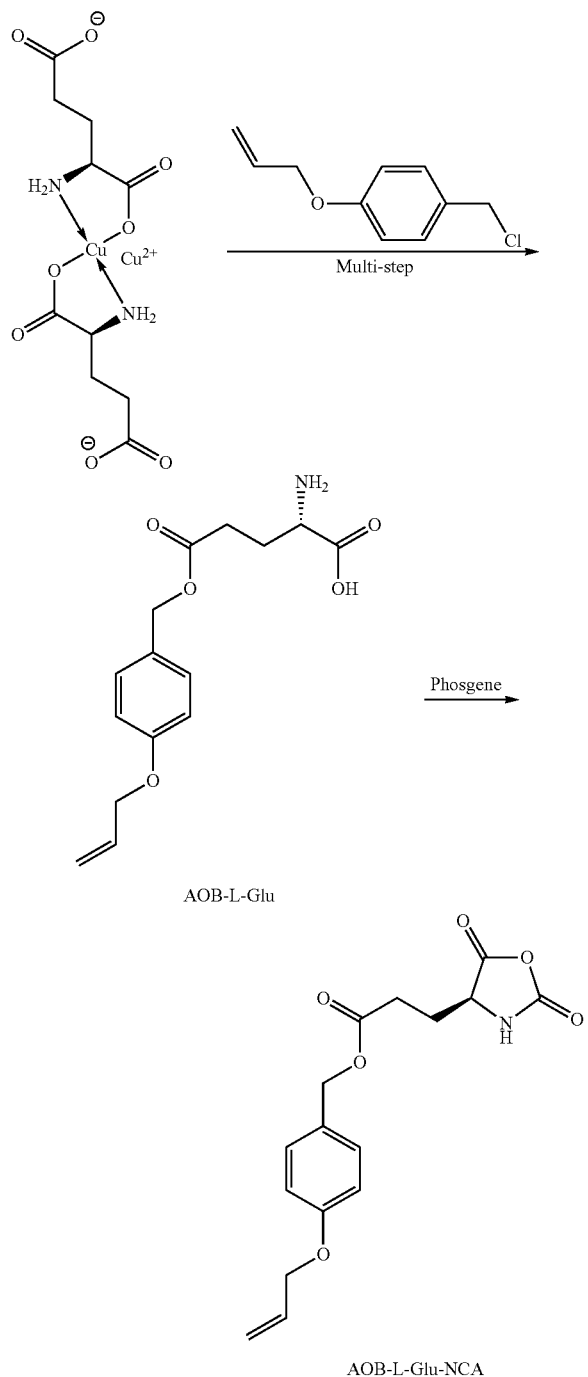

AOB-L-Glu

AOB-L-Glu-NCA

In a 500-mL round-bottom flask, N,N,N',N'-tetramethylguanidine (3.4 mL, 2.7 mmol) was added slowly to a stirred mixture of L-glutamic acid copper(II) complex copper(II) salt tetrahydrate (3.29 g, 6.7 mmol) and L-glutamic acid (1.99 g, 13.4 mmol) in a mixed solvent of dimethylformamide (DMF)/water (12 mL/1.9 mL). The mixture gradually turned dark blue. After the dissolution of all solids, DMF (9.6 mL) was added. 4-Allyloxylbenzyl chloride (5.15 g, 28.3 mmol) was added to the deep blue solution in one portion. The mixture was stirred at rt for 24 h. Acetone (300 mL) was added to the slurry and the mixture was stirred until a fine precipitate was obtained. The precipitate was collected by filtration and washed with acetone (100 mL×3) to yield crude AOB-L-Glu in violet powder form. The crude AOB-L-Glu was added a freshly-prepared EDTA disodium salt solution (EDTA (5.84 g) and sodium bicarbonate (3.36 g) in 40-45 mL water). The violet solid gradually turned white and the solution turned blue. The mixture was vigorously stirred for 3 h. The solid was collected by filtration, washed by DI water until the solid became white, recrystallized with water/isopropyl alcohol (1:2 v/v), and dried by lyophilization to give AOB-L-Glu (3.6 g, 46% yield). $^1$H-NMR (DMSO-$d_6$: DCl (20%)=9:1 v/v, 500 MHz): δ 7.24 (d, 2H, ArH), 6.89 (d, 2H, ArH), 5.95 (m, 1H, PhOCH$_2$CH=CH$_2$), 5.32 (dd, 1H, PhOCH$_2$CH=CH$_2$), 5.19 (dd, 1H, PhCH=CH$_2$), 4.95 (s, 2H, PhCH$_2$), 4.50 (d, 2H, PhOCH$_2$CH=CH$_2$), 3.86 (t, 1H, alpha-H), 2.50 (m, 2H, CH$_2$CH$_2$COOCH$_2$ and DMSO), 2.03 (t, 2H, CH$_2$CH$_2$COOCH$_2$). $^{13}$C-NMR (DMSO-$d_6$: DCl (20%)=9:1 v/v, 500 MHz): δ 172.3, 170.8, 158.6, 134.0, 130.5, 128.5, 118.3, 115.2, 68.7, 66.3, 51.5, 29.9 and 25.7. ESI-MS (m/z): calcd. $C_{15}H_{19}NO_5$ 293.1 (M). found 294.1 (M+H)$^+$.

Synthesis of γ-(4-allyloxylbenzyl)-L-glutamate N-carboxyanhydride (AOB-L-Glu-NCA)

AOB-L-Glu (2.93 g, 10 mmol) was dried under vacuum for 1 h. Anhydrous THF (30 mL) was added under nitrogen followed by the addition of phosgene (20% in toluene, 7 mL) over the course of 5 min. The suspension was stirred at 50° C. for about 2 h until a clear solution was obtained. The solvent was removed under vacuum. The crude AOB-L-Glu-NCA was recrystallized three times with anhydrous THF/hexane (10 mL/100 mL) in a glove box to yield AOB-L-Glu-NCA in needle crystalline form (2.6 g, 81%). $^1$H-NMR (CDCl$_3$, 500 MHz): δ 7.24 (d, 2H, ArH), 6.88 (d, 2H, ArH), 6.01 (m, 1H, PhOCH$_2$CH=CH$_2$), 5.39 (dd, 1H, PhOCH$_2$CH=CH$_2$), 5.26 (dd, 1H, PhCH=CH$_2$), 5.03 (s, 2H, PhCH$_2$), 4.51 (d, 2H, PhOCH$_2$CH=CH$_2$), 4.37 (t, 1H, alpha-H), 2.52 (t, 2H, CH$_2$CH$_2$COOCH$_2$), 2.14 (m, 2H, CH$_2$CH$_2$COOCH$_2$). $^{13}$C-NMR (CDCl$_3$, 500 MHz): δ 172.7, 169.6, 159.0, 152.4, 133.2, 130.5, 127.8, 118.0, 115.2, 69.1, 67.1, 56.9, 30.0, 26.8. ESI-MS (m/z): Calcd $C_{16}H_{17}NO_6$ 319.1 (M). found: 342.3 (M+Na)$^+$. Elemental analysis: calcd. $C_{16}H_{17}NO_6$ 60.18%; C, 5.37%; H, 4.39%; N. found: 60.06%; C, 5.28%; H, 4.40%; N.

General Procedure for the Polymerization of AOB-L-Glu-NCA.

In a glove box, AOB-L-Glu-NCA (32 mg, 0.1 mmol) was dissolved in DMF (1 mL) followed by the addition of HMDS (20 μL, 2 μmol). The polymerization solution was stirred for 16 h at room temperature. An aliquot of the polymerization solution was diluted to 10 mg polymer (PAOBLG)/mL using DMF containing 0.1 M LiBr and then analyzed by GPC ($M_n$=1.38×10$^3$ g/mol; $M_w/M_n$=1.05). The majority of the DMF of the polymerization solution was removed under vacuum. The polymer was precipitated with ether (15 mL). The obtained PAOBLG was sonicated for 5 min in ether and centrifuged to remove the solvent. After the sonication-centrifugation procedure was repeated two more times, PAOBLG was collected and dried under vacuum (22 mg, 80% isolated yield). $^1$H-NMR (CDCl$_3$, 500 MHz): δ

7.14 (d, 2H, ArH), 6.77 (d, 2H ArH), 5.97 (m, 1H, PhOCH$_2$CH=CH$_2$), 5.33 (dd, 1H, PhOCH$_2$CH=CH$_2$), 5.22 (dd, 1H, PhCH=CH$_2$), 5.03 (d, 2H, PhOCH$_2$CH=CH$_2$), 4.51 (s, 2H, PhCH$_2$), 3.96 (m, 1H, alpha-H), 2.63 (m, 2H, CH$_2$CH$_2$COOCH$_2$), 2.16 (m, 2H, CH$_2$CH$_2$COOCH$_2$).

Kinetic Study of the Polymerization of AOB-L-Glu-NCA.

In a glove box, AOB-L-Glu-NCA (192 mg, 0.6 mmol) was dissolved in DMF (3.0 mL). HMDS (0.1 M in DMF, 0.06 mL) (or HMDS (0.1 M in DMF, 0.06 mL) and TBD (0.01 M in DMF, 0.06 mL)) was added to the stirred NCA solution in one portion. The real-time concentration of NCA was quantified by measuring the intensity of the anhydride band at 1784 cm$^{-1}$ by FT-IR. The conversion of NCA was determined by comparing the NCA concentration in the polymerization solution versus the initial NCA concentration.

General Procedure for the Synthesis of PAOBLG-AET Via Thiol-Ene Reaction.

In a quartz bottle, PAOBLG$_n$ (16 mg, 0.06 mmol), 2-aminoethanethiol hydrochloride (34 mg, 0.3 mmol) and Irgacure®2959 photo-initiator (1 mg, 0.004 mmol) were dissolved in DMF/DI water (1.0 mL/0.1 mL). The quartz bottle was sealed with a rubber septum and the mixture was purged with nitrogen for 10 min. Irradiation with a 365 nm UV lamp (16 mW/cm$^2$) was carried out for 10 min. The crude product was dialyzed against water for 2-3 days and lyophilized (yield 70-90%). The modification efficiency was determined to be about 100% based on $^1$H-NMR analysis.

Synthesis of PAOBLG-MPA Via Thiol-Ene Reaction

PAOBLG-MPA was synthesized by following similar protocol as described above for the synthesis of PAOBLG-AET by using 3-mercaptopropionic acid instead of 2-aminoethanethiol hydrochloride as starting materials. The isolated yield was about 90%. The modification efficiency was determined to be about 100% based on $^1$H-NMR analysis.

General Procedure for the Analysis of Polypeptide Conformations by Circular dichroism (CD).

The CD study was performed on a JASCO J-700 and J-720 CD spectrometer. The polymer samples were prepared at concentrations of 0.01-0.1 mg/mL in general unless otherwise specified. The solution was placed in a quartz cell with a path length of 0.5 cm. The mean residue molar ellipticity of each polymer was calculated based on the measured apparent ellipticity by following the literature reported formulas: Ellipticity ([θ] in deg·cm$^2$·dmol$^{-1}$)=(millidegrees×mean residue weight)/(path length in millimeters×concentration of polypeptide in mg·ml$^{-1}$) (Greenfield, N. J. Nat. Prot. 2006, 1, 2876-2890). For the helix-temperature dependency study, the temperature of the sample chamber where the quartz cell was placed was controlled by a water bath (from 4° C. to 70° C.). The sample was equilibrated at corresponding temperature for at least 10 min before the CD measurements. By following similar preparation method, the polymers were dissolved in DI water or in a solution containing NaCl or urea to analyse the conformation of polymers under denaturing conditions. For the helix-pH dependency study, the pH of the polymer solution was tuned by the addition of a concentrated HCl or NaOH solution. The α-helix contents of the polypeptides were calculated using the following equation: % α-helix=(−[θ$_{222}$]+3000)/39,000 (Morrow et al., Biochemistry 2000, 39, 11657-11666).

Brief Discussion.

$^1$H-NMR studies showed that the thiol-ene reaction completed with nearly 100% efficiency, evidenced by the complete disappearance of the allyl protons of PAOBLG (δ 5.3 and 5.9 ppm (i and h) after the reaction) and the ratio of the normalized integration value of peak-k versus peak-f and e (0.63) (FIG. 84). (PAOBLG-AET)$_{50}$ has excellent water solubility (>20 mg/mL) while (PAOBLG)$_{50}$ is insoluble in water.

Example 10. De Novo Designed α-Helical Guanidine-Rich Polypeptides for Cell-Penetration Introducing hydrophobic alkyl side groups, elongating the distance between the backbone and the head groups or increasing backbone rigidities or helicity have been demonstrated to improve the cell-penetrating ability. However, guanidine-rich transporters (GRTs) with helical conformations require the design of peptides with specific sequences and time consuming stepwise synthesis. Helical guanidine-rich polypeptides (GRPs) made by polymerization have not been previously reported. A strategy for the facile generation of cationic and helical polypeptides is described herein. The helical structure of cationic polypeptides can be stabilized by increasing the hydrophobic interaction of the side chain. By following this general strategy, de novo helical GRPs can be prepared via the ring-opening polymerization.

In this example, a series of highly efficient guanidine-rich polypeptides with different main-chain/side-chain length, configurations (D, L or DL), secondary structures and hydrophobic domains have been developed.

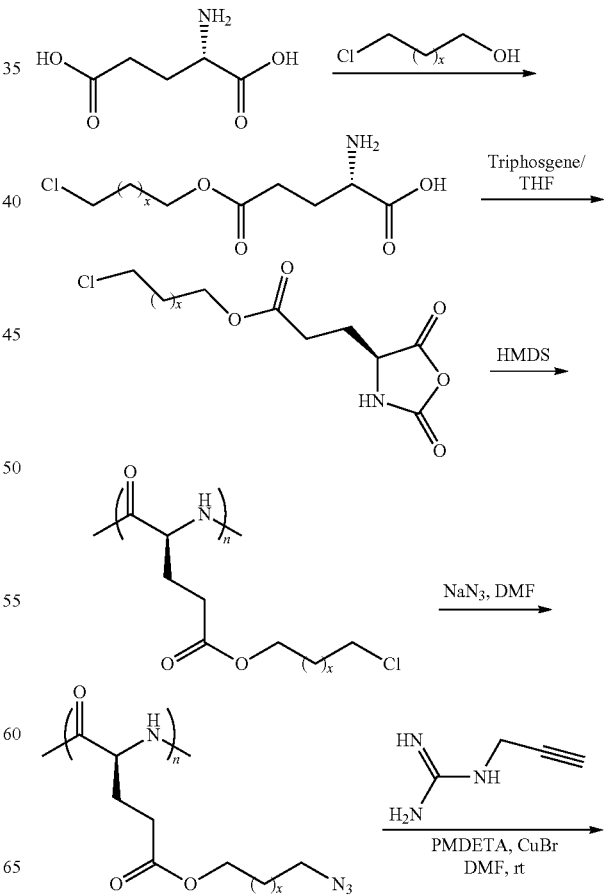

Scheme 10-1. Synthesis of guanidine-rich polypeptides.

-continued

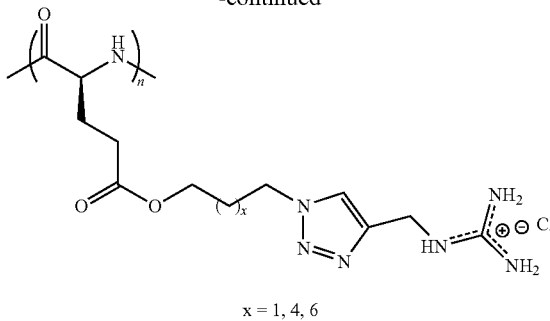

x = 1, 4, 6

Synthesis of N-Pro-2-ynyl-guanidine (PG)

Propargyl amine (0.12 g, 2 mmol), 1H-pyrazole-1-carboxamidine hydrochloride (0.29 g, 2 mmol) and triethylamine (0.26 g, 2 mmol) were dissolved in DMF (1 mL), and the mixture was stirred at room temperature for 16 h. Then, the reaction solution was poured into 10-fold ethyl ether (10 mL) to remove the DMF and other impurities. Dry under vacuum to yield an oily product. Obtained 0.24 g (yield=90%). $^1$H NMR [D$_2$O, δ, ppm]: 3.85 (s, 2H, CH≡CH$_2$—), 2.57 (s, 1H, CH≡CH$_2$—); $^{13}$C {$^1$H} NMR (D$_2$O, δ, ppm): 165.08, 77.91, 73.92 and 30.88; HR ESI-MS (m/z) [M+H]$^+$ calcd. for C$_4$H$_8$N$_3$, 98.0718. found 98.0721.

Synthesis of Poly(γ-3-azidopropanyl-L-glutamate) (PAPLG)

The polymer was synthesized by a literature procedure. $^1$H NMR (CDCl$_3$, δ, ppm): 4.18 (s, 2H, ClCH$_2$CH$_2$CH$_2$—), 3.95 (br s, 1H, CHNH), 3.40 (s, 2H, ClCH$_2$CH$_2$CH$_2$—), 2.68 (br s, 2H, —COCH$_2$CH$_2$—), 2.39 (br s, 2H, —COCH$_2$CH$_2$—), 1.92 (s, 2H, ClCH$_2$CH$_2$CH$_2$—).

Synthesis of γ-(3-Chloropropanyl)-D-glutamate, γ-(6-Chlorohexyl)-L-glutamate and γ-(8-Chlorooctyl)-L-glutamate γ-(3-Chloropropanyl)-D-glutamate was synthesized from a reported method. Obtained 10.0 g. (yield=66%). $^1$H NMR [D$_2$O, δ, ppm]: 4.13 (t, 2H, —CH$_2$OOC—), 3.61 (m, 1H, —CHNH$_2$), 3.54 (t, 2H, —CH$_2$Cl), 2.45 (t, 2H, —CH$_2$COO—), 1.97 (m, 4H, —CH$_2$CH$_2$COO— and ClCH$_2$CH$_2$CH$_2$OOC—); $^{13}$C{$^1$H} NMR (D$_2$O, δ, ppm): 174.42, 171.36, 62.65, 52.09, 41.80, 30.74, 29.70 and 24.88; HR ESI-MS (m/z) [M+H]$^+$ calcd. for C$_8$H$_{15}$ClNO$_4$, 244.0690. found 244.0690.

Typically, L-Glutamic acid (10.0 g, 68.0 mmol) and 6-chlorohexanol (15 mL) were mixed and stirred at 0° C., followed by slowly adding H$_2$SO$_4$ (4 mL). The reaction temperature allows warming up to room temperature after adding. Kept stirring for 16 h. Saturated Na$_2$CO$_3$ solution was added to the reaction mixture and the product start to precipitate after the pH value close to 7. The raw product was collected by filtration and purified by recrystallization from isopropanol/H$_2$O. Obtained 10.0 g (yield=55%). $^1$H NMR [D$_2$O/DCl (2 wt %), δ, ppm]: 3.83 (m, 3H, —CH$_2$OOC— and —CHNH$_2$) 3.32 (t, 2H, —CH$_2$Cl), 2.35 (t, 2H, —CH$_2$COO—), 1.97 (m, 2H, —CH$_2$CH$_2$COO—), 1.47-1.11 (m, 8H, ClCH$_2$—(CH$_2$)$_4$—CH$_2$OOC—); $^{13}$C{$^1$H} NMR [D$_2$O/DCl (2 wt %), δ, ppm]: 174.56, 171.32, 65.90, 52.10, 45.80, 31.81, 29.79, 27.63, 25.75, 24.95 and 24.48; HR ESI-MS (m/z) [M+H]$^+$ calcd. for C$_{11}$H$_{21}$ClNO$_4$, 266.1159. found 266.1158.

γ-(8-Chlorooctyl)-L-glutamate was synthesized using the same method. Obtained 6.0 g (yield=30%). $^1$H NMR [D$_2$O/DCl (2 wt %), δ, ppm]: 3.83 (t, 2H, —CH$_2$OOC—), 3.76 (m, 1H, —CHNH$_2$), 3.23 (t, 2H, —CH$_2$Cl), 2.33 (t, 2H, —CH$_2$COO—), 1.94 (m, 2H, —CH$_2$CH$_2$COO—), 1.45-1.03 (m, 12H, ClCH$_2$—(CH$_2$)$_6$—CH$_2$OOC—); $^{13}$C{$^1$H} NMR [D$_2$O/DCl (2 wt %), δ, ppm]: 173.74, 171.16, 65.38, 52.10, 45.22, 32.59, 29.81, 29.12, 28.73, 28.36, 26.77, 25.71 and 25.09. HR ESI-MS (m/z) [M+H]$^+$ calcd. for C$_{13}$H$_{25}$ClNO$_4$, 294.1472. found 294.1472.

Synthesis of γ-(3-Chloropropanyl)-D-glutamic Acid Based N-Carboxyanhydride (CP-D-NCA), γ-(6-Chlorohexyl)-L-glutamic Acid Based N-Carboxyanhydride (CH-L-NCA) and γ-(8-Chlorooctyl)-L-glutamic Acid Based N-Carboxyanhydride (CO-L-NCA)

A round-bottomed flask (100 mL) was charged with γ-(3-Chloropropanyl)-D-glutamate (1.2 g, 5.4 mmol), phosgene (20%, 6 mL, 10.8 mmol. 2 equiv.) and anhydrous THF (30 mL) under nitrogen. The mixture was stirred at room temperature for 24 h over which period the γ-chlorohexanyl-L-glutamate was gradually dissolved. Removal of the solvent under vacuum yielded an oily liquid. Recrystallization by layering hexane on top of a CH$_2$Cl$_2$ solution containing the oil was not successful, resulting in two separate liquid layers. The bottom layer was separated and subjected to vacuum to give a clear liquid. Obtained 0.72 g (yield=54%). $^1$H NMR [CDCl$_3$, δ, ppm]: 6.55 (s, 1H, —NH), 4.42 (t, 1H, —CHNH), 4.27 (t, 2H, —CH$_2$OOC—), 3.62 (t, 2H, —CH$_2$Cl), 2.57 (t, 2H, —CH$_2$CH$_2$COO—), 2.10-2.40 (m, 4H, —CH$_2$CH$_2$COO— and ClCH$_2$CH$_2$CH$_2$OOC—); $^{13}$C{$^1$H} NMR [CDCl$_3$, δ, ppm]: 172.70, 169.53, 151.92, 62.23, 57.15, 41.25, 31.46, 29.87 and 27.04. HR ESI-MS (m/z) [M+H]$^+$ calcd. for C$_9$H$_{13}$ClNO$_5$, 250.0482. found 250.0488.

γ-(6-Chlorohexyl)-L-glutamic Acid Based N-Carboxyanhydride (CH-L-NCA) was synthesized using the same method. Obtained 1.0 g (yield=61%). $^1$H NMR [CDCl$_3$, δ, ppm]: 6.69 (s, 1H, —NH), 4.41 (t, 1H, —CHNH), 4.10 (t, 2H, —CH$_2$OOC—), 3.54 (t, 2H, —CH$_2$Cl), 2.55 (t, 2H, —CH$_2$CH$_2$COO—), 2.13-2.26 (m, 2H, —CH$_2$CH$_2$COO—), 1.38-1.78 (m, 8H, ClCH$_2$—(CH$_2$)$_4$—CH$_2$OOC—); $^{13}$C{$^1$H} NMR [CDCl$_3$, δ, ppm]: 172.93, 169.69, 152.02, 65.47, 57.26, 45.18, 32.58, 30.05, 28.55, 27.14, 26.61 and 25.43. HR ESI-MS (m/z) [M+H]$^+$ calcd. for C$_{12}$H$_{19}$ClNO$_5$, 292.0952. found 292.0957.

γ-(8-Chlorooctyl)-L-glutamic acid-based N-carboxyanhydride (CO-L-NCA) was synthesized using the same method. Obtained 0.5 g (yield=31%). $^1$H NMR [CDCl$_3$, δ, ppm]: 6.65 (s, 1H, —NH), 4.40 (t, 1H, —CHNH), 4.09 (t, 2H, —CH$_2$OOC—), 3.53 (t, 2H, —CH$_2$Cl), 2.55 (t, 2H, —CH$_2$CH$_2$COO—), 2.12-2.26 (m, 2H, —CH$_2$CH$_2$COO—), 1.32-1.77 (m, 12H, ClCH$_2$—(CH$_2$)$_6$—CH$_2$OOC—); $^{13}$C{$^1$H} NMR [CDCl$_3$, δ, ppm]: 172.95, 169.71, 152.01, 65.66, 57.27, 45.38, 32.76, 30.08, 29.24, 28.93, 28.66, 27.16, 26.96 and 25.96. HR ESI-MS (m/z) [M+H]$^+$ calcd. for C$_{14}$H$_{23}$ClNO$_5$, 320.1265. found 320.1269.

Synthesis of Poly(γ-3-chloropropanyl-D-glutamate) (PCPDG), Poly(γ-3-chloropropanyl-DL-glutamate) (PCPDLG), Poly(γ-6-chlorohexyl-L-glutamate) (PCHLG) and Poly(γ-8-chlorooctyl-L-glutamate) (PCOLG)

Typically, inside a glove-box, CP-D-NCA (100 mg, 0.4 mmol) was dissolved in DMF (1.0 mL), followed by adding the HMDS/DMF solution (80.3 μL, 0.1 M, M/I=50). The reaction mixture was stirred for 48 h at room temperature.

The polymer was precipitated from cold methanol and collected by centrifuge. The product was dried under vacuum at 40° C. for 8 h. Obtained 55 mg (yield=67%). $^1$H NMR [CDCl$_3$/TFA-d (v/v=85/15), δ, ppm]: 4.54 (s, 1H, —CHNH), 4.28 (s, 2H, —CH$_2$OOC—), 3.59 (s, 2H, —CH$_2$Cl), 2.50 (s, 2H, —CH$_2$CH$_2$COO—), 1.95-2.40 (m, 4H, —CH$_2$CH$_2$COO— and ClCH$_2$CH$_2$CH$_2$OOC—); $^{13}$C{$^1$H} NMR [CDCl$_3$/TFA-d (v/v=85/15), δ, ppm]: 175.43, 173.13, 63.23, 53.45, 40.77, 30.99, 30.17 and 26.97.

Poly(γ-3-chloropropanyl-DL-glutamate) was synthesized using the same method by adding equivalent CP-L-NCA and CP-D-NCA. Obtained 50 mg (yield=60%). $^1$H NMR [CDCl$_3$/TFA-d (v/v=85/15), δ, ppm]: 4.61 (s, 1H, —CHNH), 4.29 (s, 2H, —CH$_2$OOC—), 3.59 (s, 2H, —CH$_2$Cl), 2.54 (s, 2H, —CH$_2$CH$_2$COO—), 1.95-2.40 (m, 4H, —CH$_2$CH$_2$COO— and ClCH$_2$CH$_2$CH$_2$OOC—); $^{13}$C{$^1$H} NMR [CDCl$_3$/TFA-d (v/v=85/15), δ, ppm]: 175.51, 173.15, 63.26, 53.44, 40.74, 30.97, 30.13 and 26.96.

Poly(γ-6-chlorohexyl-L-glutamate) was synthesized using the same method. Obtained 61 mg (yield=70%). $^1$H NMR [CDCl$_3$/TFA-d (v/v=85/15), δ, ppm]: 4.55 (s, 1H, —CHNH), 4.08 (s, 2H, —CH$_2$OOC—), 3.52 (s, 2H, —CH$_2$Cl), 2.48 (s, 2H, —CH$_2$CH$_2$COO—), 2.15-2.48 (d, 2H, —CH$_2$CH$_2$COO—), 1.34-1.98 (m, 8H, ClCH$_2$—(CH$_2$)$_4$—CH$_2$OOC—); $^{13}$C{$^1$H} NMR [CDCl$_3$/TFA-d (v/v=85/15), δ, ppm]: 176.05, 173.25, 66.79, 53.41, 44.85, 32.31, 30.21, 27.99, 27.15, 26.38, 24.94.

Poly(γ-8-chlorooctyl-L-glutamate) was synthesized using the same method. Obtained 56 mg (yield=65%). $^1$H NMR [CDCl$_3$/TFA-d (v/v=85/15), δ, ppm]: 4.56 (s, 1H, —CHNH), 4.07 (s, 2H, —CH$_2$OOC—), 3.53 (s, 2H, —CH$_2$Cl), 2.48 (s, 2H, —CH$_2$CH$_2$COO—), 1.98-2.14 (d, 2H, —CH$_2$CH$_2$COO—), 1.30-1.76 (m, 12H, ClCH$_2$—(CH$_2$)$_6$—CH$_2$OOC—); $^{13}$C{$^1$H} NMR [CDCl$_3$/TFA-d (v/v=85/15), δ, ppm]: 176.13, 173.29, 67.02, 53.39, 45.17, 32.59, 30.20, 29.04, 28.73, 27.13, 26.79 and 25.51.

Synthesis of Poly(γ-3-azidopropanyl-D-glutamate) (PAPDG), Poly(γ-3-azidopropanyl-DL-glutamate) (PAPDLG), Poly(γ-6-azidohexyl-L-glutamate) (PAHLG) and Poly(γ-8-azidooctyl-L-glutamate) (PAOLG)

A DMF (2 mL) solution of PCPDG (41 mg, 0.2 mmol of chloro groups) and sodium azide (0.16 g, 2.4 mmol) was stirred at 60° C. for 48 h and allowed to cool to room temperature. The reaction mixture was filtered to remove any inorganic salts. DMF was removed by vacuum distillation at 60° C. to yield a polymer film which was further purified by dissolution in CHCl$_3$, filtration and remove the solvent. The resulting polymer was collected by filtration and dried at under vacuum at 40° C. for 8 h. Obtained 32 mg (yield=75%). $^1$H NMR [CDCl$_3$/TFA-d (v/v=85/15), δ, ppm]: 4.56 (s, 1H, —CHNH), 4.20 (s, 2H, —CH$_2$OOC—), 3.40 (s, 2H, —CH$_2$N$_3$), 2.51 (s, 2H, —CH$_2$CH$_2$COO—), 1.90-2.20 (m, 4H, —CH$_2$CH$_2$COO— and —COOCH$_2$CH$_2$CH$_2$N$_3$); $^{13}$C{$^1$H} NMR [CDCl$_3$/TFA-d (v/v=85/15), δ, ppm]: 175.39, 173.20, 63.36, 53.62, 48.10, 30.19, 27.58 and 26.92.

Poly(γ-3-azidopropanyl-DL-glutamate) was synthesized using the same method. Obtained 30 mg (yield=70%). $^1$H NMR [CDCl$_3$/TFA-d (v/v=85/15), δ, ppm]: 4.55 (s, 1H, —CHNH), 4.18 (s, 2H, —CH$_2$OOC—), 3.38 (s, 2H, —CH$_2$N$_3$), 2.48 (s, 2H, —CH$_2$CH$_2$COO—), 1.90-2.20 (m, 4H, —CH$_2$CH$_2$COO— and —COOCH$_2$CH$_2$CH$_2$N$_3$); $^{13}$C{$^1$H} NMR [CDCl$_3$/TFA-d (v/v=85/15), δ, ppm]: 175.36, 173.05, 63.34, 53.56, 48.09, 30.13, 27.58 and 26.85.

Poly(γ-6-azidohexyl-L-glutamate) was synthesized using the same method. Obtained 38 mg (yield=75%). $^1$H NMR [CDCl$_3$/TFA-d (v/v=85/15), δ, ppm]: 4.61 (s, 1H, —CHNH), 4.12 (s, 2H, —CH$_2$OOC—), 3.33 (s, 2H, —CH$_2$N$_3$), 2.53 (s, 2H, —CH$_2$CH$_2$COO—), 1.99-2.17 (d, 2H, —CH$_2$CH$_2$COO—), 1.40-1.66 (m, 8H, —COOCH$_2$—(CH$_2$)$_4$—CH$_2$N$_3$); $^{13}$C{$^1$H} NMR [CDCl$_3$/TFA-d (v/v=85/15), δ, ppm]: 175.88, 173.22, 66.57, 53.43, 51.44, 30.19, 28.52, 28.05, 27.11, 26.26 and 25.25.

Poly(γ-8-azidooctyl-L-glutamate) was synthesized using the same method. Obtained 40 mg (yield=80%). $^1$H NMR [CDCl$_3$/TFA-d (v/v=85/15), δ, ppm]: 4.62 (s, 1H, —CHNH), 4.11 (s, 2H, —CH$_2$OOC—), 3.35 (s, 2H, —CH$_2$N$_3$), 2.53 (s, 2H, —CH$_2$CH$_2$COO—), 2.00-2.18 (d, 2H, —CH$_2$CH$_2$COO—), 1.33-1.65 (m, 12H, —COOCH$_2$—(CH$_2$)$_6$—CH$_2$N$_3$); $^{13}$C{$^1$H} NMR [CDCl$_3$/TFA-d (v/v=85/15), δ, ppm]: 175.81, 173.16, 66.75, 53.38, 51.59, 30.18, 29.04, 28.99, 28.66, 18.17, 27.08, 26.60 and 25.54.

Synthesis of Guanidine-Rich Polypeptides (P1-P11)

Typically, inside a glove-box, N-pro-2-ynyl-guanidine (10 mg, 0.1 mmol), PAPLG (21.2 mg, 0.1 mmol of the functional groups), PMDETA (70 μL, 0.5 mmol) were dissolved in DMF (1 mL), followed by adding the above solution to a vial with CuBr (14 mg, 0.1 mmol). The reaction solution was stirred at room temperature for 24 h. The reaction was quenched by exposing to air and 1N HCl$_{aq}$ was added to the reaction solution until it turned to yellow. The resulting polymer was purified by dialysis against DI water for three days in a dialysis membrane tube with a cutoff molecular weight of 1000 g·mol$^{-1}$. White solid product was obtained after freeze-dry (yield=60%-70%).

P1-P3: $^1$H NMR [D$_2$O, δ, ppm]: 7.89 (s, 1H, triazole), 4.35 (s, 4H, —COOCH$_2$— and triazole-CH$_2$NH—), 4.11 (br, 1H, —CHNH), 3.88 (s, 2H, —COOCH$_2$CH$_2$CH$_2$—), 1.83-2.28 (m, 6H, —CH$_2$CH$_2$COOCH$_2$CH$_2$—).

P4: $^1$H NMR [D$_2$O, δ, ppm]: 7.86 (s, 1H, triazole), 4.33 (s, 4H, —COOCH$_2$— and triazole-CH$_2$NH—), 3.95 (br, 1H, —CHNH), 3.87 (s, 2H, —COOCH$_2$CH$_2$CH$_2$—), 1.83-2.28 (m, 6H, —CH$_2$CH$_2$COOCH$_2$CH$_2$—).

P5: $^1$H NMR [D$_2$O, δ, ppm]: 7.89 (s, 1H, triazole), 4.32 (s, 4H, —COOCH$_2$— and triazole-CH$_2$NH—), 4.07 (br, 1H, —CHNH), 3.80 (s, 2H, —COOCH$_2$CH$_2$CH$_2$—), 1.72-2.17 (m, 6H, —CH$_2$CH$_2$COOCH$_2$CH$_2$—).

P6: $^1$H NMR [D$_2$O, δ, ppm]: 7.87 (s, 1H, triazole), 4.35 (s, 2H, —COOCH$_2$—), 4.21 (s, 2H, triazole-CH$_2$NH—), 3.85 (br, 3H, —CHNH and —COOCH$_2$CH$_2$CH$_2$—), 2.00-2.46 (m, 4H, —CH$_2$CH$_2$COO—), 1.11-1.67 (m, 8H, ClCH$_2$—(CH$_2$)$_4$—CH$_2$OOC—).

P7: $^1$H NMR [D$_2$O, δ, ppm]: 7.88 (s, 1H, triazole), 4.35 (s, 2H, —COOCH$_2$—), 4.17 (s, 2H, triazole-CH$_2$NH—), 3.84 (br, 3H, —CHNH and —COOCH$_2$CH$_2$CH$_2$—), 2.02-2.51 (m, 4H, —CH$_2$CH$_2$COO—), 1.05-1.65 (m, 12H, ClCH$_2$—(CH$_2$)$_6$—CH$_2$OOC—).

P8: $^1$H NMR [D$_2$O, δ, ppm]: 7.87 (s, 1H, triazole), 4.35 (br, 4H, —COOCH$_2$— and triazole-CH$_2$NH—), 3.89 (br, 3H, —CHNH and —COOCH$_2$CH$_2$CH$_2$—), 1.60-2.60 (m, 8H, —CH$_2$CH$_2$COOCH$_2$CH$_2$— and CH$_3$CH$_2$CH$_2$—), 0.64-1.36 (m, 5H, CH$_3$CH$_2$CH$_2$—).

P9: $^1$H NMR [D$_2$O, δ, ppm]: 7.86 (s, 1H, triazole), 4.35 (br, 4H, —COOCH$_2$— and triazole-CH$_2$NH—), 3.89 (br, 3H, —CHNH and —COOCH$_2$CH$_2$CH$_2$—), 1.60-2.60 (m, 8H, —CH$_2$CH$_2$COOCH$_2$CH$_2$— and CH$_3$(CH$_2$)$_2$CH$_2$—), 0.62-1.32 (m, 7H, CH$_3$(CH$_2$)$_2$CH$_2$—).

P10: $^1$H NMR [D$_2$O, δ, ppm]: 7.87 (s, 1H, triazole), 4.31 (br, 4H, —COOCH$_2$— and triazole-CH$_2$NH—), 3.85 (br, 3H, —CHNH and —COOCH$_2$CH$_2$CH$_2$—), 1.80-2.60 (m, 8H, —CH$_2$CH$_2$COOCH$_2$CH$_2$— and CH$_3$(CH$_2$)$_3$CH$_2$—), 0.57-1.41 (m, 9H, CH$_3$(CH$_2$)$_3$CH$_2$—).

P11: $^1$H NMR [D$_2$O, δ, ppm]: 7.87 (s, 1H, triazole), 4.36 (br, 4H, —COOCH$_2$— and triazole-CH$_2$NH—), 3.89 (br, 3H, —CHNH and —COOCH$_2$CH$_2$CH$_2$—), 1.60-2.60 (m, 8H, —CH$_2$CH$_2$COOCH$_2$CH$_2$— and CH$_3$(CH$_2$)$_4$CH$_2$—), 0.57-1.34 (m, 11H, CH$_3$(CH$_2$)$_4$CH$_2$—).

Synthesis of Guanidine-Rich Polypeptides-RhB Conjugate

Typically, guanidine-rich polypeptide (23 mg, 0.67 mmol of repeating units, 3.3×10$^{-6}$ mol of primary amine) was dissolved in NaHCO$_3$ solution (2.5 mL, 0.2 M). RhB—NCS (2 mg) was dissolved in DMSO (0.2 mL) and added to the above aqueous solution. The reaction vial was wrapped with aluminum foil. The reaction was stirring at room temperature for 12 h, followed by dialysis against DI water (the beaker was wrapped with aluminum foil) for three days in a dialysis membrane tube with a cutoff molecular weight of 1000 g·mol$^{-1}$. Red solid product was obtained after freeze-dry (yield=60%-70%).

Cell-Penetrating Test.

Cells were seeded on 96-well plates at 1×104 cells/well and cultured for 24 h followed by refreshment of the medium with serum-free DMEM and addition of the RhB-polypeptide at 2 ug/well. After incubation for 2 h at 37° C. and 4° C., the cells were washed with PBS for 3 times and lysed with RIPA buffer. The RhB-polypeptide content in the lysate were quantified by spectrofluorometry, and protein level was determined by the BCA kit. Uptake level was expressed as ug polypeptide per mg protein. To explore the mechanism involved in the uptake process, cells were pre-incubated with endocytosis inhibitor chlorpromazine (10 μg/mL), genistein (200 μg/mL), cytochilasin D (100 μg/mL), and nocodazole (20 μM) for 30 min prior to nanoparticle application and throughout the 4-h uptake experiment at 37° C. Results were expressed as percentage uptake of the control where cells were incubated with nanoparticles at 37° C. for 2 h.

CLSM.

Cells were seeded on coverslips in 6-well plates at 1×105 cells/well and cultured for 24 h followed by refreshment of the medium with serum-free DMEM and addition of poly-peptides at 2 ug/well. After incubation at 37° C. for 0.5, 1, and 4 h, respectively, the medium was discarded and cells were washed with pH 7.4 PBS for 3 times before fixation with 4% PFA at RT for 10 min. They were washed with PBS for 3 times again, and the nuclei were stained with DAPI at RT for 10 min. Cells were then washed three times with PBS before visualization using CLSM. To evaluate the membrane integrity upon polypeptide treatment, FITC as a membrane impermeable dye was co-incubated with the polypeptide (P10) for 2 h before cell visualization using CLSM.

MTT Assay.

Cells were seeded on 96-well plate at 10$^4$ cell/well and incubated for 24 h. The medium was changed to serum-free DMEM and polypeptides were added at 10, 5, 1, 0, 2, and 0.1 ug/well, respectively. Cells were incubated for 4 h followed by cell viability assessment using the MTT assay.

Results and Discussion.

Synthesis of Guanidine-Rich Polypeptides and their Rh—B Conjugates

γ-Chloroalkyl-L/D-glutamic acid-based N-carboxyanhy-dride (Glu-NCAs) has been synthesized (Scheme 1) by a multi-step synthetic route, namely the monesterification between L/D-glutamic acid and chloroalkyl alcohol using trimethylchlorosilane or H$_2$SO$_4$ as the catalyst, and the cyclization of chloroalkyl-L/D-glutamic acid in the presence of phosgene. Glu-NCAs were purified by repeatedly dissolving in anhydrous THF and precipitate from hexane. The molecular structures of the resulting NCAs have been verified by $^1$H NMR and $^{13}$C NMR.

Hexamethyldisilazane (HMDS) has been previously shown to polymerize γ-benzyl-L-glutamic acid based NCA (BLG-NCA) and γ-3-chloropropyl-L-glutamic acid based NCA (CP-L-NCA) in a controlled manner, we reasoned that it would also polymerize our new NCAs to yield corresponding copolymers with well defined structures, including controlled molecular weight (MW) and polydispersity index (PDI) (Scheme 10-1). The polymers were isolated by precipitation with cold methanol and their molecular structures were determined by $^1$H NMR. The absolute polymer MW and PDI were determined by size-exclusion chromatography coupled with multi-angle light scattering and differential refractive index detectors (SEC-MALS-DRI). To enable facile chemical modification of poly(γ-chloroalkyl-L-gluta-mate) via "click chemistry", the resulting polymers were derivatized into poly(γ-azidoalkyl-L-glutamate) by treatment with NaN$_3$ in DMF at 60° C. for two days. A quantitative conversion can be revealed by $^1$H NMR analysis. Guanidine-rich polypeptides were synthesized via the alkyne-azide [2+3] Huisgen cycloaddition with high grafting efficiency, which was verified by $^1$H NMR analysis. To conjugate the fluorescence dye (Rh—B), 5 mol % of amine groups were grafted to the polypeptides via "click chemistry", followed by reaction with RhB—NCS to yield guanidine-rich polypeptide-RhB conjugates.

Conformational Study of Guanidine-Rich Polypeptides.

Figure 85:
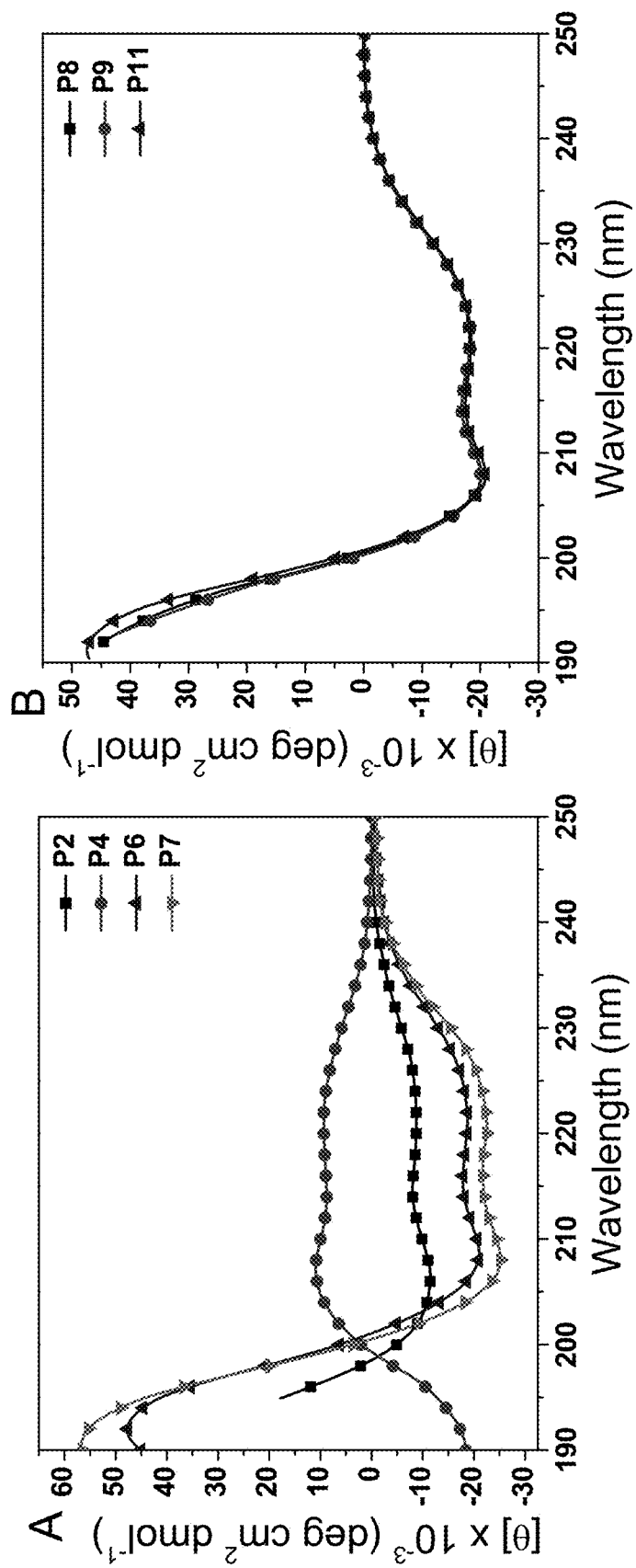

The solution conformation of guanidine-rich polypeptides with different side chain length (x=1, 4 and 6), configurations (D/L) and hydrophobic domains has been characterized by CD spectroscopy (Scheme 10-2 and FIG. 85). All the resulting copolymers adopt α-helical conformations in H$_2$O, as verified by the characteristic ellipticity at 208 nm and 222 nm. To the best of our knowledge, guanidine-rich polypeptides adopt α-helical conformation has never been reported before. To allow for comparison of the relative helical conformation content in the polypeptides. The helicity of the polypeptides were calculated by the following equation: helicity=(-[θ$_m$]+3,000)/39,000. Where [θ]222 is the mean residue ellipticity at 222 nm. The helicity increases with increasing of the side-chain length (FIG. 85A) or incorporation of alkyl side chains (FIG. 85B). For example, P2 with 13 σ-bonds (the number of C—C between backbone and charge center) shows 30% helicity while P6 (16 σ-bonds) and P7 (18 σ-bonds) show 56% and 65% helicity, respectively. This can be ascribed to the side chain hydrophobic interactions.

Scheme 10-2. Structures of guanidine-rich polypeptides.

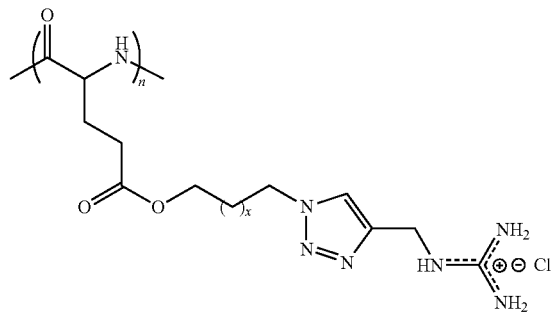

P1: n = 21, PDI = 1.19, L-Glu, x = 1
P2: n = 51, PDI = 1.11, L-Glu, x = 1
P3: n = 69, PDI = 1.10, L-Glu, x = 1
P4: n = 54, PDI = 1.17, D-Glu, x = 1
P5: n = 52, PDI = 1.16, DL-Glu, x = 1
P6: n = 50, PDI = 1.25, L-Glu, x = 4
P7: n = 55, PDI = 1.26, L-Glu, x = 6

-continued

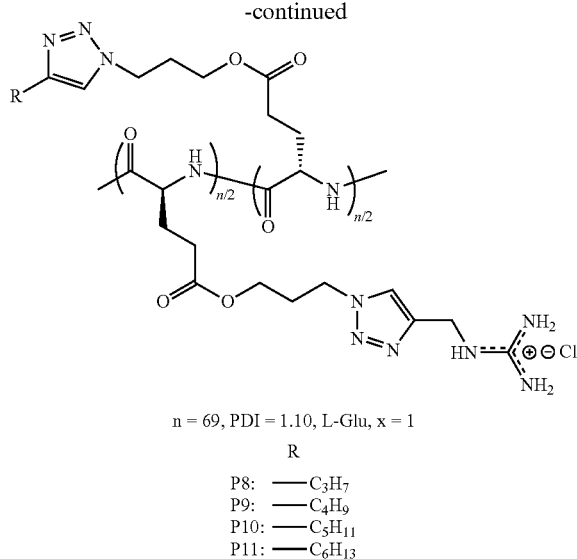

n = 69, PDI = 1.10, L-Glu, x = 1

R
P8: —C₃H₇
P9: —C₄H₉
P10: —C₅H₁₁
P11: —C₆H₁₃

Figure 86:
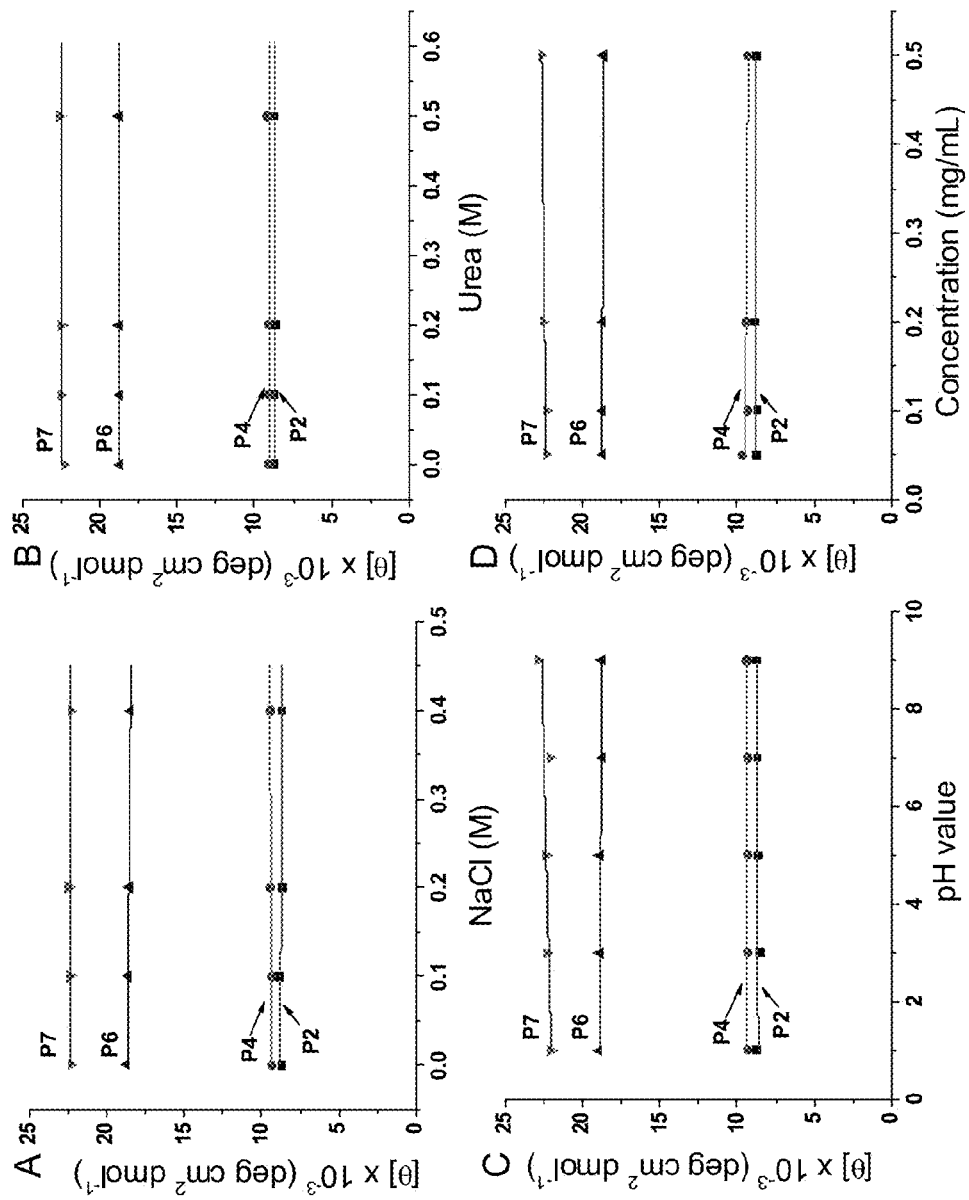

Guanidine-rich polypeptides show remarkable pH-independent helical stability at pH values ranging from 1 to 9 (FIG. 86A). High pH (pH>10) conditions were not able to perform due to protonation of the positively charged guanidino group on the side chain and a decreased solubility. These polymers also showed a lack of concentration dependence (FIG. 86B), suggesting that it remains monomeric in solution. Additionally, the resulting polymers exhibited remarkable stability against the strong denaturing reagent (i.e., urea) (FIG. 86C). All the polymers show reasonably stable helical structure in the NaCl media and the ellipticity at 222 nm remain nearly unchanged when the NaCl concentration was increased from 0 to 0.4 M at 25° C.

Cell-Penetrating Efficiency.

Figure 87:
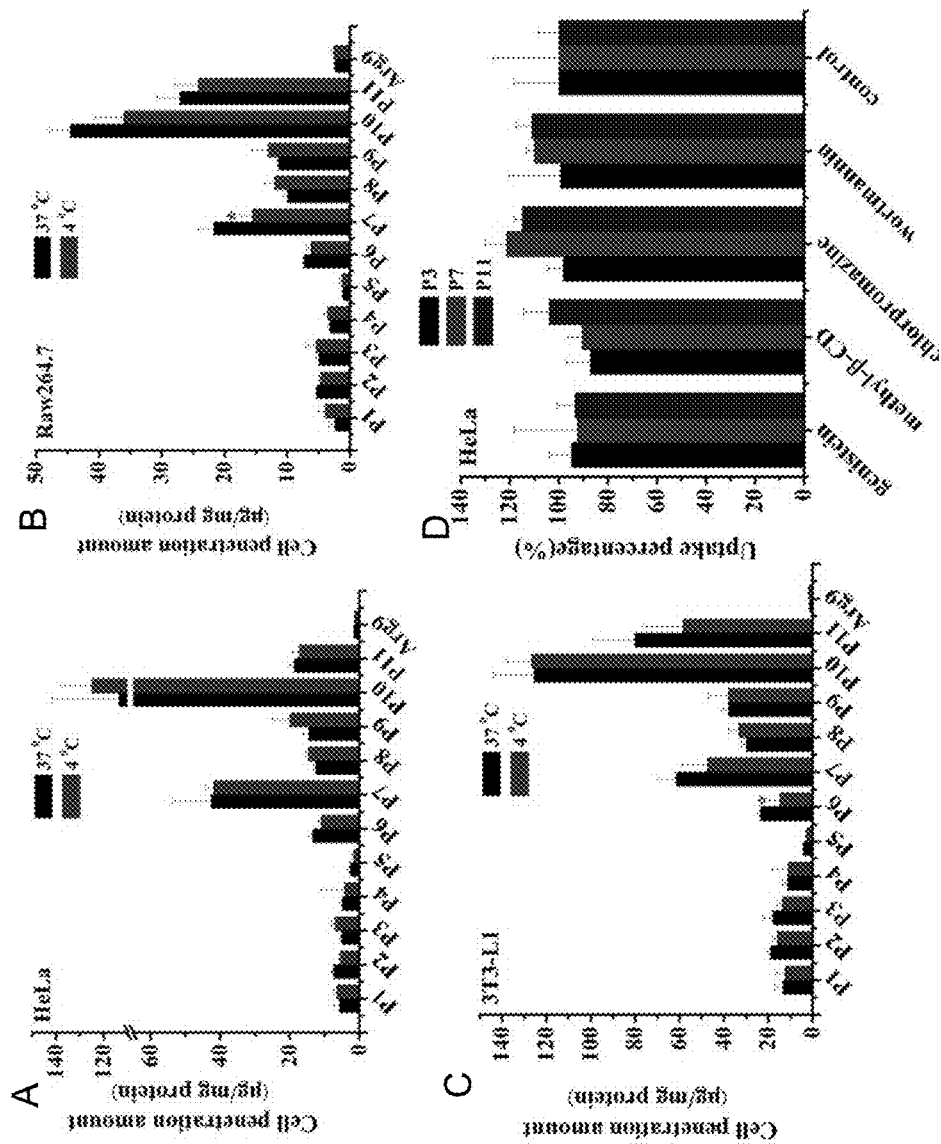

Guanidine-rich polypeptides exhibited notable cell penetration properties, which overwhelmingly outperformed Arg9 as the commonly used CPP (FIG. 87). A slight increasing of cell penetration efficiency was observed when DP increased from 21 to 51 due to the "polymer effect". α-Helical structure outperformed random-coil in facilitating cell transduction. Incorporation of hydrophobic domains (either elongating guanidine side chains via alkyl or random-copolymerizing alkyl chains) promoted the cell penetration properties which can be attributed to enhanced interaction with that played a synergistic effect. Incorporation of alkyl side chains significantly increased the cell penetration capacity, which could be attributed to the amphiphilic features of the resulting polypeptide that facilitated interaction with phospholipid layers in cells membranes. Maximal cell penetration level was noted when the alkyl chain length was 5 carbon atoms. Consistently, an increase in the hydrocarbon chain length from 3-5 corresponded to an increase in cell penetration.

By incubation at 4° C. and addition of various endocytic inhibitors, cell entry mechanism of the guanidine-rich polypeptides was revealed to be irrelevant to endocytosis. By co-incubation of membrane-impermeable FITC with the polypeptide, FITC was shown to enter the cells and distributed in the entire cytoplasmic area, suggesting that pore formation plays a key role in cell transduction.

Figure 88:
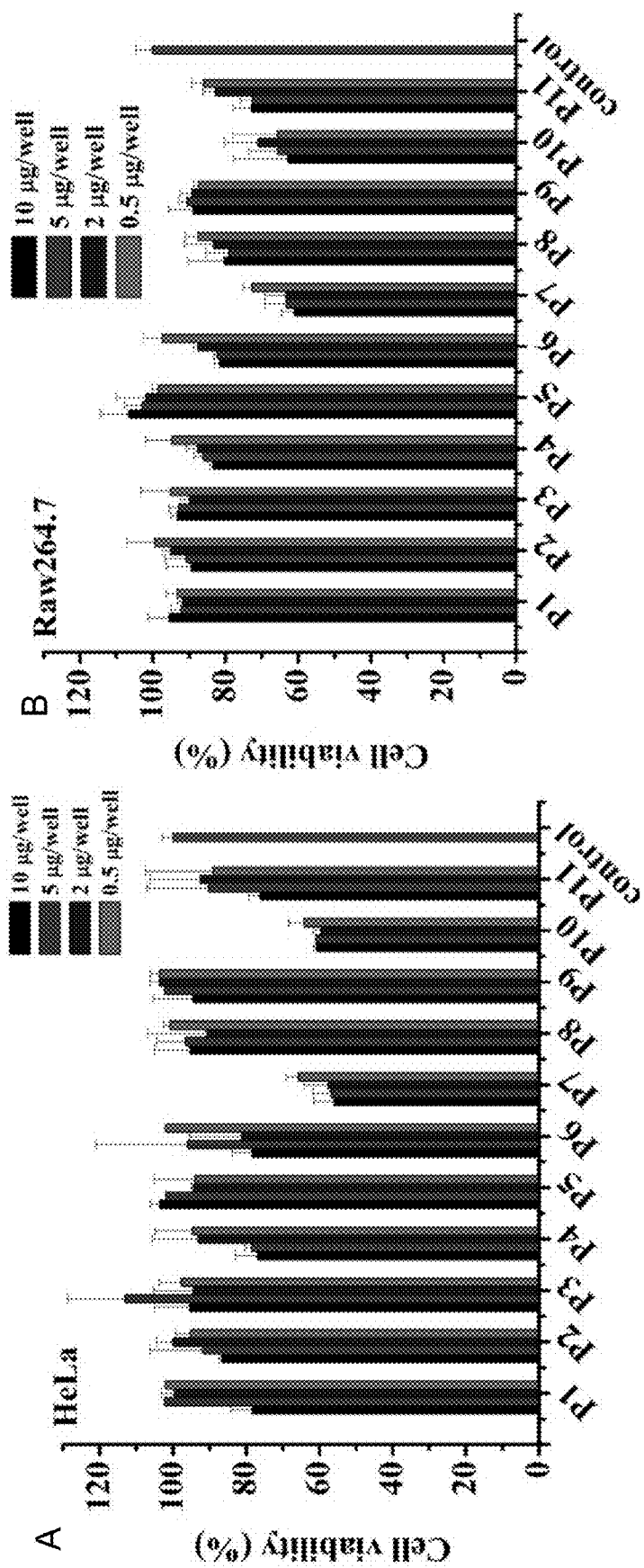

MTT assay revealed desired cyto-compatibility of the peptides, and P7 and P10 that showed the distinguished penetration capacities exhibited notable toxicity at higher concentrations, which could be attributed to the pore formation on cell membranes (FIG. 88).

In summary, a new family of α-helical guanidine-rich polypeptides with promising intracellular transduction efficiency has been created. Series of structural parameters including main-chain/side-chain length, configurations (D, L or DL), secondary structures and hydrophobic domains that influence the cell-penetrating ability have been investigated. A slight increasing of cell penetration efficiency was observed when DP increased from 21 to 51 due to the "polymer effect". GRPs with α-helical conformations show superior efficiency to P5 and Arg9 that adopt random-coil conformations. Hydrophobic domains played an essential role on the cell penetration efficiency. Significantly, the efficiency was improved by elongating the backbone to charge distance. Most significantly, GRPs bearing alkyl side-chains were found to be more efficient than P2. P10, the one bearing pentenyl groups was found to be the most efficiency transporter. Our results provide a new strategy to develop cost-effective and highly efficient molecular transporters for the delivery of molecular cargo into cells.

Example 11. Influence of Molecular Architecture on Cell-Penetration

Molecular transporters are a type of molecules that are able to delivery molecular cargos through biological barriers. Tons of evidence has shown that guanidine groups are essential motif in the molecular design of transporters. A large number of guanidine-rich transporters (GRTs) have been developed to achieve cost-effective and highly efficient transporters. Many molecular structural characteristics have been tuned including sequence length, hydrophobic domains, distance between the backbone and the head groups and backbone rigidities. However, most of the molecular transporters are linear molecules. Molecular transporters with variable architectures, such as star-shape or brush-like, have been less studied. Previously, we have demonstrated a new family of α-helical guanidine-rich polypeptides with promising intracellular transduction efficiency. Encouraging by that strategy, we are interested in investigating the influence of the molecular architecture (linear vs. star) and the secondary structures on the cell-penetrating properties (FIG. 89). In this report, a series of guanidine-rich polypeptides with different architectures (linear or star), secondary structures (helix or random-coil) and side-chain charges (amine or guanidine) have been synthesized and carefully characterized.

Scheme 11-1. Synthesis of guanidine-rich polypeptides with variable configuration and architectures.

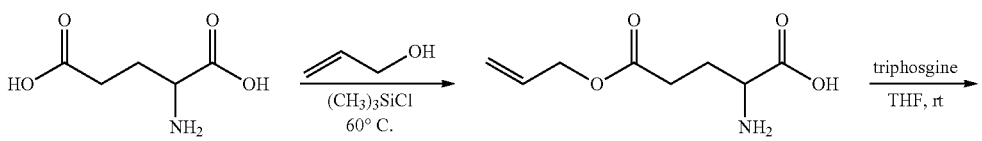

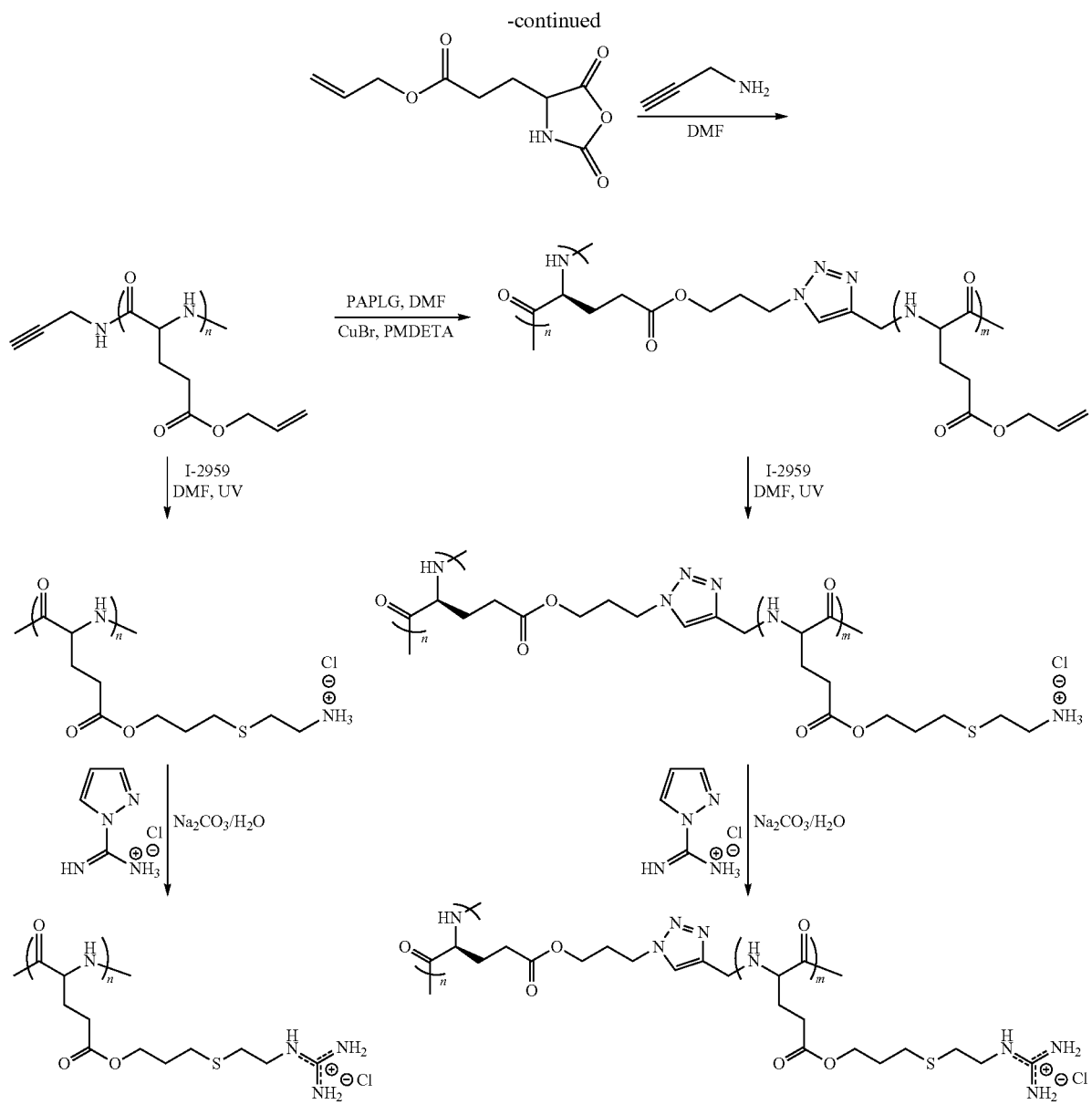

Synthesis of γ-allyl-DL-glutamate

Synthesis of γ-allyl-DL-glutamic acid-based N-carboxyanhydride

D,L-glutamic acid (10.0 g, 68 mmol) and allyl alcohol (80 mL, 1.2 mol) were mixed in a round-bottom flask (300 mL), followed by addition of chlorotrimethylsilane (10 mL, 0.8 mol) via syringe. The resulting suspension was heated to 60° C. and stirred until it became homogeneous. The solvent was removed at room temperature under vacuum to give a viscous oil. Addition of diethyl ether (200 mL) to the residue yielded a light yellow solid which was collected by filtration. Additional purification by recrystallization in ethanol/diethyl ether afforded the final product as a white solid (14.0 g, yield: 92%). $^1$H NMR (D$_2$O, δ, ppm): 5.79 (m, 1H, CH$_2$=CHCH$_2$—), 5.13 (m, 2H, CH$_2$=CHCH$_2$—), 4.48 (d, 2H, CH$_2$=CHCH$_2$—), 3.93 (t, 1H, —CHNH$_2$), 2.50 (t, 2H, —COCH$_2$CH$_2$—) and 2.10 (m, 2H, —COCH$_2$CH$_2$—); $^{13}$C NMR (D$_2$O, δ, ppm): 174.24, 172.00, 131.83, 118.77, 66.29, 52.33, 29.74 and 25.01.

γ-allyl-DL-glutamate (4.5 g, 20 mmol), triphosgene (3.0 g, 10 mmol) and anhydrous THF (60 mL) were mixed in a round-bottomed flask (100 mL). The mixture was stirred at room temperature for 24 h over which period the γ-allyl-DL-glutamate was gradually dissolved. Removal of the solvent under vacuum yielded an oily liquid. Recrystallization by layering hexane on top of a CH$_2$Cl$_2$ solution containing the oil was not successful, resulting in two separate liquid layers. The bottom layer was separated and subjected to vacuum to give a clear liquid (1.7 g, yield: 40%). $^1$H NMR (CDCl$_3$, δ, ppm): 6.79 (s, 1H, NH), 5.92 (m, 1H, CH$_2$=CHCH$_2$—), 5.33 (m, 2H, CH$_2$=CHCH$_2$—), 4.62 (m, 2H, CH$_2$=CHCH$_2$—) 4.44 (t, 1H, —CHNH$_2$), 2.61 (t, 2H, —COCH$_2$CH$_2$—) and 2.17-2.31 (m, 2H, —COCH$_2$CH$_2$—); $^{13}$C{$^1$H} NMR (CDCl$_3$, δ, ppm): 172.42, 169.77, 152.36, 131.76, 119.21, 66.10, 57.10, 29.80 and 27.07.

Synthesis of propargyl terminated poly(γ-allyl-L-glutamate) (PALG-p) and poly(γ-allyl-DL-glutamate) (PADLG-p)

A representative polymerization of AL-L-NCA is as follows. Inside a glove-box, AL-L-NCA (200 mg, 0.4 mmol) was dissolved in DMF (2.0 mL). The propargyl amine/DMF solution (186.7 μL, 0.1 M) was added. The reaction mixture was stirred for 48 h at room temperature. The solution was concentrated at room temperature under vacuum and precipitated from cold methanol. The polymer was collected by centrifuge and dried at room temperature under vacuum. Obtained 110 mg (yield: 69%). $^1$H NMR (CDCl$_3$/TFA-d, v:v=85:15, δ, ppm): 5.80 (m, 1H, CH$_2$=CHCH$_2$—), 5.23 (m, 2H, CH$_2$=CHCH$_2$—), 4.56 (m, 3H, CH$_2$=CHCH$_2$— and CHNH), 2.11 (br s, 2H, COCH$_2$CH$_2$—) and 1.90-2.30 (br b, 2H, COCH$_2$CH$_2$—).

Poly(γ-allyl-DL-glutamate) (PADLG) was synthesized by following the same method as PALG. Obtained 100 mg (yield: 63%). $^1$H NMR (CDCl$_3$/TFA-d, v:v=85:15, δ, ppm): 5.82 (m, 1H, CH$_2$=CHCH$_2$—), 5.26 (m, 2H, CH$_2$=CHCH$_2$—), 4.58 (m, 3H, CH$_2$=CHCH$_2$— and CHNH), 2.50 (br s, 2H, COCH$_2$CH$_2$—) and 1.90-2.30 (br b, 2H, COCH$_2$CH$_2$—).

Synthesis of poly(γ-3-azidopropanyl-L-glutamate) grafted PALG-p (PPLG-g-PALG) or poly(γ-3-azidopropanyl-L-glutamate) grafted PADLG-p (PPLG-g-PADLG)

Typically, in a glovebox, CuBr (2 mg, 0.012 mmol) was added to a DMF (2 mL) solution of poly(γ-3-azidopropanyl-L-glutamate) (2.5 mg, 0.012 mmol of azido group), PALG-p (80 mg, 0.012 mmol) and PMDETA (12 μL, 0.05 mmol). The reaction mixture was stirred at room temperature for 24 h and quenched by exposure to air. The copper catalyst was removed by passing though a silica gel chromatograph and eluted with THF. The solution was concentrated at room temperature under vacuum and precipitated from cold methanol. The polymer was collected by centrifuge and dried at room temperature under vacuum. Obtained 42 mg (yield: 50%). $^1$H NMR (CDCl$_3$/TFA-d, v:v=85:15, δ, ppm): 5.85 (m, 1H, CH$_2$=CHCH$_2$—), 5.28 (m, 2H, CH$_2$=CHCH$_2$—), 4.60 (m, 3H, CH$_2$=CHCH$_2$— and CHNH), 2.54 (br s, 2H, COCH$_2$CH$_2$—) and 1.90-2.30 (br b, 2H, COCH$_2$CH$_2$—).

PPLG-g-PADLG was synthesized by following the same method as PALG. Obtained 50 mg (yield: 61%). $^1$H NMR (CDCl$_3$/TFA-d, v:v=85:15, δ, ppm): 5.84 (m, 1H, CH$_2$=CHCH$_2$—), 5.26 (m, 2H, CH$_2$=CHCH$_2$—), 4.58 (m, 3H, CH$_2$=CHCH$_2$— and CHNH), 2.49 (br s, 2H, COCH$_2$CH$_2$—) and 1.90-2.30 (br b, 2H, COCH$_2$CH$_2$—).

Thiol-Ene Reaction (LP1, LP2, SP1 and SP2).

Typically, in a quartz flask, PALG (140 mg, 0.083 mmol), cysteamine hydrochloride (0.188 g, 0.17 mmol) and DMPA (7 mg, 5 wt %) were dissolved in DMF (3 mL). The flask was purged with N$_2$ for 2 min and well sealed. Then the reaction was irradiated by UV lamp (365 nm, 20 mW) for 30 min. 1N HCl$_{aq}$ (5 mL) was added and the clear solution was dialysis against DI water for three days (change water twice per day) in a dialysis membrane tube with a cutoff molecular weight of 1000 g·mol$^{-1}$. Freeze-dry to yield a white solid product (PALG-g-CA, LP1). Obtained 176 mg (yield: 75%). $^1$H NMR [D$_2$O/DCl (20 wt %), v:v=90:10, δ, ppm]: 3.94 (br s, 2H, —COOCH$_2$CH$_2$CH$_2$S—), 3.79 (br s, 1H, CHNH), 2.95 (s, 2H, —SCH$_2$CH$_2$NH$_2$), 2.59 (s, 2H, —SCH$_2$CH$_2$NH$_2$), 2.38 (br s, 2H, —COOCH$_2$CH$_2$CH$_2$S—), 2.31 (br s, 2H, COCH$_2$CH$_2$—), 1.80-2.20 (br b, 2H, COCH$_2$CH$_2$—) and 1.67 (br s, 2H, —COOCH$_2$CH$_2$CH$_2$S—).

PADLG-g-CA (LP2) was synthesized by following the same method as LP1. Obtained 187 mg (yield: 80%). $^1$H NMR [D$_2$O/DCl (20 wt %), v:v=90:10, δ, ppm]: 4.19 (br s, 1H, CHNH), 4.05 (br s, 2H, —COOCH$_2$CH$_2$CH$_2$S—), 3.08 (s, 2H, —SCH$_2$CH$_2$NH$_2$), 2.71 (s, 2H, —SCH$_2$CH$_2$NH$_2$), 2.51 (br s, 2H, —COOCH$_2$CH$_2$CH$_2$S—), 2.34 (br s, 2H, COCH$_2$CH$_2$—), 1.80-2.20 (br b, 2H, COCH$_2$CH$_2$—) and 1.97 (br s, 2H, —COOCH$_2$CH$_2$CH$_2$S—).

PPLG-g-(PALG-g-CA) (SP1) was synthesized by following the same method as LP1. Obtained 20 mg (Yield=61%). $^1$H NMR [D$_2$O/DCl (20 wt %), v:v=90:10, δ, ppm]: 4.11 (br s, 2H, —COOCH$_2$CH$_2$CH$_2$S—), 3.96 (br s, 1H, CHNH), 3.07 (s, 2H, —SCH$_2$CH$_2$NH$_2$), 2.72 (s, 2H, —SCH$_2$CH$_2$NH$_2$), 2.54 (br s, 2H, —COOCH$_2$CH$_2$CH$_2$S—), 2.51 (br s, 2H, COCH$_2$CH$_2$—), 1.90-2.30 (br b, 2H, COCH$_2$CH$_2$—) and 1.84 (br s, 2H, —COOCH$_2$CH$_2$CH$_2$S—).

PPLG-g-(PADLG-g-CA) (SP2) was synthesized by following the same method as LP1. Obtained 22 mg (Yield=65%). $^1$H NMR [D$_2$O/DCl (20 wt %), v:v=90:10, δ, ppm]: 4.18 (br s, 1H, CHNH), 4.04 (br s, 2H, —COOCH$_2$CH$_2$CH$_2$S—), 3.06 (s, 2H, —SCH$_2$CH$_2$NH$_2$), 2.70 (s, 2H, —SCH$_2$CH$_2$NH$_2$), 2.50 (br s, 2H, —COOCH$_2$CH$_2$CH$_2$S—), 2.35 (br s, 2H, COCH$_2$CH$_2$—), 1.80-2.20 (br b, 2H, COCH$_2$CH$_2$—) and 1.79 (br s, 2H, —COOCH$_2$CH$_2$CH$_2$S—).

Synthesis of Guanidine-Rich Polypeptides (LP3, LP4, SP3 and SP4)

Typically, PALG-g-CA (20 mg, 0.08 mmol of amine groups), 1H-pyrazole-1-carboxamindine hydrochloride (PCAH, 0.1 g, 10 equiv. 0.8 mmol) and Na$_2$CO$_3$ (85 mg) were mixed in DI water (8 mL). The mixture was stirred at room temperature for 12 h. Then, the solution was dialyzed against distilled water (pH=5~6) for three days in a dialysis membrane tube with a cutoff molecular weight of 1000 g/mol. Free-dry to yield the resulting polymer (PALG-g-GU, LP3). Obtained 18 mg (Yield=60%). NMR [D$_2$O/DCl (20 wt %), v:v=90:10, δ, ppm]: 3.99 (br s, 2H, —COOCH$_2$CH$_2$CH$_2$S—), 3.85 (br s, 1H, CHNH), 3.30 (s, 2H, —SCH$_2$CH$_2$NH), 2.56 (s, 2H, —SCH$_2$CH$_2$NH), 2.42 (br s, 2H, —COOCH$_2$CH$_2$CH$_2$S—), 2.39 (br s, 2H, COCH$_2$CH$_2$—), 1.80-2.20 (br b, 2H, COCH$_2$CH$_2$—) and 1.72 (br s, 2H, —COOCH$_2$CH$_2$CH$_2$S—).

PADLG-g-GU (LP4) was synthesized by following the same method as LP3. Obtained 16 mg (yield: 53%). $^1$H NMR [D$_2$O/DCl (20 wt %), v:v=90:10, δ, ppm]: 4.16 (br s, 1H, CHNH), 4.02 (br s, 2H, —COOCH$_2$CH$_2$CH$_2$S—), 3.25 (s, 2H, —SCH$_2$CH$_2$NH), 2.69 (s, 2H, —SCH$_2$CH$_2$NH), 2.47 (br s, 2H, —COOCH$_2$CH$_2$CH$_2$S—), 2.33 (br s, 2H, COCH$_2$CH$_2$—), 1.80-2.20 (br b, 2H, COCH$_2$CH$_2$—) and 1.76 (br s, 2H, —COOCH$_2$CH$_2$CH$_2$S—).

PPLG-g-(PALG-g-GU) (SP3) was synthesized by following the same method as LP3. Obtained 12 mg (yield: 40%). $^1$H NMR [D$_2$O/DCl (20 wt %), v:v=90:10, δ, ppm]: 4.05 (br s, 2H, —COOCH$_2$CH$_2$CH$_2$S—), 3.90 (br s, 1H, CHNH), 3.26 (s, 2H, —SCH$_2$CH$_2$NH), 2.69 (s, 2H, —SCH$_2$CH$_2$NH), 2.49 (br s, 2H, —COOCH$_2$CH$_2$CH$_2$S—), 2.39 (br s, 2H, COCH$_2$CH$_2$—), 1.80-2.20 (br b, 2H, COCH$_2$CH$_2$—) and 1.77 (br s, 2H, —COOCH$_2$CH$_2$CH$_2$S—).

PPLG-g-(PADLG-g-GU) (SP4) was synthesized by following the same method as LP3. Obtained 15 mg (yield:

50%). $^1$H NMR [D$_2$O/DCl (20 wt %), v:v=90:10, δ, ppm]: 4.18 (br s, 1H, CHNH), 4.05 (br s, 2H, —COOCH$_2$CH$_2$CH$_2$S—), 3.27 (s, 2H, —SCH$_2$CH$_2$NH), 2.63 (s, 2H, —SCH$_2$CH$_2$NH), 2.50 (br s, 2H, —COOCH$_2$CH$_2$CH$_2$S—), 2.36 (br s, 2H, COCH$_2$CH$_2$—), 1.80-2.20 (br b, 2H, COCH$_2$CH$_2$—) and 1.78 (br s, 2H, —COOCH$_2$CH$_2$CH$_2$S—).

Results and Discussion

Synthesis of Guanidine-Rich Polypeptides and their Rh—B Conjugates

γ-Allyl-L/D-glutamic acid-based N-carboxyanhydrides (AL-L-Glu-NCA and AL-DL-Glu-NCA) have been synthesized (Scheme 11-1) by a multi-step synthetic route, namely the monesterification between L/D-glutamic acid and allyl alcohol using trimethylchlorosilane the catalyst, and the cyclization of allyl-L/D-glutamic acid in the presence of triphosgene. NCAs were purified by repeatedly dissolving in anhydrous THF and precipitate from hexane. The molecular structures of the resulting NCAs have been verified by $^1$H NMR and $^{13}$C NMR.

The ring-opening polymerization of the resulting NCAs was initiated using propargyl amine. Targeted molecular weight (MW) was tuned by changing the M/I ratios. Polypeptides terminated propargyl groups were isolated by precipitation with cold methanol and their molecular structures were determined by $^1$H NMR. The absolute polymer MW and PDI were determined by size-exclusion chromatography coupled with multi-angle light scattering and differential refractive index detectors (SEC-MALS-DRI). Poly(γ-azido-alkyl-L-glutamate) (PAPLG) was synthesized by the literature method. Star polypeptides with different configurations was achieved via the alkyne-azide [2+3] Huisgen cycloaddition with high grafting efficiency (>70%), which was verified by SEC analysis. (Note: The grafting efficiency was calculated by SEC analysis of the relative intensity of PAD/LG side-chains before and after click reactions). Ionic polypeptides bearing amine side-groups have been synthesized via the thiol-ene reactions. A quantitatively grafting efficiency of the thiol-ene reaction was achieved by UV irradiation for 30 min, which was revealed by $^1$H NMR analysis. The side-chains of the resulting ionic polypeptides were further modified by using 1H-pyrazole-1-carboxamindine hydrochloride under a mild condition to yield a series of guanidine-rich polypeptides. High conversion (~90%) was achieved by comparing the proton integration at 3.2 ppm (methylene groups next to guanidine groups) and at 3.0 ppm (methylene groups next to amine groups) using $^1$H NMR analysis. Ionic polypeptide-RhB conjugates have also been synthesized by using RhB—NCS.

Conformational Study of the Resulting Ionic Polypeptides.

Figure 90:
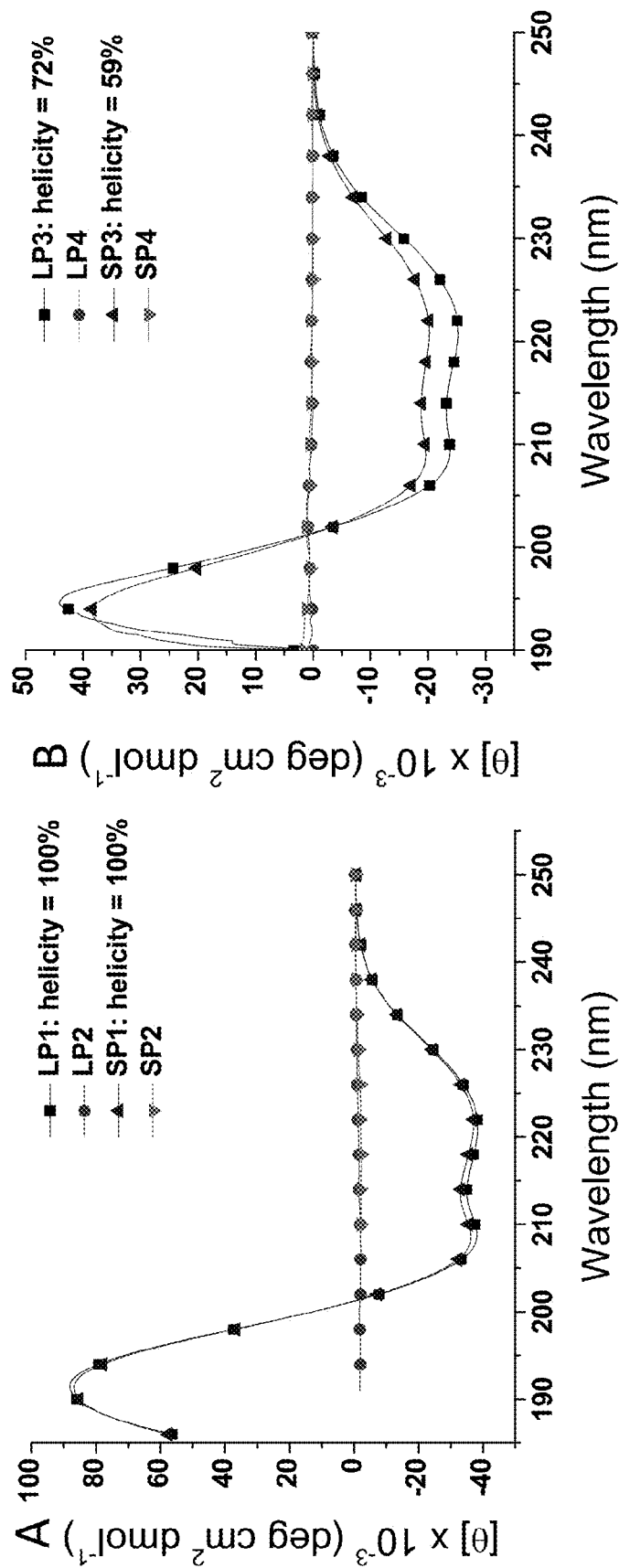

The solution conformations of the ionic polypeptides with different molecular architectures, configurations and side-chain charges have been characterized by CD spectroscopy (Scheme 11-2 and FIG. 90). All the resulting ionic polypeptides with L-configurations adopt α-helical conformations in H$_2$O, as verified by the characteristic ellipticity at 208 nm and 222 nm. To allow for comparison of the relative helical conformation content in the polypeptides. The helicity of the polypeptides were calculated by the following equation: helicity=(−[θ$_m$]+3,000)/39,000. Where [θ]$_{222}$ is the mean residue ellipticity at 222 nm. Amine-rich polypeptides (LP1 and SP1) show 100% helicity in H$_2$O. The helicity was decreased by 28-41% when the terminal charges changing from amine to guanidine groups due to the bulky size of guanidine groups (FIG. 5B). Additionally, star-shaped guanidine-rich polypeptide shows lower helicity (helicity decreased by 13%) than their corresponding amine-rich polypeptides, which was resulted from the steric repulsion of the adjacent side-chains.

Scheme 11-2. Structures of amine-/guanidine-rich polypeptides.

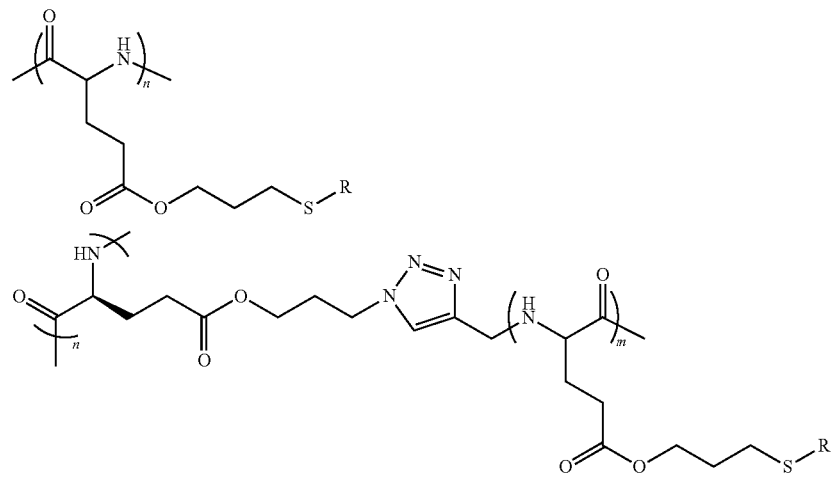

LP1: n = 50, L-Glu, R = CA
LP2: n = 49, DL-Glu, R = CA
SP1: n = 20, m = 50, L-Glu, R = CA
SP2: n = 20, m = 49, DL-Glu, R = CA
LP3: n = 50, L-Glu, R = GU
LP4: n = 49, DL-Glu, R = GU
SP3: n = 20, m = 50, L-Glu, R = GU
SP4: n = 20, m = 49, DL-Glu, R = GU

-continued

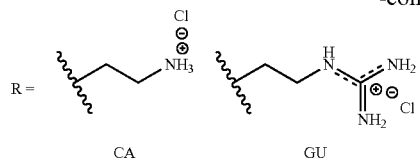

Figure 91:
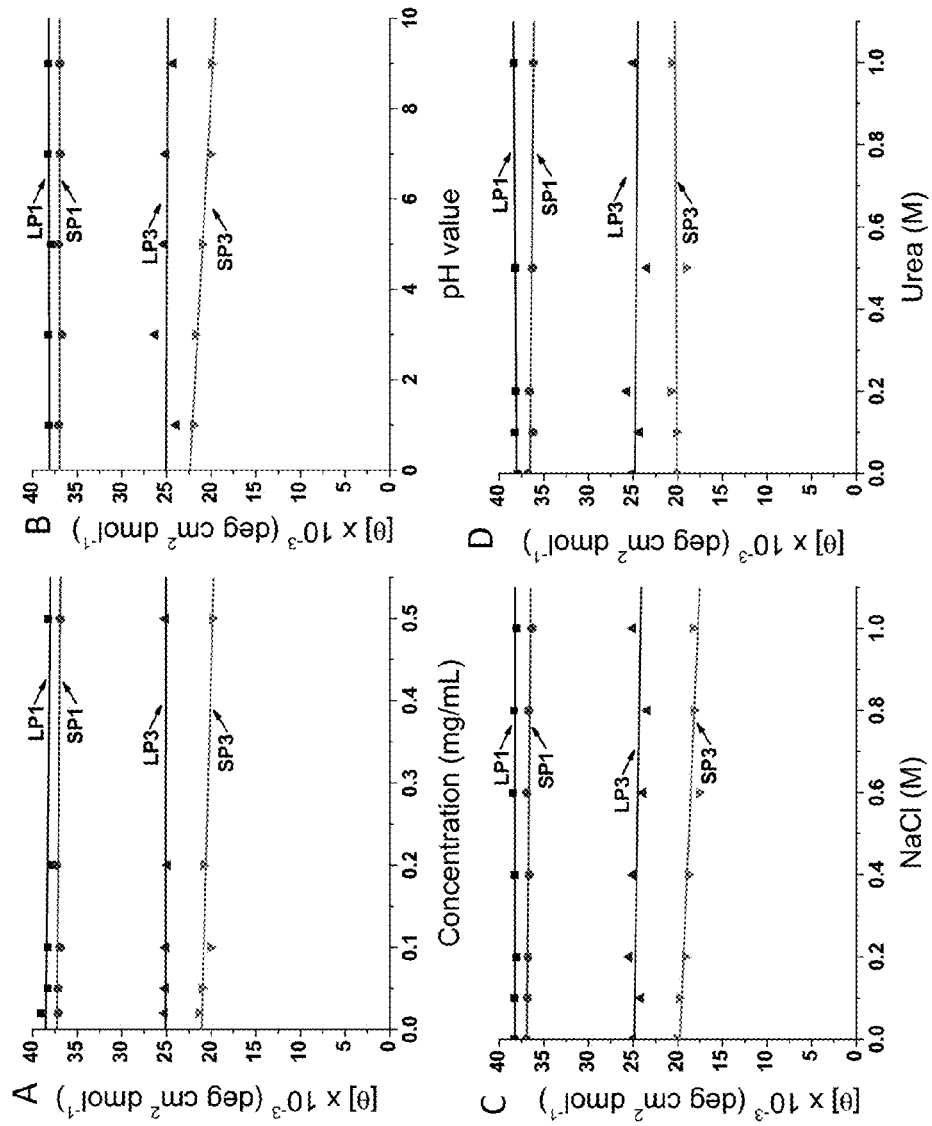

Amine-/guanidine-rich polypeptides showed a lack of concentration dependence (FIG. 91A), suggesting that it remains monomeric in solution. These polymers show remarkable pH-independent helical stability at pH values ranging from 1 to 9 (FIG. 91B). High pH (pH>10) conditions were not able to perform due to protonation of the positively charged guanidino group on the side chain and a decreased solubility. All the polymers show reasonably stable helical structure in the NaCl media and the ellipticity at 222 nm remain nearly unchanged when the NaCl concentration was increased from 0 to 0.4 M at 25° C. (FIG. 91C). Additionally, the resulting polymers exhibited remarkable stability against the strong denaturing reagent (i.e., urea) (FIG. 91D).

In summary, a series of clickable polypeptides with variable conjugations (L or DL) and molecular architectures (linear or star) have been synthesized by a combination of synthesis methods including ring-opening polymerization and copper-mediated [2+3] alkyne-azido 1,3-dipolar cycloaddition. The resulting polymers were derivatized into corresponding ionic polypeptides bearing primary amino groups via a thiol-ene reaction. $^1$H NMR analysis reveals a quantitatively grafting efficiency of amino groups by UV irradiation for 30 min. CD analysis of the resulting ionic polypeptides (LP1 and SP1) revealed that these ionic polypeptides adopt ultra-stable α-helical structures with 100% helicity. The side-chains of the resulting ionic polypeptides were further modified to achieve guanidine-rich polypeptides. The resulting GRPs (LP3 and SP3) also showed ultra-stable α-helical structures against environmental changing (pH, salts and denature reagent). A lower helicity of the GRPs was observed comparing with their precursors due to the larger size of the guanidine groups.

Example 12. Guanidine-Rich Polypeptides with Variable Alkyl-Tails: Effects of Hydrophobic Domain on Cell-Penetrating Cell-penetrating peptides (CPPs), also known as protein transduction domains have been under intense investigation as promising vectors for the cellular transportation of molecular cargos. The cellular uptake mechanisms of the CPPs involve several pathways, including endocytosis, macropinocytosis, etc, depending on the GRTs and cell line used. Guanidine groups are essential motifs in the molecular design of CPPs. A large number of guanidine-rich peptides (GRPs) have been developed to achieve highly efficiency. Additionally, hydrophobic domains and helical conformations have been demonstrated to improve the cell-penetrating ability. However, GRPs with helical conformations require the stepwise synthesis of peptides with specific sequences which is time consuming and costly.

Anew family of α-helical guanidine-rich polypeptides with promising intracellular transduction efficiency is described herein. By following that strategy, a new series of α-helical guanidine-rich polypeptides was designed with variable alkyl tails as the hydrophobic domain (FIG. 92). Large amount (gram scale) of the resulting polymer can be synthesized within few weeks via a combination of ring-opening polymerization and click chemistry.

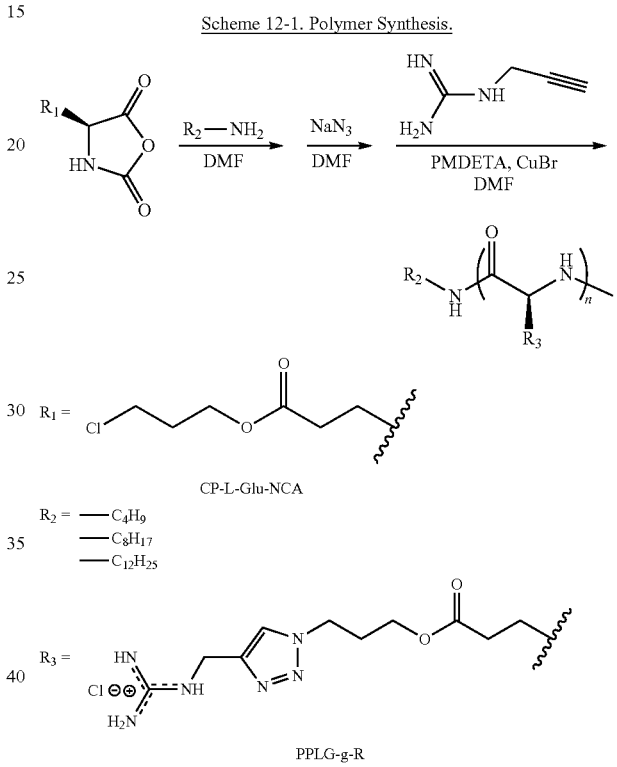

Synthesis of Alkyl Terminated Poly(γ-3-chloropropanyl-L-glutamate) (Cn-PCPLG, n=4, 8 and 12)

Typically, inside a glovebox, CP-L-Glu-NCA (200 mg, 0.8 mmol) was dissolved in DMF (2 mL) in a vial. A measured volume of n-butylamine/DMF stock solution ($C_I$=0.1 M, 400 μL, 40 μmol) was subsequently added with pipette. The polymerization solution was kept stirring at room temperature for 48 h until the monomer conversion was above 99% which was monitored by FTIR. A certain amount of the polymerization solution (0.1 mL) was draw outside the glovebox for SEC test. The solution was concentrated at room temperature under vacuum and precipitated from cold methanol. The polymer was collected by centrifuge and dried at room temperature under vacuum (the yield was 60-70%). $^1$H NMR (CDCl$_3$, δ, ppm): 4.58 (s, 1H, CHNH), 4.27 (s, 2H, ClCH$_2$CH$_2$CH$_2$—), 3.57 (s, 2H, ClCH$_2$CH$_2$CH$_2$—), 2.51 (s, 2H, —COCH$_2$CH$_2$—), 2.16 (s, 2H, —COCH$_2$CH$_2$—), 1.90-2.30 (b, 2H, ClCH$_2$CH$_2$CH$_2$—).

Synthesis of Alkyl Terminated Poly(γ-3-azidopropanyl-L-glutamate) (Cn-PAPLG, n=4, 8 and 12)

A DMF (4 mL) solution of PCPLG (125 mg, 0.6 mmol of chloro groups) and sodium azide (0.39 g, 6 mmol) was stirred at 60° C. for 48 h and allowed to cool to room temperature. The reaction mixture was filtered to remove any inorganic salts. DMF was removed by vacuum distillation at room temperature to yield a polymer film which was further purified by dissolution in CHCl$_3$, filtration and remove the solvent. The resulting polymer was collected by filtration and dried at under vacuum at 40° C. for 8 h (yield: 70-80%). $^1$H NMR (CDCl$_3$, δ, ppm): 4.58 (s, 1H, CHNH), 4.23 (s, 2H, ClCH$_2$CH$_2$CH$_2$—), 3.43 (s, 2H, ClCH$_2$CH$_2$CH$_2$—), 2.54 (s, 2H, —COCH$_2$CH$_2$—), 1.90-2.3 (br s, 2H, —COCH$_2$CH$_2$—), 1.97 (s, 2H, ClCH$_2$CH$_2$CH$_2$—).

Synthesis of Guanidine-Rich Polypeptides with Alkyl Terminated (Cn-PPLG-g-R, n=4, 8 and 12)

Typically, inside a glove-box, N-pro-2-ynyl-guanidine (40 mg, 0.4 mmol, 2 equiv.), PAPLG (50 mg, 0.2 mmol of the functional groups), PMDETA (1.2 mL) were dissolved in DMF (5 mL), followed by adding the above solution to a vial with CuBr (30 mg, 0.2 mmol). The reaction solution was stirred at room temperature for 24 h. The reaction was quenched by exposing to air and 1N HCl$_{aq}$ was added to the reaction solution until it turned to yellow. The resulting polymer was purified by dialysis against DI water for three days in a dialysis membrane tube with a cutoff molecular weight of 1000 g·mol$^{-1}$. Freeze-dry to yield the resulting polymer as a white solid (yield: 50-70%). $^1$H NMR [D$_2$O, δ, ppm]: 7.88 (s, 1H, triazole), 4.35 (s, 4H, —COOCH$_2$— and triazole-CH$_2$NH—), 3.99 (br, 1H, —CHNH), 3.88 (s, 2H, —COOCH$_2$CH$_2$CH$_2$—), 1.8-2.6 (m, 6H, —CH$_2$CH$_2$COOCH$_2$CH$_2$—).

Synthesis of Guanidine-Rich Polypeptides-RhB Conjugate

Typically, guanidine-rich polypeptide (23 mg, 0.67 mmol of repeating units, 3.3×10$^{-6}$ mol of primary amine) was dissolved in NaHCO$_3$ solution (2.5 mL, 0.2 M). RhB—NCS (2 mg) was dissolved in DMSO (0.2 mL) and added to the above aqueous solution. The reaction vial was wrapped with aluminum foil. The reaction was stirring at room temperature for 12 h, followed by dialysis against DI water (the beaker was wrapped with aluminum foil) for three days in a dialysis membrane tube with a cutoff molecular weight of 1000 g·mol$^{-1}$. Red solid product was obtained after freeze-dry (yield=60%-70%).

Results and Discussion

Synthesis of Guanidine-Rich Polypeptides with Variable Alkyl Tails

The alkyl terminated polypeptides with variable alkyl chain length have been successfully synthesized the ring-opening polymerization mediated by corresponding primary amines. The resulting polymers were verified by SEC and $^1$H NMR.

γ-Chloropropanyl-glutamic acid-based N-carboxyanhydrides (CP-L-Glu-NCA) was synthesized by a reported method. The ring-opening polymerization of the resulting NCAs was initiated using three alkyl-amines (i.e., n-butylamine, n-octylamine and dodecylamine). Targeted molecular weight (MW) was tuned by changing the M/I ratios. Alkyl terminated polypeptides were isolated by precipitation with cold methanol and their molecular structures were determined by $^1$H NMR. The absolute polymer MW and PDI were determined by size-exclusion chromatography coupled with multi-angle light scattering and differential refractive index detectors (SEC-MALS-DRI). To enable facile chemical modification of poly(γ-chloroalkyl-L-glutamate) via "click chemistry", The resulting polymers were derivatized into poly(γ-azidoalkyl-L-glutamate) by treatment with NaN$_3$ in DMF at 60° C. for two days. Quantitative conversion was revealed by $^1$H NMR analysis. Guanidine-rich polypeptides were synthesized via the alkyne-azide [2+3] Huisgen cycloaddition with high grafting efficiency, which was verified by $^1$H NMR analysis. To conjugate the fluorescence dye (Rh—B), 5 mol % of amine groups were grafted to the polypeptides via "click chemistry", followed by reaction with RhB—NCS to yield guanidine-rich polypeptide-RhB conjugates.

Conformational Study of the Guanidine-Rich Polypeptides with Variable Alkyl Tails.

The conformations of the guanidine-rich polypeptides (GRPs) with variable alkyl tails have been characterized by CD spectroscopy (Scheme 11-2). All the resulting GRPs adopt α-helical conformations in H$_2$O, as verified by the characteristic elliptrity at 208 nm and 222 nm. To allow for comparison of the relative helical conformation content in the polypeptides. The helicity of the polypeptides were calculated by the following equation: helicity=(-[θ$_m$]+3,000)/39,000. Where [θ]$_{222}$ is the mean residue ellipticity at 222 nm. The helicity of the resulting GRPs is in the range of 23-31%. A slight increasing of the helicity was observed when the degree of polymerization (DP) increases from 10 to 40. No influence on the helicity has been found when increasing the length of the alkyl tails.

Scheme 11-2. Structures of guanidine-rich polypeptides with different alkyl tails.

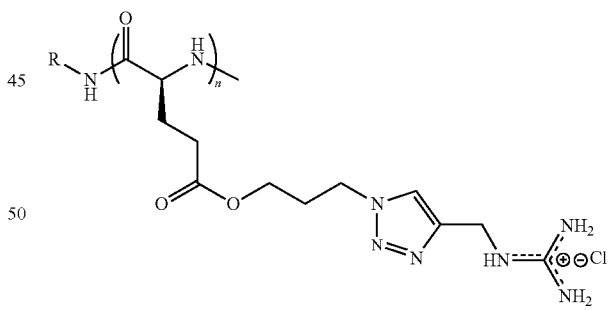

P1: n = 23, PDI = 1.20, R = —C$_4$H$_9$
P2: n = 10, PDI = 1.18, R = —C$_8$H$_{17}$
P3: n = 20, PDI = 1.15, R = —C$_8$H$_{17}$
P4: n = 41, PDI = 1.12, R = —C$_8$H$_{17}$
P5: n = 12, PDI = 1.21, R = —C$_{12}$H$_{25}$
P6: n = 22, PDI = 1.18, R = —C$_{12}$H$_{25}$
P7: n = 45, PDI = 1.13, R = —C$_{12}$H$_{25}$

The resulting GRPs show remarkable pH-independent helical stability at pH values ranging from 1 to 9. High pH (pH>10) conditions were not able to perform due to protonation of the positively charged guanidine group on the side chain and a decreased solubility. A slight decreasing of the mean residue ellipticity was observed when increasing the concentration of the GRPs, suggesting that the polymers tend to aggregated at higher concentrations (>0.1 mg/mL). Additionally, the resulting polymers exhibited remarkable stability against the strong denaturing reagent (i.e., urea). All the resulting GRPs show reasonably stable helical structure in the NaCl media and the ellipticity at 222 nm remain nearly unchanged when the NaCl concentration was increased from 0 to 0.4 M at 25° C.

In summary, a series of poly(γ-chloropropanyl-L-glutamate)s with variable alkyl end groups (Cn-PCPLG, n=4, 8 and 12) and main-chain length have been synthesized via a ring-opening polymerization using different primary amine as the initiators. The resulting polymers (Cn-PCPLG) were quantitatively derivatized into poly(γ-azidopropyl-L-glutamate) (Cn-PAPLG). Water soluble, guanidine-rich polypeptides (GRPs) have been synthesized via a copper-mediated [2+3] alkyne-azido 1,3-dipolar cycloaddition using Cn-PAPLG and Guanidium derivatives bearing propargyl groups. $^1$H NMR analysis reveals a high grafting efficiency (>95%) of guanidium groups under mild reaction conditions. CD analysis of the resulting GRPs revealed that these ionic polypeptides adopt stable α-helical structures against environmental changing (pH, salts and denature reagent).

Example 13. Side-Chain Functionalized Poly(L-Serine): Synthesis, Characterization and Conformations Ionic polypeptides such as PLGA and PLL are not able to adopt α-helix conformation at physiological pH due to side chain charge repulsion. Recently, Hua and Cheng etc. reported a strategy for the facile generation of cationic and helical polypeptides. They found that the helical structure of cationic polypeptides can be stabilized by increasing the hydrophobic interaction of the side chain, thus minimizing the effect of side chain charge repulsion. The increase in hydrophobic interaction can be achieved by maintaining a minimum separation distance of 11 σ-bonds between the peptide backbone and the side chain charge. However, all their results are based on poly(L-glutamate), ionic polypeptides with long hydrophobic side-chains based on other nature amino-acid have never been reported. Poly(L-serine)s are well known polypeptides that adopt β-sheet conformations both in the solid states and in solutions.

Scheme 13-1. The synthetic route to mPEG-b-(PALLS-g-CA) (6a) and mPEG-b-(PPELS-g-CA) (6b).

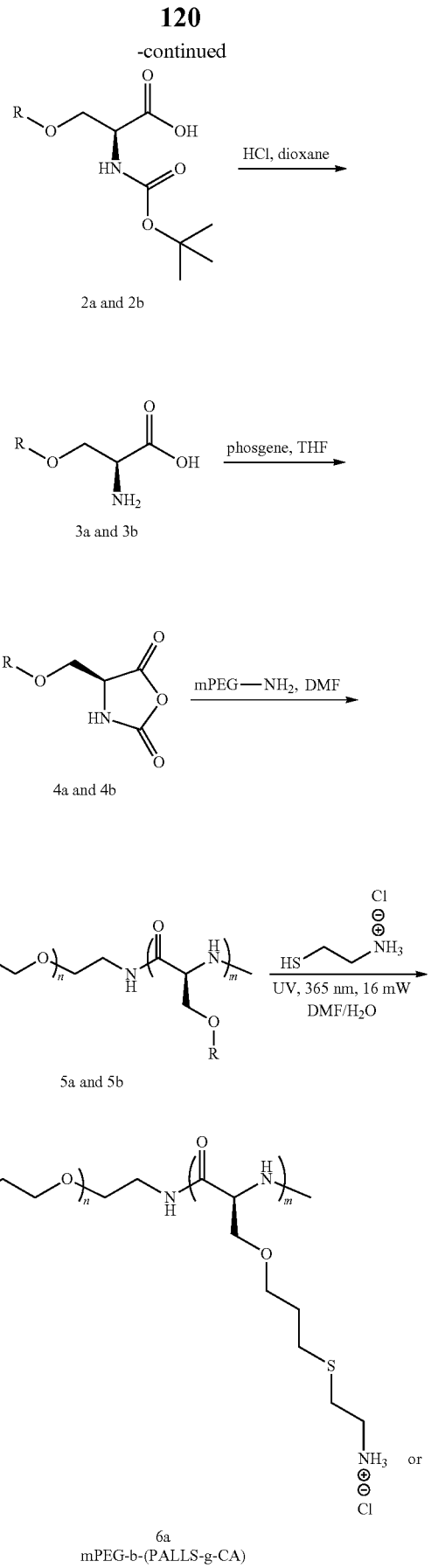

-continued

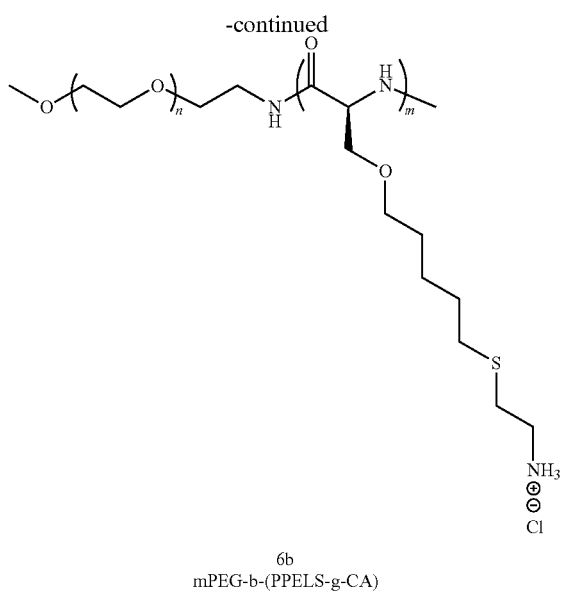

6b
mPEG-b-(PPELS-g-CA)

Synthesis of O-allyl-L-serine (3a) and O-pentenyl-L-serine (3b)

In an ice-water bath, Boc-Ser-OH (1) (5.0 g, 23 mmol) was dissolved in anhydrous DMF (100 mL) followed by slowly adding sodium hydride (1.37 g, 95%, 54 mmol). 30 min later, allyl bromide (6.7 g, 54 mmol) was added to the above mixture and kept stirring for 16 h. The temperature allows warming up to room temperature. DMF was distilled at 60° C. under vacuum. The residue was stirred in water (75 mL) for 16 h and then washed with diethyl ether (30 mL×2). The aqueous layer was acidified to pH=3 with 1N HCl and then extracted with ethyl acetate. The organic layer was dried over anhydrous $MgSO_4$ and then the solvent was distilled under vacuum to yield light yellow oil (2a). The deprotection of 2a was carried in HCl/dioxane (4 M, 50 mL) at room temperature for 4 h. All the solvents were distilled under vacuum and the solid residue was stirred in ether (100 mL) to rid the impurities. Centrifuge to collect the product (3a) and drying at room temperature under vacuum for 8 h. Obtained 0.9 g (yield: 20%). $^1$H NMR ($D_2O$, δ, ppm): 5.73 (m, 1H, $CH_2$=$CHCH_2$—), 5.12 (m, 2H, $CH_2$=$CHCH_2$—), 4.01 (t, 1H, —$CHNH_2$), 3.90 (m, 2H, $CH_2$=$CHCH_2$—) and 3.75 (m, 2H, —$OCH_2CHNH_2$).

A similar method was used to synthesize O-pentenyl-L-serine. Obtained 5.3 g. (yield: 50%). $^1$H NMR ($D_2O$, δ, ppm): 5.74 (m, 1H, $CH_2$=$CHCH_2$—), 4.88 (m, 2H, $CH_2$=$CHCH_2$—), 4.01 (m, 1H, —$CHNH_2$), 3.90 (m, 2H, —$OCH_2CHNH_2$), 3.44 (m, 2H, $CH_2$=$CHCH_2CH_2CH_2$—), 1.97 (m, 2H, $CH_2$=$CHCH_2CH_2$—) and 1.54 (m, 2H, $CH_2$=$CHCH_2CH_2$—).

Synthesis of O-allyl-L-serine-based N-carboxyanhydride (AL-L-Ser-NCA, 4a) and O-pentenyl-L-serine-based N-carboxyanhydride (PE-L-Ser-NCA, 4b)

O-Allyl-L-serine (3a) (0.9 g, 6.2 mmol) and phosgene/toluene solution (20%, 4 mL, 9.3 mmol) were dispersed in anhydrous THF (20 mL) in a round-bottomed flask. The reaction was stirred at room temperature for 16 h. THF was distilled at room temperature under vacuum. The liquid residue was purified by recrystallization from THF/Hexane three times. The product was obtained as an oil with deep color (0.46 g, yield: 44%). $^1$H NMR ($CDCl_3$, δ, ppm): 6.41 (s, 1H, —NH), 5.81 (m, 1H, $CH_2$=$CHCH_2$—), 5.22 (t, 2H, $CH_2$=$CHCH_2$—), 4.45 (t, 1H, —$CHNH_2$), 4.01 (d, 2H, $CH_2$=$CHCH_2$—) and 3.75 (d, 2H, —$OCH_2CHNH$). $^{13}$C NMR ($CDCl_3$, δ, ppm): 167.70, 152.64, 133.42, 118.67, 72.79, 68.00 and 58.61.

A similar method was used to synthesize PE-L-Ser-NCA. Obtained 0.8 g (Yield: 83%). $^1$H NMR ($CDCl_3$, δ, ppm): 6.74 (s, 1H, —NH), 5.75 (m, 1H, $CH_2$=$CHCH_2CH_2CH_2$—), 5.22 (t, 2H, $CH_2$=$CHCH_2CH_2CH_2$—), 4.43 (t, 1H, —$CHNH_2$), 3.73 (d, 2H, —$OCH_2CHNH$), 3.46 (m, 2H, $CH_2$=$CHCH_2CH_2CH_2$—), 2.04 (m, 2H, $CH_2$=$CHCH_2CH_2CH_2$—) and 1.61 (m, 2H, $CH_2$=$CHCH_2CH_2CH_2$—). $^{13}$C NMR ($CDCl_3$, δ, ppm): 168.04, 153.04, 137.96, 115.32, 71.42, 68.71, 58.78, 30.15 and 28.57.

Synthesis of methyl-terminated poly(ethylene glycol) block poly (O-allyl-L-serine) (mPEG-b-PALLS or 5a) and methyl-terminated poly(ethylene glycol) block poly (O-pentenyl-L-serine) (mPEG-b-PPELS or 5b)

Inside a glove-box, O-allyl-L-serine-based N-carboxyanhydride (4a) (100 mg, 0.58 mmol) was dissolved in DMF (4.0 mL) followed by adding to a vial containing mPEG-$NH_2$ (MW=5000, 29 mg, M/I=100). The polymerization was carried at room temperature. FTIR was used to monitor the polymerization until the conversion was above 99% (~48 h). The DMF polymerization solution was directly used for the next step due to the poor solubility of poly(L-serine). mPEG-b-PPELS was synthesized via the same method as above.

Synthesis of methyl-terminated poly(ethylene glycol) block cysteamine hydrochloride grafted poly (O-allyl-L-serine) [mPEG-b-(PALLS-g-CA) or 6a] and methyl-terminated poly(ethylene glycol) block cysteamine hydrochloride grafted poly (O-pentenyl-L-serine) [mPEG-b-(PPELS-g-CA) or 6b]

In a quartz flask, cysteamine hydrochloride (100 mg, 0.94 mmol, 1.62 equivalent of the allyl groups) and photoinitiator (DMPA, 5 mg, 5 wt %) were added to the above polymerization solution, followed by purging with $N_2$ for 5 min. The quartz flask was well sealed and irradiated with a UV lamp (365 nm, 16 mW) for 30 min. The product (6a and 6b) was purified by dialysis against DI water using a dialysis bag with a cut-off MW=1000.

Synthesis of Polymer 7

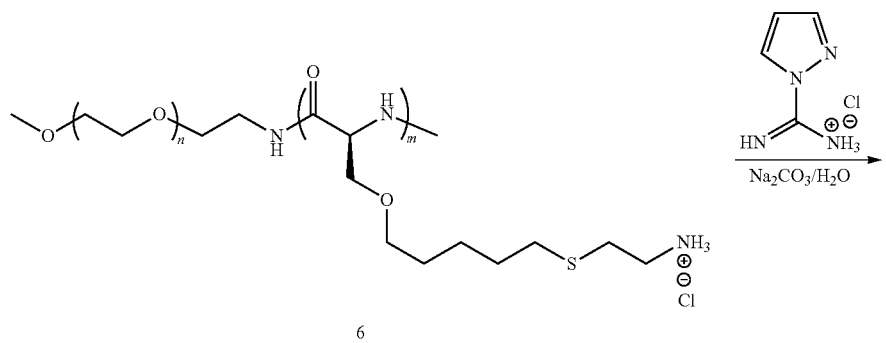

6

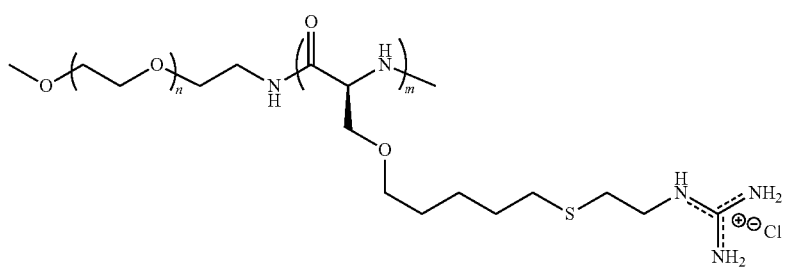

7

Results and discussion. O-Allyl-L-serine-based N-carboxyanhydride (4a) and O-1-pentene-L-serine-based N-carboxyanhydride (4b) have been synthesized via three steps with a relative low overall yield (~9%) (Scheme 13-1). The first step was an etherification in the presence of a strong base, i.e., sodium hydride due to low reactivity of alkyl hydroxide groups. Many side reactions happened in this step which is the key reason lead to low yield. Esterification of the Boc-Ser-OH was also attempted to functionalize the hydroxide groups, which end up with no success. After cyclization, liquid monomers 4a and 4b were obtained, which brought purification issues. These monomers were purified by repeatedly dissolving-and-precipitating using anhydrous THF and hexane, and then directly used for the next step. The molecular structure of 4a and 4b were verified by $^1$H NMR and $^{13}$C NMR.

Homopolymerizations of 4a and 4b were attempted firstly. However, the resulting polymers showed poor solubility in common organic solvents, such as chloroform, dichloromethane, THF etc. due to β-sheet conformation, which made them hard to purify. Furthermore, these polymers showed very weak DRI response during the SEC test, which result in troubles to figure out their molecular weights. Thus, block copolymers containing PEG building block were synthesized to solve the above problems. The MW can be calculated using $^1$H NMR, but the solubility of these polymers turned out not improved.

The polymerization solutions were directly used for the thiol-ene "click" reaction and the cysteamine hydrochloride grafted mPEG-b-PALLS or mPEG-b-PPELS was dialysis against DI water to rid of the impurities. The polymer aqueous solutions was filtered and diluted for CD tests. A typical β-sheet conformation was revealed. After lyophilization, the resulting polymers (6a and 6b) were not able to re-dissolve in DI water due to the intermolecular hydrogen bond. FTIR results revealed an amide I peak at 1622 cm$^{-1}$ for both 6a and 6b, indicating a β-sheet conformation in the solid state.

Summary.

O-Allyl-L-serine-based N-carboxyanhydride and O-1-pentene-L-serine-based N-carboxyanhydride have been successfully synthesized via etherification, deprotection reaction and cyclization reaction. These monomers can be polymerized via ring-opening polymerization using mPEG-NH$_2$ as the initiators. The resulting block copolymers were modified by cysteamine hydrochloride via thiol-ene reactions using UV irradiation. Ionic poly(L-serine)s with two different hydrophobic side-chain lengths (6a contains 9 σ-bond and 6b contains 11 σ-bond) were successfully obtained after lyophilization. These polymers (6a and 6b) showed β-sheet conformation in aqueous solution and in the solid state.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with

The invention claimed is:

1. A polymer comprising Formula IA:

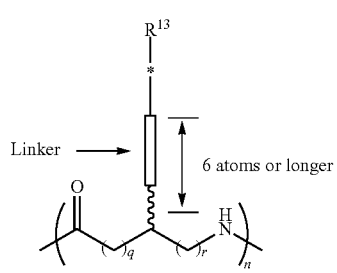
(IA)

wherein
n is about 6 to about 1000;
q is 0 to about 5;
r is 0 to about 5;
$R^{13}$ is H, absent, an aromatic group, or an aliphatic group, wherein the aromatic group or aliphatic group is optionally substituted;
Linker is a chain of atoms comprising an ester, wherein the chain is 6 atoms or longer; and
* comprises a nitrogen heterocycle, a guanidinium group, a hydrazone, a hydrazide, a sulfonate, or a carboxylate;
or a salt thereof; wherein the term "about" refers to one or two integers greater than or less than the recited integer.

2. The polymer of claim 1 wherein the polymer is positively or negatively charged and is in the form of an α-helix.

3. The polymer of claim 2 wherein the α-helix form is stable at pH 1 to about pH 11 in an aqueous solution, and in an aqueous solution containing up to a 4 M concentration of NaCl.

4. The polymer of claim 1 wherein the polymer forms an α-helix in aqueous solution wherein the helix is stable at temperatures up to about 90° C.

5. The polymer of claim 1 wherein the backbone of the polymer of Formula IA comprises glutamic acid residues or aspartic acid residues.

6. The polymer of claim 1 wherein the Linker is a $(C_6-C_{20})$alkyl group comprising an ester, wherein the $(C_6-C_{20})$alkyl group is optionally interrupted by one, two, three, or four nitrogen atoms, oxygen atoms, phenyl groups, a sulfur atom, a triazole group, or a combination thereof, and wherein the $(C_6-C_{20})$alkyl group is optionally substituted by one, two, three, four, or five oxo groups, hydroxy groups, $(C_1-C_4)$alkyl groups, pyridine groups, piperidine groups, pyrrolidine groups, monosaccharide groups, or a combination thereof.

7. The polymer of claim 2 wherein * comprises a nitrogen heterocycle, a guanidinium group, a sulfonate, or a carboxylate.

8. The polymer of claim 6 wherein the polymer comprises a polymer of Formula IIb or IIc:

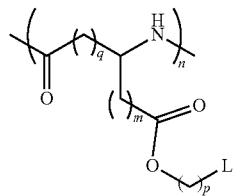
(IIb)

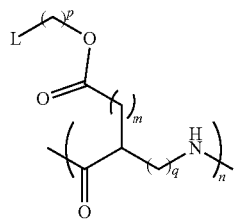
(IIc)

wherein
n is about 10 to about 500;
m is 1 to about 10;
p is 1 to about 16;
q is 0 to about 5;
L is $—R^1$, $—NH—R^2$, or $-Ph-CH_2—NH—R^2$;
$R^1$ comprises a triazole, a guanidinium, a carboxylate, a sulfonate, or a combination thereof; and
$R^2$ is $—C(=O)$-pyridine, sugar, phenyl, phenyl meta para substituted with a crown ether moiety; or $(C_2-C_{10})$alkyl optionally substituted with one or more hydroxy, pyridine, piperidine, or pyrrolidine groups;
or a salt thereof.

9. The polymer of claim 8 wherein the polymer comprises a polymer of Formula IIa:

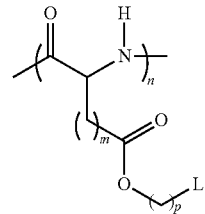
(IIa)

wherein
$R^1$ comprises a triazole a guanidinium, or a carboxylate.

10. The polymer of claim 8 wherein q is 1 to 5.

11. The polymer of claim 8 wherein q is 1 to about 5.

12. The polymer of claim 8 wherein the polymer comprises a polymer of Formula IIIa or IIIb:

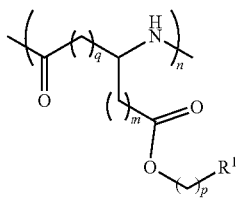
(IIIa)

-continued

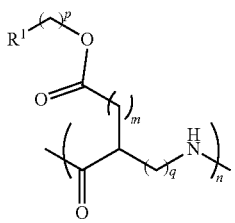

(IIIb)

wherein
R¹ comprises a triazole or a guanidinium.

13. The polymer of claim 12 wherein q is 1 to about 5.

14. The polymer of claim 9 wherein the polymer comprises Formula IIIc:

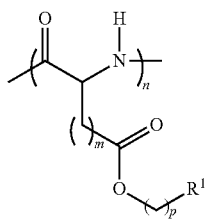

(IIIc)

wherein
R¹ comprises a triazole or a guanidinium; and
m is 1 to 9.

15. The polymer of claim 1 wherein n is 100 or greater.

16. The polymer of claim 1 wherein the polymer comprising Formula IA is a block copolymer or a random copolymer.

17. A method for delivering molecular cargo to a cell comprising:
contacting a cell with a composition comprising a polymer of claim 1 and molecular cargo, and optionally contacting the cell with an effective transfection-promoting amount of nocodazole; wherein the polymer adopts a secondary structure, where the secondary structure comprises an α-helix or a β-sheet; under conditions sufficient to transfect the cell with the molecular cargo; wherein the molecular cargo comprises, DNA, RNA, a protein, a small molecule drug, or a diagnostic agent.

18. A method for inhibiting bacterial growth comprising:
contacting bacteria with a composition comprising a polymer of claim 1, wherein the polymer adopts a secondary structure, where the secondary structure comprises an α-helix or a β-sheet; under conditions sufficient to inhibit the growth of the bacteria.

19. A method for inhibiting cancer cell growth comprising:
contacting cancer cells with a composition comprising a polymer of claim 1, wherein the polymer is in the form of a secondary structure, where the secondary structure comprises an α-helix or a β-sheet; under conditions sufficient to inhibit the growth of the cancer cells.

20. A method for destabilizing a cell membrane or causing pore formation in a cell comprising:
contacting the cell with a composition comprising a polymer claim 1, wherein the polymer is in the form of a stable α-helix; under conditions sufficient contact the cell with the polymer, whereby the polymer causes pore formation in the cell.

21. The polymer of claim 8 wherein the polymer comprises a polymer of Formula P7 or P8:

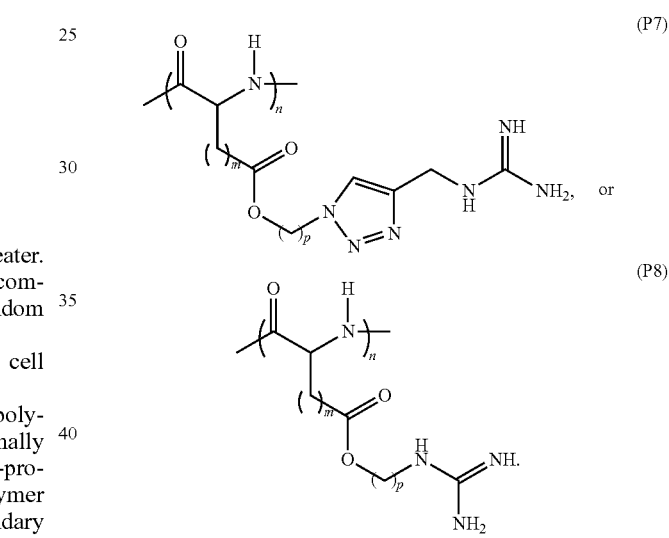

22. The polymer of claim 21 wherein n is 55, m is 2, and p is 8.

* * * * *